(12) United States Patent (10) Patent No.: US 9,315,530 B2
Singh et al. (45) Date of Patent: Apr. 19, 2016

(54) ADSORPTION OF IMMUNOPOTENTIATORS TO INSOLUBLE METAL SALTS

(75) Inventors: Manmohan Singh, Cary, NC (US);
David A. G. Skibinski, Singapore (SG);
Tom Yao-Hsiang Wu, San Diego, CA (US); Yongkai Li, San Diego, CA (US);
Alex Cortez, San Diego, CA (US);
Xiaoyue Zhang, San Diego, CA (US);
Yefen Zou, San Diego, CA (US);
Timothy Z. Hoffman, San Diego, CA (US); Jianfeng Pan, San Diego, CA (US); Kathy Yue, Minneapolis, MN (US)

(73) Assignee: Novartis AG, Basel (CH)

( * ) Notice: Subject to any disclaimer, the term of this patent is extended or adjusted under 35 U.S.C. 154(b) by 15 days.

(21) Appl. No.: 13/820,370

(22) PCT Filed: Sep. 1, 2011

(86) PCT No.: PCT/US2011/050231
§ 371 (c)(1),
(2), (4) Date: Jun. 21, 2013

(87) PCT Pub. No.: WO2012/031140
PCT Pub. Date: Mar. 8, 2012

(65) Prior Publication Data
US 2013/0274465 A1 Oct. 17, 2013

Related U.S. Application Data

(60) Provisional application No. 61/379,126, filed on Sep. 1, 2010, provisional application No. 61/448,394, filed on Mar. 2, 2011, provisional application No. 61/466,887, filed on Mar. 23, 2011.

(51) Int. Cl.
*A61K 39/39* (2006.01)
*C07F 9/6561* (2006.01)
*A61K 31/661* (2006.01)
*A61K 31/6615* (2006.01)
*A61K 31/662* (2006.01)
*A61K 39/095* (2006.01)
*C07D 471/04* (2006.01)
*C07D 487/04* (2006.01)
*C07F 9/645* (2006.01)
*C07F 9/6512* (2006.01)
*C07F 9/6558* (2006.01)
*A61K 39/00* (2006.01)

(52) U.S. Cl.
CPC .......... *C07F 9/6561* (2013.01); *A61K 31/661* (2013.01); *A61K 31/662* (2013.01); *A61K 31/6615* (2013.01); *A61K 39/095* (2013.01); *A61K 39/39* (2013.01); *C07D 471/04* (2013.01); *C07D 487/04* (2013.01); *C07F 9/645* (2013.01); *C07F 9/65122* (2013.01);

*C07F 9/65583* (2013.01); *C07F 9/65616* (2013.01); *A61K 2039/55505* (2013.01); *A61K 2039/55511* (2013.01)

(58) Field of Classification Search
CPC ............ A61K 31/661; A61K 31/6615; A61K 31/662; A61K 39/39; C07D 471/04
See application file for complete search history.

(56) References Cited

U.S. PATENT DOCUMENTS

| 4,666,886 | A | 5/1987 | Baschang |
| 5,059,258 | A | 10/1991 | Wefers et al. |
| 5,936,076 | A | 8/1999 | Higa et al. |
| 6,699,474 | B1 | 3/2004 | Cerny |
| 7,115,592 | B2 | 10/2006 | Balzarini et al. |
| 7,220,545 | B2 | 5/2007 | Binz et al. |
| 7,309,494 | B2 | 12/2007 | Corvaia et al. |
| 7,488,490 | B2 | 2/2009 | Davis et al. |
| 7,691,877 | B2 * | 4/2010 | Jones et al. .................. 514/303 |
| 7,771,726 | B2 | 8/2010 | Tsuji et al. |
| 8,222,257 | B2 | 7/2012 | Hostetler et al. |
| 8,275,711 | B2 | 9/2012 | Jackowski et al. |
| 8,338,593 | B2 * | 12/2012 | Chong et al. .................. 544/157 |
| 8,367,670 | B2 | 2/2013 | Desai et al. |
| 8,466,167 | B2 | 6/2013 | Wu et al. |
| 9,045,470 | B2 | 6/2015 | Wu et al. |
| 2004/0202668 | A1 | 10/2004 | Boutriau et al. |
| 2008/0008682 | A1 * | 1/2008 | Chong et al. ................. 424/85.6 |

(Continued)

FOREIGN PATENT DOCUMENTS

| WO | WO-9318150 A1 | 9/1993 |
| WO | WO-9527787 A1 | 10/1995 |

(Continued)

OTHER PUBLICATIONS

Bortolatto, J. et al., "Toll-like receptor 4 agonists adsorbed to aluminium hydroxide adjuvant attenuate ovalbumin-specific allergic airway disease: role of MyD88 adaptor molecule and interleukin-12/interferon-gamma axis," Clin. Exper. Aller. 38(10): 1668-1679 (2008).

(Continued)

*Primary Examiner* — D Margaret M. Seaman
(74) *Attorney, Agent, or Firm* — Helen Lee; Virginia Campen

(57) ABSTRACT

Immunopotentiators can be adsorbed to insoluble metal salts, such as aluminum salts, to modify their pharmacokinetics, pharmacodynamics, intramuscular retention time, and/or immunostimulatory effect. Immunopotentiators are modified to introduce a moiety, such as a phosphonate group, which can mediate adsorption. These modified compounds can retain or improve their in vivo immunological activity even when delivered in an adsorbed form.

**

(56) References Cited

U.S. PATENT DOCUMENTS

| | | |
|---|---|---|
| 2009/0099216 A1 | 4/2009 | Millichip et al. |
| 2009/0105212 A1 | 4/2009 | Isobe et al. |
| 2009/0118263 A1 | 5/2009 | Hashimoto et al. |
| 2009/0143400 A1 | 6/2009 | McInally et al. |
| 2009/0192153 A1 | 7/2009 | Hashimoto et al. |
| 2009/0221631 A1 | 9/2009 | Jones et al. |
| 2009/0232844 A1 | 9/2009 | Sutton et al. |
| 2010/0056031 A1 | 3/2010 | Chiu et al. |
| 2011/0028715 A1 | 2/2011 | Isobe et al. |
| 2011/0180430 A1 | 7/2011 | Rappuoli et al. |
| 2012/0177681 A1 | 7/2012 | Singh et al. |
| 2012/0237546 A1 | 9/2012 | Singh et al. |
| 2013/0122042 A1 | 5/2013 | Otten et al. |
| 2013/0236492 A1 | 9/2013 | Baudner et al. |
| 2013/0274465 A1 | 10/2013 | Singh et al. |
| 2013/0330840 A1 | 12/2013 | Skibinski et al. |
| 2014/0112950 A1 | 4/2014 | Singh et al. |
| 2014/0363461 A1 | 12/2014 | Bagnoli et al. |
| 2015/0030630 A1 | 1/2015 | Jain et al. |
| 2015/0125475 A1 | 5/2015 | Dodd et al. |
| 2015/0132339 A1 | 5/2015 | Bufali et al. |
| 2015/0190493 A1 | 7/2015 | Baudner et al. |
| 2015/0258190 A1 | 9/2015 | Grandi |

FOREIGN PATENT DOCUMENTS

| | | |
|---|---|---|
| WO | WO-9601272 A1 | 1/1996 |
| WO | WO-9601273 A1 | 1/1996 |
| WO | WO-9616046 A2 | 5/1996 |
| WO | WO-9725429 A1 | 7/1997 |
| WO | WO-98/19702 A1 | 5/1998 |
| WO | WO-0037494 A2 | 6/2000 |
| WO | WO-0202606 A2 | 1/2002 |
| WO | WO-03010317 A1 | 2/2003 |
| WO | WO-03049762 A2 | 6/2003 |
| WO | WO-03097091 A2 | 11/2003 |
| WO | WO-03105769 A2 | 12/2003 |
| WO | WO-2004032958 A1 | 4/2004 |
| WO | WO-2004111064 A1 | 12/2004 |
| WO | WO-2005002619 A2 | 1/2005 |
| WO | WO-2005/089794 A2 | 9/2005 |
| WO | WO-2005084306 A2 | 9/2005 |
| WO | WO-2005102049 A1 | 11/2005 |
| WO | WO-2006089264 A2 | 8/2006 |
| WO | WO-2006091517 A2 | 8/2006 |
| WO | WO-2006138004 A2 | 12/2006 |
| WO | WO-2007/000322 A1 | 1/2007 |
| WO | WO-2007034173 A1 | 3/2007 |
| WO | WO-2007034917 A1 | 3/2007 |
| WO | WO-2007040840 A2 | 4/2007 |
| WO | WO-2007060548 A2 | 5/2007 |
| WO | WO-2007093901 A1 | 8/2007 |
| WO | WO-2007/109813 A1 | 9/2007 |
| WO | WO-2007110700 A2 | 10/2007 |
| WO | WO-2008004948 A1 | 1/2008 |
| WO | WO-2008005555 A1 | 1/2008 |
| WO | WO-2008/020328 A2 | 2/2008 |
| WO | WO-2008020330 A2 | 2/2008 |
| WO | WO-2008/028957 A2 | 3/2008 |
| WO | WO-2008047174 A1 | 4/2008 |
| WO | WO-2008047249 A2 | 4/2008 |
| WO | WO-2008101867 A1 | 8/2008 |
| WO | WO-2008114817 A1 | 9/2008 |
| WO | WO-2008135791 A1 | 11/2008 |
| WO | WO-2009019553 A2 | 2/2009 |
| WO | WO-2009050586 A1 | 4/2009 |
| WO | WO-2009067081 A1 | 5/2009 |
| WO | WO-2009081172 A1 | 7/2009 |
| WO | WO 2009/111337 | 9/2009 |
| WO | WO-2009111337 A1 | 9/2009 |
| WO | WO-2009118296 A2 | 10/2009 |
| WO | WO-2010003009 A2 | 1/2010 |
| WO | WO-2010014913 A1 | 2/2010 |
| WO | WO-2010/067201 A2 | 6/2010 |
| WO | WO-2010077613 A1 | 7/2010 |
| WO | WO-2010/094663 A1 | 8/2010 |
| WO | WO-2010119343 A2 | 10/2010 |
| WO | WO-2010140119 A1 | 12/2010 |
| WO | WO-2010144734 A1 | 12/2010 |
| WO | WO 2011/027222 | 3/2011 |
| WO | WO-2011024072 A2 | 3/2011 |
| WO | WO-2011027222 A2 | 3/2011 |
| WO | WO 2011/057267 | 5/2011 |
| WO | WO 2011/119759 | 9/2011 |
| WO | WO-2012031140 A1 | 3/2012 |
| WO | WO-2012/117377 A1 | 9/2012 |

OTHER PUBLICATIONS

Cooper, C. L. et al., "CPG 7909, an Immunostimulatory TLR9 Agonist Oligodeoxynucleotide, as Adjuvant to Engerix-B (R) HBV Vaccine in Healthy Adults: A Double-Blind Phase I/II Study," J. Clin. Immun. 24(6): 693-701 (2004).

Hancock, G. E. et al., "Adjuvants recognized by toll-like receptors inhibit the induction of polarized type 2 T cell responses by natural attachment (G) protein of respiratory syncytial virus," Vaccines 21 (27-30): 4348-4358 (2003).

Leroux-Roels, G., "Unmet needs in Modern Vaccinology Adjuvants to Improve the Immune Response," Vaccine 28(3): C25-C36 (2010).

Barnett et al., (2001). "The ability of an oligomeric human immunodeficiency virus type 1 (HIV-1) envelope antigen to elicit neutralizing antibodies against primary HIV-1 isolates is improved following partial deletion of the second hypervariable region," J Virol, 75(12):5526-40.

Burrell et al., (1999). "Stability of aluminium-containing adjuvants to autoclaving," Vaccine, 17(20-21):2599-603.

Cassone & Torosantucci, (2006). "Opportunistic fungi and fungal infections: the challenge of a single, general antifungal vaccine," Expert Rev Vaccines, 5(6):859-67.

CDC, (1998). "Notice to readers availability of new rabies vaccine for human use," MMWR Morb Mortal Weekly Report, 47(1):12, 19.3 pages.

Chang et al., (2001). "Degree of antigen adsorption in the vaccine or interstitial fluid and its effect on the antibody response in rabbits," Vaccine, 19(20-22):2884-9.

Clausi et al., (2008). "Influence of particle size and antigen binding on effectiveness of aluminum salt adjuvants in a model lysozyme vaccine," J Pharm Sci, 97(12):5252-62.

Covacci & Rappuoli, (2000). "Tyrosine-phosphorylated bacterial proteins: Trojan horses for the host cell," J. Exp. Med. 191(4):587-592.

Covacci et al., (1993). "Molecular characterization of the 128-kDa immunodominant antigen of Helicobacter pylori associated with cytotoxicity and duodenal ulcer," Proc. Natl. Acad. Sci. USA, 90(12):5791-5795.

Dasarai et al., (2011). "Recombinant glycoprotein B vaccine formulation with Toll-like receptor 9 agonist and immune-stimulating complex induces specific immunity against multiple strains of cytomegalovirus," J Gen Virol, 92:1021-31.

De Libero et al, (2005). "Recognition of lipid antigens by T cells," Nature Reviews Immunology, 5:485-496.

Earl et al., (2001). "Immunogenicity and protective efficacy of oligomeric human immunodeficiency virus type 1 gp140," J Virol, 75(2):645-53.

Evans et al., (1995). "Identification of four new prokaryotic bacterioferritins, from Helicobacter pylori, Anabaena variabilis, Bacillus subtilis and Treponema pallidum, by analysis of gene sequences," Gene, 153:123-127.

Gennaro, (2000). Remington: The Science and Practice of Pharmacy, 20th edition, ISBN: 0683306472. Table of Contents, 4 pages.

Giuliani et al., (2006). "A universal vaccine for serogroup B meningococcus," Proc Natl Acad Sci USA, 103(29):10834-9.

Goff et al, (2004). "Effects of lipid chain lengths in alpha-galactosylceramides on cytokine release by natural killer T cells," J. Am. Chem. Soc., 126(42):13602-13603.

(56) References Cited

OTHER PUBLICATIONS

Harper et al., (2004). "Efficacy of a bivalent L1 virus-like particle vaccine in prevention of infection with human papillomavirus types 16 and 18 in young women: a randomised controlled trial," Lancet, 364(9447): 1757-65.
Hashiro et al. (2009). "Rapid and Efficient Induction of an Endogenous Cell Signaling Event by Subcellular Targeting of a Synthetic Ligand" JAGS, 131(38):13568-13569.
Hockova et al., (2003), "5-Substituted-2,4-diamino-6-[2-(phosphonomethoxy)ethoxy]pyrimidines-acyclic nucleoside phosphonate analogues with antiviral activity," J. Med. Chem., 46:5064-5073.
Iyer et al., (2004). "Mechanism of adsorption of hepatitis B surface antigen by aluminum hydroxide adjuvant," Vaccine, 22:1475-9.
Keitel et al., (1996). "Increasing doses of purified influenza virus hemagglutinin and subvirion vaccines enhance antibody responses in the elderly," Clin Diagn Lab Immunol, 3(5):507-10.
Levesque & de Alwis, (2005). "Mechanism of adsorption of three recombinant *Streptococcus* pneumoniae (Sp) vaccine antigens by an aluminum adjuvant," Human Vaccines, 1(2):70-3.
Marchetti et al., (1998), "Protection against Helicobacter pylori infection in mice by intragastric vaccination with H. pylori antigens is achieved using a non-toxic mutant of *E. coli* heat-labile enterotoxin (LT) as adjuvant," Vaccine, 16(1):33-37.
Mendez et al., (2007). "Potentiation of the immune response to non-adsorbed antigens by aluminum-containing adjuvants," Vaccine, 25(5):825-33.
Morefield et al., (2005). "Effect of phosphorylation of ovalbumin on adsorption by aluminum-containing adjuvants and elution upon exposure to interstitial fluid," Vaccine 23(13): 1502-6.
Nencioni et al., (1991), "Properties of pertussis toxin mutant PT-9K/129G after formaldehyde treatment," Infect Immun, 59(2): 625-30.
Oki et al., (2004). "The clinical implication and molecular mechanism of preferential IL-4 production by modified glycolipid-stimulated NKT cells," J. Clin. Investig, 113(11):1631-1640.
Powell & Newman, (1995). Vaccine Design: The Subunit and Adjuvant Approach. Pharmaceutical Biotechnology, vol. 6. ISBN: 030644867X. Table of Contents, 23 pages.
Rappuoli et al., (1991). "Towards third-generation whooping cough vaccines," TIBTECH 9:232-238.
Rosenberg et al., (2010). "TLR reporter cell lines for screening TLR agonists and antagonists," J Immunol 184: 136.20. Meeting Abstract. 2 pages.
Shi et al., (2002), "Change in the degree of adsorption of proteins by aluminum-containing adjuvants following exposure to interstitial fluid: freshly prepared and aged model vaccines," Vaccine 20:80-5.
Telford et al., (1994). "Gene structure of the Helicobacter pylori cytotoxin and evidence of its key role in gastric disease," J. Exp. Med., 179:1653-1658.
Treanor et al., (1996). "Evaluation of a recombinant hemagglutinin expressed in insect cells as an influenza vaccine in young and elderly adults," J Infect Dis, 173:1467-70.
Tummuru et al., (1993). "Cloning and expression of a high-molecular-mass major antigen of Helicobacter pylori: evidence of linkage to cytotoxin production," Infect. Immun., 61(5):1799-1809.
Yang et al., (2004). "The C-glycoside analogue of the immunostimulant alpha-galactosylceramide (KRN7000): synthesis and striking enhancement of activity," Angew Chem Int Ed, 43: 3818-3822.
Zhang et al., (2001), "Expression, purification, and characterization of recombinant HIV gp140. The gp41 ectodomain of HIV or simian immunodeficiency virus is sufficient to maintain the retroviral envelope glycoprotein as a trimer," J. Biol. Chem. 276(43):39577-85.
Abarca (2003). "Reduced-Antigen Combined Diphtheria-Tetanus-Acellular Pertussis Vaccine (Boostrix) a Viewpoint by Katia Abarca," Drugs, Adis International Ltd, NZ, 63(13): 1415.
Banus et al. (2008). "The role of Toll-like receptor-4 in pertussis vaccine-induced immunity." BMC Immunol. 9:21:1471-2172.
Billaudelle et al. (1962). "[Triple vaccine without aluminium-"carrier"]," Nord Med, 68:1339-40. [Article in Swedish].

Brewer (2006). "(How) do aluminium adjuvants work?" Immunol Lett, 102(1):10-5.
Davis et al. (1998). "CpG DNA is a potent enhancer of specific immunity in mice immunized with recombinant hepatitis B surface antigen," J Immunol, 160(2):870-6.
Garcon et al (2006). "Development and evaluation of AS04, a novel and improved adjuvant system containing MPL and aluminum salt," Immunopotentiators in Modern Vaccines, p. 161-177.
Geurtsen et al. (2007). "Lipopolysaccharide analogs improve efficacy of acellular pertussis vaccine and reduce type I hypersensitivity in mice." Clin Vaccine Immunol. 14(7):821-9.
Gröndahl-Yli-Hannuksela et al. (2012). "Gene polymorphism in toll-like receptor 4: effect on antibody production and persistence after acellular pertussis vaccination during adolescence," J Infect Dis. 205(8):1214-9.
Hem and White. (1995). "Structure and Properties of Aluminum-Containing Adjuvants," Vaccine Design: The subunit 1 and adjuvant approach, ed. M.F. Powell and M.J. Newman (Plenum Press, New York), vol. 6, Chapter 9, pp. 249-276.
Hem et al. (2007). "Relationship between physical and chemical properties of aluminum-containing adjuvants and immunopotentiation," Expert Review Vaccines, 6(5): 685-698.
International Search Report for International Application No. PCT/EP2013/054672, mailed Oct. 2, 2014. 9 pages.
International Search Report for International Application No. PCT/IB2010/002386, mailed Feb. 18, 2011, 5 pages.
International Search Report, mailed Aug. 14, 2012, for International Application No. PCT/IB2012/050989, filed Mar. 2, 2012.
Mansour et al. (2007). "Improved Efficacy of a Licensed Acellular Pertussis Vaccine, Reformulated in an Adjuvant Emulsion of Liposomes in Oil, in a Murine Model," Clin Vaccine Immunol. 14(10): 1381-1383.
Munoz, F.M. (2006). "Pertussis in infants, children, and adolescents: Diagnosis, treatment, and Prevention," Seminars in Pediatric Infectious Diseases, 17(1):14-9.
Racke et al. (2005). "PTX cruiser: driving autoimmunity via TLR4," Trends Immunol. 26(6):289-291.
Response to Final Office Action mailed Dec. 4, 2014, for U.S. Appl. No. 13/394,036, 22 pages.
Response to Notice of Non-Compliant Amendment dated Jul. 21, 2014, for U.S. Appl. No. 13/790,948, filed Mar. 8, 2013.
Response to Office Action mailed Jul. 24, 2015, for U.S. Appl. No. 13/223,793, 54 pages.
Response to United States Advisory Action, mailed on Jan. 8, 2015, for U.S. Appl. No. 13/394,036, filed May 30, 2012.
Response to United States Final Office Action, mailed on Dec. 4, 2014, for U.S. Appl. No. 13/394,036, filed May 30, 2012.
Scheifele et al. (1995). "Can reductions in diphtheria toxoid or aluminum content reduce the reactogenicity of booster doses of DPT vaccine?" Immunology and Infectious Diseases (Oxford, GB), 5(1):73-77.
Singh et al. (2006). "A preliminary evaluation of alternative adjuvants to alum using a range of established and new generation vaccine antigens," Vaccine, 24(10):1680-6.
Steinhagen et al. (2011). "TLR-based immune adjuvants," Vaccine. 29(17):3341-55.
Sugai et al. (2005). "A CpG-containing oligodeoxynucleotide as an efficient adjuvant counterbalancing the Th1/Th2 immune response in diphtheria-tetanus-pertussis vaccine." Vaccine. 23(46-47):5450-6.
United States Advisory Action mailed on Dec. 11, 2014, for U.S. Appl. No. 13/394,036, filed May 30, 2012.
United States Final Office Action mailed Oct. 5, 2015, for U.S. Appl. No. 13/223,793, 16 pages.
United States Final Office Action mailed on May 28, 2015, for U.S. Appl. No. 13/790,948, filed Mar. 8, 2013.
United States Final Office Action mailed on Sep. 8, 2014, for U.S. Appl. No. 13/394,036, filed May 30, 2012.
United States Office Action mailed Aug. 14, 2015, for U.S. Appl. No. 13/394,036, 10 pages.
United States Office Action mailed on Sep. 16, 2015, for U.S. Appl. No. 14/002,700, filed Jan. 10, 2014.
van Duin D (2006). "Triggering TLR signaling in vaccination." Trends Immunol. Jan. 2006; 27(1):49-55.

(56) References Cited

OTHER PUBLICATIONS

Vecchi et al. (2012). "Aluminum adjuvant dose guidelines in vaccine formulation for preclinical evaluations," J Pharm Sci, 101(1):17-20.

Vergara et al. (2005). "Reduced-antigen-content-diphtheria-tetanus-acellular-pertussis and inactivated polio vaccine as a booster for adolescents 10 to 14 years of age," Eur J Pediatr, 164(6):377-82.

Wack et al. (2008). "Combination adjuvants for the induction of potent, long-lasting antibody and T-cell responses to influenza vaccine in mice," Vaccine, 26(4):552-61.

Wendorf et al. (2008). "A comparison of anionic nanoparticles and microparticles as vaccine delivery systems," Hum Vaccin, 4(1):44-9.

Written Opinion for International Application No. PCT/EP2013/054672, mailed Sep. 8, 2014. 13 pages.

Written Opinion for International Application No. PCT/IB2010/002386, mailed Mar. 2, 2013, 6 pages.

Wu et al. (2014). "Rational design of small molecules as vaccine adjuvants," Sci Transl Med, 6(263):263ra160.

* cited by examiner

ADSORPTION OF IMMUNOPOTENTIATORS TO INSOLUBLE METAL SALTS

This application is the U.S. National Phase of International Application No. PCT/US2011/050231, filed Sep. 1, 2011 and published in English, which claims the benefit of U.S. Provisional Application No. 61/379,126, which was filed Sep. 1, 2010, U.S. Provisional Application No. 61/448,394, which was filed Mar. 2, 2011 and U.S. Provisional Application No. 61/466,887, which was filed Mar. 23, 2011, the complete contents of all of which are hereby incorporated herein by reference for all purposes.

TECHNICAL FIELD

The invention is in the field of formulating immunopotentiating compounds for in vivo use. More particularly, the invention relates to the design of immunopotentiating agents for formulation by association with insoluble metal salts e.g. by adsorption.

SEQUENCE LISTING

The instant application contains a Sequence Listing which has been submitted via EFS-Web and is hereby incorporated by reference in its entirety. The ASCII copy, created on Mar. 1, 2013, is named 54166_SeqList.TXT, and is 25,327 bytes in size.

BACKGROUND ART

Early detection of specific classes of pathogens is accomplished by the innate immune system with help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs).

Toll-like receptors (TLRs) are an important family of PRRs and are widely expressed on innate immune cells, including dendritic cells (DCs), macrophages, mast cells, neutrophils, endothelial cells and fibroblasts. TLRs have broad specificity for conserved molecular patterns shared by bacteria, viruses and parasites.

A number of different TLRs have been characterized. These TLRs bind and become activated by different ligands, which in turn are located on different organisms or structures. The development of immunopotentiator compounds that are capable of eliciting responses in specific TLRs is of interest in the art.

For example, reference 1 describes certain lipopeptide molecules that are TLR2 agonists. References 2 to 5 each describe classes of small molecule agonists of TLR7. References 6 & 7 describe TLR7 and TLR8 agonists for treatment of diseases. These various compounds include small molecule immunopotentiators (SMIPs).

These compounds have typically been selected for their TLR-modulating activity, without attention to their pharmacokinetic or pharmacodynamic (PK/PD) properties or for their retention at an injection site where they can usefully exert an immunostimulatory effect. The compounds may thus have poor PK/PD or retention profiles when introduced in vivo. Moreover, it may be desirable to modify the systemic exposure of the compounds e.g. to minimise potential systemic side effects in widespread prophylactic immunisations, or to maintain systemic exposure in an emergency immunotherapeutic setting. As shown in FIGS. 1 to 5, injection of a TLR7 active SMIP into a subject initially results in high serum concentration which quickly drops, and injected compounds can be fully cleared from muscle within 24 hours.

It is an object of the invention to provide new formulations of immunopotentiators, and in particular of SMIPs, which can modify or improve the immunopotentiators' pharmacological properties, such as PK/PD profiles, cellular uptake, retention at injection sites, reduced general activation of B cells, etc. It is a further object to provide formulations which can improve their immunostimulating activity.

DISCLOSURE OF THE INVENTION

The inventors have surprisingly found that the PK/PD of immunopotentiators (and in particular TLR agonists), and their retention at sites of injection, can be modified by adsorbing them to insoluble metal salts, such as aluminium salts. Stable adsorption of the compounds ideally takes place by ligand exchange, but known SMIPs typically lack suitable functional groups. Thus SMIPs can be modified to introduce an adsorptive moiety, such as a phosphonate group, which can then mediate adsorption. The inventors have found that these modified SMIPs (in particular, TLR7 agonists) can retain their in vivo immunological activity even when delivered in an adsorbed form, and so the improved PK/PD properties are not at the expense of immunostimulating activity. Indeed, adsorption of TLR7 agonists is shown herein to improve their immunostimulatory activity. Furthermore, adsorption of the compounds can reduce peak serum concentrations and increase residence times at sites of intramuscular injection, which can contribute to modifying and controlling the level of systemic exposure. High systemic exposure can elicit the production of high levels of proinflammatory cytokines in the blood, so higher residence time at an injection site can help to minimise the production of proinflammatory cytokines in the blood, thus improving safety and/or tolerability of the compounds. Cellular uptake of the compounds can also be enhanced by adsorption.

The invention enables the modification of SMIPs to contain at least one adsorptive moiety such that the modified SMIP has the ability to adsorb to insoluble metal salt adjuvants. The inventors have realised the broad applicability of this modification and subsequent formulation for immunopotentiating agents as a whole. Therefore, described herein are a broad range of functionalised immunopotentiating compounds and compositions comprising these functionalised compounds that are illustrative of the present invention.

In a first aspect, the invention provides a TLR agonist comprising at least one adsorptive moiety, with the proviso that the TLR agonist:
 (a) is not a TLR4 agonist;
 (b) is not a TLR9 agonist;
 (c) is not a compound according to formula (I) or (II) as defined below;
 (d) is not a compound according to formula (III) as defined below;
 (e) is not a compound according to Formula (I-A) as defined below.

The presence of the adsorptive moiety enables the TLR agonist to be formulated with an insoluble metal salt adjuvant in order to modify or improve its pharmacokinetic and pharmacodynamic profile, to increase the duration of its retention at a site of intramuscular injection, and/or to increase its immunostimulatory effect.

In a second aspect, the invention provides a water-soluble TLR agonist comprising at least one adsorptive moiety, with the proviso that the water-soluble TLR agonist:

(a) is not a TLR4 agonist;
(b) is not a TLR9 agonist;
(c) is not a compound according to formula (I) or (II) as defined below; and
(d) is not a compound according to formula (III) as defined below.

In a third aspect, the invention provides a TLR agonist comprising at least one phosphonate group, with the proviso that the TLR agonist:
  (a) is not a phosphonate-containing compound according to formula (I) or (II) as defined below;
  (b) is not a phosphonate-containing compound according to formula (III), as defined below.
  (c) is not a phosphonate-containing compound according to formula (I-A), as defined below.

In a fourth aspect, the invention provides a compound comprising at least one adsorptive moiety, wherein the compound is an agonist of TLR1, TLR3, TLR5, TLR6, TLR8 or TLR11. The invention also provides such a compound adsorbed to an insoluble metal salt. Thus the invention provides a composition comprising the agonist compound and an insoluble metal salt, wherein the agonist compound is adsorbed onto the insoluble metal salt.

In a fifth aspect, the invention provides a compound comprising at least one adsorptive moiety, wherein the compound is an agonist of TLR1, TLR2, TLR3, TLR5, TLR6, TLR7, TLR8, or TLR11, with the proviso that the compound:
  (a) is not a compound according to formula (I) or (II) as defined below;
  (b) is not a compound according to formula (III), as defined below; and
  (c) is not a compound according to formula (I-A), as defined below.

In a sixth aspect, the invention provides a composition comprising a TLR agonist and an insoluble metal salt, wherein the TLR agonist is adsorbed onto the insoluble metal salt, with the proviso that the TLR agonist:
  (a) is not a TLR4 agonist;
  (b) is not a TLR9 agonist;
  (c) is not a compound according to formula (III) as defined below; and
  (d) is not a compound according to Formula (I-A) as defined below.

In some embodiments of this sixth aspect, the compound does not include an acyl chain or a cytosine nucleotide. In some embodiments of this sixth aspect, the agonist compound has a molecular weight below 1500 Da e.g. below 1300 Da, or preferably below 1000 Da.

According to a seventh aspect, the invention provides a composition comprising a TLR agonist and an insoluble metal salt, wherein the TLR agonist is adsorbed onto the insoluble metal salt, with the proviso that the TLR agonist:
  (a) is not a compound according to formula (III) as defined below;
  (b) is not a compound according to Formula (I-A) as defined below;
  (c) does not include an acyl chain; and
  (d) does not include a cytosine nucleotide.

Preferably, agonists of this seventh aspect have a molecular weight below 1000 Da.

According to an eighth aspect, the invention provides a TLR4 agonist comprising at least one adsorptive moiety, provided that the TLR4 agonist does not include an acyl chain. The invention also provides such a TLR4 agonist adsorbed to an insoluble metal salt. Thus the invention provides a composition comprising the TLR4 agonist compound and an insoluble metal salt, wherein the TLR4 agonist compound is adsorbed onto the insoluble metal salt.

According to a ninth aspect, the invention provides a TLR9 agonist comprising at least one adsorptive moiety, provided that the TLR9 agonist does not include a cytidine nucleoside. The invention also provides such a TLR9 agonist adsorbed to an insoluble metal salt. Thus the invention provides a composition comprising the TLR9 agonist compound and an insoluble metal salt, wherein the TLR9 agonist compound is adsorbed onto the insoluble metal salt.

According to a tenth aspect, the invention provides a TLR2 agonist comprising at least one adsorptive moiety, provided that the TLR2 agonist is not a compound according to formula (III) as defined below. The invention also provides such a TLR2 agonist adsorbed to an insoluble metal salt. Thus the invention provides a composition comprising the TLR2 agonist compound and an insoluble metal salt, wherein the TLR2 agonist compound is adsorbed onto the insoluble metal salt.

According to an eleventh aspect, the invention provides a TLR7 agonist comprising at least one adsorptive moiety, provided that the TLR7 agonist is not: (a) a compound according to formula (I) as defined below; (b) a compound according to formula (II) as defined below; or (c) a compound according to formula (I-A) as defined below. The invention also provides such a TLR7 agonist adsorbed to an insoluble metal salt. Thus the invention provides a composition comprising the TLR7 agonist compound and an insoluble metal salt, wherein the TLR7 agonist compound is adsorbed onto the insoluble metal salt.

According to a twelfth aspect, the invention provides a TLR4 agonist comprising at least one adsorptive moiety, wherein the TLR agonist has a molecular weight of less than 1000 Da. The invention also provides such a TLR4 agonist adsorbed to an insoluble metal salt. Thus the invention provides a composition comprising the TLR4 agonist compound and an insoluble metal salt, wherein the TLR4 agonist compound is adsorbed onto the insoluble metal salt.

According to a thirteenth aspect, the invention provides a TLR9 agonist comprising at least one adsorptive moiety, wherein the TLR agonist has a molecular weight of less than 1000 Da. The invention also provides such a TLR9 agonist adsorbed to an insoluble metal salt. Thus the invention provides a composition comprising the TLR9 agonist compound and an insoluble metal salt, wherein the TLR9 agonist compound is adsorbed onto the insoluble metal salt.

According to a fourteenth aspect, the invention provides a TLR agonist including between two and fifteen adsorptive moieties. In some embodiments of this aspect, the TLR agonist is (i) not a TLR4 agonist (ii) not a TLR9 agonist (iii) not a compound of formula (III) and/or (iv) not a compound of formula (IV). The invention also provides such an agonist adsorbed to an insoluble metal salt. Thus the invention provides a composition comprising the agonist compound and an insoluble metal salt, wherein the agonist compound is adsorbed onto the insoluble metal salt.

According to a fifteenth aspect, the invention provides a composition comprising a TLR agonist, an insoluble metal salt, and a buffer, wherein the TLR agonist is adsorbed onto the insoluble metal salt, with the proviso that (i) the buffer is not a phosphate buffer. In some embodiments of this aspect, the TLR agonist is (i) not a TLR4 agonist (ii) not a TLR9 agonist (iii) not a compound of formula (III) and/or (iv) not a compound of formula (IV).

According to a sixteenth aspect, the invention provides a TLR7 agonist selected from compounds according to any of formulae (C), (D), (E), and (H):

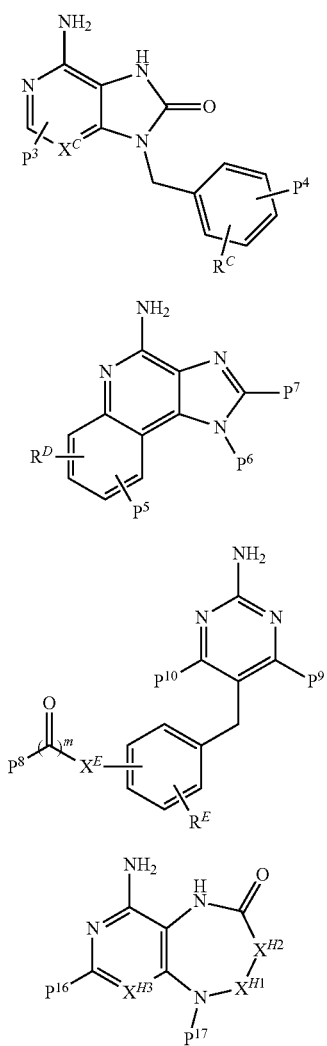

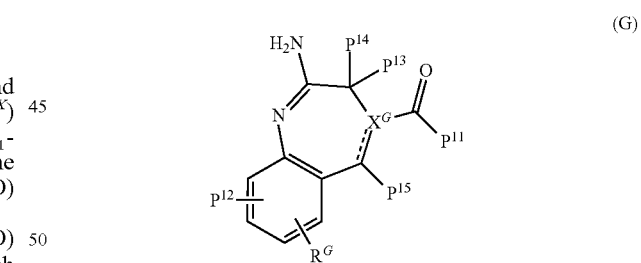

wherein:
(a) P³ is selected from H, C₁-C₆alkyl, CF₃, and —((CH₂)ₚO)_q(CH₂)ₚO_s— and —Y-L-X—P(O)(OR^X)(OR^Y); and P⁴ is selected from H, C₁-C₆alkyl, —C₁-C₆alkylaryl and —Y-L-X—P(O)(OR^X)(OR^Y); with the proviso that at least one of P³ and P⁴ is —Y-L-X—P(O)(OR^X)(OR^Y), (b) P⁵ is selected from H, C₁-C₆alkyl, and —Y-L-X—P(O)(OR^X)(OR^Y); P⁶ is selected from H, C₁-C₆alkyl each optionally substituted with 1 to 3 substituents selected from C₁-C₄alkyl and OH, and —Y-L-X—P(O)(OR^X)(OR^Y); and P⁷ is selected from H, C₁-C₆alkyl, —((CH₂)ₚO)_q(CH₂)ₚO_s—, —NHC₁-C₆alkyl and —Y-L-X—P(O)(OR^X)(OR^Y); with the proviso that at least one of P⁵, P⁶ and P⁷ is —Y-L-X—P(O)(OR^X)(OR^Y);

(c) P⁸ is selected from H, C₁-C₆alkyl, C₁-C₆alkoxy, —NHC₁-C₆alkyl each optionally substituted with OH, and —Y-L-X—P(O)(OR^X)(OR^Y); and P⁹ and P¹⁰ are each independently selected from H, C₁-C₆alkyl, C₁-C₆alkoxy, —NHC₁-C₆alkyl each optionally substituted with OH and C₁-C₆alkyl, and —Y-L-X—P(O)(OR^X)(OR^Y); with the proviso that at least one of P⁸, P⁹ or P¹⁰ is —Y-L-X—P(O)(OR^X)(OR^Y);

(d) P¹⁶ and each P¹⁸ are each independently selected from H, C₁-C₆alkyl, and —Y-L-X—P(O)(OR^X)(OR^Y); P¹⁷ is selected from H, C₁-C₆alkyl, aryl, heteroaryl, C₁-C₆alkylaryl, C₁-C₆alkyl heteroaryl, C₁-C₆alkylaryl-Y-L-X—P(O)(OR^X)(OR^Y) and —Y-L-X—P(O)(OR^X)(OR^Y), each optionally substituted with 1 to 2 substituents selected from C₁-C₆alkyl or heterocyclyl with the proviso that at least one of P¹⁶, P¹⁷ or a P¹⁸ contains a —Y-L-X—P(O)(OR^X)(OR^Y) moiety;

R^X and R^Y are independently selected from H and C₁-C₆alkyl;

R^C, R^D and R^H are each independently selected from H and C₁-C₆alkyl;

X^C is selected from CH and N;

R^E is selected from H, C₁-C₆alkyl, C₁-C₆alkoxy, C(O)C₁-C₆alkyl, halogen and —((CH₂)ₚO)_q(CH₂)ₚ—;

X^E is selected from a covalent bond, CR^{E2}R^{E3} and NR^{E4};

R^{E2}, R^{E3} and R^{E4} are independently selected from H and C₁-C₆alkyl;

X^{H1}—X^{H2} is selected from —CR^{H2}R^{H3}—, —CR^{H2}R^{H3}—CR^{H2}R^{H3}—, —C(O)CR^{H2}R^{H3}—, —C(O)CR^{H2}R^{H3}—, —CR^{H2}R^{H3}C(O)—, —NR^{H4}C(O)—, C(O)NR^{H4}—, CR^{H2}R^{H3}S(O)₂ and —CR^{H2}=CR^{H2}—;

R^{H2}, R^{H3} and R^{H4} are each independently selected from H, C₁-C₆alkyl and P¹⁸;

X^{H3} is selected from N and CN;

X is selected from a covalent bond, O and NH;

Y is selected from a covalent bond, O, C(O), S and NH;

L is selected from, a covalent bond C₁-C₆alkylene, C₁-C₆alkenylene, arylene, heteroarylene, C₁-C₆alkyleneoxy and —((CH₂)ₚO)_q(CH₂)ₚ— each optionally substituted with 1 to 4 substituents independently selected from halo, OH, C₁-C₄alkyl, —OP(O)(OH)₂ and —P(O)(OH)₂;

m is selected from 0 or 1;

each p is independently selected from 1, 2, 3, 4, 5 and 6;

q is selected from 1, 2, 3 and 4; and s is selected from 0 and 1.

According to a seventeenth aspect, the invention provides a TLR8 agonist selected from compounds according to formula (G):

wherein:
P¹¹ is selected from H, C₁-C₆alkyl, C₁-C₆ alkoxy, NR^V R^W and —Y-L-X—P(O)(OR^X)(OR^Y);

P¹² is selected from H, C₁-C₆alkyl, aryl optionally substituted by C(O)NR^V R^W, and —Y-L-X—P(O)(OR^X)(OR^Y);

P¹³, P¹⁴ and P¹⁵ are independently selected from H, C₁-C₆alkyl, C₁-C₆ alkoxy and —Y-L-X—P(O)(OR^X)(OR^Y);

with the proviso that at least one of P¹¹, P¹², P¹³, P¹⁴ or P¹⁵ is —Y-L-X—P(O)(OR^X)(OR^Y);

R^V and R^W are independently selected from H, C₁-C₆alkyl or together with the nitrogen atom to which they are attached form a 4 to 7 remembered heterocyclic ring;

X^G is selected from C, CH and N;

----- represents an optional double bond, wherein $X^G$ is C if ----- is a double bond; and
$R^G$ is selected from H and $C_1$-$C_6$alkyl;
X is selected from a covalent bond, O and NH;
Y is selected from a covalent bond, O, C(O), S and NH;
L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6 and q is selected from 1, 2, 3 and 4.

According to an eighteenth aspect, the invention provides a compound of formulae (B) or (F) or (J):

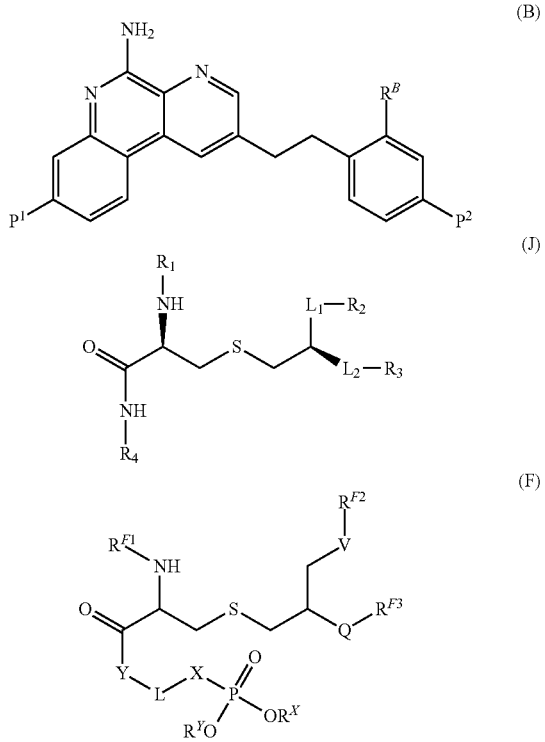

as defined below.

The seventeenth and eighteenth aspects include such agonists of formulae (B) or (G) adsorbed to an insoluble metal salt. Thus the invention provides a composition comprising the agonist compound and an insoluble metal salt, wherein the agonist compound is adsorbed onto the insoluble metal salt.

According to a nineteenth aspect, the invention provides a process for preparing an adjuvant complex, comprising a step of mixing a TLR agonist with an insoluble metal salt such that the TLR agonist adsorbs to the insoluble metal salt to form the complex. The TLR agonist is preferably a TLR agonist as variously described above e.g. in some embodiments the agonist is not a TLR4 agonist, a TLR9 agonist, a compound of formula (III), or a compound of formula (I-A). The invention also provides an adjuvant complex obtained or obtainable by this process. The complex can be mixed with an immunogen to provide an immunogenic composition.

According to a twentieth aspect, the invention provides a process for preparing a sterile adjuvant complex, comprising steps of: (i) mixing a TLR agonist with an insoluble metal salt such that the TLR agonist adsorbs to the insoluble metal salt to form the complex; and (ii) sterilising the complex. The agonist is preferably an agonist as variously described above e.g. in some embodiments the agonist is not a TLR4 agonist or a TLR9 agonist. The invention also provides a sterile adjuvant complex obtained or obtainable by this process. The sterile complex can be mixed with an immunogen to provide an immunogenic composition. Sterilisation can be conveniently achieved by autoclaving (or similar procedures [8]).

The invention also provides a process for preparing a sterile adjuvant complex, comprising steps of: (i) sterilising a solution or suspension of a TLR agonist; and (ii) combining the sterilised solution or suspension with a sterile insoluble metal salt. The invention also provides a process for preparing a sterile adjuvant complex, comprising steps of: (i) sterilising an insoluble metal salt; and (ii) combining the sterilised insoluble metal salt with a sterile solution or suspension of a TLR agonist. The invention also provides a process for preparing a sterile adjuvant complex, comprising a step of combining a sterile solution or suspension of a TLR agonist with a sterile insoluble metal salt. Sterilisation of the TLR agonist solution/suspension can conveniently be achieved by sterile filtration, and this material can be prepared in concentrated form. Sterilisation of the insoluble metal salt can conveniently be achieved by autoclaving. The sterile insoluble metal salt will typically be an aqueous suspension.

According to a twenty-first aspect, the invention provides a process for preparing an immunogenic composition, wherein the process comprises mixing a TLR agonist, an insoluble metal salt, and an immunogen, thereby providing the immunogenic composition. The invention also provides an immunogenic composition obtained or obtainable by this process. In some embodiments of this aspect, the TLR agonist is not compound 13 herein. In some embodiments of this aspect, the immunogen is not a three-protein mixture of 287-953, 936-741 and 961c as disclosed in references 40 & 73. In some embodiments of this aspect, the TLR agonist is (i) not a TLR4 agonist (ii) not a TLR9 agonist (iii) not a compound of formula (III) and/or (iv) not a compound of formula (IV).

According to a twenty-second aspect, the invention provides a process for preparing an immunogenic composition, comprising one of: (i) combining an immunogen with a mixture comprising a TLR agonist and an insoluble metal salt; (ii) combining an insoluble metal salt with a mixture comprising a TLR agonist and an immunogen; or (iii) combining a TLR agonist with a mixture comprising an insoluble metal salt and an immunogen. The invention also provides an immunogenic composition obtained or obtainable by this process. In some embodiments of this aspect, the TLR agonist is not compound 13 herein. In some embodiments of this aspect, the immunogen is not a three-protein mixture of 287-953, 936-741 and 961c as disclosed in references 40 & 73. In some embodiments of this aspect, the TLR agonist is (i) not a TLR4 agonist (ii) not a TLR9 agonist (iii) not a compound of formula (III) and/or (iv) not a compound of formula (IV).

According to a twenty-third aspect, the invention provides a method for modifying or improving the pharmacokinetic profile of an immunopotentiator, and/or for increasing the time for which an immunopotentiator is retained at a site of intramuscular injection, the method comprising: chemically modifying the immunopotentiator to form a modified immunopotentiator by the introduction of an adsorptive group. The adsorptive group may be joined to the immunopotentiator via a linker group (e.g. selected from, $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$, etc.). The modified compound can adsorb to an insoluble metal salt. Thus the method may further comprise: adsorbing the modified immunopotentiator to an insoluble metal salt. This adsorption can modify or improve the pharmacokinetic profile of the modified immunopotentiator, and/or can increase the time for which it is retained at a site of intramuscular injection, relative to the unmodified immunopotentiator. The method may further comprise a step of combining a modified adsorptive immunopotentiator with an immunogen e.g. to provide a vaccine composition.

According to a twenty-fourth aspect, the invention provides a composition comprising (a) a compound according to formula (I) or formula (II), and (b) an immunogen.

According to a twenty-fifth-aspect, the invention provides a composition comprising: (a) an adjuvant complex comprising a TLR agonist adsorbed to an insoluble metal salt; and (b) at least two different immunogens. The TLR agonist is preferably a TLR agonist as variously described above e.g. in some embodiments the agonist is not a TLR4 agonist, in some embodiments the agonist is not a TLR9 agonist, in some embodiments it is of formula (I-A), etc. In some embodiments of this aspect, the TLR agonist is not compound 13 herein. In some embodiments of this aspect, the immunogen is not a three-protein mixture of 287-953, 936-741 and 961c as disclosed in references 40 & 73. The invention also provides a process for preparing an immunogenic composition, comprising one of: (i) combining at least two different immunogens with a mixture comprising a TLR agonist and an insoluble metal salt; (ii) combining an insoluble metal salt with a mixture comprising a TLR agonist and at least two different immunogens; (iii) combining a TLR agonist with a mixture comprising an insoluble metal salt and at least two different immunogens; or (iv) combining in any order a TLR agonist, an insoluble metal salt, a first immunogen and a second immunogen.

According to a twenty-sixth aspect, the invention provides a composition comprising: (a) an adjuvant complex comprising a first TLR agonist adsorbed to an insoluble metal salt; and (b) an adjuvant complex comprising a second TLR agonist adsorbed to an insoluble metal salt. The composition can also include one or more immunogens.

According to a twenty-seventh aspect, the invention provides a process for preparing an adjuvant complex, comprising steps of (i) preparing an aqueous mixture of a TLR agonist and a soluble aluminium salt; then (ii) adding a non-aluminium salt to the aqueous mixture in order to form a precipitated aluminium salt to which the TLR agonist is adsorbed. The TLR agonist is preferably a TLR agonist as variously described above. The invention also provides an adjuvant complex obtained or obtainable by this process. The complex can be mixed with an immunogen to provide an immunogenic composition.

According to a twenty-eighth aspect, the invention provides a process for preparing an immunogenic composition, comprising a step of mixing (i) an aqueous mixture of a TLR agonist and a soluble aluminium salt with (ii) a buffered aqueous mixture of an immunogen, wherein the mixing step causes precipitation of an aluminium salt to which the TLR agonist and the immunogen are adsorbed. The TLR agonist is preferably a TLR agonist as variously described above. The invention also provides an immunogenic composition obtained or obtainable by this process.

According to a twenty-ninth aspect, the invention provides an assay for analysing an adjuvant complex which comprises a TLR agonist adsorbed to an insoluble metal salt, comprising steps of: (i) treating the complex to desorb TLR agonist from the insoluble metal salt; then (ii) detecting the desorbed TLR agonist. Various other assays are also provided (see below).

In a thirtieth aspect, the invention provides a composition comprising a TLR agonist and an aluminium hydroxyphosphate adjuvant, wherein at least 50% (e.g. ≥60%, ≥70%, ≥80%, ≥85%, ≥90%, ≥95%, ≥98%, ≥99%) of the TLR agonist is adsorbed onto the aluminium hydroxyphosphate, with the proviso that the TLR agonist:

(a) is not a TLR4 agonist; and (b) is not a TLR9 agonist.

In some embodiments of this thirtieth aspect the TLR agonist is not a compound according to formula (III) as defined below and/or is not a compound of formula (I-A) as defined below.

According to a thirty-first aspect, the invention provides a method for preparing an adjuvant complex, comprising steps of mixing an insoluble aluminium salt with a complex of a TLR agonist and an insoluble aluminium salt, thereby lowering the ratio of TLR agonist to aluminium. After mixing, the new mixture can be incubated to permit redistribution of the TLR agonist onto the added aluminium salt. This method permits a bulk complex having a high SMIP:Al$^{+++}$ ratio to be diluted to a complex having a desired SMIP:Al$^{+++}$ ratio. The bulk can be used as the basis of several dilutions, thus simplifying overall manufacture of multiple different end products. The insoluble aluminium salt which is added is ideally free from TLR agonists, or else has a different SMIP:Al$^{+++}$ ratio than the other material, thus permitting an overall change in ratio. The aluminium salt in the two mixed materials is preferably the same salt.

Formulae (I) & (II)

In some embodiments of the invention, a TLR agonist of the invention is not a compound according to formula (I) or (II). In other embodiments, however, TLR agonists of these formulae can be used e.g. in embodiments according to the sixth aspect, where the TLR agonist is adsorbed to an insoluble metal salt.

Formulae (I) and (II) correspond to the compounds disclosed in reference 3. As used herein, formulae (I) and (II) are defined as follows:

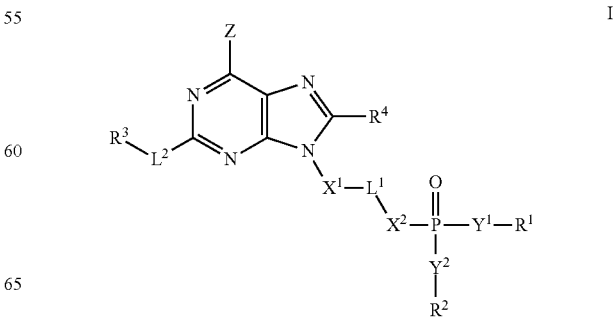

-continued

II wherein:
- Z is —NH$_2$ or —OH;
- X$^1$ is alkylene, substituted alkylene, alkenylene, substituted alkenylene, alkynylene, substituted alkynylene, carbocyclylene, substituted carbocyclylene, heterocyclylene, or substituted heterocyclylene;
- L$^1$ is a covalent bond, arylene, substituted arylene, heterocyclylene, substituted heterocyclylene, carbocyclylene, substituted carbocyclylene, —S—, —S(O)—, S(O)$_2$, —NR$^5$—, or —O—
- X$^2$ is a covalent bond, alkylene, or substituted alkylene;
- L$^2$ is NR$^5$—, —N(R$^5$)C(O)—, —O—, —S—, —S(O)—, S(O)$_2$, or a covalent bond;
- R$^3$ is H, alkyl, substituted alkyl, heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl;
- Y$^1$ and Y$^2$ are each independently a covalent bond, —O— or —NR$^5$—; or —Y$^1$—R$^1$ and —Y$^2$—R$^2$ are each independently —O—N═C(R$^6$R$^7$);
- R$^1$ and R$^2$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$
- R$^4$ is H, halogen, —OH, —O-alkyl, —O-alkylene-O—C(O)—O—R$^5$, —O—C(O)—O—R$^5$, —SH, or —NH(R$^5$);
- each R$^5$, R$^6$, and R$^7$ are independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

Reference 3 discloses some compounds of formulae (I) and (II) which include adsorptive moieties, but had not reported that these moieties could be used for adsorption. Thus reference 3 does not realise that these moieties could be exploited to provide an adsorbed compound.

The invention also provides a composition comprising (a) a compound of formula (I) or formula (II) and (b) an insoluble metal salt; wherein the compound of formula (I) or (II) is adsorbed onto the insoluble metal salt.

Formula (III)

In some embodiments of the invention, a TLR agonist of the invention is not a compound according to formula (III). In other embodiments, however, TLR agonists of formula (III) can be used e.g. in embodiments according to the twentieth aspect, where the TLR agonist is adsorbed to an insoluble metal salt and then sterilised.

Formula (III) corresponds to compounds disclosed in reference 9. As used herein, formula (III) is defined as follows:

(III)

wherein:
- R$^1$ is H, —C(O)—C$_{10}$-C$_{18}$alkyl; R$^2$ is C$_{10}$-C$_{18}$alkyl; R$^3$ is C$_{10}$-C$_{18}$alkyl;
- L$_1$ is —CH$_2$O—, —CH$_2$OC(O)—, —CH$_2$NR$^7$C(O)— or —C(O)NR$^7$—;
- L$_2$ is —O—, —OC(O)— or —NR$^7$C(O)—;
- R$^4$ is -L$_3$R$^5$ or -L$_4$R$^5$;
- R$^5$ is —N(R$^7$)$_2$, —OR$^7$, —P(O)(OR$^7$)$_2$, —C(O)OR$^7$, —NR$^7$C(O)L$_3$R$^8$, —OL$_3$R$^6$, —C(O)NR$^7$L$_3$R$^8$, C$_1$-C$_6$alkyl, a C$_6$ aryl, a C$_{10}$ aryl, a C$_{14}$ aryl, 5 to 14 membered heteroaryl containing 1 to 3 heteroatoms selected from O, S and N, C$_3$-C$_8$cycloalkyl or a 5 to 6 membered heterocycloalkyl containing 1 to 3 heteroatoms selected from O, S and N, wherein the aryl, heteroaryl, cycloalkyl and heterocycloalkyl of R$^5$ are each optionally substituted with 1 to 3 substituents independently selected from —OR$^9$, —OL$_3$R$^6$, —OL$_4$R$^6$, —OR$^7$, and —C(O)OR$^2$;
- L$_3$ is a C$_1$-C$_{10}$alkylene, wherein the C$_1$-C$_6$alkylene of L$_3$ is optionally substituted with 1 to 4 R$^6$ groups, or the C$_1$-C$_6$alkylene of L$_3$ is substituted with 2 C$_1$-C$_6$alkyl groups on the same carbon atom which together, along with the carbon atom they are attached to, form a C$_3$-C$_8$cycloakyl;
- L$_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each R$^{11}$ is a C$_1$-C$_6$alkyl groups which together, along with the carbon atom they are attached to, form a C$_3$-C$_8$cycloakyl;
- each R$^6$ is independently selected from halo, C$_1$-C$_6$alkyl, —OR$^7$, —N(R$^7$)$_2$, —C(O)N(R$^7$)$_2$, —P(O)(OR$^7$)$_2$, a C$_6$ aryl, a C$_{10}$ aryl and a C$_{14}$ aryl;
- each R$^7$ is independently selected from H and C$_1$-C$_6$alkyl;
- R$^8$ is selected from —SR$^7$, —C(O)OH and a 5 to 6 membered heterocycloalkyl containing 1 to 3 heteroatoms selected from O and N;
- R$^9$ is phenyl;
- each R$^{10}$ is independently selected from H and halo;
- each p is independently selected from 1, 2, 3, 4, 5 and 6, and
- q is 1, 2, 3 or 4.

In some embodiments of the invention, a TLR agonist of the invention is a compound which is according to formula (IIIa) but which is not according to formula (III):

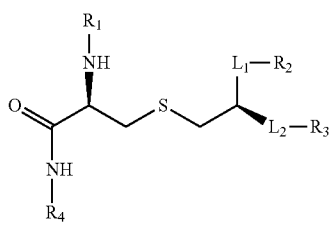

(IIIa)

wherein:
- R¹ is H, —C(O)—C₇-C₁₈alkyl or —C(O)—C₁-C₆alkyl;
- R² is C₇-C₁₈alkyl;
- R³ is C₇-C₁₈alkyl;
- L₁ is —CH₂OC(O)—, —CH₂O—, —CH₂NR⁷C(O)— or —CH₂OC(O)NR⁷—;
- L₂ is —OC(O)—, —O—, —NR⁷C(O)— or —OC(O)NR⁷—;
- R⁴ is -L₃R⁵ or -L₄R⁵;
- R⁵ is —N(R⁷)₂, —OR⁷, —P(O)(OR⁷)₂, —C(O)OR⁷, —NR⁷C(O)L₃R⁸, —NR⁷C(O)L₄R⁸, —OL₃R⁶, —C(O)NR⁷L₃R⁸, —C(O)NR⁷L₄R⁸, —S(O)₂OR⁷, —OS(O)₂OR⁷, C₁-C₆alkyl, a C₆aryl, a C₁₀aryl, a C₁₄aryl, 5 to 14 ring membered heteroaryl containing 1 to 3 heteroatoms selected from O, S and N, C₃-C₈cycloalkyl or a 5 to 6 ring membered heterocycloalkyl containing 1 to 3 heteroatoms selected from O, S and N, wherein the aryl, heteroaryl, cycloalkyl and heterocycloalkyl of R⁵ are each unsubstituted or the aryl, heteroaryl, cycloalkyl and heterocycloalkyl of R⁵ are each substituted with 1 to 3 substituents independently selected from —OR⁹, —OL₃R⁶, —OL₄R⁶, —OR⁷, and —C(O)OR⁷;
- L₃ is a C₁-C₁₀alkylene, wherein the C₁-C₁₀alkylene of L₃ is unsubstituted, or the C₁-C₁₀alkylene of L₃ is substituted with 1 to 4 R⁶ groups, or the C₁-C₁₀alkylene of L₃ is substituted with 2 C₁-C₆alkyl groups on the same carbon atom which together, along with the carbon atom they are attached to, form a C₃-C₈cycloakyl;
- L₄ is —((CR⁷R⁷)ᵖO)_q(CR¹⁰R¹⁰)_p— or —(CR¹¹R¹¹)((CR⁷R⁷)_pO)_q(CR¹⁰R¹⁰)_p—, wherein each R¹¹ is a C₁-C₆alkyl groups which together, along with the carbon atom they are attached to, form a C₃-C₈cycloakyl;
- each R⁶ is independently selected from halo, C₁-C₆alkyl, C₁-C₆alkyl substituted with 1-2 hydroxyl groups, —OR⁷, —N(R⁷)₂, —C(O)OH, —C(O)N(R⁷)₂, —P(O)(OR⁷)₂, a C₆aryl, a C₁₀aryl and a C₁₄aryl;
- each R⁷ is independently selected from H and C₁-C₆alkyl;
- R⁸ is selected from —SR⁷, —C(O)OH, —P(O)(OR⁷)₂, and a 5 to 6 ring membered heterocycloalkyl containing 1 to 3 heteroatoms selected from O and N;
- R⁹ is phenyl;
- each R¹⁰ is independently selected from H and halo;
- each p is independently selected from 1, 2, 3, 4, 5 and 6, and q is 1, 2, 3 or 4.

These compounds which fall inside formula (IIIa), but outside formula (III), may overlap with formula (F) and/or formula (J).

Even where compounds of formula (III) are disclaimed, in some embodiments the invention may nevertheless use one of the following compounds 72 to 101:

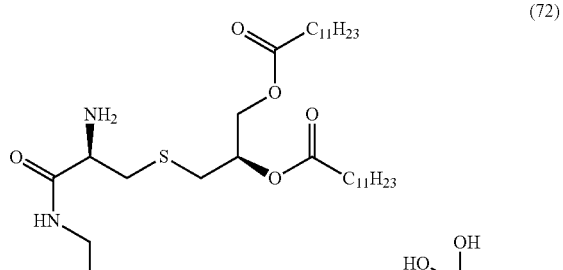

(72)

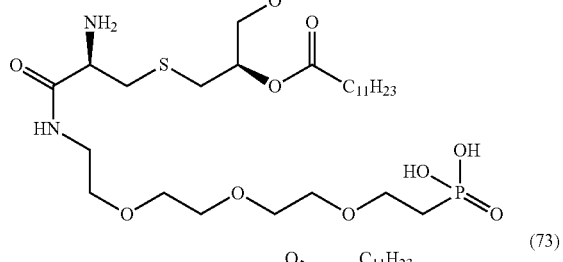

(73)

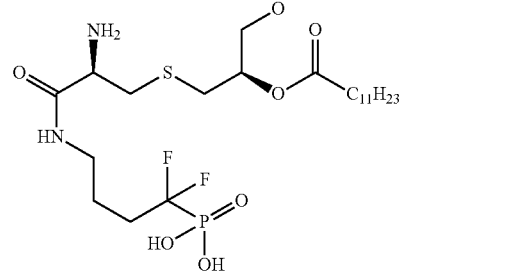

(74)

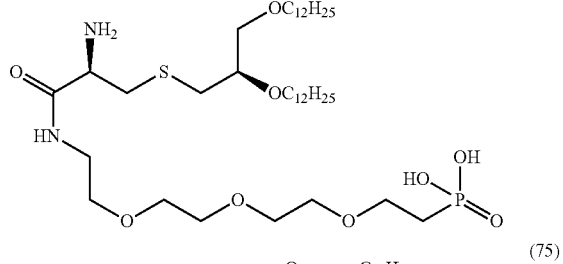

(75)

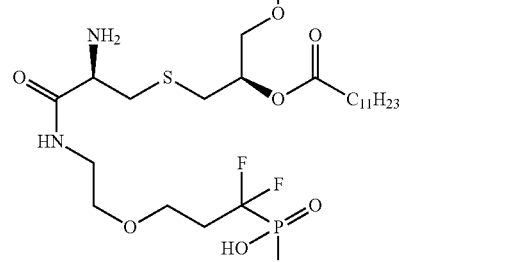

(76)

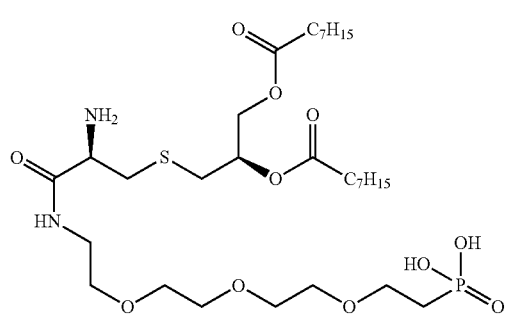
(77)
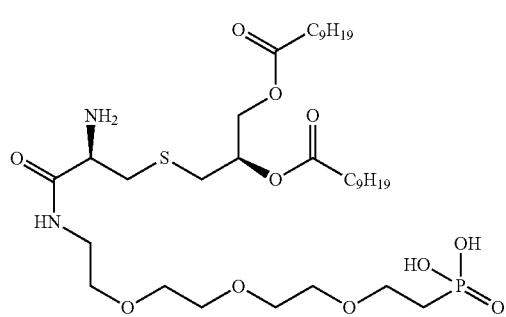
(78)
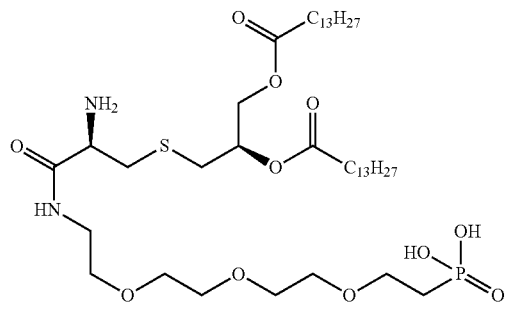
(79)
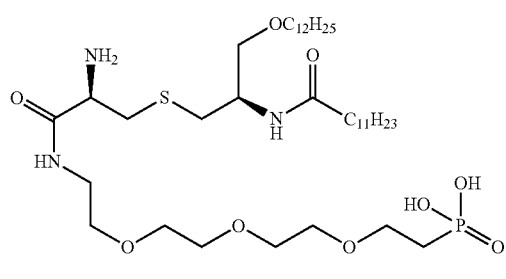
(80)
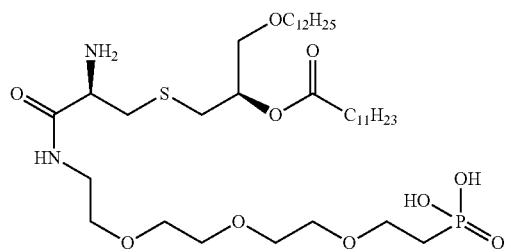
(81)
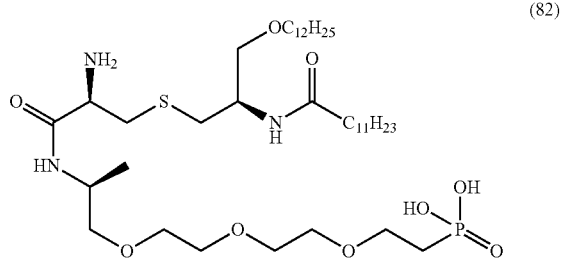
(82)
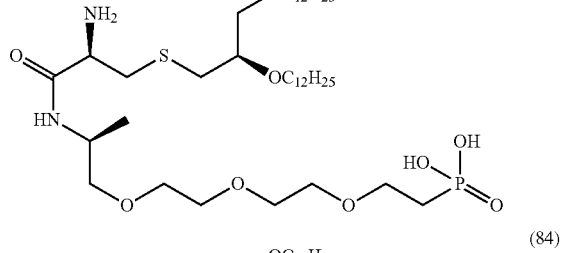
(83)
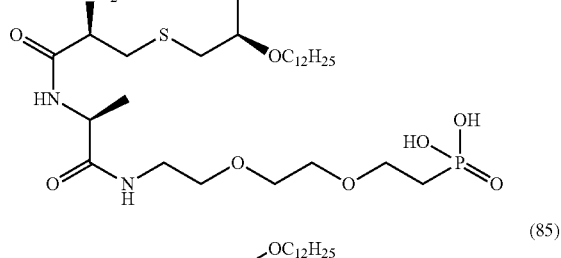
(84)
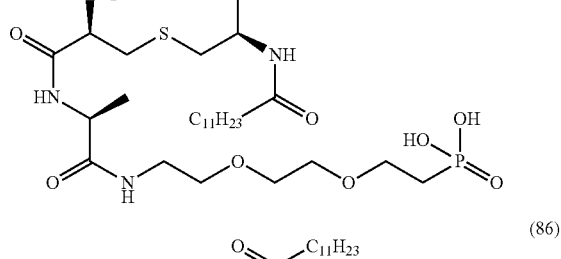
(85)
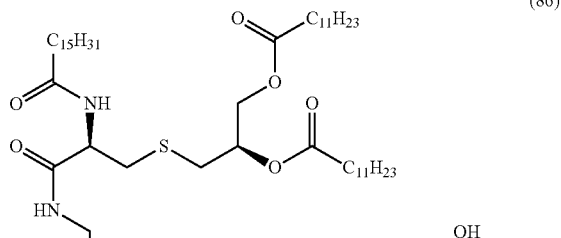
(86)
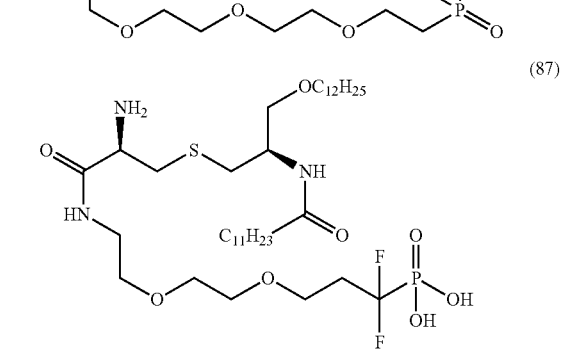
(87)

17
-continued
(88)
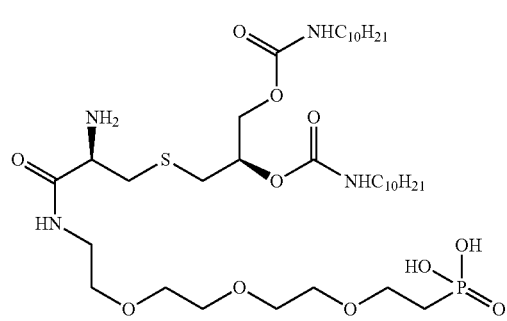
(89)
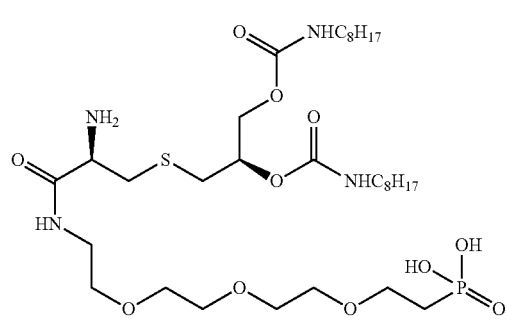
(90)
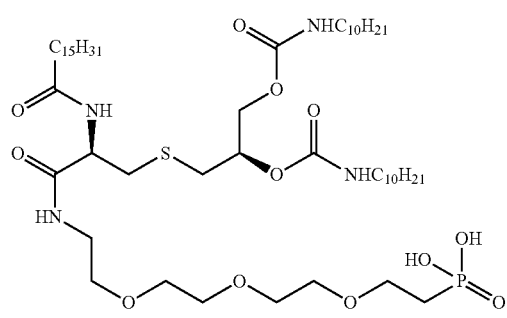
(91)
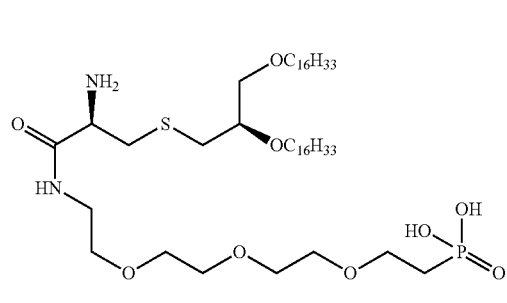
(92)
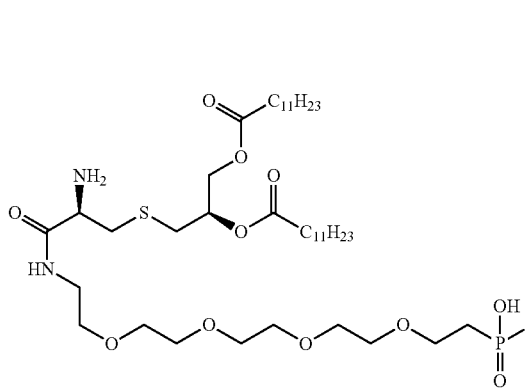
18
-continued
(93)
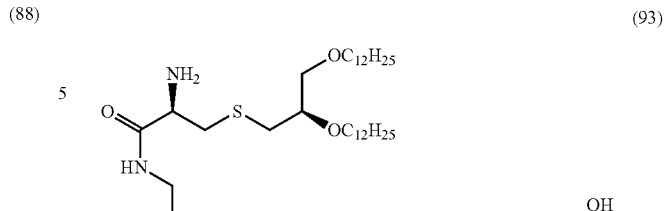
(94)
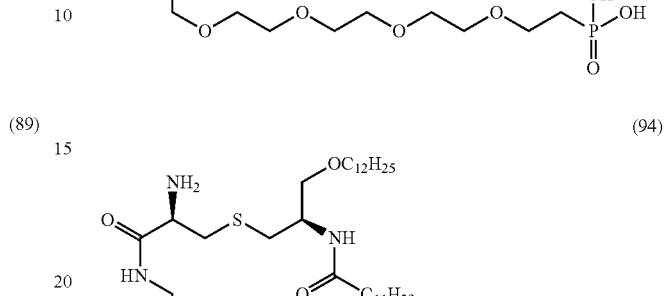
(95)
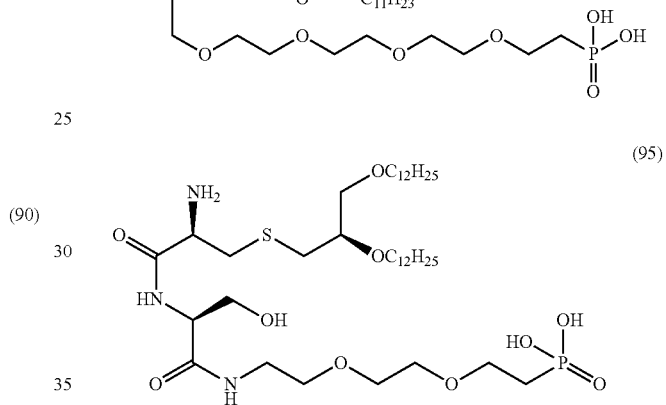
(96)
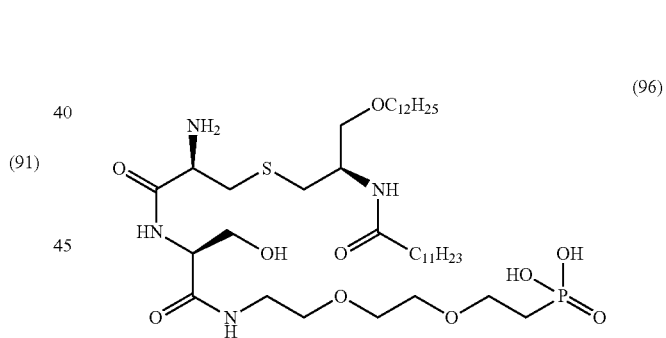
(97)
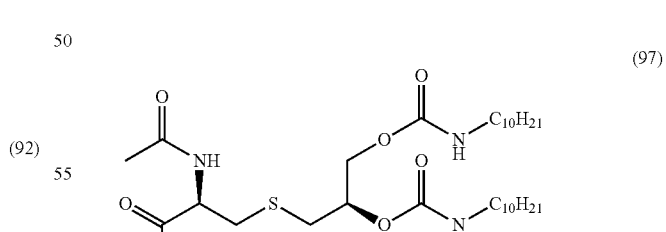

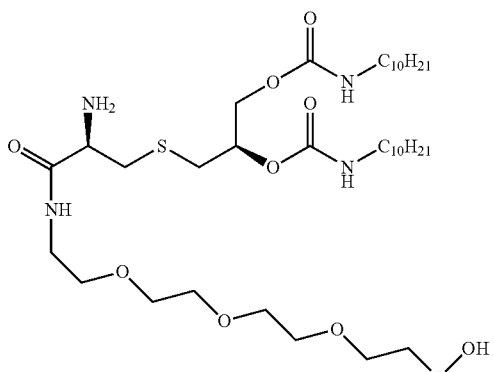
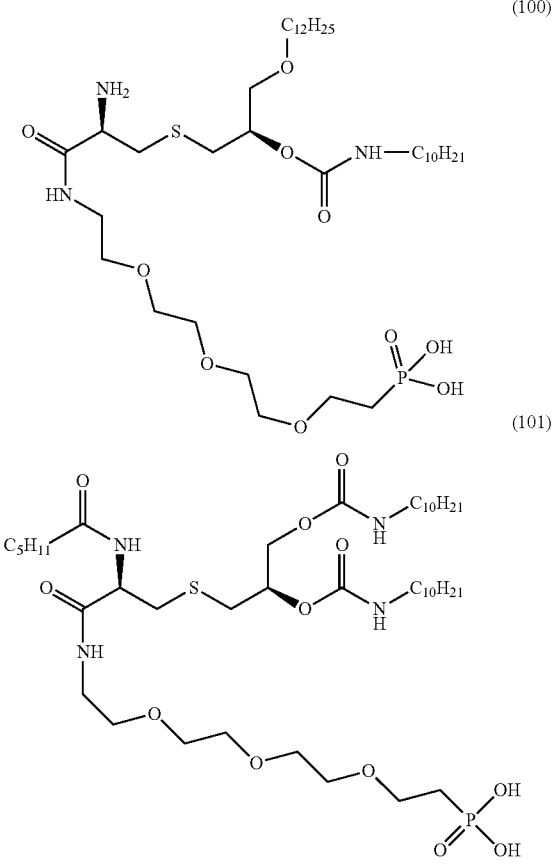

These 30 compounds (compounds 72 to 101, collectively the "TLR2p" compounds), which are generally of use with the invention, can be made using the protocols described in reference 9. An exemplary synthesis is included below.

Formula (I-A)

In some embodiments of the invention, a TLR agonist of the invention is not a compound according to formula (I-A). In other embodiments, however, TLR agonists of formula (I-A) can be used e.g. in embodiments according to the twentieth aspect, where the TLR agonist is adsorbed to an insoluble metal salt and then sterilised.

Formula (I-A) corresponds to the compounds disclosed in reference 4. As used herein, formula (I-A) is defined as follows:

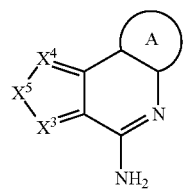

Formula (I-A)

wherein:
$X^3$ is N;
$X^4$ is N or $CR^3$
$X^5$ is —$CR^4$=$CR^5$—;
$R^1$ and $R^2$ are H;
$R^3$ is H;
$R^4$ and $R^5$ are each independently selected from H, halogen, —C(O)$OR^7$, —C(O)$R^7$, —C(O)N($R^{11}R^{12}$), —N($R^{11}R^{12}$), —N($R^9$)$_2$, —NHN($R^9$)$_2$, —$SR^7$, —(CH$_2$)$_n$$OR^2$, —(CH$_2$)$_n$$R^7$, -$LR^8$, - $LR^{10}$, —$OLR^8$, —$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —NO$_2$, —$R^7$, —$OR^8$, —C(O)$R^8$, —OC(O)$R^8$, —C(O)$OR^8$, —N($R^9$)$_2$, —P(O)($OR^8$)$_2$, —OP(O) ($OR^8$)$_2$, —P(O)($OR^{10}$)$_2$, —OP(O)($OR^{10}$)$_2$, —C(O)N ($R^9$)$_2$, —S(O)$_2$$R^8$, —S(O)$R^8$, —S(O)$_2$N($R^9$)$_2$, and —N$R^9$S(O)$_2$$R^8$;
or, $R^3$ and $R^4$, or $R^4$ and $R^5$, or $R^5$ and $R^6$, when present on adjacent ring atoms, can optionally be linked together to form a 5-6 membered ring, wherein the 5-6 membered ring is optionally substituted with $R^7$;
each L is independently selected from a bond, —(O (CH$_2$)$_m$)$_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —N($R^9$)$_2$, —P(O)($OR^8$)$_2$, —OP(O)($OR^8$)$_2$, —P(O) ($OR^{10}$)$_2$, and —OP(O)($OR^{10}$)$_2$;
$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups, and each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, —$OLR^8$, -$LSR^8$, -$LSR^{10}$, -$LC(O)R^8$, —$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, —$OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{10})_2$ and —$OLP(O)(OR^{10})_2$;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_6$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{10}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, $OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$ and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$;

$R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, $C(O)R^8$, $OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

ring A is an aryl or a heteroaryl, wherein the aryl and heteroaryl groups of Ring A are optionally substituted with 1 to 3 $R^4$ groups, wherein each $R^4$ is independently selected from —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —CH=$CHCO_2R^8$, —$C(=NH)$—$N(R^9)_2$, and —$(CH_2)_nNHC(O)R^8$ or two adjacent $R^4$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

Reference 4 discloses compounds of formula (I-A) which have intrinsic adsorptive properties, but the inventors did not report at the time of filing reference 4 that these properties exist and thus did not report that they could be exploited to provide an adsorbed compound.

Formula (IV)

In some embodiments of the invention, a TLR agonist of the invention is not a compound according to formula (IV). Formula (IV) corresponds to compounds disclosed in reference 10. As used herein, formula (IV) is defined as follows:

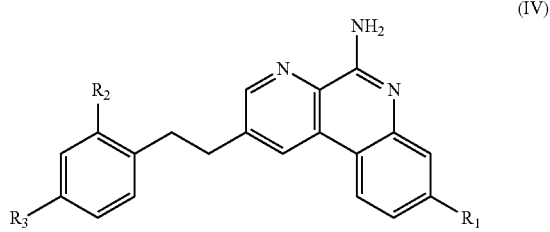

(IV)

wherein:
$R^1$ is H, $C_1$-$C_6$alkyl, —$C(R^5)_2OH$, -$L^1R^5$, -$L^1R^6$, -$L^2R^5$, -$L^2R^6$, —$OL^2R^5$, or —$OL^2R^6$;

$L^1$ is —C(O)— or —O—;

$L^2$ is $C_1$-$C_6$alkylene, $C_2$-$C_6$alkenylene, arylene, heteroarylene or —$((CR^4R^4)_pO)_q(CH_2)_p$—, wherein the $C_1$-$C_6$alkylene and $C_2$-$C_6$alkenylene of $L^2$ are optionally substituted with 1 to 4 fluoro groups;

each $L^3$ is independently selected from $C_1$-$C_6$alkylene and —$((CR^4R^4)_pO)_q(CH_2)_p$—, wherein the $C_1$-$C_6$alkylene of $L^3$ is optionally substituted with 1 to 4 fluoro groups;

$L^4$ is arylene or heteroarylene;
$R^2$ is H or $C_1$-$C_6$alkyl;
$R^3$ is selected from $C_1$-$C_4$alkyl, -$L^3R^5$, -$L^1R^5$, -$L^3R^7$, -$L^3L^4L^3R^7$, -$L^3L^4R^5$, -$L^3L^4L^3R^5$, —$OL^3R^5$, —$OL^3R^7$, —$OL^3L^4R^7$, —$OL^3L^4L^3R^7$, —$OR^8$, —$OL^3L^4R^5$, —$OL^3L^4L^3R^5$ and —$C(R^5)_2OH$;
each $R^4$ is independently selected from H and fluoro;
$R^5$ is —$P(O)(OR^9)_2$,
$R^6$ is —$CF_2P(O)(OR^9)_2$ or —$C(O)OR^{10}$;
$R^7$ is —$CF_2P(O)(OR^9)_2$ or —$C(O)OR^{10}$;
$R^8$ is H or $C_1$-$C_4$alkyl;
each $R^9$ is independently selected from H and $C_1$-$C_6$alkyl;
$R^{10}$ is H or $C_1$-$C_4$alkyl;
each p is independently selected from 1, 2, 3, 4, 5 and 6, and q is 1, 2, 3 or 4.

Formulae (C), (D), (E), (G) and (H)

As discussed above, the sixteenth aspect of the invention provides TLR7 agonists of formulae (C), (D), (E), or (H). The sixteenth aspect of the invention provides compounds of formula (C). The sixteenth aspect of the invention also and independently provides compounds of formula (D). The sixteenth aspect of the invention also and independently provides compounds of formula (E). The sixteenth aspect of the invention also and independently provides compounds of formula (H).

The 'parent' compounds of formulae (C), (D), (E) and (H) are useful TLR7 agonists (see references 2-5 and 11-27) but are modified herein by attachment of a phosphorus-containing moiety. Compounds of formulae (C), (D), (E) and (H) can thus be used with various aspects of the invention.

In some embodiments of formulae (C), (D) and (E) the compounds have structures according to formulae (C'), (D') and (E'), shown below:

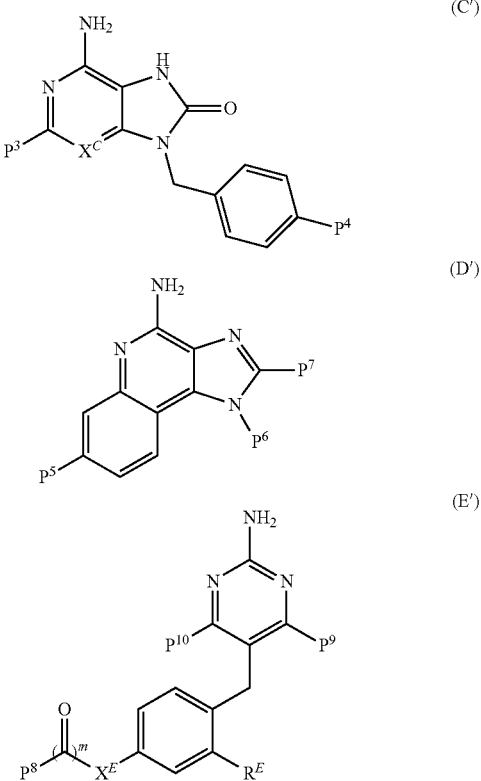

The embodiments of the invention of formulae (C), (D), (E) and (H) also apply to formulae (C'), (D'), (E') and (H').

In some embodiments of formulae (C), (D), (E), and (H): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is CH; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is 1 or 2.

In other embodiments of formulae (C), (D), (E), and (H): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (C): $P^3$ is selected from $C_1$-$C_6$alkyl, $CF_3$, and —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is N; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

In other embodiments of formula (D): $P^5$ is selected from $C_1$-$C_6$alkyl, and —Y-L-X—P(O)(OR$^X$)(OR$^Y$).

In other embodiments of formula (D): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (D): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

In other embodiments of formula (E): $X^E$ is $CH_2$, $P^8$ is $C_1$-$C_6$alkoxy optionally substituted with —Y-L-X—P(O)(OR$^X$)(OR$^Y$).

In other embodiments of formula (E): $P^9$ is —$NHC_1$-$C_6$alkyl optionally substituted with OH and $C_1$-$C_6$alkyl, and —Y-L-X—P(O)(OR$^X$)(OR$^Y$).

In some embodiments, a compound of formula (C) is not a compound in which $P^4$ is —Y-L-X—P(O)(OR$^X$)(OR$^Y$).

In some embodiments, in a compound of formula (C), P⁴ is selected from H, $C_1$-$C_6$alkyl, —$C_1$-$C_6$alkylaryl.

Preferred compounds of formulae (C), (D) and (E) are compounds (6), (7), (8), (67), (68), (69) and (70) as disclosed below. The invention provides each of compounds (6), (7), (8), (67), (68), (69) and (70).

In some embodiments of formula (H): $X^{H1}$—$X^{H2}$ is $CR^{H2}R^{H3}$, $R^{H2}$ and $R^{H3}$ are H, $X^{H3}$ is N, X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂; each p is independently selected from 1, 2 and 3; and q is selected from 1 and 2.

In some embodiments of formula (H): $X^{H1}$—$X^{H2}$ is $CR^{H2}R^{H3}$, $R^{H2}$ and $R^{H3}$ are H, $X^{H3}$ is N, X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂; each p is independently selected from 1, 2 and 3; and q is selected from 1 and 2.

In some embodiments, a TLR agonist of the invention, for example, a compound of formula (H), is not one of the following two compounds;

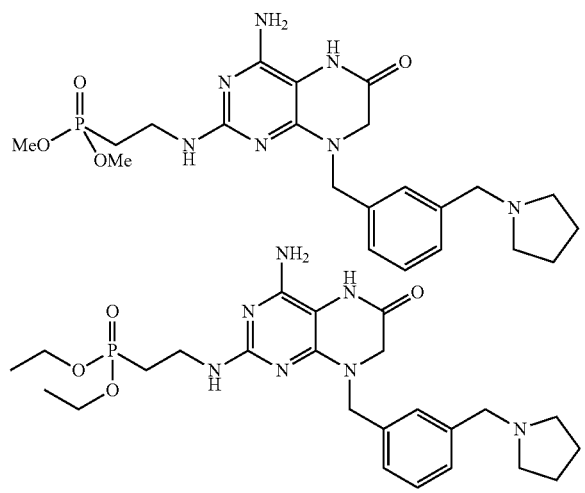

As discussed above, the seventeenth aspect of the invention provides compounds of formula (G).

The 'parent' compounds of formula (G) are useful TLR8 agonists (see references 6 & 7) but are modified herein by attachment of a phosphorus-containing moiety. Compounds of formulae (G) can thus be used with various aspects of the invention.

In some embodiments of formula (G), the compounds have structures according to formula (G');

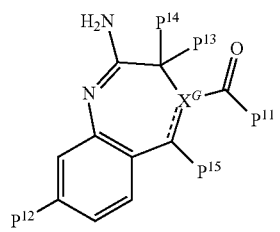

In some embodiments of formula (G) or (G'): $X^G$ is C and ----- represents a double bond.

In some embodiments of formula (G) or (G'): X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂; each p is independently selected from 1, 2 and 3; and q is selected from 1 and 2.

In some embodiments of formula (G) or (G'): X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂; each p is independently selected from 1, 2 and 3; and q is selected from 1 and 2.

Formula (B)

The eighteenth aspect of the invention provides a compound according to formula (B)

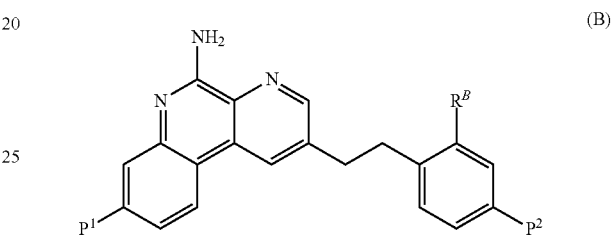

wherein:

P¹ is selected from H, $C_1$-$C_6$alkyl optionally substituted with COOH and —Y-L-X—P(O)(OR^X)(OR^Y);

P² is selected from H, $C_1$-$C_6$alkyl, $C_1$-$C_6$alkoxy and —Y-L-X—P(O)(OR^X)(OR^Y);

with the proviso that at least one of P¹ and P² is —Y-L-X—P(O)(OR^X)(OR^Y);

$R^B$ is selected from H and $C_1$-$C_6$alkyl;

$R^X$ and $R^Y$ are independently selected from H and $C_1$-$C_6$alkyl;

X is selected from a covalent bond, O and NH;

Y is selected from a covalent bond, O, C(O), S and NH;

L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂;

each p is independently selected from 1, 2, 3, 4, 5 and 6; and q is selected from 1, 2, 3 and 4.

In some embodiments of formula (B): P¹ is selected from $C_1$-$C_6$alkyl optionally substituted with COOH and —Y-L-X—P(O)(OR^X)(OR^Y); P² is selected from $C_1$-$C_6$alkoxy and —Y-L-X—P(O)(OR^X)(OR^Y); $R^B$ is $C_1$-$C_6$alkyl; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)₂ and —P(O)(OH)₂; each p is independently selected from 1, 2 and 3; q is selected from 1 and 2.

In some embodiments of the invention (e.g. those where the compound of formula (B) is adsorbed to an aluminium salt), a TLR agonist of the invention is not one of the following four compounds:

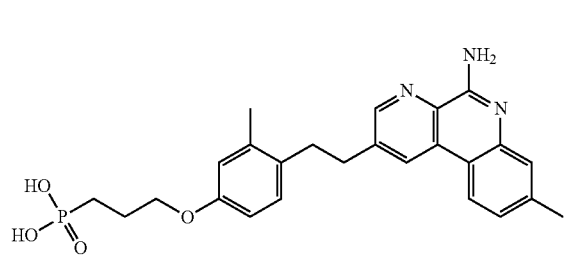
(13)

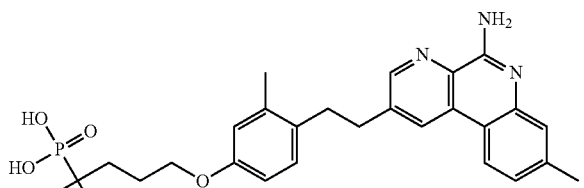
(12)

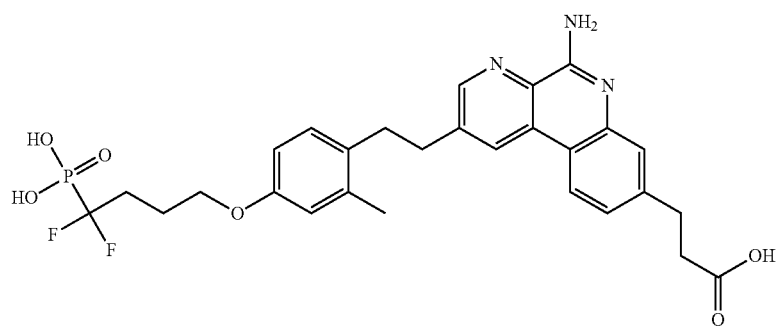
(3)

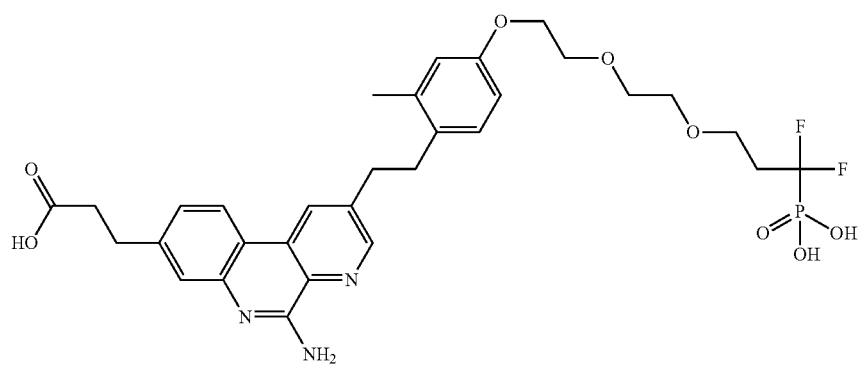
(4)

In some embodiments of the invention (e.g. the 25th and 26th aspects) preferred compounds of formula (B) are compounds 1, 2, 5, and 13 herein.

Formula (F)

The eighteenth aspect of the invention provides a compound according to formula (F):

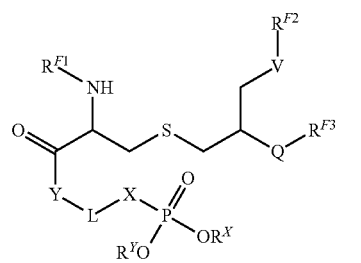
(F)

wherein:

$R^X$ and $R^Y$ are independently selected from H and $C_1$-$C_6$alkyl;

Q and V are independently selected from a covalent bond, NH, S, C(O) and O;

X is selected from a covalent bond, O and NH;

Y is selected from a covalent bond, O, C(O), S and NH;

L is selected from, a covalent bond $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; and $R^{F1}$, $R^{F2}$ and $R^{F3}$ are independently selected from H, $C_1$-$C_{18}$ alkyl, $C_1$-$C_{18}$alkenyl, C(O)$C_1$-$C_{18}$alkyl and C(O)$C_1$-$C_{18}$alkenyl;

each p is independently selected from 1, 2, 3, 4, 5 and 6; and q is selected from 1, 2, 3 and 4.

The 'parent' compounds of formula (F) are useful TLR2 agonists (see reference 9) but are modified herein by attachment of a phosphorus-containing moiety. Compounds of formulae (F) can thus be used with various aspects of the invention.

In some embodiments, compounds of formula (F) are not compounds according to formula (III), as defined above.

In some embodiments, a TLR agonist of the invention, for example, a compound of formula (F), is not one of the following seven compounds (16) to (22):

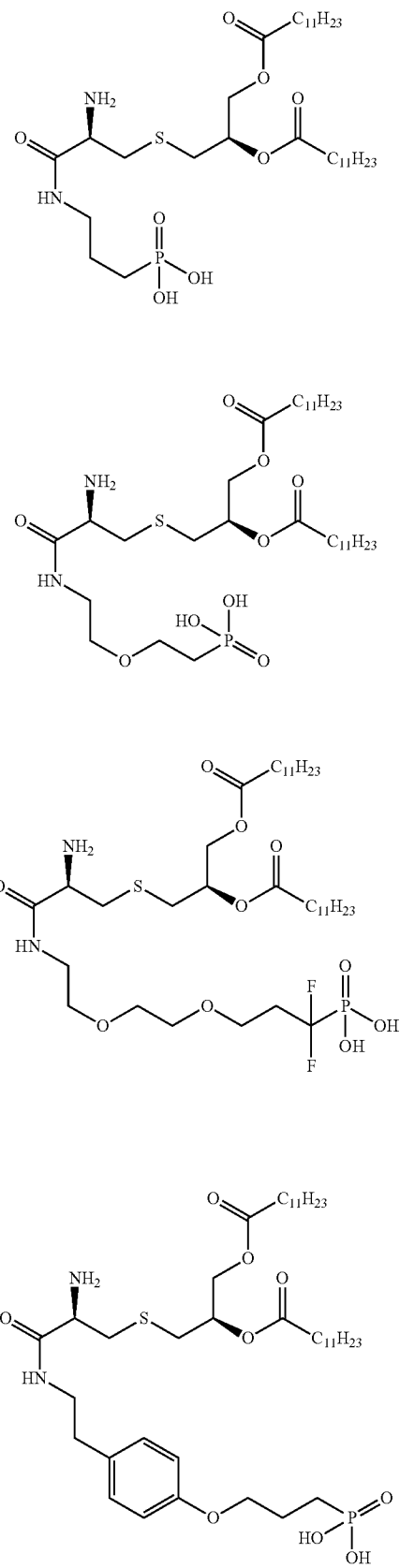
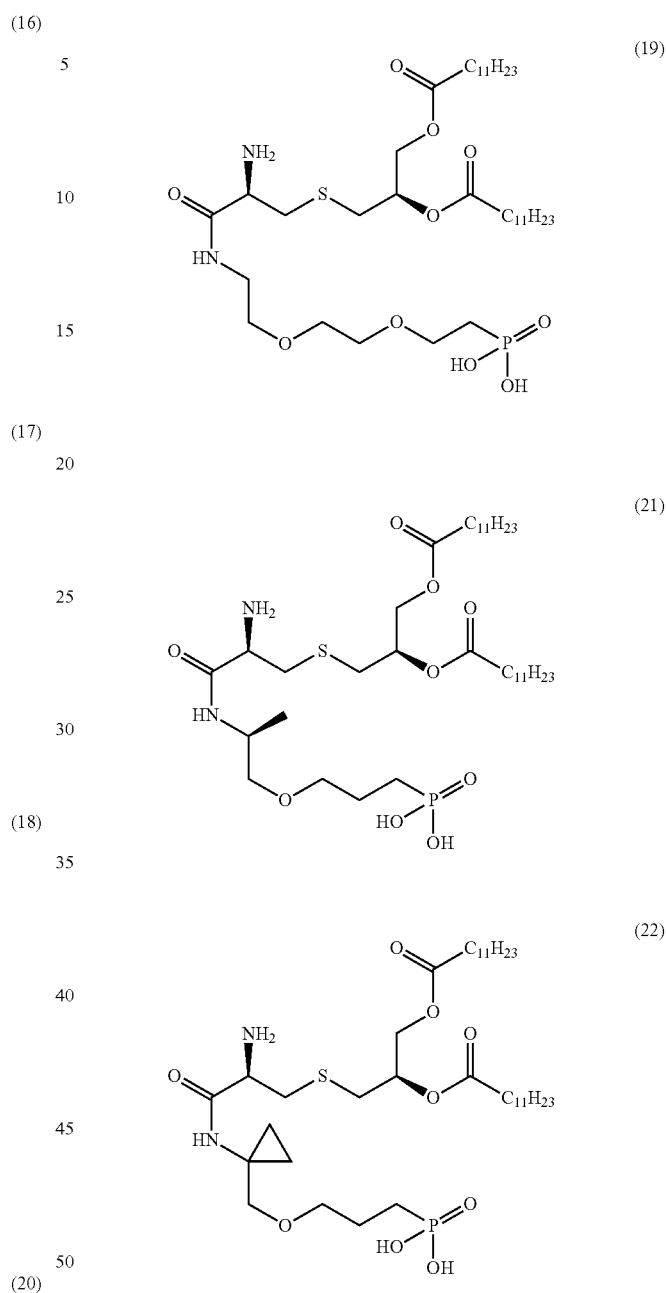

In some embodiments (e.g. those where the compound of formula (F) is adsorbed to an aluminium salt), a TLR agonist of the invention is not one of compounds (17), (19) or (22).

In some embodiments of formula (F): Q and V are O.
In some embodiments of formula (F): X is O.
In some embodiments of formula (F): Y is O.
In some embodiments of formula (F): $R^X$ and $R^Y$ are H; Q and V are O; X is selected from a covalent bond and O; Y is NH; L is selected from $C_1$-$C_6$alkylene, arylene, heteroarylene, —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; $R^{F1}$, $R^{F2}$ and $R^{F3}$ are selected from $C_1$-$C_{18}$ alkyl and C(O) $C_1$-$C_{18}$alkyl; each p is independently selected from 1, 2 and 3; and q is selected from 1 and 2.

Formula (J)

The eighteenth aspect of the invention provides a compound according to formula (J):

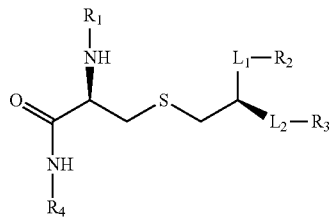

(J)

wherein:
R$^1$ is H, —C(O)—C$_7$-C$_{18}$alkyl or C(O)—C$_1$-C$_6$alkyl;
R$^2$ is C$_7$-C$_{18}$alkyl;
R$^3$ is C$_7$-C$_{18}$alkyl;
L$_1$ is —CH$_2$OC(O)—, —CH$_2$O—, —CH$_2$NR$^7$C(O)— or —CH$_2$OC(O)NR$^7$—;
L$_2$ is —OC(O)—, —O—, —NR$^7$C(O)— or —OC(O)NR$^7$—;
R$^4$ is -L$_3$R$^5$ or -L$_4$R$^5$;
R$^5$ is P(O)(OR$^7$)$_2$, —NR$^7$C(O)L$_3$-P(O)(OR$^7$)$_2$, —NR$^7$C(O)L$_4$-P(O)(OR$^7$)$_2$, —OL$_3$-P(O)(OR$^7$)$_2$, —C(O)NR$^7$L$_3$-P(O)(OR$^7$)$_2$, or —C(O)NR$^7$L$_4$-P(O)(OR$^7$)$_2$,
L$_3$ is a C$_1$-C$_{10}$alkylene, wherein the C$_1$-C$_{10}$alkylene of L$_3$ is unsubstituted, or the C$_1$-C$_{10}$alkylene of L$_3$ is substituted with 1 to 4 R$^6$ groups, or the C$_1$-C$_{10}$alkylene of L$_3$ is substituted with 2 C$_1$-C$_6$alkyl groups on the same carbon atom which together, along with the carbon atom they are attached to, form a C$_3$-C$_8$cycloakyl;
L$_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each R$^{11}$ is a C$_1$-C$_6$alkyl groups which together, along with the carbon atom they are attached to, form a C$_3$-C$_8$cycloakyl;
each R$^6$ is independently selected from halo, C$_1$-C$_6$alkyl, C$_1$-C$_6$alkyl substituted with 1-2 hydroxyl groups, —OR$^7$, —N(R$^7$)$_2$, —C(O)OH, —C(O)N(R$^7$)$_2$, —P(O)(OR$^7$)$_2$, a C$_6$aryl, a C$_{10}$aryl and a C$_{14}$aryl;
each R$^7$ is independently selected from H and C$_1$-C$_6$alkyl;
each R$^{10}$ is independently selected from H and halo;
each p is independently selected from 1, 2, 3, 4, 5 and 6; and q is 1, 2, 3 or 4.

In some embodiments of (J), R$_1$ is H. In other embodiments of (J), R$_1$ is —C(O)—C$_{15}$alkyl;

In some embodiments of (J): (i) L$_1$ is —CH$_2$OC(O)— and L$_2$ is —OC(O)—, —O—, —NR$^7$C(O)— or —OC(O)NR$^7$—; or (ii) or L$_1$ is —CH$_2$O— and L$_2$ is —OC(O)—, —O—, —NR$^7$C(O)— or —OC(O)NR$^7$—; or (iii) L$_1$ is —CH$_2$NR$^7$C(O)— and L$_2$ is —OC(O)—, —O—, —NR$^7$C(O)— or —OC(O)NR$^7$—; or (iv) L$_1$ is —CH$_2$OC(O)NR$^7$— and L$_2$ is —OC(O)—, —O—, NR$^7$C(O)— or —OC(O)NR$^7$—.

In some embodiments of (J): (i) L$_1$ is —CH$_2$OC(O)— and L$_2$ is —OC(O)—; or (ii) L$_1$ is —CH$_2$O— and L$_2$ is —O—; or (iii) L$_1$ is —CH$_2$O— and L$_2$ is —NHC(O)—; or (iv) L$_1$ is —CH$_2$OC(O)NH— and L$_2$ is —OC(O)NH—.

In some embodiments of (J), (i) R$^2$ is —C$_{11}$alkyl and R$^3$ is —C$_{11}$alkyl; or (ii) R$^2$ is —C$_{16}$alkyl and R$^3$ is —C$_{16}$alkyl; or (iii) R$^2$ is —C$_{16}$alkyl and R$^3$ is —C$_{11}$alkyl; or (iv) R$^2$ is —C$_{12}$alkyl and R$^3$ is —C$_{12}$alkyl and R$^3$ is —C$_7$alkyl; or (v) R$^2$ is —C$_7$alkyl and R$^3$ is —C$_7$alkyl; or (vi) R$^2$ is —C$_9$alkyl and R$^3$ is —C$_9$alkyl; or (vii) R$^2$ is —C$_8$alkyl and R$^3$ is —C$_8$alkyl; or (viii) R$^2$ is —C$_{13}$alkyl and R$^3$ is —C$_{13}$alkyl; or (ix) R$^2$ is —C$_{12}$alkyl and R$^3$ is —C$_{11}$alkyl; or (x) R$^2$ is —C$_{12}$alkyl and R$^3$ is —C$_{12}$alkyl; or (xi) R$^2$ is —C$_{10}$alkyl and R$^3$ is —C$_{10}$alkyl; or (xii) R$^2$ is —C$_{15}$alkyl and R$^3$ is —C$_{15}$alkyl.

In some embodiments of (J), R$^2$ is —C$_{11}$alkyl and R$^3$ is —C$_{11}$alkyl.

In some embodiments of (J), L$_3$ is a C$_1$-C$_{10}$alkylene, wherein the C$_1$-C$_{10}$alkylene of L$_3$ is unsubstituted or is substituted with 1 to 4 R$^6$ groups.

In some embodiments of (J): L$_4$ is —((CR$^7$R$^7$)$_p$O)$_q$(CR$^{10}$R$^{10}$)$_p$—; each R$^{10}$ is independently selected from H and F; and each p is independently selected from 2, 3, and 4.

In some embodiments of (J), each R$^6$ is independently selected from methyl, ethyl, i-propyl, i-butyl, —CH$_2$OH, —OH, —F, —NH$_2$, —C(O)OH, —C(O)NH$_2$, —P(O)(OH)$_2$ and phenyl.

In some embodiments of (J), each R$^7$ is independently selected from H, methyl and ethyl.

Specific compounds of formula (J) which are useful with the invention include the "TLR2p" group disclosed above. Further specific compounds of formula (J) which are useful include:
(3-((R)-2-amino-3-(((R)-2,3-bis(dodecanoyloxy)propyl)thio)propanamido)propyl)phosphonic acid; (16)
((8R,12R)-8-amino-12-(dodecanoyloxy)-7,15-dioxo-3,14-dioxa-10-thia-6-azahexacosyl)phosphonic acid; (17)
((12R,16R)-12-amino-16-(dodecanoyloxy)-1,1-difluoro-11,19-dioxo-4,7,18-trioxa-14-thia-10-azatriacontyl)phosphonic acid; (18)
((11R,15R)-11-amino-15-(dodecanoyloxy)-10,18-dioxo-3,6,17-trioxa-13-thia-9-azanonacosyl)phosphonic acid; (19)
((6S,9R,13R)-9-amino-13-(dodecanoyloxy)-6-methyl-8,16-dioxo-4,15-dioxa-11-thia-7-azaheptacosyl)phosphonic acid; (21)
(3-((1-((R)-2-amino-3-(((R)-2,3-bis(dodecanoyloxy)propyl)thio)propanamido)cyclopropyl)methoxy)propyl)phosphonic acid; (22)
(3-(4-(2-((R)-2-amino-3-(((R)-2,3-bis(dodecanoyloxy)propyl)thio)propanamido)ethyl)phenoxy)propyl)phosphonic acid; (20)
((14R,18R)-14-amino-18-(dodecanoyloxy)-13,21-dioxo-3,6,9,20-tetraoxa-16-thia-12-azadotriacontyl)phosphonic acid; (72)
(4-((R)-2-amino-3-(((R)-2,3-bis(dodecanoyloxy)propyl)thio)propanamido)-1,1-difluorobutyl)phosphonic acid; (73)
((14R,18R)-14-amino-18-(dodecyloxy)-13-oxo-3,6,9,20-tetraoxa-16-thia-12-azadotriacontyl)phosphonic acid; (74)
((9R,13R)-9-amino-13-(dodecanoyloxy)-1,1-difluoro-8,16-dioxo-4,15-dioxa-11-thia-7-azaheptacosyl)phosphonic acid; (75)
((12R,16R)-12-amino-16-(dodecyloxy)-1,1-difluoro-11-oxo-4,7,18-trioxa-14-thia-10-azatriacontyl)phosphonic acid; (76)
((14R,18R)-14-amino-18-(octanoyloxy)-13,21-dioxo-3,6,9,20-tetraoxa-16-thia-12-azaoctacosyl)phosphonic acid; (77)
((14R,18R)-14-amino-18-(decanoyloxy)-13,21-dioxo-3,6,9,20-tetraoxa-16-thia-12-azatriacontyl)phosphonic acid; (78)
((14R,18R)-14-amino-13,21-dioxo-18-(tetradecanoyloxy)-3,6,9,20-tetraoxa-16-thia-12-azatetratriacontyl)phosphonic acid; (79)
((14R,18R)-14-amino-18-dodecanamido-13-oxo-3,6,9,20-tetraoxa-16-thia-12-azadotriacontyl)phosphonic acid; (80)

((14R,18R)-14-amino-18-(dodecanoyloxy)-13-oxo-3,6,9,
20-tetraoxa-16-thia-12-azadotriacontyl)phosphonic acid;
(81)

((11S,14R,18R)-14-amino-18-dodecanamido-11-methyl-
13-oxo-3,6,9,20-tetraoxa-16-thia-12-azadotriacontyl)
phosphonic acid; (82)

((11S,14R,18R)-14-amino-18-(dodecyloxy)-11-methyl-13-
oxo-3,6,9,20-tetraoxa-16-thia-12-azadotriacontyl)phosphonic acid; (83)

((11S,14R,18R)-14-amino-18-(dodecyloxy)-11-methyl-10,
13-dioxo-3,6,20-trioxa-16-thia-9,12-diazadotriacontyl)
phosphonic acid; (84)

((11S,14R,18R)-14-amino-18-dodecanamido-11-methyl-
10,13-dioxo-3,6,20-trioxa-16-thia-9,12-diazadotriacontyl)phosphonic acid; (85)

((14R,18R)-18-(dodecanoyloxy)-13,21-dioxo-14-palmitamido-3,6,9,20-tetraoxa-16-thia-12-azadotriacontyl)phosphonic acid; (86)

((12R,16R)-12-amino-16-dodecanamido-1,1-difluoro-11-
oxo-4,7,18-trioxa-14-thia-10-azatriacontyl)phosphonic
acid; (87)

((14R,18R)-14-amino-18-((decylcarbamoyl)oxy)-13,21-di-
oxo-3,6,9,20-tetraoxa-16-thia-12,22-diazadotriacontyl)
phosphonic acid; (88)

((14R,18R)-14-amino-18-((octylcarbamoyl)oxy)-13,21-di-
oxo-3,6,9,20-tetraoxa-16-thia-12,22-diazatriacontyl)
phosphonic acid; (89)

((14R,18R)-18-((decylcarbamoyl)oxy)-13,21-dioxo-14-
palmitamido-3,6,9,20-tetraoxa-16-thia-12,22-diazadotriacontyl)phosphonic acid; (90)

((14R,18R)-14-amino-18-(hexadecyloxy)-13-oxo-3,6,9,20-
tetraoxa-16-thia-12-azahexatriacontyl)phosphonic acid;
(91)

((17R,21R)-17-amino-21-(dodecanoyloxy)-16,24-dioxo-3,
6,9,12,23-pentaoxa-19-thia-15-azapentatriacontyl)phosphonic acid; (92)

((17R,21R)-17-amino-21-(dodecyloxy)-16-oxo-3,6,9,12,
23-pentaoxa-19-thia-15-azapentatriacontyl)phosphonic
acid; (93)

((17R,21R)-17-amino-21-dodecanamido-16-oxo-3,6,9,12,
23-pentaoxa-19-thia-15-azapentatriacontyl)phosphonic
acid; (94)

((11S,14R,18R)-14-amino-18-(dodecyloxy)-11-(hydroxymethyl)-10,13-dioxo-3,6,20-trioxa-16-thia-9,12-diazadotriacontyl)phosphonic acid; (95)

((11S,14R,18R)-14-amino-18-dodecanamido-11-(hydroxymethyl)-10,13-dioxo-3,6,20-trioxa-16-thia-9,12-diazadotriacontyl)phosphonic acid; (96)

((14R,18R)-14-acetamido-18-((decylcarbamoyl)oxy)-13,
21-dioxo-3,6,9,20-tetraoxa-16-thia-12,22-diazadotriacontyl)phosphonic acid; (97)

((14R,18R)-14-amino-18-((decylcarbamoyl)oxy)-13,21-di-
oxo-3,6,9,20-tetraoxa-16-thia-12,22-diazadotriacontyl)
phosphonic acid; (98)

((14R,18R)-18-((decylcarbamoyl)oxy)-14-heptanamido-13,
21-dioxo-3,6,9,20-tetraoxa-16-thia-12,22-diazadotriacontyl)phosphonic acid; (99)

((14R,18R)-14-amino-18-((dodecyloxy)methyl)-13,20-di-
oxo-3,6,9,19-tetraoxa-16-thia-12,21-diazahentriacontyl)
phosphonic acid; (100)

((14R,18R)-18-((decylcarbamoyl)oxy)-14-hexanamido-13,
21-dioxo-3,6,9,20-tetraoxa-16-thia-12,22-diazadotriacontyl)phosphonic acid. (101)

In some embodiments, a compound of formula (J) is not one of the compounds 16 to 22.

In some embodiments (e.g. those where the compound is adsorbed to an aluminium salt), a compound of formula (J) is not one of compounds (17), (19) or (22).

The invention can use compounds of formula (J), or pharmaceutically acceptable salts or esters thereof.

Compounds Useful with the Invention

In general, and subject to provisos mentioned herein, TLR agonists useful with the invention are represented by formula (A1):

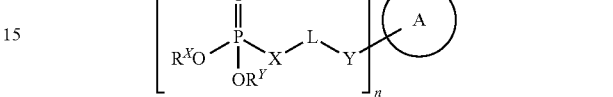

wherein:

$R^X$ and $R^Y$ are independently selected from H and $C_1$-$C_6$ alkyl;

X is selected from a covalent bond, O and NH;

Y is selected from a covalent bond, O, C(O), S and NH;

L is a linker e.g. selected from, $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;

each p is independently selected from 1, 2, 3, 4, 5 and 6;

q is selected from 1, 2, 3 and 4;

n is selected from 1, 2 and 3; and

A is a TLR agonist moiety.

In one embodiment, the TLR agonist according to formula (A1) is as follows: $R^X$ and $R^Y$ are H; X is O; L is selected from $C_1$-$C_6$ alkylene and —$((CH_2)_pO)_q(CH_2)_p$— each optionally substituted with 1 to 2 halogen atoms; p is selected from 1, 2 and 3; q is selected from 1 and 2; and n is 1. Thus in these embodiments the adsorptive moiety comprises a phosphate group.

In other embodiments, the TLR agonist according to formula (A1) is as follows: $R^X$ and $R^Y$ are H; X is a covalent bond; L is selected from $C_1$-$C_6$ alkylene and —$((CH_2)_pO)_q(CH_2)_p$— each optionally substituted with 1 to 2 halogen atoms; p is selected from 1, 2 or 3; q is selected from 1 or 2; and n is 1. Thus in these embodiments the adsorptive moiety comprises a phosphonate group.

Useful 'A' moieties for formula (A1) include, but are not limited to, radicals of any of the following compounds, defined herein or as disclosed in references 1-7 and 9-27:

Compounds of formula (I) or (II) as defined above;

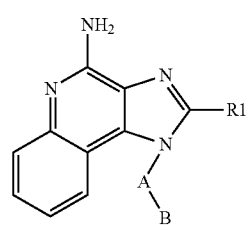

as defined on pages 6 and 7 of reference 2;

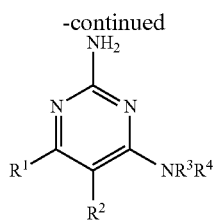

as defined on pages 2 to 5 of reference 5;

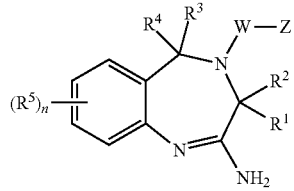

as defined on pages 5 to 6 of reference 6;

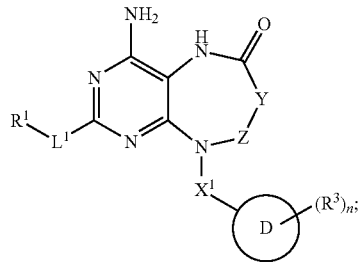

as defined on pages 2 to 3 of reference 27

In some embodiments, the TLR agonist moiety 'A' has a molecular weight of less than 1000 Da. In some embodiments, the TLR agonist of formula (A1) has a molecular weight of less than 1000 Da.

Preferred TLR agonists are water-soluble. Thus they can form a homogenous solution when mixed in an aqueous buffer with water at pH 7 at 25° C. and 1 atmosphere pressure to give a solution which has a concentration of at least 50 µg/ml. The term "water-soluble" thus excludes substances that are only sparingly soluble under these conditions.

In addition to being water-soluble at pH 7, preferred water-soluble TLR agonists are soluble in water at a pH between 4 and 10 e.g. between 5 and 9, between 6 and 8, or preferably between 6.5 and 7.5.

Adsorptive Moieties

The adsorptive moieties referred to above are functional groups which are capable of adsorbing to an insoluble metal salt (for example to an insoluble aluminium salt, such as aluminium oxyhydroxide) e.g. by ligand exchange or any other suitable mechanism. Thus the adsorptive moiety can endow an active compound (e.g. the TLR agonist) with the ability to be adsorbed to an insoluble metal salt.

Ligand exchange is a mechanism of adsorption whereby chemical moieties on an immunopotentiator compound exchange with chemical moieties on the surface of an insoluble metal salt, thereby resulting in adsorption of the immunopotentiator to the surface of the metal salt. This is the major mechanism of adsorption for phosphorylated proteins such as HBsAg [28,29]. Thus an immunopotentiator can comprise an adsorptive moiety such as a phosphonate group, which can exchange with groups on the surface of the salt, such as hydroxyl groups on aluminium oxyhydroxide. In some embodiments, however, adsorption can take place by any other suitable mechanism e.g. by electrostatic or hydrophobic means [30] (or by a combination of mechanisms). In some embodiments actual physicochemical adsorption may not occur and a TLR agonist may instead be trapped in void spaces within aggregates of the metal salt (e.g. as discussed in reference 31), but this entrapment can be enhanced by the presence of the adsorptive group. In other embodiments there may be a mixture of adsorbed and entrapped TLR agonist.

Phosphorus-containing adsorptive moieties are particularly useful, and so an adsorptive moiety may comprise a phosphate, a phosphonate, a phosphinate, a phosphonite, a phosphinite, etc. One useful adsorptive moiety comprises at least one phosphate group. A preferred adsorptive moiety comprises at least one phosphonate group.

A group of useful phosphorus-containing adsorptive moieties are shown in [square brackets] in formula A1, and a TLR agonist may thus include a phosphate (optionally substituted) or phosphonate (optionally substituted) by which it can adsorb to an insoluble metal salt.

Phosphorous-containing groups employed with the invention may exist in a number of protonated and deprotonated forms depending on the pH of the surrounding environment, for example the pH of the solvent in which they are dissolved. Therefore, although a particular form may be illustrated it is intended, unless otherwise mentioned, for these illustrations to merely be representative and not limiting to a specific protonated or deprotonated form.

For example, in the case of a phosphate group, this has been illustrated as —OP(O)(OH)$_2$ but the definition includes the protonated forms —[OP(O)(OH$_2$)(OH)]$^+$ and —[OP(O)(OH$_2$)$_2$]$^{2+}$ that may exist at a pH below 7, and the deprotonated forms —[OP(O)(OH)(O)]$^-$ and [OP(O)(O)$_2$]$^{2-}$ that may exist at a pH above 7.

Compounds disclosed herein can exist as pharmaceutically acceptable salts. Thus, the compounds may be used in the form of their pharmaceutically acceptable salts i.e. physiologically or toxicologically tolerable salt (which includes, when appropriate, pharmaceutically acceptable base addition salts and pharmaceutically acceptable acid addition salts).

Alternatives to phosphorus-containing functional groups to provide an adsorptive TLR agonist are nitrate and/or sulphate groups.

Compounds useful with the invention may include a single adsorptive moiety, or may include more than one e.g. between 2 and 15 adsorptive moieties. Typically a compound will include 1, 2 or 3 adsorptive moieties.

Insoluble Metal Salts

As disclosed herein, immunopotentiators can adsorb to insoluble metal salts, thereby forming an adsorbed complex. For instance, they can be adsorbed to insoluble calcium salts (e.g. calcium phosphate) or, preferably, to insoluble aluminium salts. Such aluminium salts have a long history of use in vaccines. Aluminium salts which include hydroxide ions are the preferred insoluble metal salts for use with the present invention.

Thus the invention provides various embodiments in which a TLR agonist is adsorbed to such insoluble salts e.g. a compound of formula (I), (II), (III), (I-A), (B), (C), (D), (E), (F), (G), (H) or (J).

Useful aluminium salts include, but are not limited to, aluminium hydroxide, aluminium oxyhydroxide, and aluminium hydroxyphosphates (including aluminium hydroxyphosphate sulfate). Such salts are described e.g. in chapters 8 & 9 of reference 32.

Preferred salts for adsorption of immunopotentiators are aluminium oxyhydroxides and/or aluminium hydroxyphosphate. These have surface hydroxyl moieties which can readily undergo ligand exchange with phosphorus-containing groups (e.g. phosphates, phosphonates) to provide stable adsorption.

The adjuvants commonly known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ (chapter 9 of ref. 32). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants e.g. with needle-like particles with diameters about 2 nm. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants commonly known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls (chapter 9 of reference 32).

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs, with primary particles in the range of 50 nm). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

In solution both aluminium phosphate and hydroxide adjuvants tend to form stable porous aggregates 1-10 µm in diameter [33].

A composition including an TLR agonist of the invention adsorbed to a metal salt can also include a buffer (e.g. a phosphate or a histidine or a Tris buffer). When such a composition includes a phosphate buffer, however, it is preferred that the concentration of phosphate ions in the buffer should be less than 50 mM e.g. <40 mM, <30 mM, <20 mM, <10 mM, or <5 mM, or between 1-15 mM. In embodiments of the fifteenth aspect, however, using a phosphate buffer is not permitted.

Because of the insolubility of adsorptive metal salts which are useful with the invention, compositions containing adsorbed immunopotentiators will generally be suspensions having a cloudy appearance. This can mask contaminating bacterial growth and so a composition of the invention may include a preservative such as thiomersal or 2-phenoxyethanol. It is preferred that a composition should be substantially free from (e.g. <10 µg/ml) mercurial material e.g. thiomersal-free. Vaccines containing no mercury are more preferred.

A composition can include a mixture of both an aluminium oxyhydroxide and an aluminium hydroxyphosphate, and an immunopotentiator may be adsorbed to one or both of these salts.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range of Al$^{+++}$ in a composition of the invention is between 0.3 and 1 mg/ml or between 0.3-0.5 mg/ml. A maximum of 0.85 mg/dose is preferred. Because the inclusion of a TLR agonist can improve the adjuvant effect of aluminium salts then the invention advantageously permits lower amounts of Al$^{+++}$ per dose, and so a composition of the invention can usefully include between 10 and 250 µg of Al$^{+++}$ per unit dose. Current pediatric vaccines typically include at least 300 µg Al$^{+++}$. In concentration terms, a composition of the invention may have an Al$^{+++}$ concentration between 10 and 500 µg/ml e.g. between 10-300 µg/ml, between 10-200 µg/ml, or between 10-100 µg/ml.

In general, when a composition includes both a TLR agonist and an aluminium salt, the weight ratio of agonist to Al$^{+++}$ will be less than 5:1 e.g. less than 4:1, less than 3:1, less than 2:1, or less than 1:1. Thus, for example, with an Al$^{+++}$ concentration of 0.5 mg/ml the maximum concentration of TLR agonist would be 2.5 mg/ml. But higher or lower levels can be used; a lower mass of TLR agonist than of Al$^{+++}$ is typical e.g. per dose, 100 µg of TLR agonist with 0.2 mg Al$^{+++}$.

Where a composition includes a TLR agonist and an insoluble metal salt, it is preferred that at least 50% (by mass) of the immunopotentiator in the composition is adsorbed to the metal salt e.g. ≥60%, ≥70%, ≥80%, ≥85%, ≥90%, ≥92%, ≥94%, ≥95%, ≥96%, ≥97%, ≥98%, ≥99%, or even 100%. A minimum of 80% adsorption is typical, and at least 90% or 95% is preferred.

As discussed above, as a result of adsorption to an insoluble metal salt can modify the in vivo behaviour of SMIPs. Thus an adsorbed SMIP can display a longer residence time (e.g. at least 2× longer) in muscle after intramuscular injection, relative to the same SMIP injected in non-adsorbed form. Some clearance can occur, but a detectable portion of the injected SMIP will still be present. Thus, for instance, an adsorbed SMIP can, when injected intramuscularly, still be present in the injected muscle at least 12 hours later e.g. 24 hours later.

In some embodiments, an adsorbed SMIP can display a lower peak serum concentration, relative to the same SMIP injected in non-adsorbed form. This peak is usually expressed as a Cmax value. For instance, an adsorbed SMIP can, when injected intramuscularly, have a lower serum Cmax value than the same SMIP when injected intramuscularly in non-adsorbed form (e.g. <95% of the non-adsorbed Cmax, <80% of the non-adsorbed Cmax, <50% of the non-adsorbed Cmax, or even <30% of the non-adsorbed Cmax).

In some embodiments, an adsorbed SMIP can display a lower total systemic exposure after injection, relative to the same SMIP injected in non-adsorbed form. Levels of systemic exposure are usually expressed as AUC (area under the concentration-time curve) values (e.g. in nM·hr). Advantageously, for instance, an adsorbed SMIP can, when injected intramuscularly, have a lower serum AUC value in the 24 hours following injection than the same SMIP when injected intramuscularly in non-adsorbed form (e.g. <90% of the non-adsorbed AUC, <80% of the non-adsorbed AUC, or even <50% of the non-adsorbed AUC, etc.).

Immunogens

Adsorbed immunopotentiators of the invention are useful during immunisation. An adsorbed complex of the invention can thus be used in conjunction with one or more immunogen(s). The complex and immunogen(s) can be provided as an admixture, or can be provided separately for use after mixing. In some embodiments, an immunopotentiators of the invention can be combined with an immunogen in the absence of an insoluble metal salt, and can thereafter either be administered to a mammal or can be combined with an insoluble metal salt for later administration to a mammal.

The invention can be used with a wide range of immunogens, for treating or protecting against a wide range of diseases. The immunogen may elicit an immune response that protects against a viral disease (e.g. due to an enveloped or non-enveloped virus), a bacterial disease (e.g. due to a Gram negative or a Gram positive bacterium), a fungal disease, a parasitic disease, an auto-immune disease, or any other disease. The immunogen may also be useful in immunotherapy e.g. for treating a tumour/cancer, Alzheimer's disease, or an addiction.

The immunogen may take various forms e.g. a whole organism, an outer-membrane vesicle, a polypeptide, a saccharide, a liposaccharide, a conjugate (e.g. of a carrier and a hapten, or of a carrier and a saccharide or liposaccharide), etc. Where the immunogen is a polypeptide, it will typically be a surface polypeptide e.g. an adhesin, a hemagglutinin, an envelope glycoprotein, a spike glycoprotein, etc.

The immunogen may elicit an immune response against an influenza virus, including influenza A and B viruses. Various forms of influenza virus immunogen are currently available, typically based either on live virus or on inactivated virus. Inactivated vaccines may be based on whole virions, split virions, or on purified surface antigens. Influenza antigens can also be presented in the form of virosomes. Hemagglutinin is the main immunogen in current inactivated vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [34,35]). Thus compositions may include between 0.1 and 150 μg of HA per influenza strain, preferably between 0.1 and 50 μg e.g. 0.1-20 μg, 0.1-15 μg, 0.1-10 μg, 0.5-5 μg, etc. Particular doses include e.g. about 45, about 30, about 15, about 10, about 7.5, about 5, about 3.8, about 3.75, about 1.9, about 1.5, etc. per strain. It is usual to include substantially the same mass of HA for each strain included in the vaccine e.g. such that the HA mass for each strain is within 10% of the mean HA mass per strain, and preferably within 5% of the mean. For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical. Rather than use SPF eggs as the substrate for viral growth, where virus is harvested from infected allantoic fluids of hens' eggs, cell lines that support influenza virus replication may be used. The cell line will typically be of mammalian origin e.g. MDCK. Influenza A virus immunogens may be from any suitable HA subtype strain e.g. H1, H3, H5, H7, H9 etc., such as a H1N1, H3N2 and/or H5N1 strain.

The immunogen may elicit an immune response against a Candida fungus such as C. albicans. For instance, the immunogen may be a ft-glucan, which may be conjugated to a carrier protein. The glucan may include β-1,3 and/or β-1,6 linkages. Suitable immunogens include those disclosed in references 36 & 37.

The immunogen may elicit an immune response against a Streptococcus bacterium, including S. agalactiae, S. pneumoniae and S. pyogenes. For instance, the immunogen may be a capsular saccharide, which may be conjugated to a carrier protein. For S. agalactiae the saccharide may be from one or more of serotypes Ia, Ib, II, III, and/or V. For S. pneumoniae the saccharide may be from one or more of serotypes 1, 3, 4, 5, 6B, 7F, 9V, 14, 18C, 19F, and/or 23F. In addition to (or in place of) capsular saccharide immunogen(s), polypeptide immunogens may be used to elicit a protective anti-streptococcal immune response e.g. comprising RrgB, as disclosed in reference 38.

The immunogen may elicit an immune response against a Staphylococcus bacterium, including S. aureus or S. epidermidis. For instance, the immunogen may comprise an IsdA antigen, an IsdB antigen, a ClfA antigen, a ClfB antigen, a SdrD antigen, a Spa antigen, an EsxA antigen, an EsxB antigen, a Sta006 antigen, a hemolysin, and/or a Sta011 antigen. Suitable S. aureus immunogens and their combinations are disclosed in reference 39.

The immunogen may elicit an immune response against a meningococcal bacterium (Neisseria meningitidis). For instance, the immunogen may be a capsular saccharide, which may be conjugated to a carrier protein. Capsular saccharides are particularly useful for protecting against meningococcal serogroups A, C, W135 and/or Y. In addition to (or in place of) capsular saccharide immunogen(s), polypeptide immunogens and/or outer membrane vesicles may be used to elicit a protective anti-meningococcal immune response, particularly for use against serogroup B e.g. as disclosed in reference 40. A typical amount of capsular saccharide per unit dose of a vaccine is between 2.5-10 μg, although lower doses can be used with the invention due to the antigen-sparing nature of the adjuvants.

The immunogen may elicit an immune response against a hepatitis virus, such as a hepatitis A virus, a hepatitis B virus, a hepatitis C virus and/or a hepatitis E virus. For instance, the immunogen may be hepatitis B virus surface antigen (HBsAg). A typical amount of HBsAg per unit dose of a vaccine is between 5-20 μg, but lower doses can be used with the invention due to the antigen-sparing nature of the adjuvants.

The immunogen may elicit an immune response against a respiratory syncytial virus. Immunogens may be from a group A RSV and/or a group B RSV. Suitable immunogens may comprise the F and/or G glycoproteins or fragments thereof e.g. as disclosed in references 41 & 42.

The immunogen may elicit an immune response against a Chlamydia bacterium, including C. trachomatis and C. pneumoniae. Suitable immunogens include those disclosed in references 43-49.

The immunogen may elicit an immune response against an *Escherichia coli* bacterium, including extraintestinal pathogenic strains. Suitable immunogens include those disclosed in references 50-52.

The immunogen may elicit an immune response against a coronavirus, such as the human SARS coronavirus. Suitable immunogens may comprise the spike glycoprotein.

The immunogen may elicit an immune response against a *Helicobacter pylori* bacterium. Suitable immunogens include CagA [53-56], VacA [57,58], and/or NAP [59-61].

The immunogen may elicit an immune response against a *Corynebacterium diphtheriae* bacterium. Suitable immunogens include diphtheria toxoid ("DT"). A typical amount of DT per unit dose of a pediatric vaccine is between 15-30 Lf ("limes flocculating dose"), although lower doses can be used with the invention due to the antigen-sparing nature of the adjuvants. Lower amounts are also typical in adolescent or adult booster vaccines e.g. between 1-10 Lf/dose.

The immunogen may elicit an immune response against a *Clostridium tetani* bacterium. Suitable immunogens include tetanus toxoid ("TT"). A typical amount of TT per unit dose of a pediatric vaccine is between 5-15 Lf ("limes flocculating dose"), although lower doses can be used with the invention due to the antigen-sparing nature of the adjuvants. Lower amounts are also typical in adolescent or adult booster vaccines e.g. between 1-5 Lf/dose.

The immunogen may elicit an immune response against a *Bordetella pertussis* bacterium. Pertussis antigens are either cellular (whole cell, in the form of inactivated *B. pertussis* cells; 'wP') or acellular ('aP'). Where acellular antigens are used, one, two or (preferably) three of the following antigens are included: (1) detoxified pertussis toxin (pertussis toxoid, or 'PT'); (2) filamentous hemagglutinin ('FHA'); (3) pertactin (also known as the '69 kiloDalton outer membrane protein'). The PT may be chemically detoxified or may be a mutant PT in which enzymatic activity has been reduced by mutagenesis [62] e.g. the 9K/129G double mutant [63]. As well as PT, FHA and pertactin, it is also possible to include fimbriae (e.g. agglutinogens 2 and 3) in an acellular pertussis antigen component. A typical amount of PT in a pediatric vaccine is 10-30 µg/dose. A typical amount of FHA in a pediatric vaccine is 15-30 µg/dose. A typical amount of pertactin in a pediatric vaccine is 2-10 µg/dose. Lower doses can be used with the invention due to the antigen-sparing nature of the adjuvants. Lower amounts are also typical in booster vaccines e.g. ~3 times lower.

The immunogen may elicit an immune response against a *Haemophilus influenzae* type B bacterium ("Hib"). Suitable immunogens include conjugates of the Hib capsular saccharide ("PRP") e.g. conjugated to tetanus toxoid, diphtheria toxoid, the CRM197 derivative of diphtheria toxoid, *H. influenzae* protein D, and an outer membrane protein complex from serogroup B meningococcus. A typical amount of Hib conjugate (measured as saccharide) is between 2.5-15 µg per dose, although lower doses can be used with the invention due to the antigen-sparing nature of the adjuvants.

The immunogen may elicit an immune response against a poliovirus. Suitable immunogens include inactivated viruses. A typical composition will include three poliovirus antigens—poliovirus Type 1 (e.g. Mahoney strain), poliovirus Type 2 (e.g. MEF-1 strain), and poliovirus Type 3 (e.g. Saukett strain). A typical amount of poliovirus per dose is 40 DU ("D-antigen unit") for Type 1, 8 DU for Type 2, and 32 DU for Type 3, although lower doses can be used with the invention due to the antigen-sparing nature of the adjuvants.

The immunogen may elicit an immune response against a cytomegalovirus ('CMV'). For example, the immunogen may be a recombinant glycoprotein B e.g. the soluble antigen used in reference 64.

The immunogen may elicit an immune response against a human immunodeficiency virus e.g. against HIV-1 or HIV-2. For example, the immunogen may be a HIV envelope glycoprotein. For instance, engineered envelope glycoproteins are available, such as gp140, which can form oligomers (referred to as 'o-gp140'). The gp140 polypeptide includes the gp120 sequence and the ectodomain of gp41 [65], and has been reported to be a better immunogen than gp120 [66]. Thus a useful envelope glycoprotein may include a portion of gp41 but not include its transmembrane domain. The gp140 form of the envelope glycoprotein can have its V2 loop deleted, to give gp140ΔV2 mutants, and such deletions have been reported to improve immunogenicity. The ΔV2 mutants of gp140 have been shown to form trimers [67].

The immunogen may elicit an immune response against rabies virus. A suitable immunogen is an inactivated rabies virus [68, RabAvert™].

The immunogen may elicit an immune response against a human papillomavirus. Useful immunogens are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [69]. In addition to HPV-16 and HPV-18 strains, it is also possible to include L1 VLPs from HPV-6 and HPV-11 strains.

The immunogen may elicit an immune response against a tumour antigen, such as MAGE-1, MAGE-2, MAGE-3 (MAGE-A3), MART-1/Melan A, tyrosinase, gp100, TRP-2, etc. The immunogen may elicit an immunotherapeutic response against lung cancer, melanoma, breast cancer, prostate cancer, etc.

The immunogen may elicit an immune response against a hapten conjugated to a carrier protein, where the hapten is a drug of abuse [70]. Examples include, but are not limited to, opiates, marijuana, amphetamines, cocaine, barbiturates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

Various other immunogens may be used.

Compositions for Immunisation Against *Neisseria meningitidis*

The invention is particularly useful for immunising against meningococcus e.g. against serogroup B.

One preferred immunogenic composition of the invention comprises: (i) an aluminium hydroxide adjuvant; (ii) compound 1, 2 or 5 herein; (iii) a first polypeptide comprising SEQ ID NO: 1; (iv) a second polypeptide comprising SEQ ID NO: 2; and (v) a third polypeptide comprising SEQ ID NO: 3; wherein the compound of (ii) is adsorbed to the aluminium hydroxide.

Another preferred immunogenic composition of the invention comprises: (i) an aluminium hydroxide adjuvant; (ii) compound 1, 2 or 5 herein; (iii) a first polypeptide comprising SEQ ID NO: 1; (iv) a second polypeptide comprising SEQ ID NO: 2; and (v) a third polypeptide comprising SEQ ID NO: 4; Wherein the compound of (ii) is adsorbed to the aluminium hydroxide.

Another preferred immunogenic composition of the invention comprises: (i) an aluminium hydroxide adjuvant; (ii) compound 1, 2 or 5 herein; (iii) a first polypeptide comprising SEQ ID NO: 1; (iv) a second polypeptide comprising SEQ ID NO: 2; and (v) a third polypeptide comprising SEQ ID NO: 5; wherein the compound of (ii) is adsorbed to the aluminium hydroxide.

Any of the first, second and/or third polypeptides can differ from the relevant SEQ ID NO: 1, 2, 3, 4 or 5 by up to 3 amino acids, provided that the polypeptide can still elicit antibodies which bind to a polypeptide which consists of SEQ ID NO: 1, 2, 3, 4 or 5, as appropriate.

Ideally, 1 2 or 3 of the first second and/or third polypeptides is/are also adsorbed to the aluminium hydroxide. These polypeptides are disclosed in more detail in references 40, 71 and 91. The composition may include 5-100 µg of each polypeptide. The composition ideally does not include any bacterial outer membrane vesicles.

The composition may include from 5-100 µg of compound 1, 2 or 5. For example, it may include from 5-100 µg of compound 2, or it may include from 5-100 µg of compound 5.

The composition may include a histidine buffer e.g. a 10 mM histidine buffer. It may include sucrose and/or sodium chloride. It may be administered in a dosage volume of 0.5 ml e.g. for intramuscular injection.

Further immunogenic compositions of the invention may comprise: (i) an aluminium hydroxide adjuvant; (ii) a TLR7 agonist of formula (I-A) or of formula (IV); (iii) a meningococcal factor H binding protein antigen, provided that this antigen is not a fusion protein having an amino acid sequence comprising SEQ ID NO: 8 from reference 73. The factor H binding protein antigen can be adsorbed to the aluminium hydroxide too.

Compositions with Multiple Different Immunogens

According to a twenty-fifth aspect, the invention provides a composition comprising an adjuvant complex of the invention in combination with at least two different immunogens.

The invention also provides a kit comprising (i) an adjuvant complex in a first container and (ii) at least one immunogen in a second container. The first container can optionally include at least one immunogen in addition to the complex.

The TLR agonist in the adjuvant complex can be any agonist as disclosed herein.

In some embodiments the TLR agonist is a TLR7 agonist according to any of formulae (B), (C), (D), (E), or (H). In some embodiments the TLR agonist is a TLR2 agonist according to formula (F) or (J). In some embodiments the TLR agonist is a TLR8 agonist according to formula (G).

In some embodiments the TLR agonist is not a TLR4 agonist. In some embodiments the TLR agonist is not a TLR9 agonist. In some embodiments the TLR agonist is not a compound according to formula (I) as defined herein. In some embodiments the TLR agonist is not a compound according to formula (II) as defined herein. In some embodiments the TLR agonist is not a compound according to formula (III) as defined herein. In some embodiments the TLR agonist is not a compound according to Formula (I-A) as defined herein.

In preferred embodiments the TLR agonist is a TLR7 agonist according to formula (B). Specific TLR7 agonists of interest include compounds 1A to 27A in Table A on pages 79-84 of reference 72.

Where the TLR agonist is a TLR7 agonist according to formula (B), the "at least two different immunogens" in some embodiments does not consist of: (i) a combination of a measles virus immunogen, a mumps virus immunogen, and a rubella virus immunogen; (ii) a combination of a measles virus immunogen, a mumps virus immunogen, a rubella virus immunogen, and a varicella virus immunogen; (iii) a diphtheria vaccine, a tetanus vaccine, and a pertussis vaccine; (iv) a tetravalent combination of conjugates from meningococcus serogroups A, C, W135 and Y; (v) a combination of bacterial antigens from serogroups A, B, C, W135 and/or Y of N. meningitidis; (vi) a combination including antigens from two or more different strains of influenza viruses; (vii) a combination of outer-membrane vesicles from serogroups A, C, W135, Y, X and/or B of N. meningitidis; (viii) a combination of saccharides from different pneumococcal serotypes; (ix) a combination of Moraxella catarrhalis antigens; (x) a combination of Bordetella pertussis holotoxin, filamentous haemagglutinin, pertactin and/or agglutinogens 2 and 3; (xi) a combination of multiple different polypeptide antigens from N. meningitidis.

Where the TLR agonist is a TLR7 agonist which is Compound 1, 2, 3, 4, 5 or 13 herein then the "at least two different immunogens" in some embodiments does not consist of a combination of multiple different polypeptide antigens from N. meningitidis such as the combination disclosed in references 40 and 73.

The "at least two different immunogens" can include at least one bacterial antigen and at least one viral antigen.

If the "at least two different immunogens" include only bacterial immunogens then they ideally include immunogens for at least two different species of bacteria (thus, for instance, excluding a combination of different meningococcal capsular saccharides, as these are all from a single species).

The "at least two different immunogens" should not be conjugated to each other. Thus a conjugate of a Hib saccharide and a tetanus toxoid is not "at least two different immunogens" as used herein.

Preferred embodiments of "at least two different immunogens" include compositions including: (i) a diphtheria toxoid, a tetanus toxoid, and an acellular pertussis antigen e.g. comprising a pertussis toxoid, filamentous hemagglutinin and/or pertactin; (ii) a diphtheria toxoid, a tetanus toxoid, a pertussis antigen, and a H. influenzae type B capsular saccharide conjugate; (iii) a diphtheria toxoid, a tetanus toxoid, a pertussis antigen, and a hepatitis B virus surface antigen; (iv) a diphtheria toxoid, a tetanus toxoid, a pertussis antigen, a hepatitis B virus surface antigen and a H. influenzae type B capsular saccharide conjugate; (v) a diphtheria toxoid, a tetanus toxoid, a pertussis antigen, and an inactivated poliovirus antigen; (vi) a diphtheria toxoid, a tetanus toxoid, a pertussis antigen, a H. influenzae type B capsular saccharide conjugate, a hepatitis B virus surface antigen, and an inactivated poliovirus antigen; or (vii) a hepatitis A virus antigen and a hepatitis B virus antigen.

Where a composition includes an inactivated poliovirus antigen it preferably includes antigens from each of poliovirus Type 1 (e.g. Mahoney strain), poliovirus Type 2 (e.g. MEF-1 strain), and poliovirus Type 3 (e.g. Saukett strain).

Where a composition includes a pertussis antigen it ideally does not include whole inactivated B. pertussis cells i.e. it is ideally an acellular vaccine.

As well as including D, T, Pa, HBsAg, Hib and/or poliovirus antigens, a composition of the invention may include further antigens e.g. from further pathogens. For example, these antigens may be from N. meningitidis (one or more of serogroups A, B, C, W135 and/or Y) or S. pneumoniae. Thus a composition may include two or three of: (i) one or more of D, T, Pa, HBsAg, Hib and/or poliovirus antigens; (ii) a conjugated capsular saccharide from one or more of meningococcal serogroups A, C, W135 and/or Y; (iii) a polypeptide antigen from meningococcus, such as a fHbp.

Compositions of the invention which include multiple immunogens preferably do not include any bacterial outer membrane vesicles.

TLR Agonism

The invention utilises TLR agonists which comprise an adsorptive moiety and a TLR agonist moiety.

The adsorptive moiety confers the ability to adsorb to an insoluble metal salt (see above), whereas the TLR agonist moiety confers the ability to agonise a Toll-like receptor. Typically a TLR agonist of the invention would thus function as a TLR agonist even without its adsorptive moiety. Except where otherwise stated, TLR agonists of the invention can activate any of TLR1, TLR2, TLR3, TLR4, TLR5, TLR6, TLR7, TLR8, TLR9 or TLR11.

Where the invention provides or refers to a compound as a TLR agonist, the compound is preferably an agonist of TLR1, TLR2, TLR3, TLR4, TLR5, TLR6, TLR7, TLR8, TLR9, TLR10 or TLR11. From this group, a preferred sub-group is TLR1, TLR2, TLR3, TLR5, TLR6, TLR7, TLR8 and TLR11. A more preferred subgroup is TLR2, TLR7 and TLR8. Another preferred subgroup is TLR2 and TLR7.

Most preferably, a TLR agonist is an agonist of a human TLR.

A compound of the invention may be an agonist of human TLR1. A compound of the invention may be an agonist of human TLR2. A compound of the invention may be an agonist of human TLR3. A compound of the invention may be an agonist of human TLR4. A compound of the invention may be an agonist of human TLR5. A compound of the invention may be an agonist of human TLR6. A compound of the invention may be an agonist of human TLR7. A compound of the invention may be an agonist of human TLR8. A compound of the invention may be an agonist of human TLR9. A compound of the invention may be an agonist of human TLR11.

Agonist activity of a compound against any particular Toll-like receptor can be determined by standard assays. Companies such as Imgenex, Invivogen supply cell lines which are stably co-transfected with human TLR genes and NFκB, plus suitable reporter genes, for measuring TLR activation pathways. They are designed for sensitivity, broad working range dynamics and can be used for high-throughput screening. Constitutive expression of one or two specific TLRs is typical in such cell lines. See also reference 74.

According to a twenty-sixth aspect, a composition includes first and second TLR agonists. These two agonists are different from each other and they target different TLRs. Both agonists are adsorbed to an aluminium salt. They may be co-adsorbed to an aluminium salt or they may be separately adsorbed to aluminium salts (preferably the same salt e.g. both to aluminium hydroxide) and then combined. TLR combinations are known from e.g. reference 75.

In Situ Precipitation Processes

According to a twenty-seventh aspect, the invention provides a process for preparing an adjuvant complex, comprising steps of (i) preparing an aqueous mixture of a TLR agonist and a soluble aluminium salt; then (ii) adding a non-aluminium salt to the aqueous mixture in order to form a precipitated aluminium salt to which the TLR agonist is adsorbed.

According to a twenty-eighth aspect, the invention provides a process for preparing an immunogenic composition, comprising a step of mixing (i) an aqueous mixture of a TLR agonist and a soluble aluminium salt with (ii) a buffered aqueous mixture of an immunogen, wherein the mixing step causes precipitation of an aluminium salt to which the TLR agonist and the immunogen are adsorbed.

The invention also provides a process for preparing an immunogenic composition, comprising a step of mixing (i) an aqueous solution of a soluble aluminium salt with (ii) a buffered aqueous mixture of an immunogen and a TLR agonist, wherein the mixing step causes precipitation of an aluminium salt to which the TLR agonist and the immunogen are adsorbed.

The invention also provides a process for preparing an immunogenic composition, comprising a step of mixing (i) an aqueous solution of a soluble aluminium salt and an immunogen with (ii) a buffered aqueous mixture of a TLR agonist, wherein the mixing step causes precipitation of an aluminium salt to which the TLR agonist and the immunogen are adsorbed.

The invention also provides immunogenic compositions obtained or obtainable by these processes.

In these processes the soluble aluminium salt will typically be alum ($KAl(SO_4)_2$, typically as $KAl(SO_4)_2.12H_2O$) or aluminium chloride. Adding an alternative anion to this soluble salt can cause an aluminium salt adjuvant to precipitate in situ.

The alternative anion is typically added as part of a buffer. Thus, for instance, if a phosphate buffer is added to the soluble aluminium salt then an aluminium phosphate adjuvant can precipitate. The buffer will typically be an acetate, carbonate, or phosphate buffer. Addition of the buffer to an alum solution leads to precipitation of an amorphous aluminium hydroxy(buffer anion)sulfate e.g. aluminium hydroxyphosphatesulfate (see chapter 9 of reference 32). The immunogen and the TLR agonist can adsorb to the precipitated salt.

The process may involve addition of a solution of a desired immunogen in a phosphate buffer. These processes can lead to compositions in which immunogen and/of TLR agonist are adsorbed to an aluminium hydroxyphosphatesulfate.

Analytical Assays

According to a twenty-ninth aspect, the invention provides an assay for analysing an adjuvant complex which comprises a TLR agonist adsorbed to an insoluble metal salt, comprising steps of: (i) treating the complex to desorb TLR agonist from the insoluble metal salt; then (ii) detecting the desorbed TLR agonist.

Various techniques are available for desorption, as required by step (i). For example, the complex can be treated with an adsorptive compound which has higher affinity for the metal salt and which thus displaces the adsorbed TLR agonist. Another method involves incubating the complex with a high concentration of a phosphate buffer, such that the buffer ions displace the adsorbed TLR agonist. Another method uses mixtures of salts and detergents e.g. see reference 76. Another method dissolves the insoluble metal salt, thus destroying adsorption at the same time; suitable ways of dissolving such salts include e.g. citrate at an appropriate pH can be used to dissolve aluminium salt adjuvants, as can other polybasic or α-hydroxy-carboxylic acids.

Detection in step (ii) can be qualitative, quantitative, or semi-quantitative. Thus the detection step can merely confirm that desorption has occurred, or can be used to quantify the amount of agonist which had been adsorbed to the metal salt. Techniques such as HPLC can be used for quantitative detection of desorbed agonists.

In another aspect the invention provides an assay for analysing an adjuvant complex which comprises a TLR agonist adsorbed to an insoluble metal salt, comprising steps of: (i) treating the complex to desorb TLR agonist from the insoluble metal salt; then (ii) testing the biological activity of the desorbed TLR agonist. Techniques for testing for the agonists' activity are well known in the art (see above). This assay, particularly when activity is analysed quantitatively, can be used to confirm the stability of adsorbed material e.g. to check that the total activity of material which was adsorbed to the salts is retained after desorption. If all material is desorbed, but activity has been lost, this can indicate that the material has degraded while it was adsorbed.

Pharmaceutical Compositions and Products

The invention provides a pharmaceutical composition comprising a TLR agonist of the invention. This composition can also include an insoluble metal salt and/or an immunogen.

The invention also provides a pharmaceutical composition comprising a TLR agonist of the invention and an insoluble metal salt. This composition can also include an immunogen.

The invention also provides an immunogenic pharmaceutical composition comprising a TLR agonist of the invention and an immunogen. This composition can also include an insoluble metal salt.

The invention also provides a method for preparing a pharmaceutical composition, comprising a step of combining a TLR agonist of the invention with one or more pharmaceutically acceptable excipients.

The invention also provides a method for preparing a pharmaceutical composition, comprising a step of combining a complex of the invention with one or more pharmaceutically acceptable excipients.

Pharmaceutical compositions usually include components in addition to the TLR agonist, insoluble metal salt and/or immunogen e.g. they typically include one or more pharmaceutical carrier(s) and/or excipient(s). A thorough discussion of such components is available in reference 77.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions can include a physiological salt, such as a sodium salt e.g. to control tonicity. Sodium chloride (NaCl) is typical, which may be present at between 1 and 20 mg/ml e.g. 10±2 mg/ml or 9 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg, e.g. between 240-360 mOsm/kg, or between 290-310 mOsm/kg.

Pharmaceutical compositions may include compounds (with or without an insoluble metal salt) in plain water (e.g. w.f.i.) but will usually include one or more buffers. Typical buffers include: a phosphate buffer (except in the fifteenth aspect); a Tris buffer; a borate buffer; a succinate buffer; a histidine buffer (particularly with an aluminium hydroxide adjuvant); or a citrate buffer. Buffer salt s will typically be included in the 5-20 mM range. If a phosphate buffer is used then the concentration of phosphate ions should, in some embodiments, be <50 mM (see above) e.g. <10 mM.

Pharmaceutical compositions typically have a pH between 5.0 and 9.5 e.g. between 6.0 and 8.0.

Pharmaceutical compositions are preferably sterile.

Pharmaceutical compositions preferably non-pyrogenic e.g. containing <1 EU (endotoxin unit, a standard measure) per dose, and preferably <0.1 EU per dose.

Pharmaceutical compositions are preferably gluten free.

Pharmaceutical compositions are suitable for administration to animal (and, in particular, human) patients, and thus include both human and veterinary uses. They may be used in a method of raising an immune response in a patient, comprising the step of administering the composition to the patient. Compositions may be administered before a subject is exposed to a pathogen and/or after a subject is exposed to a pathogen.

Pharmaceutical compositions may be prepared in unit dose form. In some embodiments a unit dose may have a volume of between 0.1-1.0 ml e.g. about 0.5 ml.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

The invention also provides a kit comprising first and second kit components, wherein: (i) the first kit component comprises an insoluble metal salt and an immunogen; and (ii) the second kit component comprises a TLR agonist compound of the invention. The second component ideally does not include an insoluble metal salt and/or does not include an immunogen. The first and second components can be combined to provide a composition suitable for administration to a subject.

The invention also provides a kit comprising first and second kit components, wherein: (i) the first kit component comprises an insoluble metal salt and a TLR agonist compound of the invention; and (ii) the second kit component comprises an immunogen. The second component ideally does not include an insoluble metal salt and/or a TLR agonist. In some embodiments, the second component is lyophilised. The first and second components can be combined to provide a pharmaceutical composition suitable for administration to a subject.

The invention also provides a kit comprising first and second kit components, wherein: (i) the first kit component comprises an immunogen and a TLR agonist compound of the invention; and (ii) the second kit component comprises an insoluble metal salt. The second component ideally does not include an immunogen and/or a TLR agonist. The first and second components can be combined to provide a pharmaceutical composition suitable for administration to a subject.

In some embodiments these kits comprise two vials. In other embodiments they comprise one ready-filled syringe and one vial, with the contents of the syringe being mixed with the contents of the vial prior to injection. A syringe/vial arrangement is useful where the vial's contents are lyophilised. Usually, though, the first and second kit components will both be in aqueous liquid form.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository or pessary. The composition may be prepared for nasal, aural or ocular administration e.g. as a spray or drops. The composition may be in kit form, designed such that a combined composition is reconstituted just prior to administration to a patient. Such kits may comprise one or more antigens in liquid form and one or more lyophilised antigens. Injectables for intramuscular administration are typical.

Compositions comprise an effective amount of a TLR agonist i.e. an amount which, when administered to an individual, either in a single dose or as part of a series, is effective for enhancing the immune response to a co-administered immunogen. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. The amount will fall in a relatively broad range that can be determined through routine trials. An amount of between 1-1000 µg/dose can be used e.g. from 5-100 µg per dose or from 10-100 µg per dose, and ideally ≤300 µg per dose e.g. about 5 µg, 10 µg, 20 µg, 25 µg, 50 µg or 100 µg per dose. Thus the concentration of a TLR agonist in a composition of the invention may be from 2-2000 µg/ml e.g. from 10-200 µg/ml, or about 10, 20, 40, 50, 100 or 200 µg/ml, and ideally ≤600 µg/ml. These ranges of doses, and specific dosages, are particularly useful for compounds of formula (I-A) or (IV).

Methods of Treatment, and Administration of Immunogenic Compositions

The invention provides a method of raising an immune response in a subject, comprising the step of administering to the subject a TLR agonist, complex and/or composition of the invention.

The invention also provides a TLR agonist, complex and/or composition of the invention, for use in a method of raising an immune response in a subject.

The invention also provides the use of a TLR agonist or complex of the invention in the manufacture of a medicament for raising an immune response in a subject.

The invention also provides the use of (i) a TLR agonist as defined herein and (ii) an insoluble metal salt in the manufacture of a medicament for raising an immune response in a subject. Similarly, the invention also provides the use of (i) a TLR agonist as defined herein (ii) an insoluble metal salt and (iii) an immunogen in the manufacture of a medicament (e.g. a vaccine) for raising an immune response in a subject.

The invention is suitable for raising immune responses in human or non-human animal (in particular mammal) subjects. Compositions prepared according to the invention may be used to treat both children and adults.

The immune response stimulated by these methods and uses will generally include an antibody response, preferably a protective antibody response. Methods for assessing antibody responses after immunisation are well known in the art.

Treatment can be by a single dose schedule or a multiple dose schedule. Multiple doses may be used in a primary immunisation schedule and/or in a booster immunisation schedule. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, etc.).

Exemplary Compounds

Compounds 1 to 102 below contain adsorptive moieties coupled to core structures that have been shown to be TLR agonists. Thus, these compounds can be adsorbed to insoluble metal salts as described herein. Thus the invention provides each of the following compounds:

Compound 1

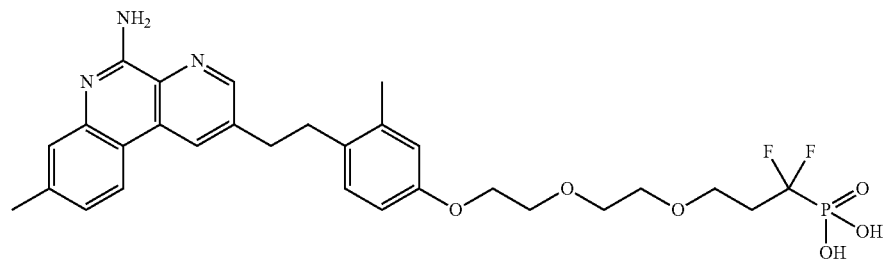

(3-(2-(2-(4-(2-(5-amino-8-methylbenzo[f][1,7]naphthyridin-2-yl)ethyl)-3-methylphenoxy)ethoxy)ethoxy)-1,1-difluoropropyl)phosphonic acid Compound 2

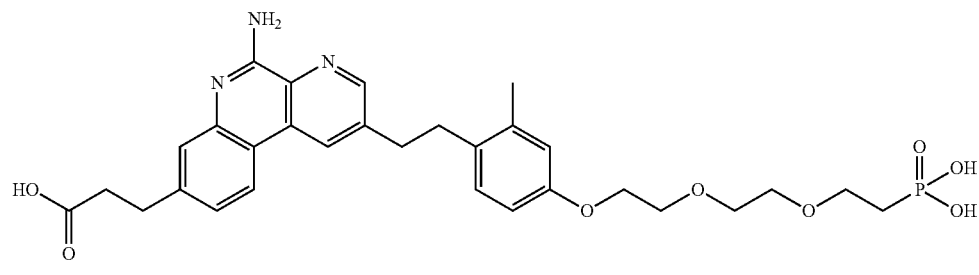

3-(5-amino-2-(2-methyl-4-(2-(2-(2-phosphonoethoxy)ethoxy)ethoxy)phenethyl)benzo[f][1,7]naphthyridin-8-yl)propanoic aicd Compound 3

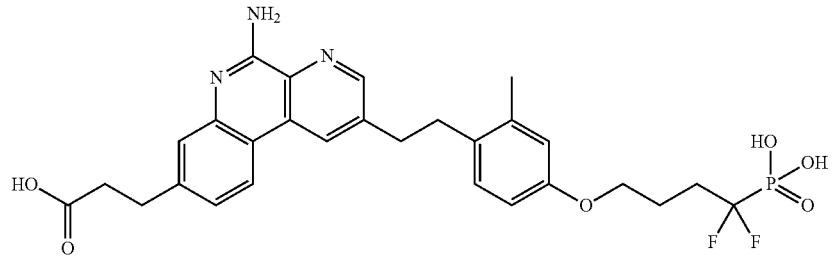

3-(5-amino-2-(4-(4,4-difluoro-4-phosphonobutoxy)-2-methylphenethyl)benzo[f][1,7]naphthyridin-8-yl)propanoic acid Compound 4

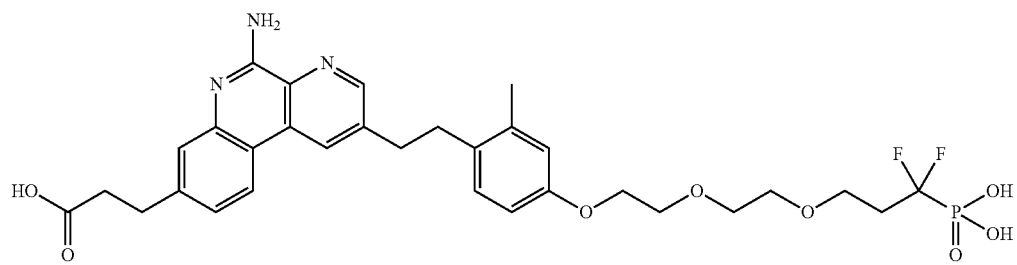

3-(5-amino-2-(4-(2-(2-(3,3-difluoro-3-phosphonopropoxy)ethoxy)ethoxy)-2-methylphenethyl)benzo[f][1,7]naphthyridin-8-yl)propanoic acid Compound 5

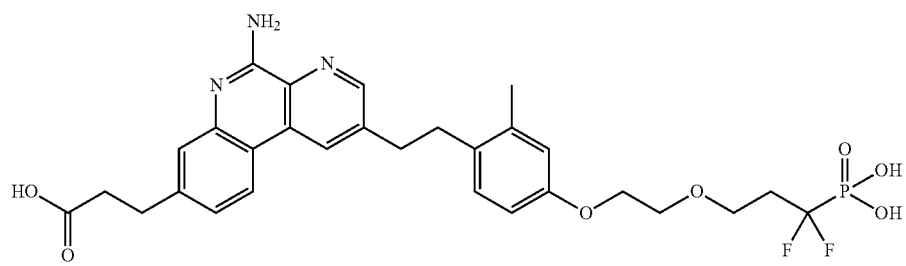

3-(5-amino-2-(4-(2-(3,3-difluoro-3-phosphonopropoxy)ethoxy)-2-methylphenethyl)benzo[f][1,7]naphthyridin-8-yl)propanoic acid Compound 6

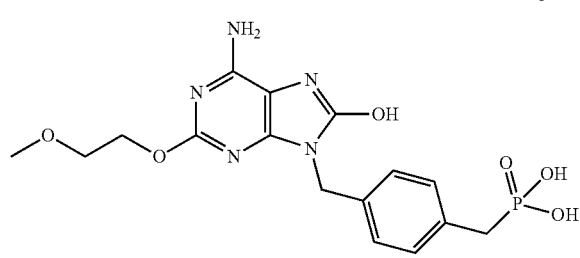

(4-((6-amino-8-hydroxy-2-(2-methoxyethoxy)-9H-purin-9-yl)methyl)benzyl)phosphonic acid Compound 7

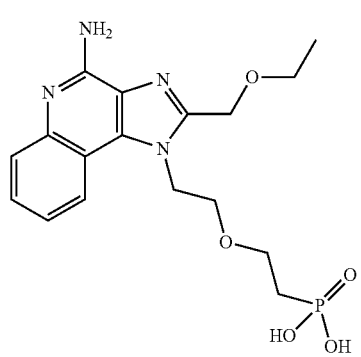

(2-(2-(4-amino-2-(ethoxymethyl)-1H-imidazo[4,5-c]quinolin-1-yl)ethoxy)ethyl)phosphonic acid -continued Compound 8

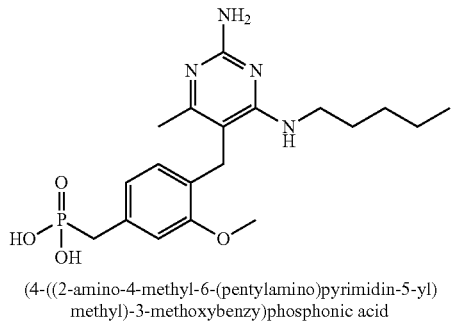

(4-((2-amino-4-methyl-6-(pentylamino)pyrimidin-5-yl)
methyl)-3-methoxybenzy)phosphonic acid Compound 9

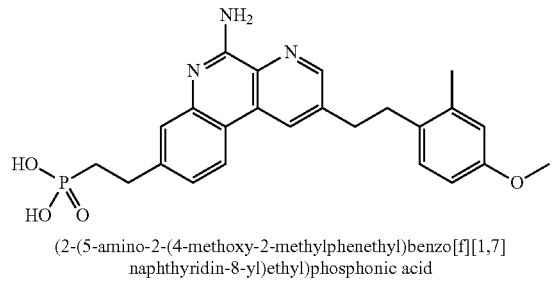

(2-(5-amino-2-(4-methoxy-2-methylphenethyl)benzo[f][1,7]
naphthyridin-8-yl)ethyl)phosphonic acid Compound 10

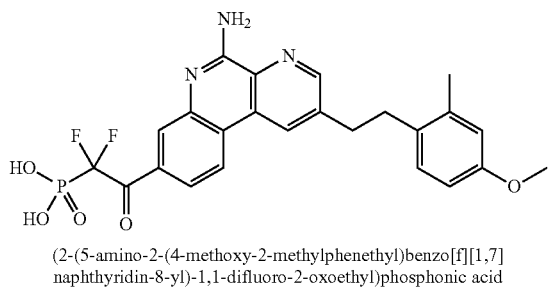

(2-(5-amino-2-(4-methoxy-2-methylphenethyl)benzo[f][1,7]
naphthyridin-8-yl)-1,1-difluoro-2-oxoethyl)phosphonic acid Compound 11

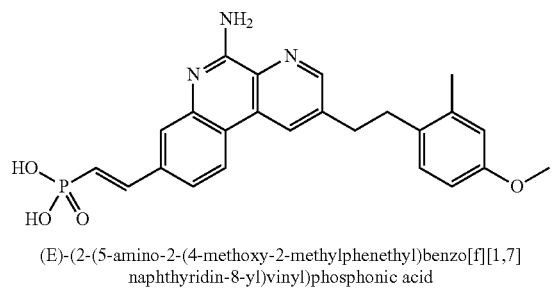

(E)-(2-(5-amino-2-(4-methoxy-2-methylphenethyl)benzo[f][1,7]
naphthyridin-8-yl)vinyl)phosphonic acid Compound 12

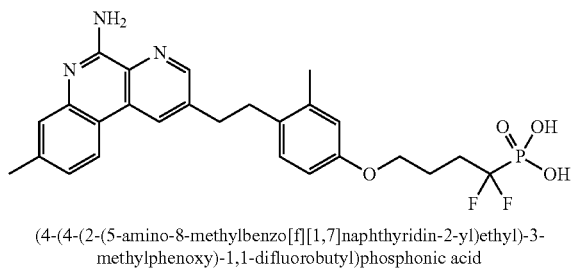

(4-(4-(2-(5-amino-8-methylbenzo[f][1,7]naphthyridin-2-yl)ethyl)-3-
methylphenoxy)-1,1-difluorobutyl)phosphonic acid Compound 13

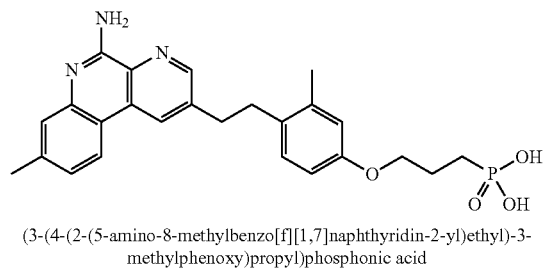

(3-(4-(2-(5-amino-8-methylbenzo[f][1,7]naphthyridin-2-yl)ethyl)-3-
methylphenoxy)propyl)phosphonic acid Compound 14

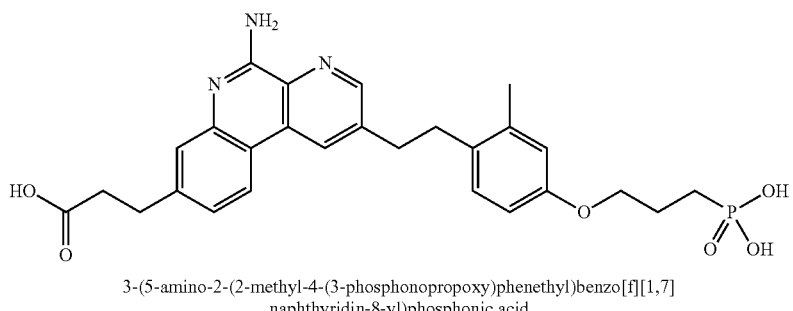

3-(5-amino-2-(2-methyl-4-(3-phosphonopropoxy)phenethyl)benzo[f][1,7]
naphthyridin-8-yl)phosphonic acid Compound 15

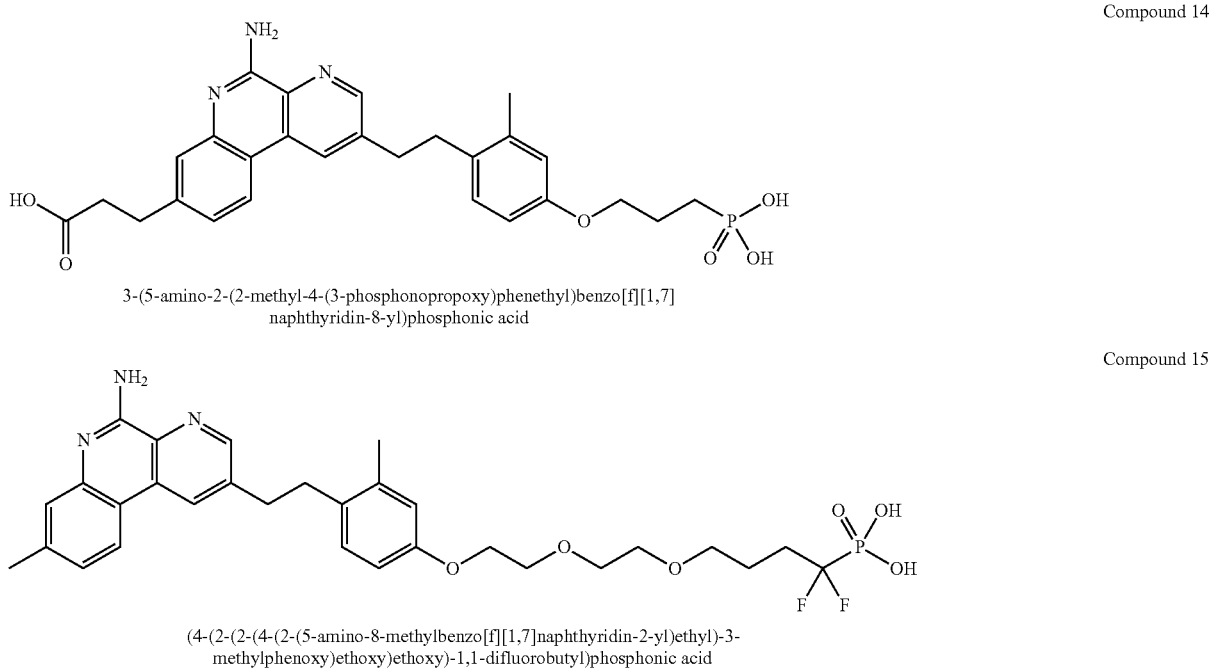

(4-(2-(2-(4-(2-(5-amino-8-methylbenzo[f][1,7]naphthyridin-2-yl)ethyl)-3-
methylphenoxy)ethoxy)ethoxy)-1,1-difluorobutyl)phosphonic acid -continued Compound 16

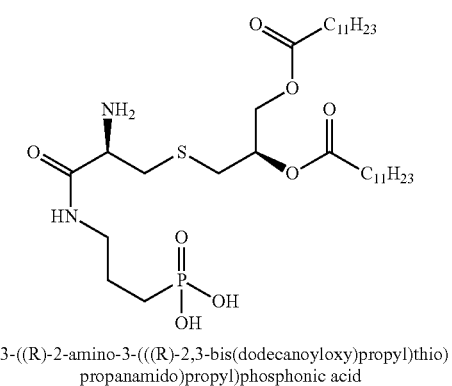

(3-(((R)-2-amino-3-(((R)-2,3-bis(dodecanoyloxy)propyl)thio)
propanamido)propyl)phosphonic acid Compound 17

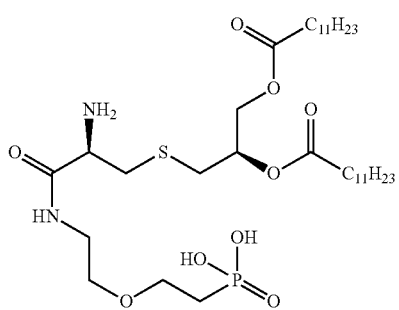

((8R,12R)-8-amino-12-(dodecanoyloxy)-7,15-dioxo-3,
14-dioxa-10-thia-6-azahexacosyl)phosphonic acid Compound 18

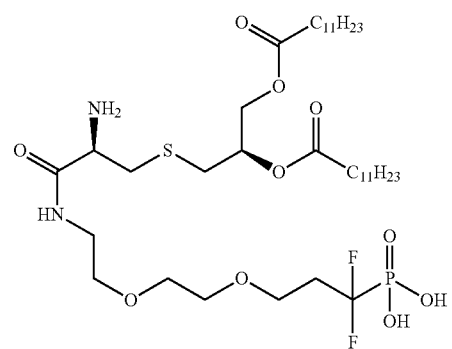

((12R,16R)-12-amino-16-(dodecanoyloxy)-1,1-difluoro-11,19-
dioxo-4,7,18-trioxa-14-thia-10-azatriacontyl)phosphonic acid Compound 19

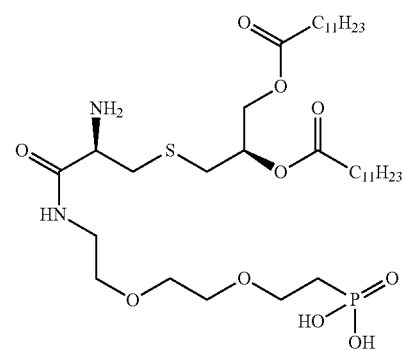

((11R,15R)-11-amino-15-(dodecanoyloxy)-10,18-dioxo-
3,6,17-trioxa-13-thia-9-azanonacosyl)phosphonic acid Compound 20

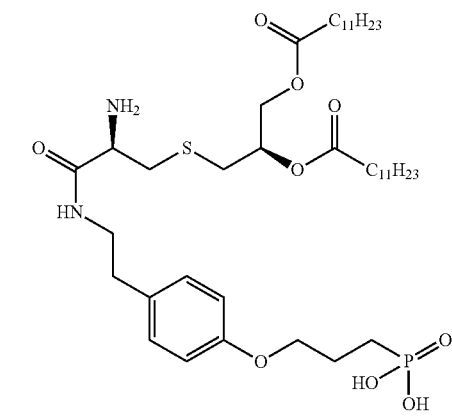

(3-(4-(2-((R)-2-amino-3-(((R)-2,3-bis(dodecanoyloxy)propyl)thio)
propanamido)ethyl)phenoxy)propyl)phosphonic acid Compound 21

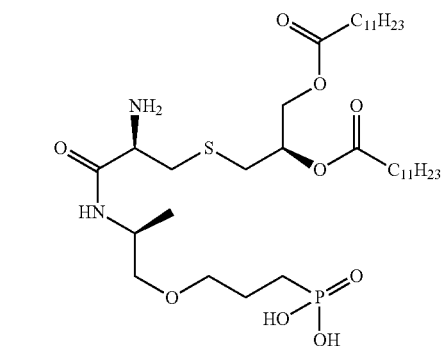

((6S,9R,13R)-9-amino-13-(dodecanoyloxy)-6-methyl-8,16-dioxo-
4,15-dioxa-11-thia-7-azaheptacosyl)phosphonic acid Compound 22

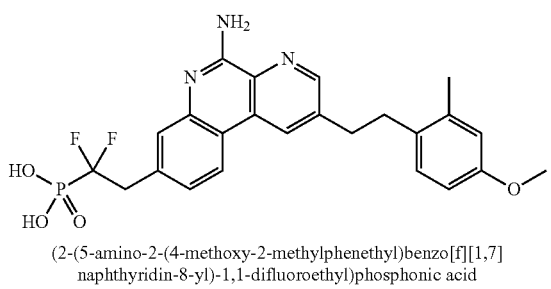

(3-((1-((R)-2-amino-3-(((R)-2,3-bis(dodecanoyloxy)propyl)thio)
propanamido)cyclopropyl)methoxy)propyl)phosphonic acid Compound 23

(2-(5-amino-2-(4-methoxy-2-methylphenethyl)benzo[f][1,7]
naphthyridin-8-yl)-1,1-difluoroethyl)phosphonic acid -continued Compound 24

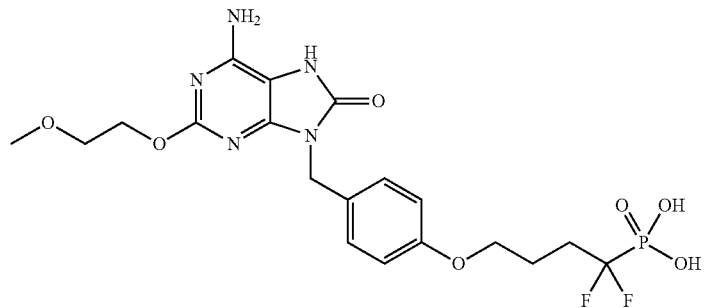

(4-(4-((6-amino-2-(2-methoxyethoxy)-8-oxo-7H-purin-9(8H)-yl)
methyl)phenoxy)-1,1-difluorobutyl)phosphonic acid Compound 25

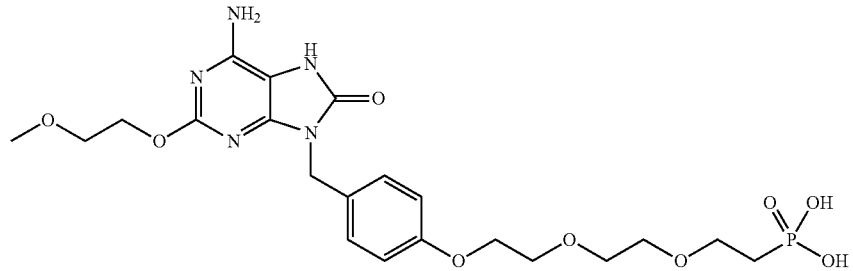

(2-(2-(2-(4-((6-amino-2-(2-methoxyethoxy)-8-oxo-7H-purin-9(8H)-yl)
methyl)phenoxy)ethoxy)ethoxy)ethyl)phosphonic acid Compound 26

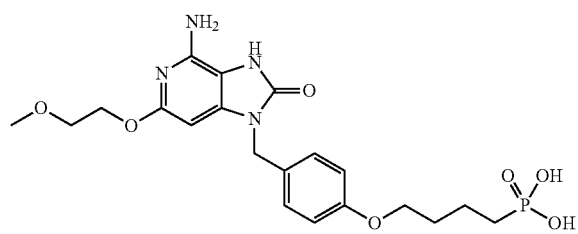

(4-(4-((4-amino-6-(2-methoxyethoxy)-2-oxo-2,3-dihydro-1H-imidazo
[4,5-c]pyridin-1-yl)methyl)phenoxy)butyl)phosphonic acid Compound 27

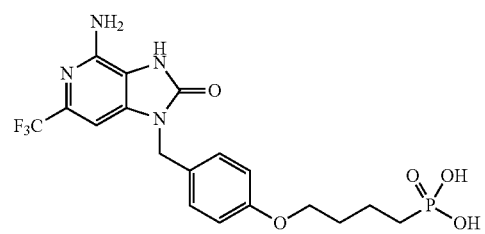

(4-4-((4-amino-2-oxo-6-(trifluoromethyl)-2,3-dihydro-1H-imidazo
[4,5-c]pyridin-1-yl)methyl)phenoxy)butyl)phosphonic acid Compound 28

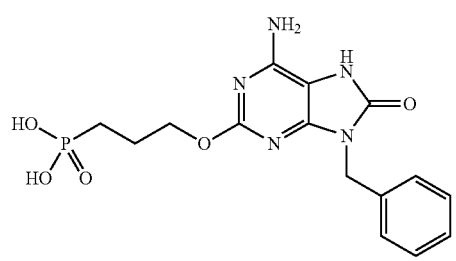

(3-((6-amino-9-benzyl-8-oxo-8,9-dihydro-7H-
purin-2-yl)oxy)propyl)phosphonic acid Compound 29

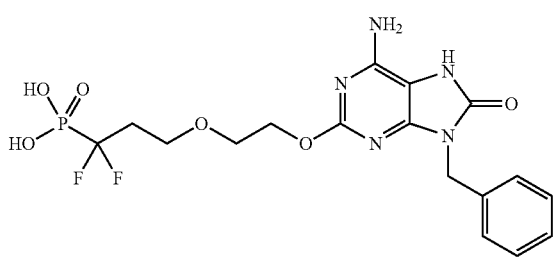

(3-(2-((6-amino-9-benzyl-8-oxo-8,9-dihydro-7H-purin-2-yl)
oxy)ethoxy)-1,1-difluoropropyl)phosphonic acid Compound 30

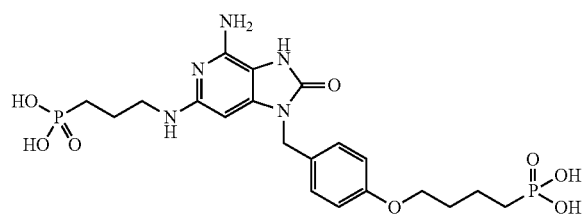

(3-((4-amino-1-(4-(butyloxyphosphonate)benzyl)-2-oxo-2,3-
dihydro-1H-imidazo[4,5-c]pyridin-6-yl)amino)propyl)phosphonic acid Compound 31

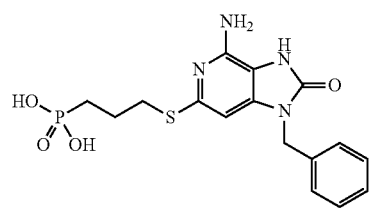

(3-((4-amino-1-benzyl-2-oxo-2,3-dihydro-1H-imidazo
[4,5-c]pyridin-6-yl)thio)propyl) phosphonic acid -continued Compound 32

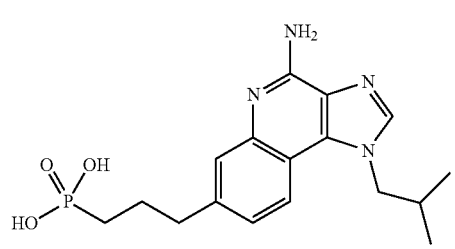

(3-(4-amino-1-isobutyl-1H-imidazo[4,5-c]
quinolin-7-yl)propyl)phosphonic acid

Compound 33

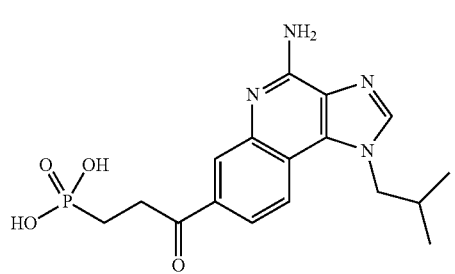

(3-(4-amino-1-isobutyl-1H-imidazo[4,5-c]
quinolin-7-yl)-3-oxopropyl)phosphonic acid Compound 34

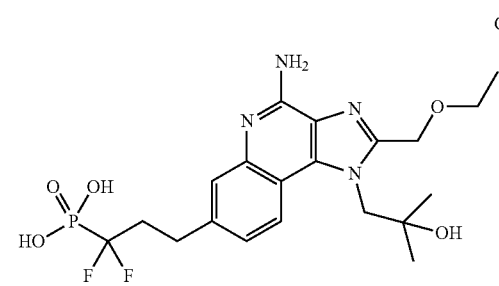

(3-(4-amino-2-(ethoxymethyl)-1-(2-hydroxy-2-methylpropyl)-1H-
imidazo[4,5-c]quinolin-7-yl)-1,1-difluoropropyl)phosphonic acid Compound 35

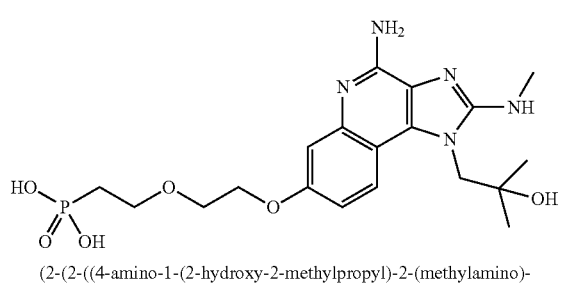

(2-(2-((4-amino-1-(2-hydroxy-2-methylpropyl)-2-(methylamino)-
1H-imidazo[4,5-c]quinolin-7-yl)oxy)ethoxy)ethyl)phosphonic acid Compound 36

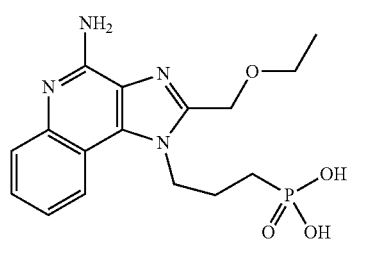

(3-(4-amino-2-(ethoxymethyl)-1H-imidazo
[4,5-c]quinolin-1-yl)propyl)phosphonic acid Compound 37

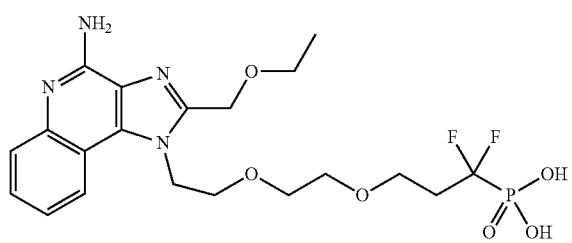

(3-(2-(2-(4-amino-2-(ethoxymethyl)-1H-imidazo[4,5-c]
quinolin-1-yl)ethoxy)ethoxy)-1,1-difluoropropyl)phosphonic acid Compound 38

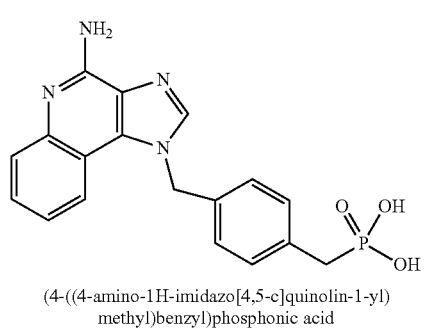

(4-((4-amino-1H-imidazo[4,5-c]quinolin-1-yl)
methyl)benzyl)phosphonic acid

Compound 39

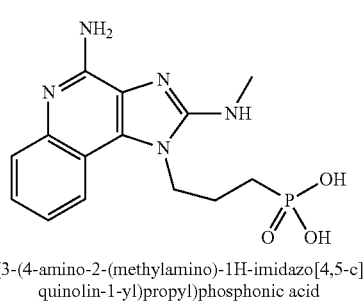

(3-(4-amino-2-(methylamino)-1H-imidazo[4,5-c]
quinolin-1-yl)propyl)phosphonic acid

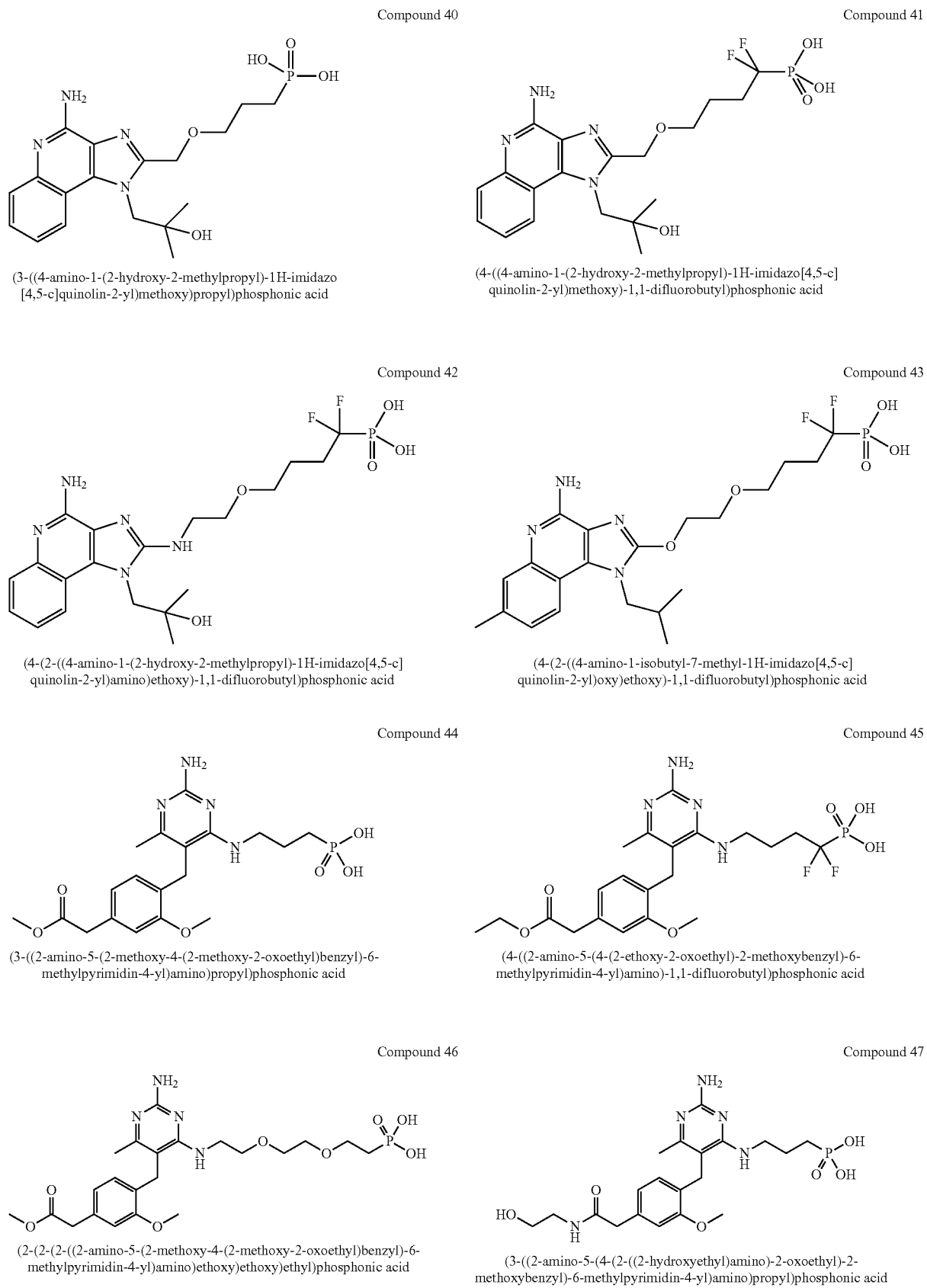

-continued

Compound 48

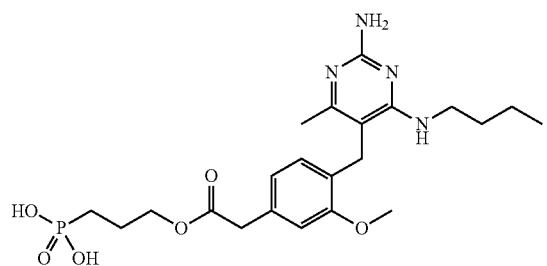

(3-(2-(4-((2-amino-4-(butylamino)-6-methylpyrimidin-5-yl)
methyl)-3-methoxyphenyl)acetoxy)propyl)phosphonic acid Compound 49

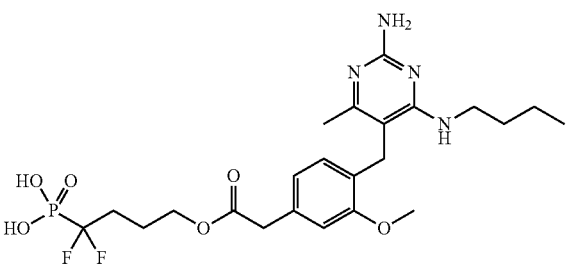

(4-(2-(4-((2-amino-4-(butylamino)-6-methylpyrimidin-5-yl)methyl)-3-
methoxyphenyl)acetoxy)-1,1-difluorobutyl)phosphonic acid Compound 50

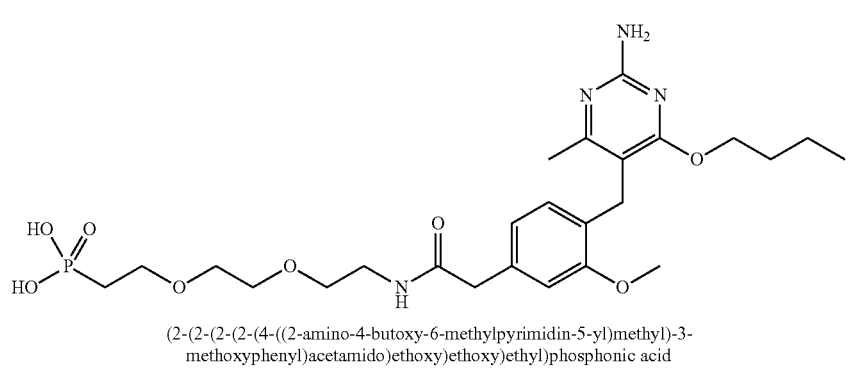

(2-(2-(2-(2-(4-((2-amino-4-butoxy-6-methylpyrimidin-5-yl)methyl)-3-
methoxyphenyl)acetamido)ethoxy)ethoxy)ethyl)phosphonic acid Compound 51

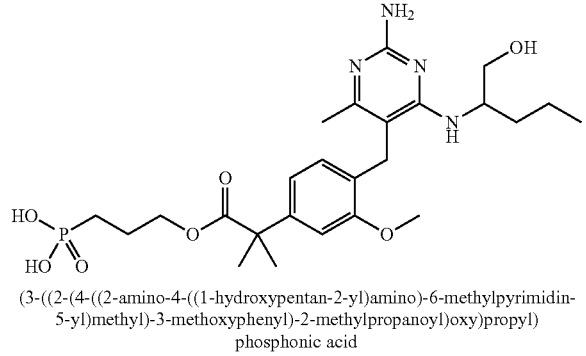

(3-((2-(4-((2-amino-4-((1-hydroxypentan-2-yl)amino)-6-methylpyrimidin-
5-yl)methyl)-3-methoxyphenyl)-2-methylpropanoyl)oxy)propyl)
phosphonic acid Compound 52

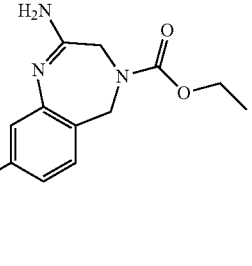

(4-(2-amino-4-(ethoxycarbonyl)-4,5-dihydro-3H-
benzo[e][1,4]diazepin-8-yl)phenyl)phosphonic acid Compound 53

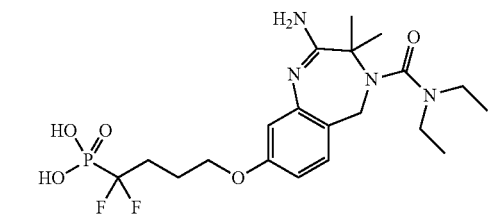

(4-((2-amino-4-(diethylcarbamoyl)-3,3-dimethyl-4,5-dihydro-3H-
benzo[e][1,4]diazepin-8-yl)oxy)-1,1-difluorobutyl)phosphonic acid Compound 54

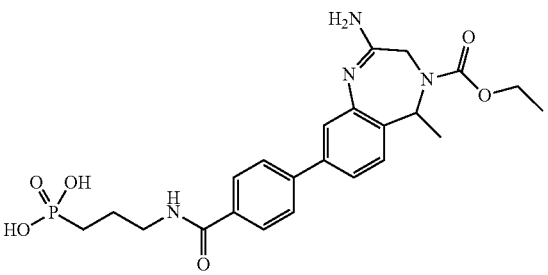

(3-(4-(2-amino-4-(ethoxycarbonyl)-5-methyl-4,5-dihydro-3H-
benzo[e][1,4]diazepin-8-yl)benzamido)propyl)phosphonic acid Compound 55

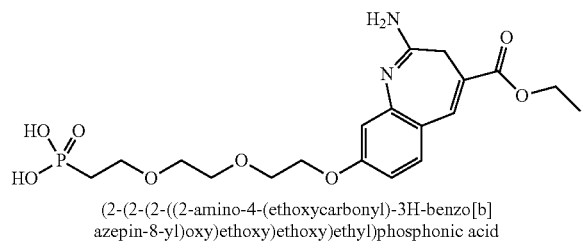

(2-(2-(2-((2-amino-4-(ethoxycarbonyl)-3H-benzo[b]
azepin-8-yl)oxy)ethoxy)ethoxy)ethyl)phosphonic acid Compound 56

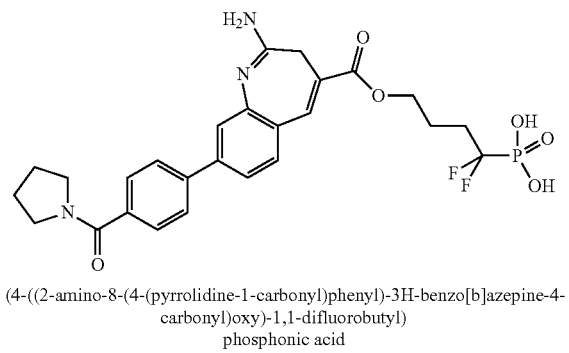

(4-((2-amino-8-(4-(pyrrolidine-1-carbonyl)phenyl)-3H-benzo[b]azepine-4-
carbonyl)oxy)-1,1-difluorobutyl)
phosphonic acid Compound 57

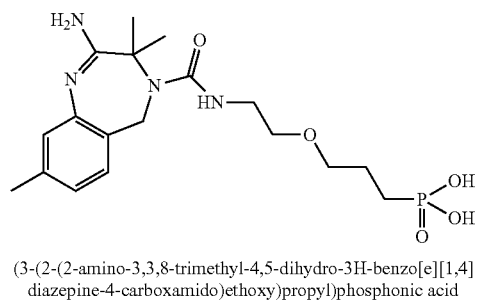

(3-(2-(2-amino-3,3,8-trimethyl-4,5-dihydro-3H-benzo[e][1,4]
diazepine-4-carboxamido)ethoxy)propyl)phosphonic acid Compound 58

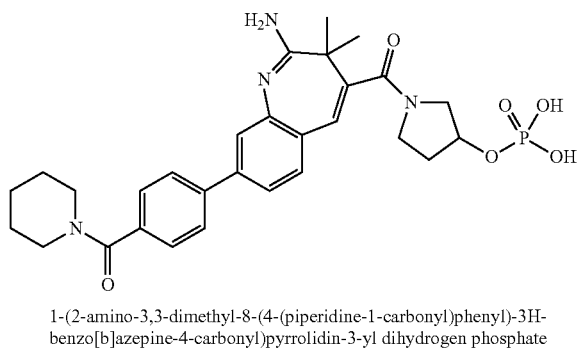

1-(2-amino-3,3-dimethyl-8-(4-(piperidine-1-carbonyl)phenyl)-3H-
benzo[b]azepine-4-carbonyl)pyrrolidin-3-yl dihydrogen phosphate Compound 59

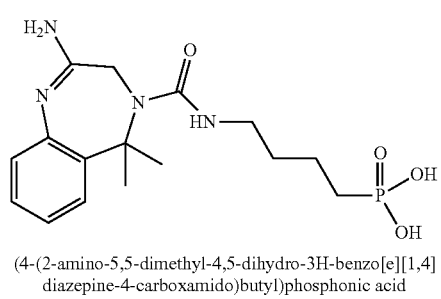

(4-(2-amino-5,5-dimethyl-4,5-dihydro-3H-benzo[e][1,4]
diazepine-4-carboxamido)butyl)phosphonic acid Compound 60

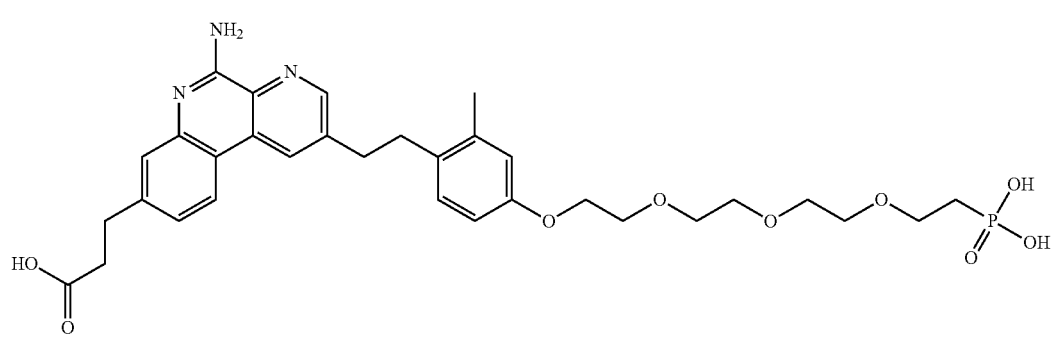

3-(5-amino-2-(2-methyl-4-(2-(2-(2-(2-phosphonoethoxy)ethoxy)ethoxy)
ethoxy)phenethyl)benzo[f][1,7]naphthyridin-8-yl)propanoic acid Compound 61

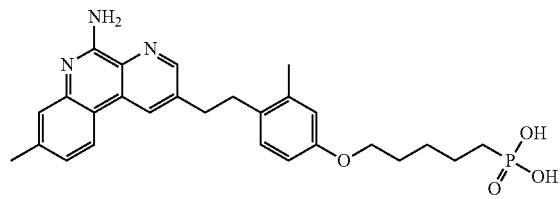

(5-(4-(2-(5-amino-8-methylbenzo[f][1,7]naphthyridin-2-yl)ethyl)-3-methylphenoxy)pentyl)phosphonic acid Compound 62

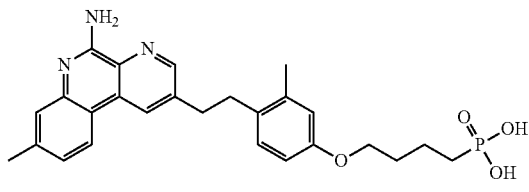

(4-(4-(2-(5-amino-8-methylbenzo[f][1,7]naphthyridin-2-yl)ethyl)-3-methylphenoxy)butyl)phosphonic acid Compound 63

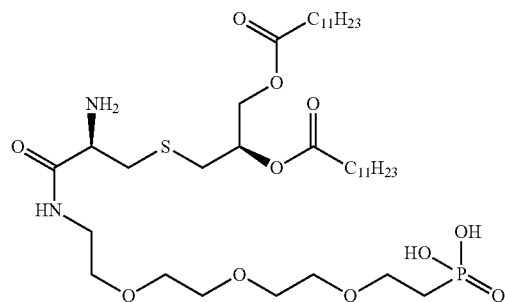

(14R,18R)-14-amino-18-(dodecanoyloxy)-13,21-dioxo-3,6,9,20-tetraoxa-16-thia-12-azadotriacontylphosphonic acid Compound 64

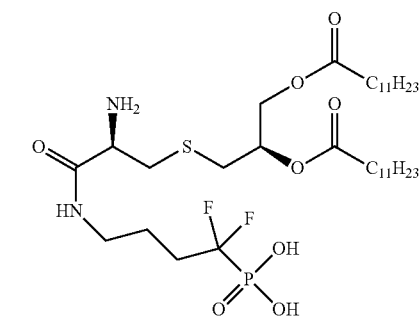

4-((R)-2-amino-3-((R)-2,3-bis(dodecanoyloxy)propylthio)propanamido)-1,1-difluorobutylphosphonic acid Compound 65

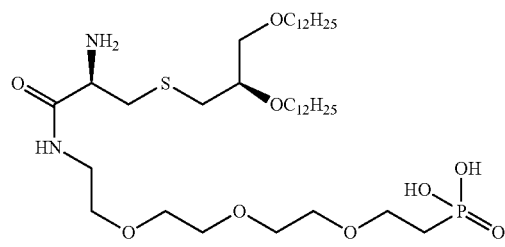

(14R,18R)-14-amino-18-(dodecyloxy)-13-oxo-3,6,9,20-tetraoxa-16-thia-12-azadotriacontylphosphonic acid Compound 66

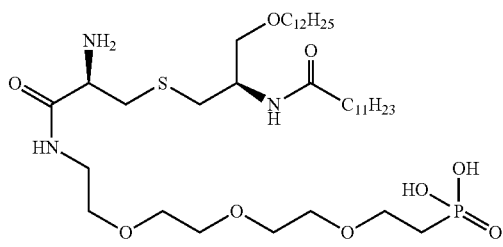

((14R,18R)-14-amino-18-dodecanamido-13-oxo-3,6,9,20-tetraoxa-16-thia-12-azadotriacontyl)phosphonic acid Compound 67

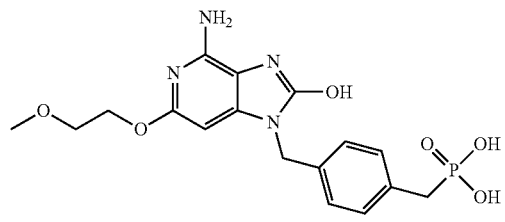

(4-((4-amino-6-(2-methoxyethoxy)-2-oxo-2,3-dihydro-1H-imidazo[4,5-c]pyridin-1-yl)methyl)benzyl)phosphonic acid Compound 68

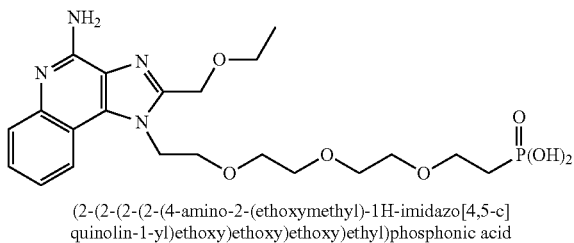

(2-(2-(2-(2-(4-amino-2-(ethoxymethyl)-1H-imidazo[4,5-c]quinolin-1-yl)ethoxy)ethoxy)ethoxy)ethyl)phosphonic acid Compound 69

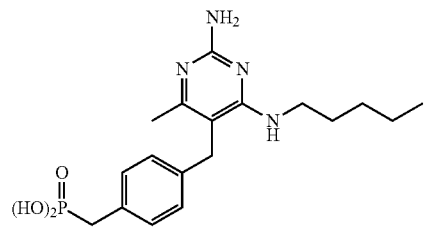

(4-((2-amino-4-methyl-6-(pentylamino)pyrimidin-5-yl)methyl)benzyl)phosphonic acid Compound 70

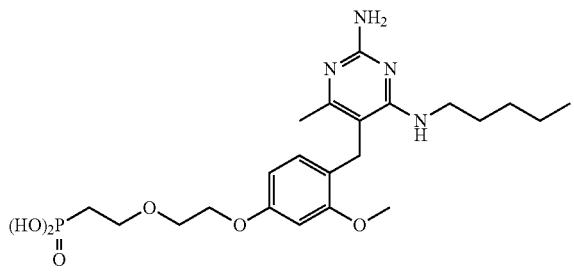

(2-(2-(4-((2-amino-4-methyl-6-(pentylamino)pyrimidin-5-yl)methyl)-3-methoxyphenoxy)ethoxy)ethyl) phosphonic acid Compound 71

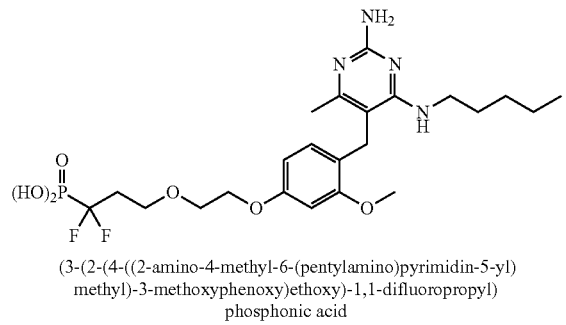

(3-(2-(4-((2-amino-4-methyl-6-(pentylamino)pyrimidin-5-yl)
methyl)-3-methoxyphenoxy)ethoxy)-1,1-difluoropropyl)
phosphonic acid Compound 72

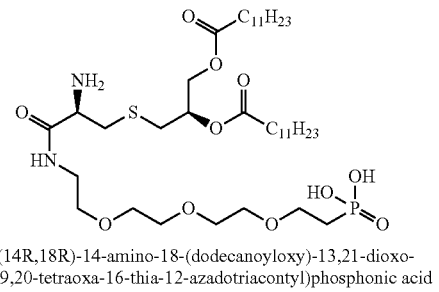

((14R,18R)-14-amino-18-(dodecanoyloxy)-13,21-dioxo-
3,6,9,20-tetraoxa-16-thia-12-azadotriacontyl)phosphonic acid Compound 73

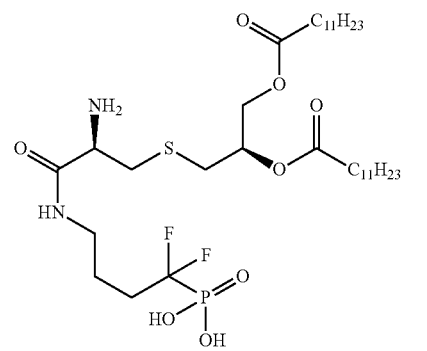

(4-((R)-2-amino-3-(((R)-2,3-bis(dodecanoyloxy)propyl)thio)
propanamido)-1,1-difluorobutyl)phosphonic acid;

Compound 74

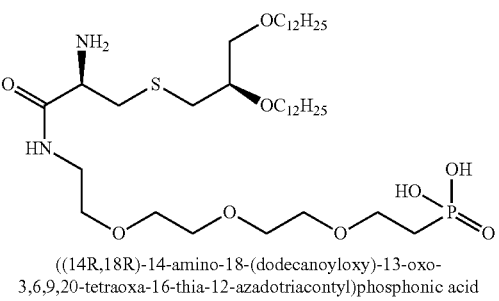

((14R,18R)-14-amino-18-(dodecanoyloxy)-13-oxo-
3,6,9,20-tetraoxa-16-thia-12-azadotriacontyl)phosphonic acid Compound 75

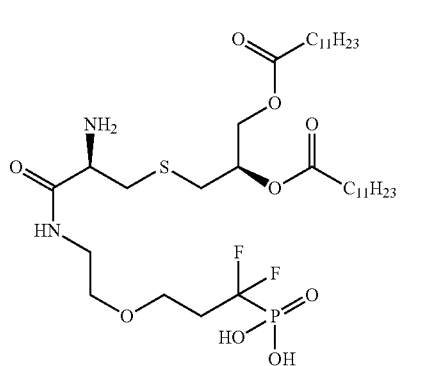

((9R,13R)-9-amino-13-(dodecanoyloxy)-1,1-difluoro-8,16-
dioxo-4,15-dioxa-11-thia-7-azaheptacosyl)phosphonic acid Compound 76

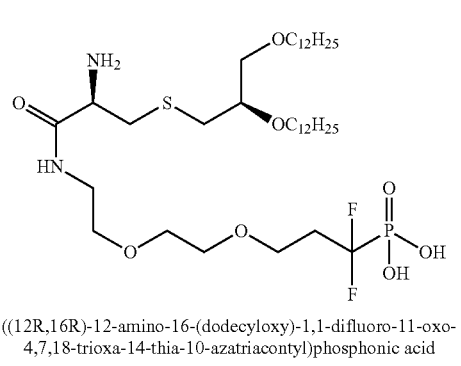

((12R,16R)-12-amino-16-(dodecyloxy)-1,1-difluoro-11-oxo-
4,7,18-trioxa-14-thia-10-azatriacontyl)phosphonic acid Compound 77

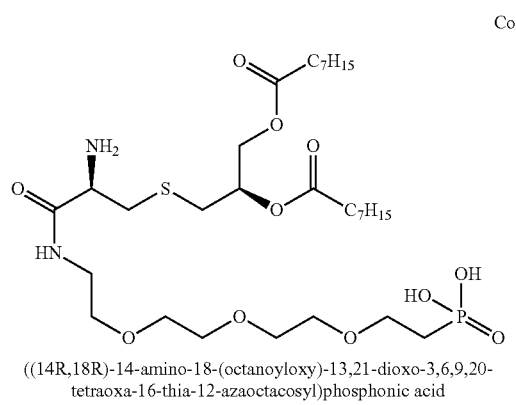

((14R,18R)-14-amino-18-(octanoyloxy)-13,21-dioxo-3,6,9,20-
tetraoxa-16-thia-12-azaoctacosyl)phosphonic acid Compound 78

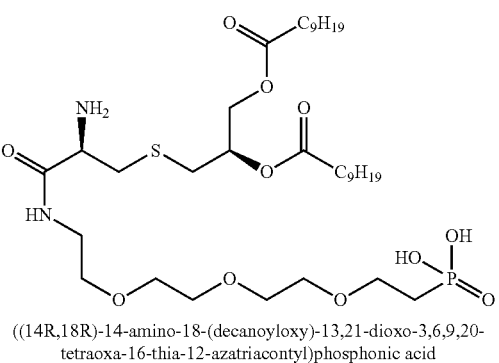

((14R,18R)-14-amino-18-(decanoyloxy)-13,21-dioxo-3,6,9,20-
tetraoxa-16-thia-12-azatriacontyl)phosphonic acid Compound 79

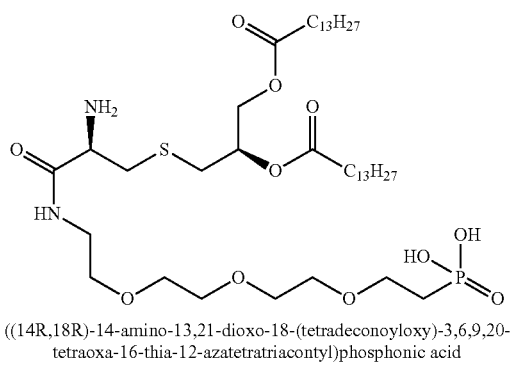

((14R,18R)-14-amino-13,21-dioxo-18-(tetradeconoyloxy)-3,6,9,20-tetraoxa-16-thia-12-azatetratriacontyl)phosphonic acid Compound 80

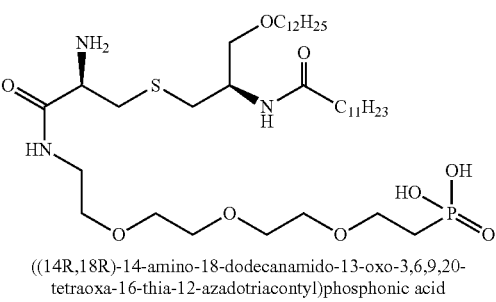

((14R,18R)-14-amino-18-dodecanamido-13-oxo-3,6,9,20-tetraoxa-16-thia-12-azadotriacontyl)phosphonic acid Compound 81

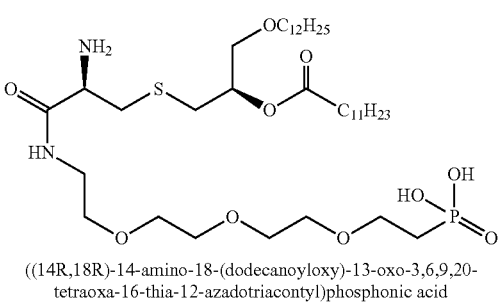

((14R,18R)-14-amino-18-(dodecanoyloxy)-13-oxo-3,6,9,20-tetraoxa-16-thia-12-azadotriacontyl)phosphonic acid Compound 82

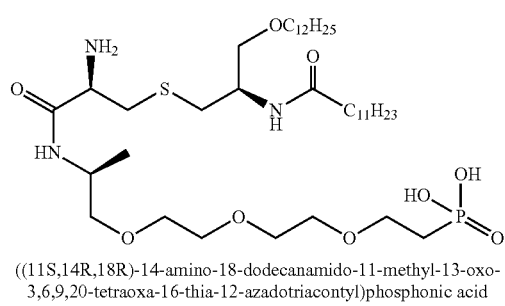

((11S,14R,18R)-14-amino-18-dodecanamido-11-methyl-13-oxo-3,6,9,20-tetraoxa-16-thia-12-azadotriacontyl)phosphonic acid Compound 83

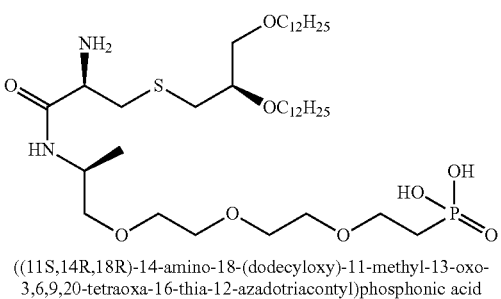

((11S,14R,18R)-14-amino-18-(dodecyloxy)-11-methyl-13-oxo-3,6,9,20-tetraoxa-16-thia-12-azadotriacontyl)phosphonic acid Compound 84

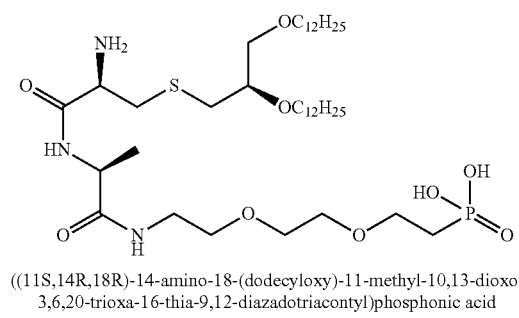

((11S,14R,18R)-14-amino-18-(dodecyloxy)-11-methyl-10,13-dioxo-3,6,20-trioxa-16-thia-9,12-diazadotriacontyl)phosphonic acid Compound 85

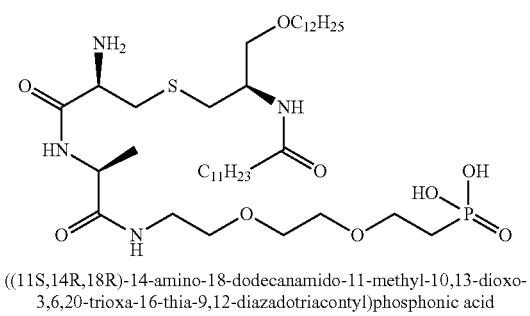

((11S,14R,18R)-14-amino-18-dodecanamido-11-methyl-10,13-dioxo-3,6,20-trioxa-16-thia-9,12-diazadotriacontyl)phosphonic acid Compound 86

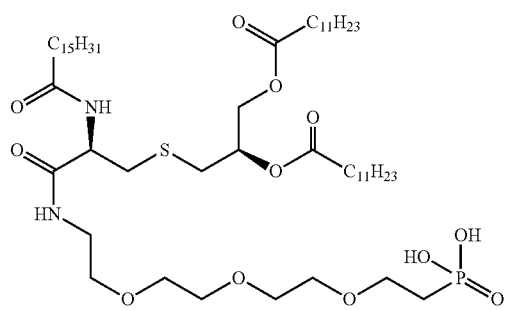

((14R,18R)-18-(dodecanoyloxy)-13,21-dioxo-14-palmitamido-3,6,9,20-tetraoxa-16-thia-12-azadotriacontyl)phosphonic acid Compound 87

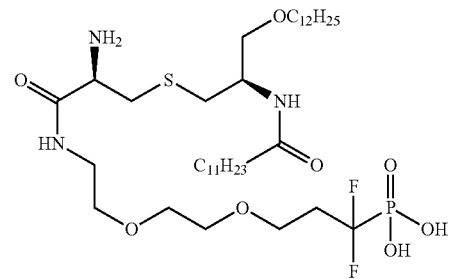

((12R,16R)-12-amino-16-dodecanamido-1,1-difluoro-11-oxo-4,7,18-trioxa-14-thia-10-azatriacontyl)phosphonic acid Compound 88

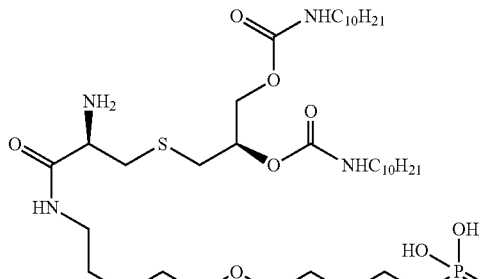

((14R,18R)-14-amino-18-((decylcarbamoyl)oxy)-13,21-dioxo-3,6,9,20-tetraoxa-16-thia-12,22-diazadotriacontyl)phosphonic acid Compound 89

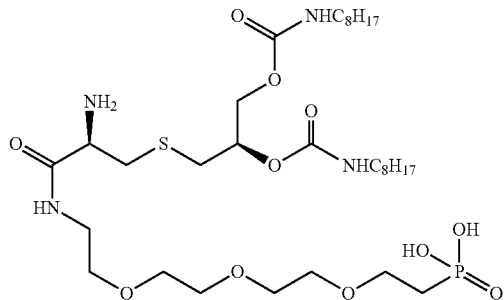

((14R,18R)-14-amino-18-((octylcarbamoyl)oxy)-13,21-dioxo-3,6,9,20-tetraoxa-16-thia-12,22-diazatriacontyl)phosphonic acid Compound 90

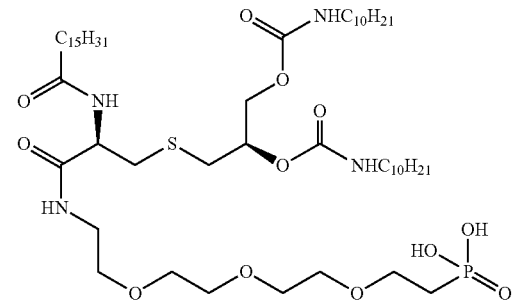

((14R,18R)-18-((decylcarbamoyl)oxy)-13,21-dioxo-14-palmitamido-3,6,9,20-tetraoxa-16-thia-12,22-diazadotriacontyl)phosphonic acid Compound 91

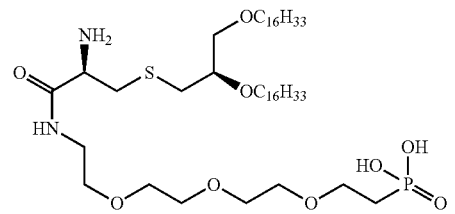

((14R,18R)-14-amino-18-(hexadecyloxy)-13-oxo-3,6,9,20-tetraoxa-16-thia-12-azahexatriacontyl)phosphonic acid Compound 92

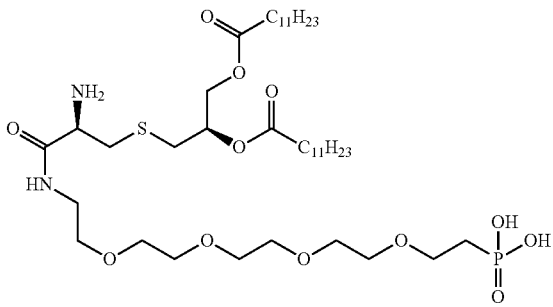

((17R,21R)-17-amino-21-(dodecanoyloxy)-16,24-dioxo-3,6,9,12,23-pentaoxa-19-thia-15-azapentatriacontyl)phosphonic acid Compound 93

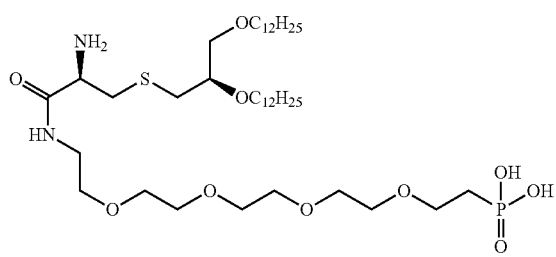

((17R,21R)-17-amino-21-(dodecyloxy)-16-oxo-3,6,9,12,23-pentaoxa-19-thia-15-azapentatriacontyl)phosphonic acid Compound 94

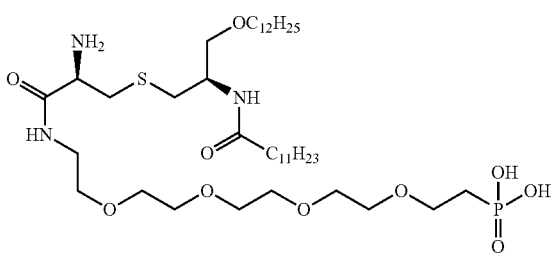

((17R,21R)-17-amino-21-dodecanamido-16-oxo-3,6,9,12,23-pentaoxa-19-thia-15-azapentatriacontyl)phosphonic acid Compound 95

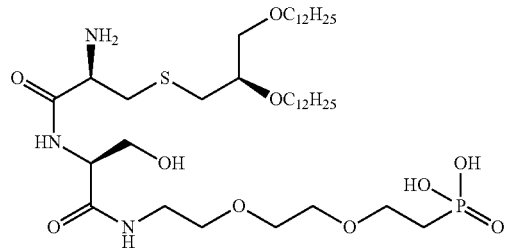

(((11S,14R,18R)-14-amino-18-(dodecyloxy)-11-(hydroxymethyl)-10,13-dioxo-3,6,20-trioxa-16-thia-9,12-diazadotriacontyl)phosphonic acid Compound 96

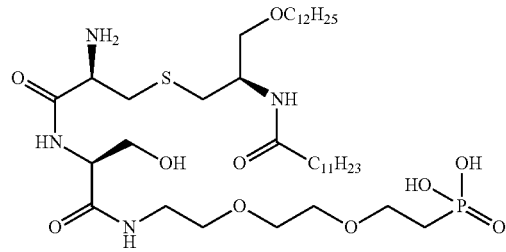

(((11S,14R,18R)-14-amino-18-dodecanamido-11-(hydroxymethyl)-10,13-dioxo-3,6,20-trioxa-16-thia-9,12-diazadotriacontyl)phosphonic acid Compound 97

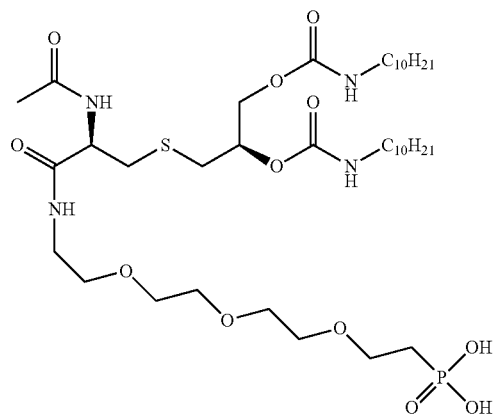

((14R,18R)-14-acetamido-18-((decylcarbamoyl)oxy)-13,21-dioxo-3,6,9,20-tetraoxa-16-thia-12,22-diazadotriacontyl)phosphonic acid Compound 98

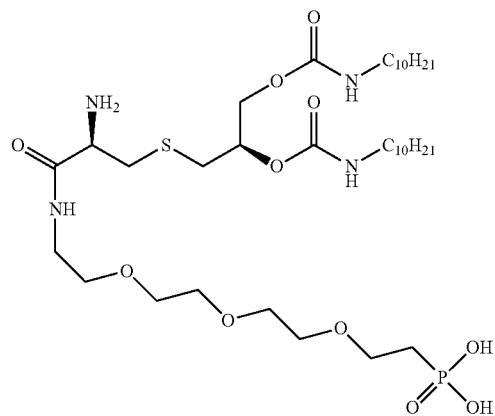

((14R,18R)-14-amino-18-((decylcarbamoyl)oxy)-13,21-dioxo-3,6,9,20-tetraoxa-16-thia-12,22-diazadotriacontyl)phosphonic acid Compound 99

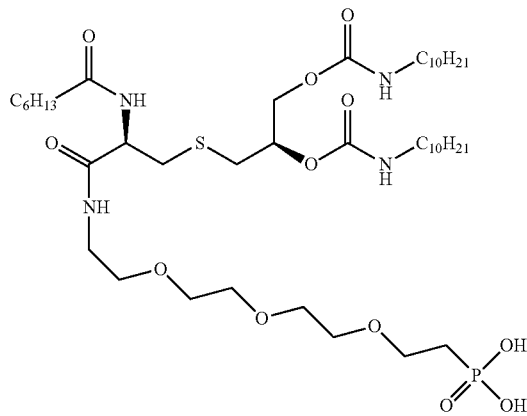

((14R,18R)-18-((decylcarbamoyl)oxy)-14-heptanamido-13,21-dioxo-3,6,9,20-tetraoxa-16-thia-12,22-diazadotriacontyl)phosphonic acid Compound 100

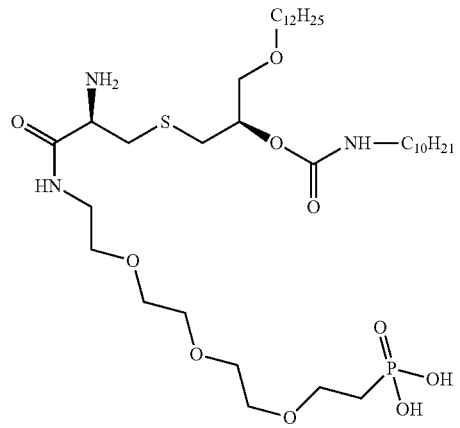

((14R,18R)-14-amino-18-((dodecyloxy)methyl)-13,20-dioxo-3,6,9,19-tetraoxa-16-thia-12,21-diazahentriacontyl)phosphonic acid

Compound 101

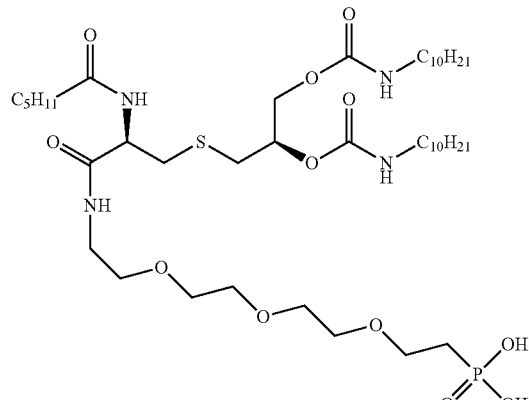

((14R,18R)-18-((decylcarbamoyl)oxy)-14-hexanamido-13,21-dioxo-3,6,9,20-tetraoxa-16-thia-12,22-diazadotriacontyl)phosphonic acid

Compound 102

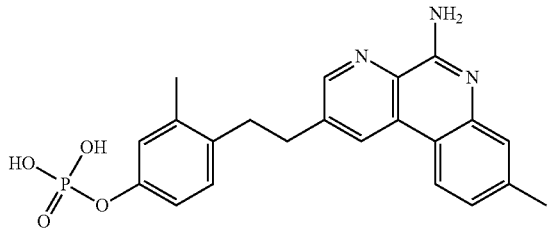

4-(2-(5-amino-8-methylbenzo[f][1,7]naphthyridin-2-yl)ethyl)-3-methylphenyl dihydrogen phosphate The invention also provides a composition comprising two or more of said compounds 1 to 62. The invention also provides a composition comprising two or more of said compounds 1 to 66. The invention also provides a composition comprising two or more of said compounds 1 to 102.

Compounds 1 to 15, 23 to 51, 60 to 62, 67 to 71, and 102 are phospho-modified TLR7 agonists which are useful with the invention.

Compounds 16 to 22, 63 to 66 and 72 to 101 are phospho-modified TLR2 agonists which are useful with the invention.

Compounds 52 to 59 are phospho-modified TLR8 agonists which are useful with the invention.

Other Biological Receptors

The invention is defined above by reference to TLR agonists, but it can be more widely applied to other SMIPS which do not act via TLRs. In particular, SMIPs which may be used with the invention may agonise C-type lectin receptors (CLRs) or CD1d rather than (or in addition to) a TLR. Thus the present disclosure includes the invention as described above with reference to TLR agonism, but wherein references to a TLR agonist (or similar) are replaced by reference either to a CLR agonist or to a CD1d agonist. Thus CLR or CD1d agonists can be modified to contain at least one adsorptive moiety to provide the ability to adsorb to insoluble metal salt adjuvants.

CLR agonists include, but are not limited to, trehalose-6,6'-dimycolate (TDM), its synthetic analog D-(+)-trehalose-6,6'-dibehenate (TDB), and other 6,6'-diesters of trehalose and fatty acids. These trehalose esters can readily be modified (e.g. as disclosed for the twenty-third aspect) to include an adsorptive group. The adsorptive group may be joined to the immunopotentiator via a linker group, as discussed above. The modified compound can adsorb to an insoluble metal salt. Thus the invention can be applied to trehalose esters and diacyl trehaloses which are CLR agonists. These agonists may have formula (T):

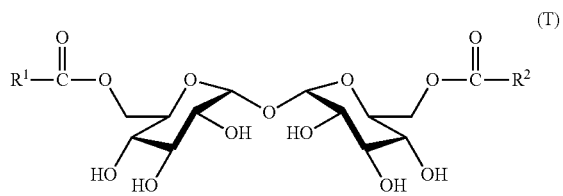

(T)

where $R^1C(O)$— and $R^2C(O)$— are the same or different and are acyl groups, provided that (i) one of the monosaccharide rings (ii) $R^1$ or (iii) $R^2$ includes an adsorptive moiety. Suitable acyl groups may be saturated or unsaturated. They may be selected from the acyl residues of a mycolic acid, a corynomycolic acid, a 2-tetradecyl-3-hydroxyoctadecanoic acid, a 2-eicosyl-3-hydroxytetracosanoic acid, a bourgeanic acid, a behenic acid, a palmitic acid, etc. Useful mycolic acids include alpha-, methoxy-, and keto-mycolic acids, in cis- and or trans-forms.

CD1d agonists include, but are not limited to, α-glycosylceramides [78-87] such as α-galactosylceramides. These can readily be modified (e.g. as disclosed for the twenty-third aspect) to include an adsorptive group. The adsorptive group may be joined to the immunopotentiator via a linker group, as discussed above. The modified compound can adsorb to an insoluble metal salt. Thus the invention can be applied to glycosylceramides which are CD1d agonists, including α-galactosylceramide, phytosphingosine-containing α-glycosylceramides, [(2S,3S,4R)-1-O-(α-D-galactopyranosyl)-2-(N-hexacosanoylamino)-1,3,4-octadecanetriol], OCH, KRN7000 CRONY-101, 3"-O-sulfo-galactosylceramide, etc., provided that the CD1d agonist includes an adsorptive group.

Chemical Groups

Unless specifically defined elsewhere, the chemical groups discussed herein have the following meaning when used in present specification:

The term "alkyl" includes saturated hydrocarbon residues including:

linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited, to $C_1$-methyl, $C_2$-ethyl, $C_3$-propyl and $C_4$-n-butyl.

branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkylene" refers to the divalent hydrocarbon radical derived from an alkyl group, and shall be construed in accordance with the definition above.

The term "alkenyl" includes monounsaturated hydrocarbon residues including:

linear groups of between 2 and 6 atoms ($C_2$-$C_6$). Examples of such alkenyl groups include, but are not limited to, $C_2$-vinyl, $C_3$-1-propenyl, $C_3$-allyl, $C_4$-2-butenyl branched groups of between 3 and 8 atoms ($C_3$-$C_8$). Examples of such alkenyl groups include, but are not limited to, $C_4$-2-methyl-2-propenyl and $C_6$-2,3-dimethyl-2-butenyl.

The term alkenylene refers to the divalent hydrocarbon radical derived from an alkenyl group, and shall be construed in accordance with the definition above.

The term "alkoxy" includes O-linked hydrocarbon residues including:

linear groups of between 1 and 6 atoms ($C_1$-$C_6$), or of between 1 and 4 atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 atoms ($C_3$-$C_6$) or of between 3 and 4 atoms ($C_3$-$C_4$). Examples of such alkoxy groups include, but are not limited to, $C_3$-iso-propoxy, and $C_4$-sec-butoxy and tert-butoxy.

Halo is selected from Cl, F, Br and I. Halo is preferably F.

The term "aryl" includes a single or fused aromatic ring system containing 6 or 10 carbon atoms; wherein, unless otherwise stated, each occurrence of aryl may be optionally substituted with up to 5 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined above. Typically, aryl will be optionally substituted with 1, 2 or 3 substituents. Optional substituents are selected from those stated above. Examples of suitable aryl groups include phenyl and naphthyl (each optionally substituted as stated above). Arylene refers the divalent radical derived from an aryl group, and shall be construed in accordance with the definition above.

The term "heteroaryl" includes a 5, 6, 9 or 10 membered mono- or bi-cyclic aromatic ring, containing 1 or 2 N atoms and, optionally, an $NR^{14}$ atom, or one $NR^{14}$ atom and an S or an O atom, or one S atom, or one O atom; wherein, unless otherwise stated, said heteroaryl may be optionally substituted with 1, 2 or 3 substituents independently selected from ($C_1$-$C_6$)alkyl, ($C_1$-$C_6$)alkoxy, OH, halo, CN, $COOR^{14}$, $CF_3$ and $NR^{14}R^{15}$; as defined below. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Heteroarylene refers the divalent radical derived from heteroaryl, and shall be construed in accordance with the definition above.

The term "heterocyclyl" is a C-linked or N-linked 3 to 10 membered non-aromatic, mono- or bi-cyclic ring, wherein said heterocycloalkyl ring contains, where possible, 1, 2 or 3 heteroatoms independently selected from N, $NR^{14}$, $S(O)_q$ and O; and said heterocycloalkyl ring optionally contains, where possible, 1 or 2 double bonds, and is optionally substituted on carbon with 1 or 2 substituents independently selected from ($C_1$-$C_6$)alkyl, ($C_1$-$C_6$)alkoxy, OH, CN, $CF_3$, halo, $COOR^{14}$, $NR^{14}R^{15}$ and aryl.

In the above definitions $R^{14}$ and $R^{15}$ are independently selected from H and ($C_1$-$C_6$)alkyl.

When a structural formula is defined with a substituent attached to the core of the molecule by an unspecified, or "floating" bond, for example, as for the group $P^3$ in the case of formula (C), this definition encompasses the cases where the unspecified substituent is attached to any of the atoms on the ring in which the floating bond is located, whilst complying with the allowable valence for that atom.

In the case of compounds of the invention which may exist in tautomeric forms (i.e. in keto or enol forms), for example the compounds of formula (C) or (H), reference to a particular compound optionally includes all such tautomeric forms.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encapsulopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a disclaimer is defined above, the disclaimed compounds should include at least one adsorptive moiety.

MODES FOR CARRYING OUT THE INVENTION

Phospho-Modified Benzonaphthyridines

Compound 'O', a useful TLR7 agonist, is prepared as disclosed in example 48 of reference 4:

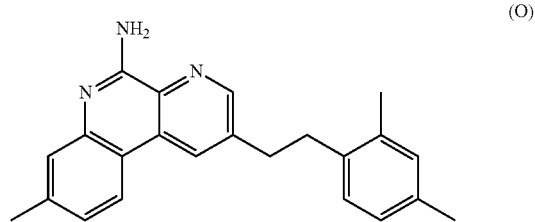

(O)

Various modifications to this 'parent' benzonaphthyridine compound are made to improve its physicochemical properties, and in particular to increase its solubility in water and to confer on it the ability to adsorb to an aluminium hydroxide adjuvant, thereby ensuring in vivo delivery in a controlled manner with prolonged persistence at the site of injection. With this intent, the compounds referred to above as Compounds 1-15 and 60-62 are synthesized as disclosed in reference 10 (see also reference 72).

Figure 12:
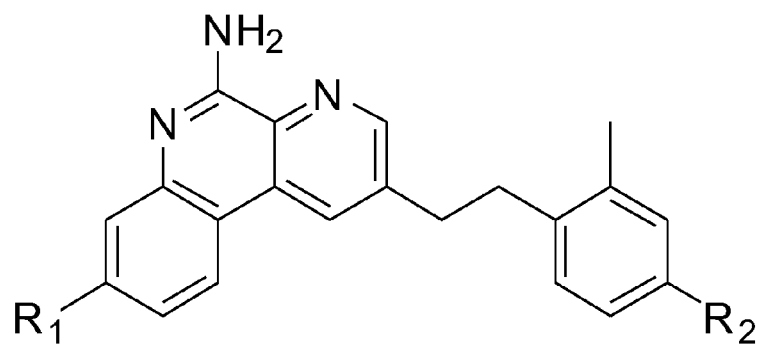
FIG. 12 shows structures of compounds 1, 2, 3, 4, 5 and 13.

Example compounds 1, 2, 3, 4, 5, and 13 (FIG. 12) include a phosphonate group attached to compound O's phenyl ring via ethylene glycol linkers. The phosphonate provides a group which could undergo ligand exchange with an aluminium salt whereas the ethylene glycol linkers increase water solubility of the compounds. Compounds 2, 3, 4 & 5 additionally include a carboxyl moiety which also serves to improve water solubility. The phosphonate in compounds 1, 3, 4 and 5 includes two electronegative fluoro substituents on the α carbon, aiming to improve solubility.

Example compound 102 includes a phosphate group attached to compound O's phenyl ring. The phosphate provides a group which could undergo ligand exchange with an aluminium salt. Compound 102 is synthesised as disclosed in reference 10.

Adsorption Studies—Aluminium Hydroxide

Adsorption of compounds to aluminium hydroxide (Al—H) is studied at various pH.

Compound 13 (0.5 mg/mL) is dissolved in 10 mM NaOH (pH 6.5 or pH 9) and added to aluminium hydroxide adjuvant (2 mg/mL) resulting in a 100 µg/dose formulation. The supernatant is evaluated with HPLC using a ballistic gradient (from 10% CH$_3$CN-0.1% TFA to 100% CH$_3$CN-0.1% TFA in 2.5 minutes) on a C18 (50 cm×4.6 mm) ACE column at 45° C. To evaluate the effect of supernatant temperature and incubation time on binding, the supernatant is evaluated at room temperature and at 37° C. after 1 hour, 5 hours and 24 hours. A control without aluminium hydroxide is also evaluated. HPLC chromatograms for compound 1 formulations with and without aluminium hydroxide, at either temperature, and at either pH, show that compound 1 is not present in the supernatant at any time point when aluminium hydroxide is present, suggesting it has adsorbed to the metal salt.

Compound 12 (1 mg/mL) is tested in the same way at pH 9. Compound 12 is also tested at pH 6.7 in 10 mM histidine buffer. Again, compound 10 is not present in the supernatant when aluminium hydroxide is included in the formulation, at either pH and either temperature.

An organic solvent extraction method is used to evaluate whether compound 13 is covalently bound to the aluminium hydroxide. The formulation is prepared as follows: 2 mg/ml aluminium hydroxide, 100 μg/dose compound 13, 10 mM histidine buffer; adjust pH to 9. A control formulation without aluminium hydroxide is also prepared. 1 ml of the formulation is mixed with 1 ml of $KH_2PO_4$ 1 M pH 9 (0.5M final conc, pH 9) and left in gentle agitation overnight at 37° C. If the compound adsorbs to the aluminium salt by ligand exchange then the free phosphate anions will displace it. Organic extraction is then performed: 1 ml of each sample is mixed with 1 ml of n-butanol and vortexed.

After the formation of 2 phases, the upper phase (butanol) is recovered, dried with $N_2$ and resuspended in MeOH/10 mM NaOH. HPLC analysis is run both for the formulation supernatants and for the butanol-extracted samples (C18 column; 0-100% B in 2 min; A=0.1% TFA in H2O; B=0.1% TFA in ACN). Increased quantities of compound 13 are observed in the supernatant of the formulation treated with $KH_2PO_4$, indicating displacement of compound 13 by the phosphate anions i.e. desorption.

Adsorption of compounds 1, 2, 3, 4, 5 (and also of further compounds 6, 67, 68 and 71 described below) in 10 mM histidine buffer, pH 6.5, is also assessed and quantified. These compounds are water-soluble at >1 mg/ml and adsorption to Al—H is as follows:

| Compound | 1 | 2 | 3 | 4 | 5 | 6 | 67 | 68 | 71 |
|---|---|---|---|---|---|---|---|---|---|
| % | 98.2% | 97.0% | 96.2% | 96.0% | 94.5% | 88% | 82% | 94% | 85% |

In contrast to the high proportion of adsorption seen with these phospho-modified compounds, 'parent' compound O fails to adsorb to the Al—H adjuvant.

Phospho compound 1 is intrinsically fluorescent. Confocal microscopy of the Al—H adjuvant (3 mg/ml) before and after mixing with compound 1 (0.25 mg/ml) visually shows that the phospho compound associates with particles of the insoluble metal salt. Flow cytometry with compound 2 shows similar results: compound O is seen as a separate population in the presence of Al—H, whereas compound 2 co-localizes with the Al—H.

A desorption protocol is used to further confirm binding of the phospho-compounds to Al—H. The compound/Al—H formulation (fluorescent) is treated with 0.5 M phosphate buffer and then washed with either water (for water soluble compounds) or butanol (for poorly water soluble compounds). The washed Al—H is then analyzed and, like Al—H before having been mixed with a phospho-compound, shows no fluorescence.

Stability studies show that the adsorbed compounds are stable for several weeks, both in terms of compound stability and adsorption. All of compounds 1, 2, 3, 4, 5 & 13 show at least 95% adsorption over at least a 3 week period. Continued study of compounds 2 and 5 show that they are stable for 6 weeks or more. Continued RP-HPLC studies of compound 2 with Al—H, even in the presence of the 5CVMB antigens (see below), showed that the antigens and the TLR7 agonist both remained stably adsorbed without degradation for at least 24 weeks in aqueous conditions at 4° C., or for at least 4 weeks at 37° C. Osmolarity and pH also remained within acceptable ranges over the storage period.

Figure 14:
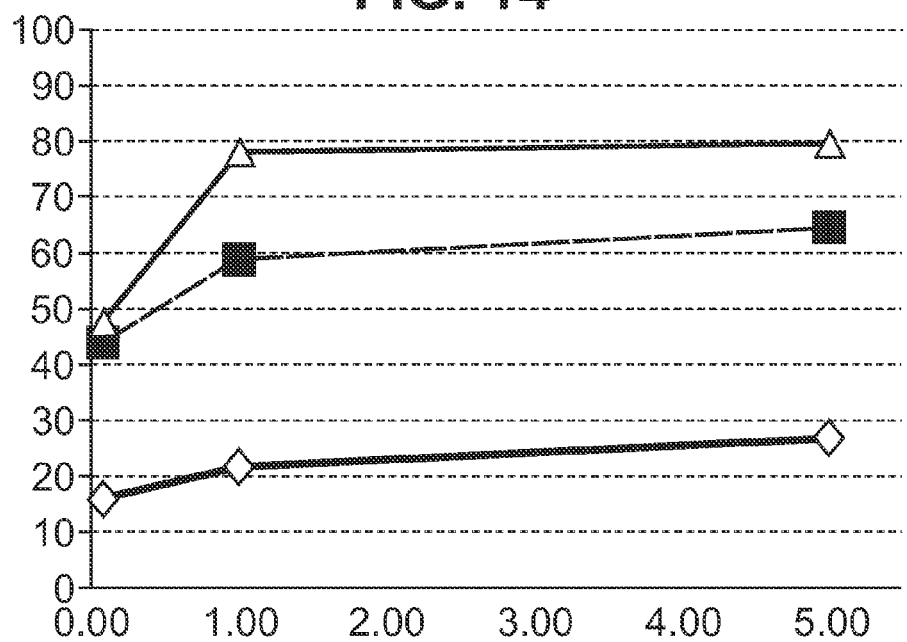
FIG. 14 shows the degree of desorption (%) of compound 1 over a period of 5 hours after treatment with potassium phosphate at 10 mM (♦), 100 mM (■) or 500 mM (▲).

FIG. 14 shows desorption of compound 1 stored at 100° C., pH 7, for up to 5 hours. Desorption begins quickly, with increasing levels of potassium phosphate (10 mM, 100 mM, 500 mM) leading to increased desorption (20%, 60%, 80%) after an hour, but not increasing much further after 5 hours. At 10 mM phosphate the compound remains >70% bound after 5 hours at 100° C., and >80% bound after 5 hours at 70° C.

Various buffer anions were tested for desorption of compound 1, using both intrinsic fluorescence and HPLC to follow the compound. As expected, $KH_2PO_4$ (0.5M, pH 9) was able to completely desorb compound 1 from Al—H. A slight reduction in binding (partial desorption) was seen with glutamate, ascorbate and citrate. In contrast, NaCl and Tris-HCl did not change the adsorption; nor did sodium sulfate or HEPES, or $KH_2PO_4$ at pH 7.

Compound 102 was tested for adsorption to Al—H. Method: 1. Compound 2 Solution: 2 mg of the compound was dissolved in 2 mL water to prepare 1 mg/mL solution. Briefly, 2 mL water was added to 2 mg of compound 2 and the suspension was sonicated for 10 min. 1N NaOH was added in 2 μL increments until solution went clear; a total of 12 μL of 1N NaOH was added. Final pH of solution was determined using a pH strip as ~10. Solution was further sonicated for 5 min and maintained at room temperature. 2. Alum Adsorption: Alum adsorption samples were prepared with 3 mg/mL aluminum hydroxide and 0.5 mg/mL of compound 2 without a buffer. a) Experimental: 303 μL of water+197 μL of aluminum hydroxide (15.22 mg/mL, lot 1050)+500 μL of 1 mg/mL compound 2, rock at room temperature overnight. b) Control: 500 μL water+500 μL of 1 mg/mL compound 2, rock at room temperature overnight. Results: 1) Visual: Upon addition of compound 2 for experimental vial, the suspension became whitish and cloudy, similar to that observed with phosphonates and fluorophosphonates (Compounds 2 and 5). 2) RP-HPLC: Adsorption and recovery were determined by RP-HPLC. Standards used were 400, 40 and 4 μg/mL; Slope was Area=18000× Concentration (μg/mL). a) Adsorption Efficiency: 10× diluted supernatant was analyzed. i) Experimental: Area=133708; Concentration (1×)=74.3 μg/mL; Efficiency=85.1%. ii) Control: Area=923681; Concentration (1×)=513.2 μg/mL; Efficiency=−2.6% (equivalent to 0%). b) Recovery: 10× diluted supernatant after boiling with 0.5M $Na_2HPO_4$ (pH9). i) Experimental: Area=931578; Concentration (1×)=517.5 μg/mL; Recovery=103.5%. ii) Control: Area=870826; Concentration (1×)=483.8 μg/mL; Recovery=96.8%. Conclusions: Phosphate-containing TLR7 modulator compound 102 adsorbs to aluminum hydroxide at >80% adsorption efficiency to deliver 50 μg dose in 100 μL injection volume.

Zeta Potential

The surface charge of Al—H particles (2 mg/ml) was measured in the absence of compound 2, or with increasing concentrations from 10-200 µg. The zeta potential measurement is based on the scattering of light of particulate systems. Formulations were prepared in 10 mM histidine buffer with NaCl, then diluted 1:10 in formulation buffer. Results were as follows:

| Compound 2 (µg) | ζ potential (mV) | % adsorption |
|---|---|---|
| 0 | +20 ± 2 | — |
| 10 | +23.5 ± 0.6 | 100 |
| 25 | +17 ± 1 | 100 |
| 50 | +10.6 ± 0.7 | 100 |
| 100 | −11.5 ± 0.8 | 100 |
| 150 | −28.9 ± 0.1 | 99 |
| 200 | −41 ± 2 | 98.8 |

Thus the net charge on the Al—H particles decreases as the SMIP is added, inverting polarity between 50 and 100 µg of SMIP. This shows that the SMIP is associating with the Al—H particles and modifies the aluminium salt's surface charge.

A net negative charge with 100 µg of SMIP does not exclude the possibility that the Al—H surface has regions with a partial positive charge. Such regions may be available for antigen adsorption by charge-based mechanisms.

Adsorption Studies—Aluminium Phosphate

Adsorption of compounds 1, 2 and 5 to an aluminium phosphate (Al—P) adjuvant is also studied. The Al—P adjuvant is chemically a hydroxyphosphate salt with a $PO_4/Al$ molar ratio of about 0.9 and a PZC about 5.7. The adjuvant is tested in 'plain' form or after pre-treatment with increasing concentrations of phosphate buffer (10 mM, 50 mM, 100 mM, 250 mM and 500 mM) in an attempt to saturate adsorptive sites on the adjuvant. Incubation was for 8 hours in 10 mM histidine buffer with 0.4 mg/ml of the compound and 3 mg/ml Al—P.

Results are as follows, showing % adsorption for two experiments per compound:

| | Pre-treatment with phosphate buffer (mM) | | | | | |
|---|---|---|---|---|---|---|
| | 0 | 10 | 50 | 100 | 250 | 500 |
| Cmpd 1 | 91.6 | 84.2 | 21.4 | 10.1 | 17.1 | 14.6 |
| Cmpd 1 | | 85.3 | 8.7 | 10.9 | 14.5 | 18.2 |
| Cmpd 2 | 97.4 | 92.3 | 81.6 | 61.6 | 51.9 | 67.5 |
| Cmpd 2 | | 94.0 | 81.5 | 59.2 | 5.2.0 | 62.2 |
| Cmpd 5 | 60 | 0.4 | 5.9 | 0.0 | 1.8 | 0.0 |
| Cmpd 5 | | 0.0 | 2.4 | 0.0 | 2.0 | 0.0 |

Thus compounds 2 and 5 adsorb to Al—P with good efficiency (>90%) whereas compound 5 adsorbs at lower efficiency (60%). Pre-treatment of Al—P with phosphate solution inhibits adsorption of all compounds, and the degree of adsorption is dependent on the concentration of phosphate in the pre-treatment solution. For compound 5 a 10 mM Pi solution is enough to inhibit completely adsorption, whereas for compound 1a 50 mM solution lowers the adsorption to a 20% and for compound 2 a 100 mM solution lowers the adsorption to ~60%.

Separate experiments with compound 1 showed that pre-treatment of an aluminium phosphate adjuvant with 10 mM potassium phosphate reduced adsorption from 79.8% to 23.5%, and that pre-treatment with 50 mM or 100 mM completely inhibited adsorption.

Adsorption Studies—Calcium Phosphate

Adsorption of compound 2 to a commercially-available calcium phosphate adjuvant was studied at pH 6.4, without histidine buffer. Two formulations are prepared, both with 1.12 mg/ml $Ca^{++}$ but with either 0.25 mg/mL or 0.125 mg/ml compound 2. Adsorption was around 90% for both formulations.

Autoclaving

Figure 22:
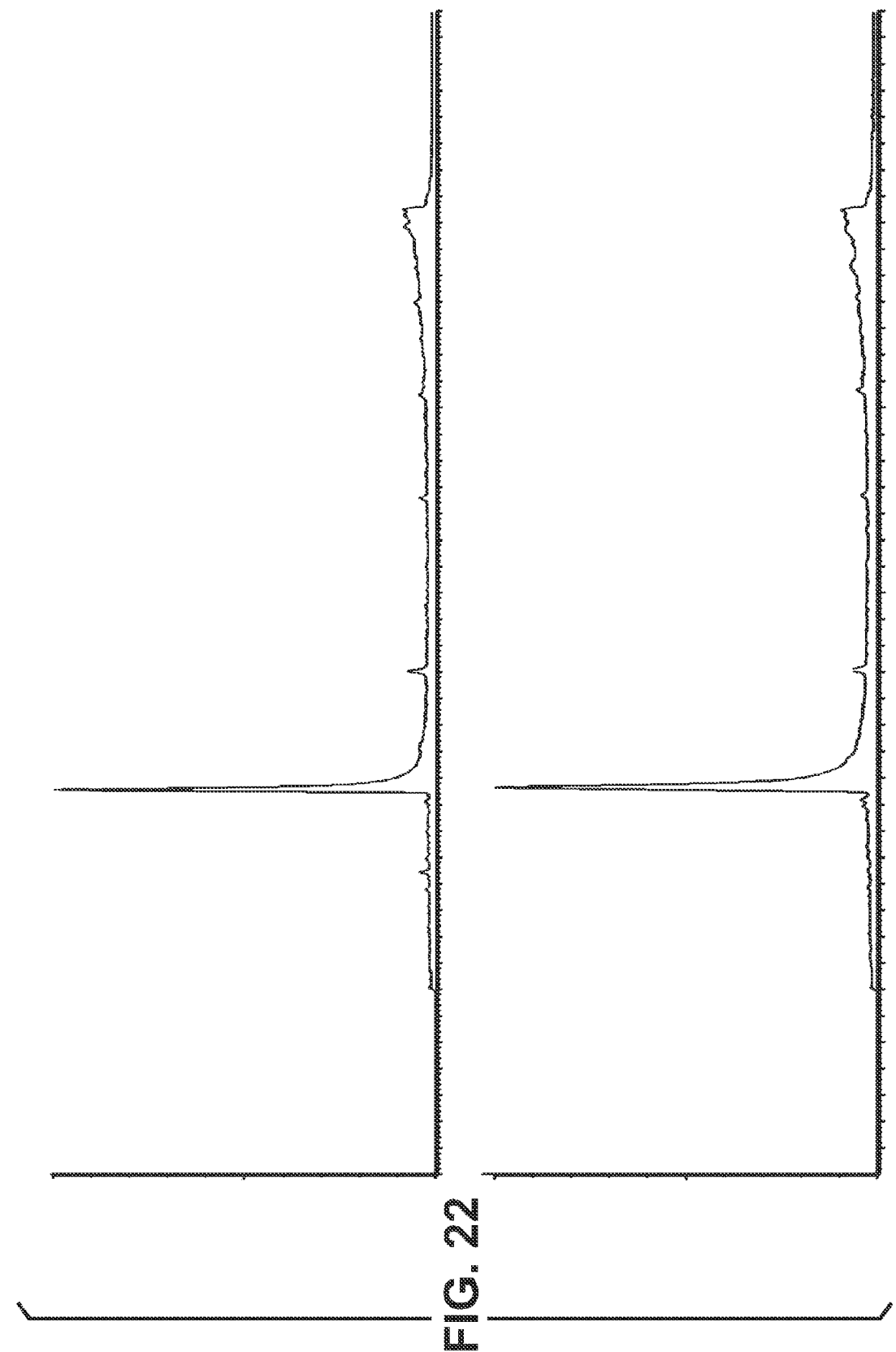
FIG. 22 shows chromatograms of Al—H/compound 2 before and after autoclaving.
Figure 23A:
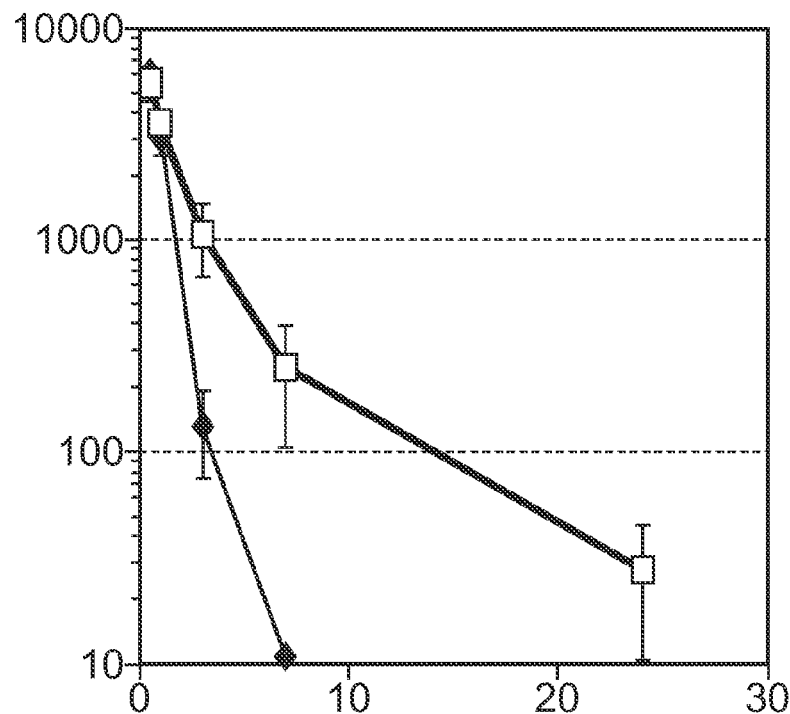
FIG. 23 shows serum levels (nM) over time (hours on X-axis) of compounds (A) 6 (B) 67 (C) 68 and (D) 71 after intramuscular injection (100 µg).
Figure 23B:
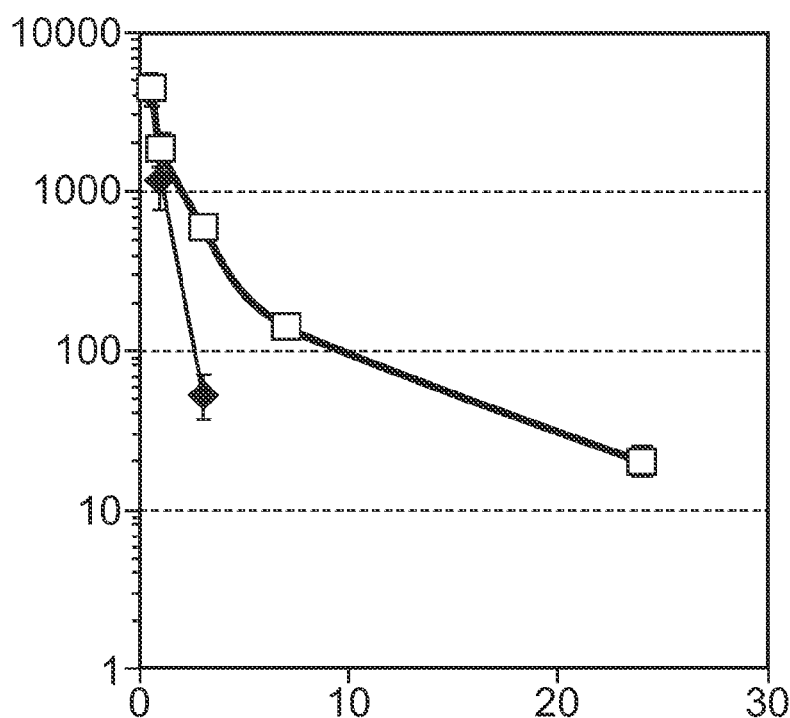
Figure 23C:
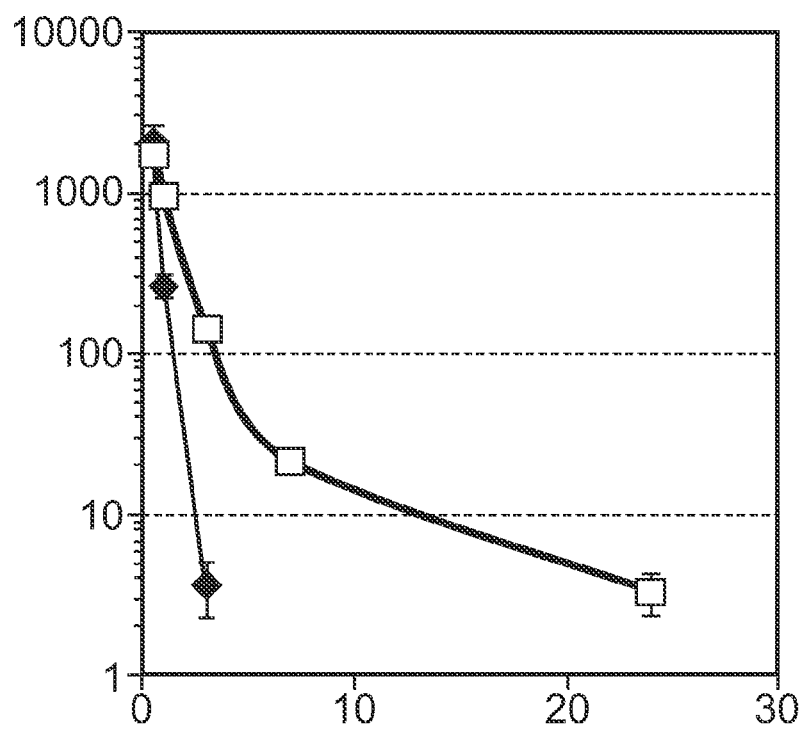
Figure 23D:
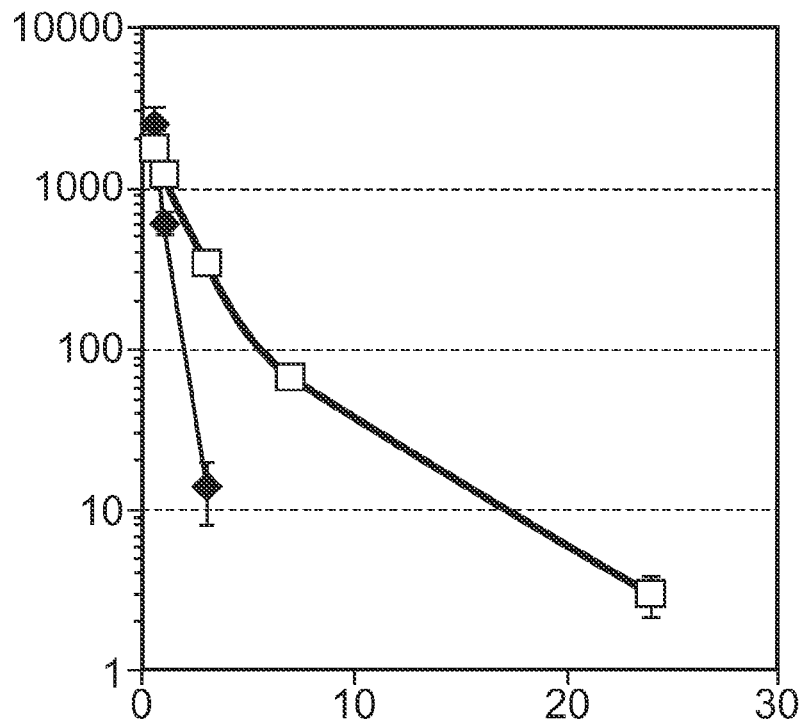

Compound 2 was adsorbed to Al—H and was analysed by HPLC before and after autoclaving. FIG. 22 shows that there is no change in the chromatographic profile. Mass spectrometry was also used and there was also no change in MS peaks in pre- and post-autoclaved material. Thus the SMIPs can be sterilised by autoclaving even when adsorbed.

Formula (C)—Adenine Compounds

The following phospho-compound is synthesized, based on the parent adenine compounds disclosed in references 3, 11-17, 21 & 23-25 (in particular, references 3 & 24):

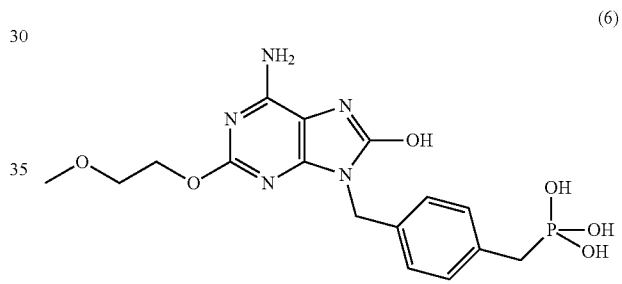

(6)

Compound 6 can be synthesized according to according to the scheme shown below, the reference numerals referring to the compounds shown in the scheme below, and not relating to the compound numbering established elsewhere in this application. The compound identified with reference numeral 29 in the scheme below is Compound 6 of the invention.

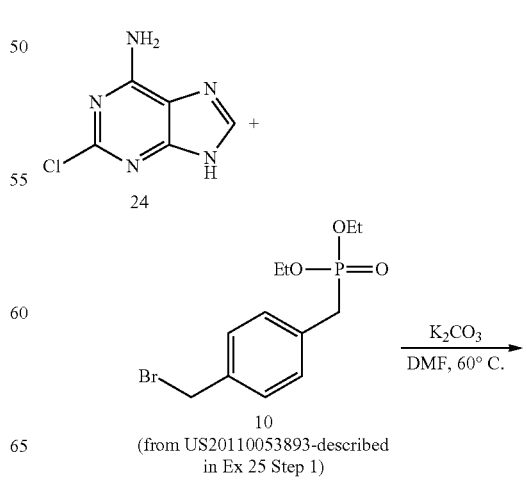

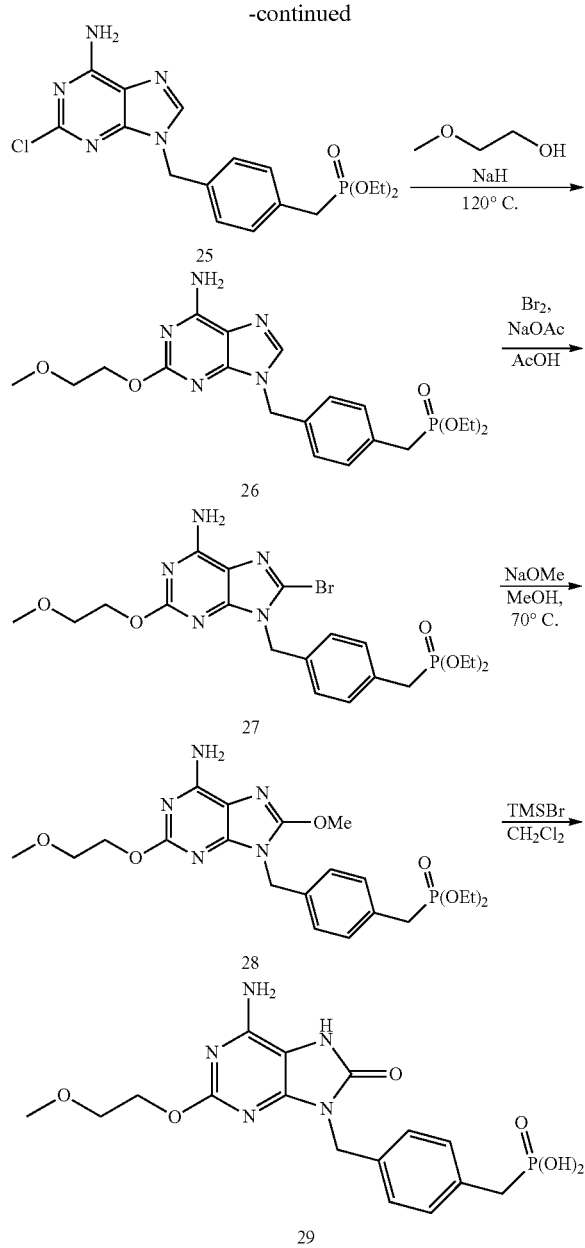

The reaction mixture was then heated to 60° C. for 5 h. At this point the reaction mixture was allowed to cool to room temperature and the volatiles were removed in vacuo. The resulting residue was purified by a COMBIFLASH™ system (ISCO) using a gradient of 0-5% MeOH/DCM to provide the title compound (18%) as a solid.

Step 2: diethyl 4-((6-amino-2-(2-methoxyethoxy)-9H-purin-9-yl)methyl)benzylphosphonate To a solution of diethyl 4-((6-amino-2-chloro-9H-purin-9-yl)methyl)benzylphosphonate (1 equiv.) in 2-methoxyethanol (0.10 M) was added sodium hydride (1.3 equiv.). The reaction mixture was then heated to 120° C. for 18 h. At this point the reaction mixture was allowed to cool to room temperature. The mixture was then diluted with water and EtOAc. This mixture was transferred to a separatory funnel and washed with water three times. The organic layer was then separated, dried over anhydrous $Na_2SO_4$ and the volatiles were removed in vacuo. The resulting residue was purified by a COMBIFLASH™ system using a gradient of 0-10% MeOH/DCM to provide the title compound in quantitative yield as a solid.

Step 3: diethyl 4-((6-amino-8-bromo-2-(2-methoxyethoxy)-9H-purin-9-yl)methyl)benzylphosphonate To a solution of diethyl 4-((6-amino-2-(2-methoxyethoxy)-9H-purin-9-yl)methyl)benzylphosphonate (1 equiv.) in acetic acid (0.20 M) was added sodium acetate (15 equiv.) and bromine (13 equiv.). The reaction mixture was then allowed to stir at room temperature for 18 h. At this point the reaction was quenched by the addition of sodium thiosulfate. The mixture was then diluted with water and DCM. This mixture was transferred to a separatory funnel and washed with DCM three times. The combined organic layers were then dried over anhydrous $Na_2SO_4$ and the volatiles were removed in vacuo. The resulting residue was purified by a COMBIFLASH™ system using a gradient of 0-5% MeOH/DCM to provide the title compound (14%) as a solid.

Step 4: diethyl 4-((6-amino-8-methoxy-2-(2-methoxyethoxy)-9H-purin-9-yl)methyl)benzylphosphonate To a solution of diethyl 4-((6-amino-8-bromo-2-(2-methoxyethoxy)-9H-purin-9-yl)methyl)benzylphosphonate in methanol (0.10 M) was added sodium methoxide (20 equiv.). The reaction mixture was then allowed to stir at 70° C. for 18 h. At this point the reaction mixture was allowed to cool to room temperature and then quenched by the addition of ammonium chloride. The mixture was then diluted with DCM, transferred to a separatory funnel and washed with DCM three times. The combined organic layers were then dried over anhydrous $Na_2SO_4$ and the volatiles were removed in vacuo. The resulting solid compound (38%) was carried onto the next step without further purification.

Step 5: (4-((6-amino-2-(2-methoxyethoxy)-8-oxo-7H-purin-9(8H)-yl)methyl)benzyl)phosphonic acid To a solution of diethyl 4-((6-amino-8-methoxy-2-(2-methoxyethoxy)-9H-purin-9-yl)methyl)benzylphosphonate (1 equiv.) in $CH_2Cl_2$ (0.10 M) at 0° C. was slowly added trimethylsilyl bromide (10 equiv.). After 1 h the ice-bath was removed and the reaction mixture was allowed to stir at 22° C. for 2 h. At this point the volatiles were removed in vacuo and With reference to the above scheme, alkylation of commercially available adenine 24 with benzyl bromide 10 (described in ref. 88, Ex 25 Step 1) provides intermediate 25. The aryl chloride of 25 is then substituted with 2-methoxyethanol to provide intermediate 26. Bromination of 26 then furnishes intermediate 27. Treatment of 27 with sodium methoxide then provides 28. Intermediate 28 is then hydrolyzed with bromotrimethyl silane to deliver phosphonic acid 29.

The experimental details of the above synthesis of Compound 6 are as follows.

Step 1: diethyl 4-((6-amino-2-chloro-9H-purin-9-yl)methyl)benzylphosphonate

To a solution of commercially available 2-chloro-9H-purin-6-amine (1 equiv.) in DMF (0.50 M) was added potassium carbonate (1.2 equiv.) and diethyl 4-(bromomethyl)benzylphosphonate (1 equiv.) (described in ref. 88, Ex 25 Step 1).

the resulting residue was purified by Reverse Phase-HPLC using a 20-90% 0.5 mM NH$_4$OAc (in MeCN) to 10 mM NH$_4$OAc (in water) gradient to deliver the title compound (29%) as a solid.

$^1$H NMR (Dimethylsulfoxide-d6): δ 7.16-7.11 (br, 4H), 6.58 (br, 2H), 4.77 (s, 2H), 4.25 (t, 2H, J=4.0 Hz), 3.58 (t, 2H, J=4.0 Hz), 3.27 (s, 3H), 2.73 (s, 1H), 2.67 (s, 1H). LRMS [M+H]=410.1

The activity of this compound is assessed in an assay using HEK293 cells which are stably transfected with human TLR7 and an NF-κB-driven luciferase reporter vector (pNifty-Luciferase). As a control assay, normal HEK293 transfected with pNifty-Luc are used. Cells are cultured in DMEM supplemented with 2 mM L-glutamine, 10% heart inactivated FBS, 1% penicillin and streptomycin, 2 μg/ml puromycin and 5 μg/ml of blasticidin. Bright-Glo™ Luciferase assay buffer and substrate are supplied by Promega. Cells are plated at 25,000 cells/well in 384-well plates in a final volume of 50 μl of media. Cells are allowed to adhere to the plates after overnight (18 hours) culture at 37° C. and 5% CO$_2$. Serially-diluted experimental and positive control compounds are then dispensed to each well and incubated for 7 hours at 37° C. and 5% CO$_2$. Cells stimulated with DMSO alone serve as negative controls. After the incubation, 30 μl of the pre-mix assay buffer and substrate buffer are added to each well according to manufacturer's instructions. The luminescence signal is read on a CLIPR machine with an integration time of 20 seconds per plate. Dose response curves are generated for each compound and EC$_{50}$ values were determined as the concentration that gives 50% of the maximal signal. EC$_{50}$ values are also compared to the activity of resiquimod (set to 100%).

Compound 6 shows an EC$_{50}$ of 0.41 μM or 93%. In splenocytes it shows an EC$_{50}$ of 0.98 μM (210%). In human PBMCs it shows an EC$_5$=of 1.0 (35%). It is soluble in histidine buffer at pH 6.8.

Formula (C)—Deazapurine Compounds

The following phospho-compound 67 is synthesized (a deazapurine analog of adenine compound 6), based on the parent deazapurine compounds disclosed in references 18-20:

(67)

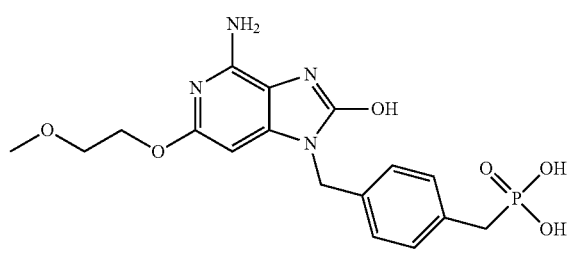

Compound 67 can be synthesized according to according to the scheme shown below, the reference numerals referring to the compounds shown in the scheme below, and not relating to the compound numbering established elsewhere in this application. The compound identified with reference numeral 16 in the scheme below is Compound 67 of the invention.

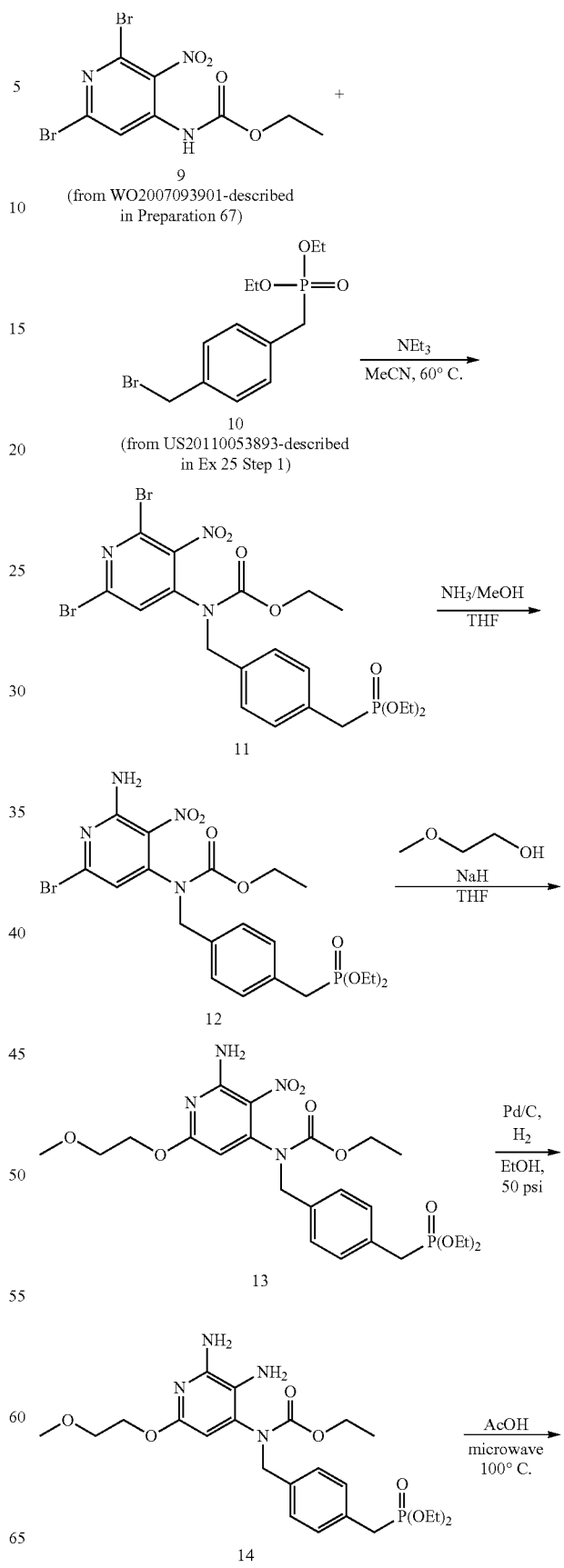

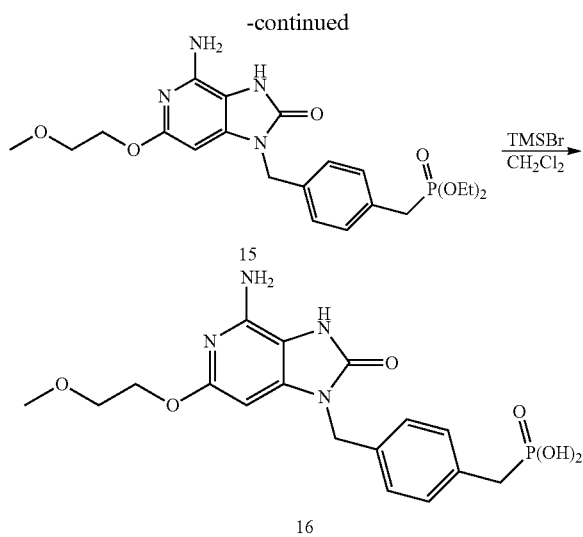

With reference to the above scheme, alkylation of pyridine 9 (described in ref. 18, Preparation 67) with benzyl bromide 10 (described in ref. 88, Ex 25 Step 1) furnishes intermediate 11. Amination of 11 with ammonia then delivers pyridine 12. The aryl bromide of 12 is then substituted with 2-methoxyethanol to provide intermediate 13. Hydrogenation of 13 then furnishes diamine 14. Treatment of 14 with acetic acid under microwave conditions then delivers deazapurine 15. Intermediate 15 is then hydrolyzed with bromotrimethyl silane to deliver phosphonic acid 16.

The experimental details of the above synthesis of Compound 67 are as follows.

Step 1: ethyl (2,6-dibromo-3-nitropyridin-4-yl)(4-((diethoxyphosphoryl)methyl)benzyl)carbamate To a solution of ethyl (2,6-dibromo-3-nitropyridin-4-yl) carbamate (1 equiv.) (described in ref. 18, Preparation 67) in acetonitrile (0.40 M) was added triethyl amine (1.5 equiv.) and diethyl 4-(bromomethyl)benzylphosphonate (1.3 equiv.) (described in ref. 88, Ex 25 Step 1). The reaction mixture was then heated to 60° C. for 18 h. At this point the reaction mixture was allowed to cool to room temperature and the volatiles were removed in vacuo. The resulting residue was purified by a COMBIFLASH™ system using a gradient of 0-5% MeOH/DCM to provide the title compound (38%) as a solid.

Step 2: ethyl (2-amino-6-bromo-3-nitropyridin-4-yl)(4-((diethoxyphosphoryl)methyl)benzyl)carbamate To a solution of ethyl (2,6-dibromo-3-nitropyridin-4-yl)(4-((diethoxyphosphoryl)methyl)benzyl)carbamate (1 equiv.) in THF (0.40 M) was added a 7 M solution of ammonia in methanol (5 equiv.). The reaction mixture was then allowed to stir at room temperature for 48 h. At this point the volatiles were removed in vacuo. The resulting residue was purified by a COMBIFLASH™ system using a gradient of 0-5% MeOH/DCM to provide the title compound (68%) as a solid.

Step 3: ethyl (2-amino-6-(2-methoxyethoxy)-3-nitropyridin-4-yl)(4-((diethoxyphosphoryl)methyl)benzyl)carbamate To a solution of ethyl (2-amino-6-bromo-3-nitropyridin-4-yl)(4-((diethoxyphosphoryl)methyl)benzyl)carbamate (1 equiv.) in THF (0.30 M) was added sodium hydride (5 equiv.) in a solution of 2-methoxyethanol (0.50 M). The reaction mixture was allowed to stir at room temperature for 2 h. At this point the volatiles were removed in vacuo. The resulting residue was purified by a COMBIFLASH™ system using a gradient of 0-5% MeOH/DCM to provide the title compound (68%) as a solid.

Step 4: ethyl (2,3-diamino-6-(2-methoxyethoxy)pyridin-4-yl)(4-((diethoxyphosphoryl)methyl)benzyl)carbamate To a solution of ethyl (2-amino-6-(2-methoxyethoxy)-3-nitropyridin-4-yl)(4-((diethoxyphosphoryl)methyl)benzyl) carbamate (1 equiv.) in EtOH (0.05 M) was added 10% Pd/C (50% equiv. by weight) in a Paar Shaker Flask. The reaction mixture was placed in a Paar Shaker at 55 psi for 4 h. At this point the reaction mixture was passed through a pad of Celite, washing with a 2:1 mixture of $CHCl_3$:MeOH. The combined organic layers were dried over anhydrous $Na_2SO_4$ and the volatiles were removed in vacuo. The resulting residue was used in the next step without further purification.

Step 5: diethyl 4-((4-amino-6-(2-methoxyethoxy)-2-oxo-2,3-dihydro-1H-imidazo[4,5-c]pyridin-1-yl)methyl)benzylphosphonate A solution of ethyl (2,3-diamino-6-(2-methoxyethoxy)pyridin-4-yl)(4-((diethoxyphosphoryl)methyl)benzyl)carbamate (1 equiv.) in AcOH (0.15 M) was heated in a microwave at 100° C. for 5 min. At this point the volatiles were removed in vacuo. The resulting residue was purified by a COMBIFLASH™ system using a gradient of 0-10% MeOH/DCM to provide the title compound (63% over two steps) as a solid.

Step 6: (4-((4-amino-6-(2-methoxyethoxy)-2-oxo-2,3-dihydro-1H-imidazo[4,5-c]pyridin-1-yl)methyl) benzyl)phosphonic acid To a solution of diethyl 4-((4-amino-6-(2-methoxyethoxy)-2-oxo-2,3-dihydro-1H-imidazo[4,5-c]pyridin-1-yl) methyl)benzylphosphonate (1 equiv.) in $CH_2Cl_2$ (0.10 M) at 0° C. was slowly added trimethylsilyl bromide (10 equiv.). After 1 h the ice-bath was removed and the reaction mixture was allowed to stir at 22° C. for 18 h. At this point the volatiles were removed in vacuo and the resulting residue was purified by Reverse Phase-HPLC using a 20-90% 0.5 mM $NH_4OAc$ (in MeCN) to 10 mM $NH_4OAc$ (in water) gradient to deliver the title compound (41%) as a solid.

$^1$H NMR (Dimethylsulfoxide-d6): δ 7.09-7.05 (br, 4H), 5.79 (s, 1H), 5.63 (br, 2H), 4.78 (s, 2H), 4.17 (t, 2H, J=4.8 Hz), 3.55 (t, 2H, J=4.8 Hz), 3.23 (s, 3H), 2.71 (s, 1H), 2.66 (s, 1H). LRMS [M+H]=409.1

Compound 67 shows an $EC_{50}$ of 6.5 µM or 103% in HEK293 cells. In splenocytes it shows an $EC_{50}$ of 9.3 µM (142%). In human PBMCs it shows an $EC_5$=of 0.8 (59%). It is soluble in histidine buffer at pH 6.8.

Formula (D)

The following phospho-compound is synthesized, based on the parent substituted imidazoquinoline compounds disclosed in references 2 & 22:

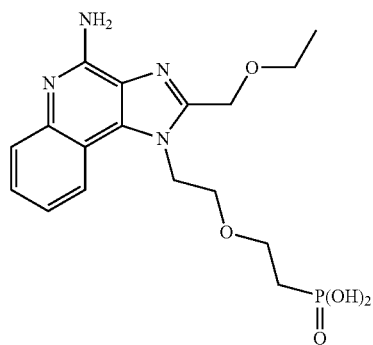

(7)

Compound 7 has a $EC_{50}$ of 66 μM (55%) in the HEK293 assay disclosed above but is inactive in splenocytes and hPBMCs. It is insoluble in histidine buffer at pH 6.8.

Modified forms of compound 7, with longer ethylene glycol linkers, are also prepared (compounds 37 and 68). Compound 68 has a $EC_{50}$ of 28 μM (75%) in HEK293 cells but, again, is inactive in splenocytes and hPBMCs. Unlike compound (7) it is soluble in histidine buffer at pH 6.8.

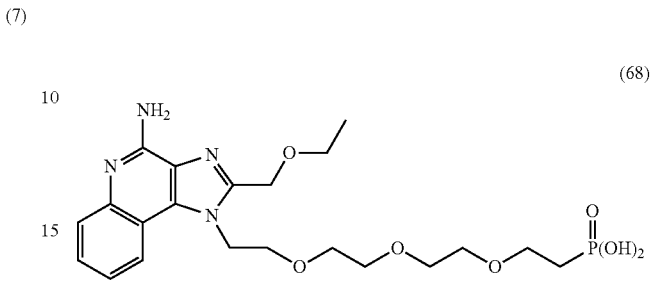

(68)

Compound 68 can be synthesized according to according to the scheme shown below, the reference numerals referring to the compounds shown in the scheme below, and not relating to the compound numbering established elsewhere in this application. The compound identified with reference numeral 23 in the scheme below is Compound 68 of the invention.

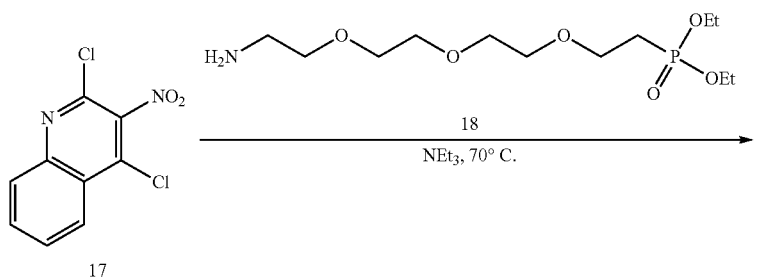

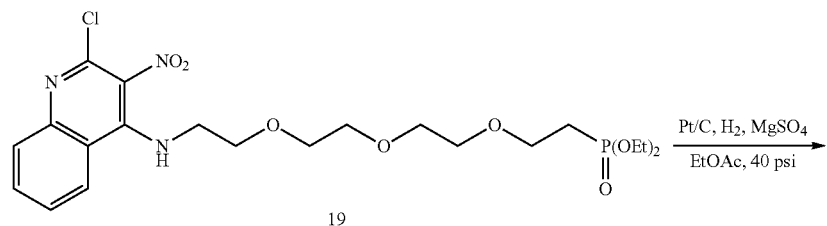

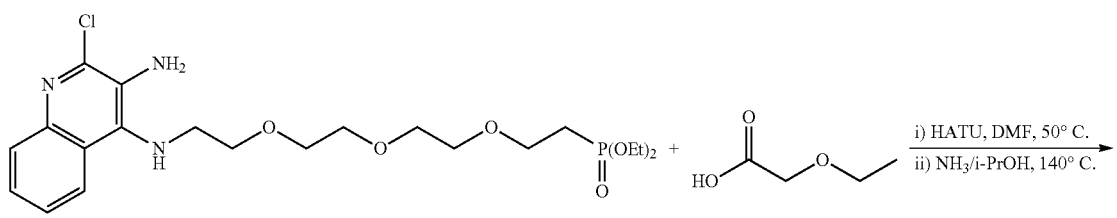

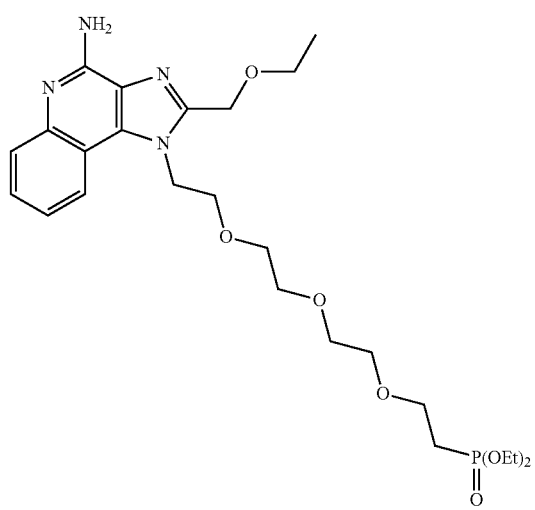

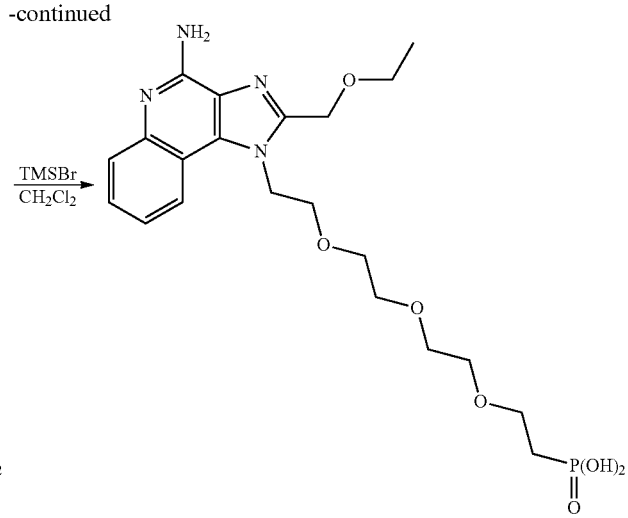

With reference to the above scheme, commercially available quinoline 17 is substituted with amine 18 to deliver intermediate 19. Reduction of the nitro group in 19 then provides intermediate 20. Coupling of intermediate 20 with 2-ethyoxyacetic acid then furnishes intermediate 21. Amination of intermediate 21 with ammonia then affords imidazoquinoline 22. Hydrolysis of 22 with bromotrimethyl silane then furnishes phosphonic acid 23.

The experimental details of the above synthesis of Compound 68 are as follows.

Step 1: diethyl (2-(2-(2-(2-((2-chloro-3-nitroquinolin-4-yl)amino)ethoxy)ethoxy)ethoxy)ethyl)phosphonate To a solution of commercially available 2,4-dichloro-3-nitroquinoline (1 equiv.) in triethyl amine (0.30 M) was added commercially available diethyl (2-(2-(2-(2-aminoethoxy)ethoxy)ethoxy)ethyl)phosphonate (1.3 equiv.) (provided by PHARMARON). The resulting reaction mixture was stirred at 70° C. for 2 h. At this point the volatiles were removed in vacuo. The resulting residue was purified by a COMBIFLASH™ system using a gradient of 0-5% MeOH/DCM to provide the title compound (63%) as a solid.

Step 2: diethyl (2-(2-(2-(2-((3-amino-2-chloroquinolin-4-yl)amino)ethoxy)ethoxy)ethoxy)ethyl)phosphonate To a solution of diethyl (2-(2-(2-(2-((2-chloro-3-nitroquinolin-4-yl)amino)ethoxy)ethoxy)ethoxy)ethyl)phosphonate (1 equiv.) in EtOAc (0.10 M) was added 10% PUC (5% equiv. by weight) and $MgSO_4$ (2 equiv.) in a Paar Shaker Flask. The reaction mixture was placed in a Paar Shaker at 40 psi for 7 h. At this point the reaction mixture was passed through a pad of Celite, washing with a 2:1 mixture of $CHCl_3$:MeOH. The combined organic layers were dried over anhydrous $Na_2SO_4$ and the volatiles were removed in vacuo. The resulting residue was purified by a COMBIFLASH™ system using a gradient of 0-10% MeOH/DCM to provide the title compound (97%) as a solid.

Step 3: diethyl (2-(2-(2-(2-(4-amino-2-(ethoxymethyl)-1H-imidazo[4,5-c]quinolin-1-yl)ethoxy)ethoxy)ethoxy)ethyl)phosphonate To a solution of diethyl (2-(2-(2-(2-((3-amino-2-chloroquinolin-4-yl)amino)ethoxy)ethoxy)ethoxy)ethyl)phosphonate (1 equiv.) in DMF (0.25 M) was added (2-(7-Aza-1H-benzotriazole-1-yl)-1,1,3,3-tetramethyluronium hexafluorophosphate (1 equiv.) and 2-ethoxyacetic acid 21 (1.2 equiv.). The resulting reaction mixture was heated to 50° C. for 18 h. At this point the reaction mixture was allowed to cool to room temperature. The mixture was then diluted with water and EtOAc. This mixture was transferred to a separatory funnel and washed with water three times. The organic layer was then separated, dried over anhydrous $Na_2SO_4$ and the volatiles were removed in vacuo. The resulting residue was purified by a COMBIFLASH™ system using a gradient of 0-10% MeOH/DCM to provide the coupled intermediate (19%) as a solid. A solution of this intermediate (1 equiv.) in 2 M ammonia in isopropanol (0.06 M) was then heated at 100° C. for three days. At this point the volatiles were removed in vacuo. The resulting residue was purified by a COMBIFLASH system using a gradient of 0-10% MeOH/DCM to provide the title compound (62%) as a solid.

Step 4: (2-(2-(2-(2-(4-amino-2-(ethoxymethyl)-1H-imidazo[4,5-c]quinolin-1-yl)ethoxy)ethoxy)ethoxy)ethyl)phosphonic acid To a solution of diethyl (2-(2-(2-(2-(4-amino-2-(ethoxymethyl)-1H-imidazo[4,5-c]quinolin-1-yl)ethoxy)ethoxy)ethoxy)ethyl)phosphonate (1 equiv.) in $CH_2Cl_2$ (0.10 M) at 0° C. was slowly added trimethylsilyl bromide (10 equiv.). After 1 h the ice-bath was removed and the reaction mixture was allowed to stir at 22° C. for 18 h. At this point the volatiles were removed in vacuo and the resulting residue was purified by Reverse Phase-HPLC using a 20-90% 0.5 mM $NH_4OAc$ (in MeCN) to 10 mM $NH_4OAc$ (in water) gradient to deliver the title compound (26%) as a solid.

$^1$H NMR ($CDCl_3$): δ 8.00-7.76 (m, 2H), 7.51-7.28 (m, 2H), 4.91-4.72 (m, 4H), 3.98-3.84 (m, 2H), 3.72-3.54 (m, 4H), 3.48-3.38 (m, 2H), 3.30-3.29 (m, 2H), 3.13-3.00 (m, 2H), 2.10-1.96 (m, 2H), 1.31-1.11 (m, 3H). LRMS [M+H]=483.1.

Formula (E)

The following phospho-compound is synthesized, based on the parent pyrimidine compounds disclosed in reference 5 e.g. the ester in example 21:

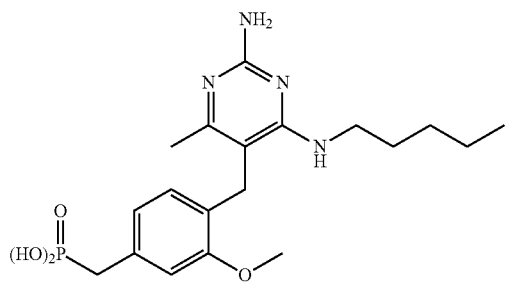
(8)

Compound 8 has a $EC_{50}$ of 7.3 µM (81%) in the HEK293 assay disclosed above. In splenocytes it shows an $EC_{50}$ of 3.1 µM (184%). In hPBMCs it shows an $EC_{50}$ of 10.4 (50%). It is insoluble in histidine buffer at pH 6.8.

Further compounds of formula (E) are prepared:

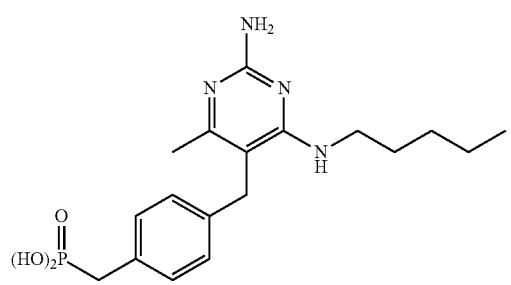
(69)

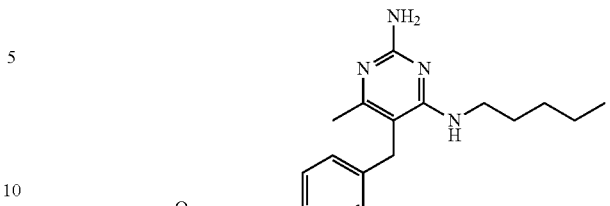
(70)

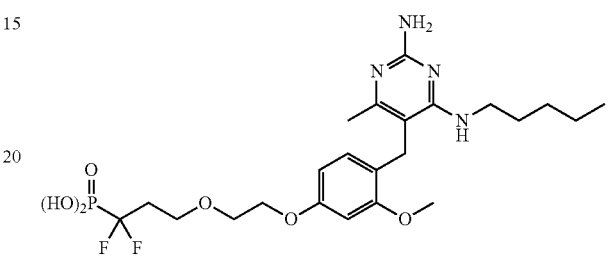
(71)

Compound (69) shows an $EC_{50}$ of 47.4 µM (36%) in HEK293 cells but is inactive in splenocytes and hPBMCs. It is insoluble in histidine buffer at pH 6.8. Compound 70 also had poor solubility.

Compound 71 shows an $EC_{50}$ of 2.7 µM (53%) in HEK293. In splenocytes it shows an $EC_{50}$ of 10.5 µM (239%). In hPBMCs it shows an $EC_{50}$ of 9.5 (50%). It is soluble in histidine buffer at pH 6.8.

Compound 71 can be synthesized according to according to the scheme shown below, the reference numerals referring to the compounds shown in the scheme below, and not relating to the compound numbering established elsewhere in this application. The compound identified with reference numeral 8 in the scheme below is Compound 71 of the invention.

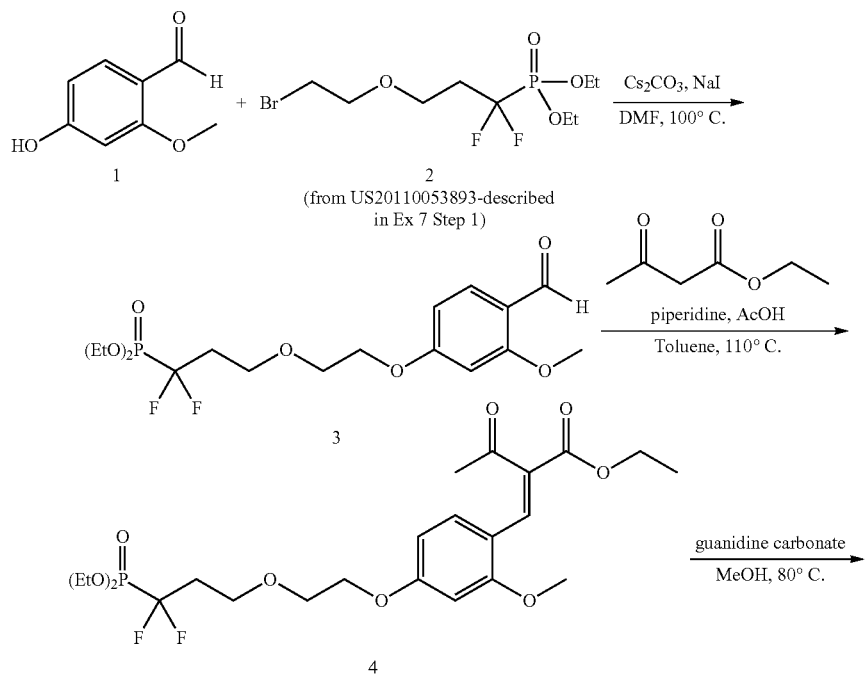

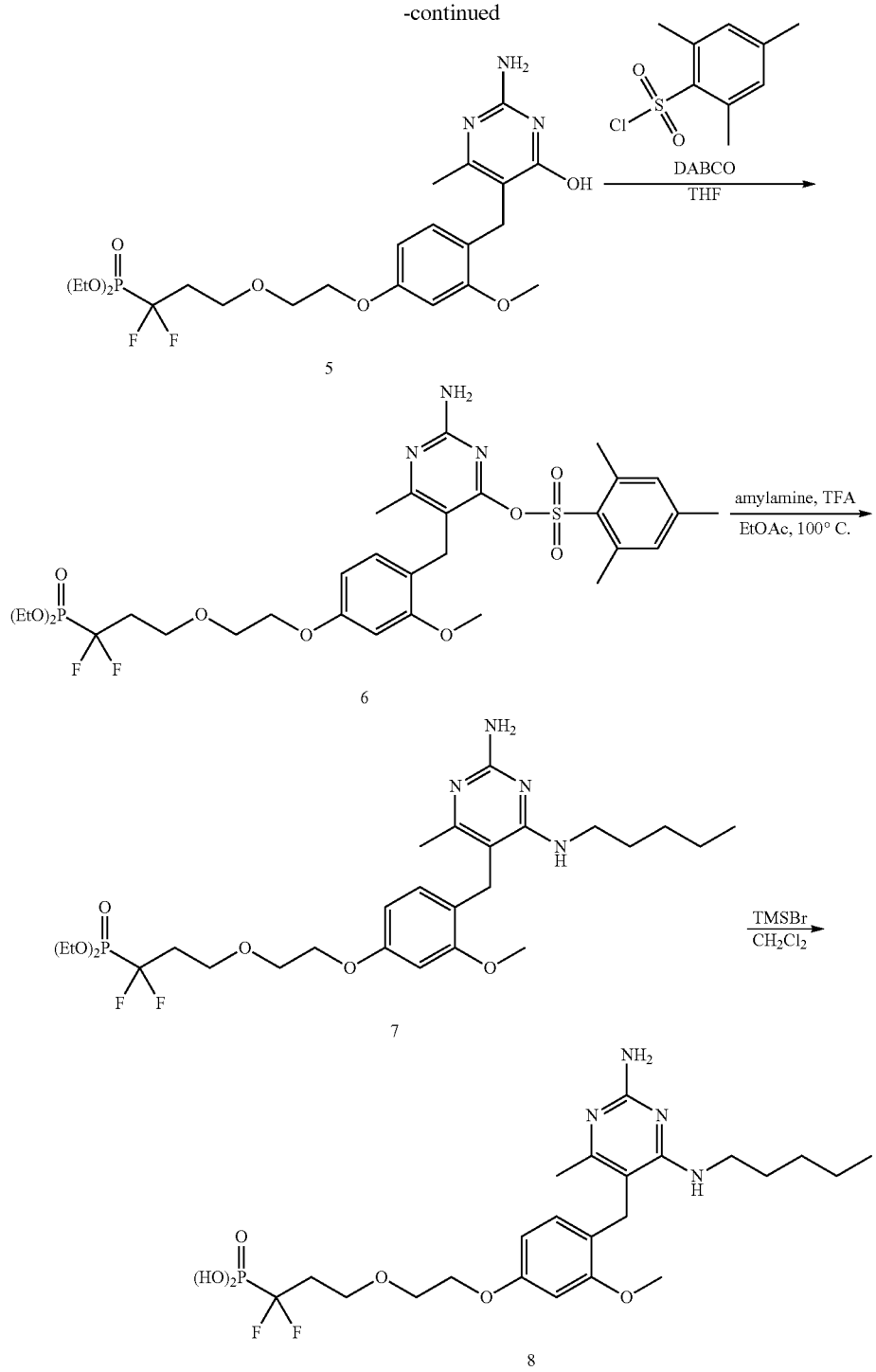

With reference to the above scheme, commercially available phenol 1 is alkylated with bromide 2 (described in ref. 88, Ex 7 Step 1) to deliver intermediate 3. Condensation of intermediate 3 with ethyl acetoacetate then provides enoate 4. Cyclization of 4 with guanidine carbonate then provides pyrimidine 5. Intermediate 5 is then converted to sulfone 6 which is substituted with amylamine do deliver pyrimidine 7. Hydrolysis of 7 with bromotrimethyl silane then furnishes phosphonic acid 8.

Step 1: diethyl (1,1-difluoro-3-(2-(4-formyl-3-methoxyphenoxy)ethoxy)propyl)phosphonate To a solution of 4-hydroxy-2-methoxybenzaldehyde (1 equiv.) in DMF (0.25 M) was added cesium carbonate (2 equiv.), sodium iodide (0.20 equiv.) and diethyl (3-(2-bromoethoxy)-1,1-difluoropropyl)phosphonate (1.2 equiv.) (described in ref. 88, Ex 7 Step 1). The reaction mixture was stirred at 100° C. for 3 h, after which it was allowed to cool to room temperature. The resulting mixture was then diluted with water and EtOAc. This mixture was transferred to a separatory funnel and washed with water three times. The organic layer was then separated, dried over anhydrous $Na_2SO_4$ and the volatiles were removed in vacuo. The resulting residue was purified by a COMBIFLASH™ system using a gradient of 0-5% MeOH/DCM to provide the title compound (79%) as a solid.

Step 2: (E)-ethyl 2-(4-(2-(3-(diethoxyphosphoryl)-3,3-difluoropropoxy)ethoxy)-2-methoxybenzylidene)-3-oxobutanoate To a solution of diethyl (1,1-difluoro-3-(2-(4-formyl-3-methoxyphenoxy)ethoxy)propyl)phosphonate (1 equiv.) in toluene (0.50 M) was added piperidine (0.10 equiv.), acetic acid (0.50 equiv.) and ethyl acetoacetate (1.2 equiv.). The reaction mixture was then heated to 110° C. for 18 h. At this point additional piperidine (0.10 equiv.), acetic acid (0.50 equiv.) and ethyl acetoacetate (0.50 equiv.) were added to the reaction mixture and heating at 110° C. was continued for 4 h. At this point the reaction mixture was allowed to cool to room temperature and the volatiles were removed in vacuo. The resulting residue was purified by a COMBIFLASH™ system using a gradient of 0-5% MeOH/DCM to provide the title compound (78%) as a solid.

Step 3: diethyl (3-(2-(4-((2-amino-4-hydroxy-6-methylpyrimidin-5-yl)methyl)-3-methoxyphenoxy)ethoxy)-1,1-difluoropropyl)phosphonate To a solution of (E)-ethyl 2-(4-(2-(3-(diethoxyphosphoryl)-3,3-difluoropropoxy)ethoxy)-2-methoxybenzylidene)-3-oxobutanoate (1 equiv.) in MeOH (0.20 M) was added guanidine carbonate (1.1 equiv.) and the reaction mixture was heated to 80° C. for 3 h. At this point the reaction mixture was allowed to cool to room temperature and it was then diluted with water and EtOAc. The resulting mixture was transferred to a separatory funnel and washed with EtOAc three times. The combined organic layers were dried over anhydrous $Na_2SO_4$ and the volatiles were removed in vacuo. The resulting residue was purified by a COMBIFLASH™ system using a gradient of 0-10% MeOH/DCM to provide the title compound (15%) as a solid.

Step 4: 2-amino-5-(4-(2-(3-(diethoxyphosphoryl)-3,3-difluoropropoxy)ethoxy)-2-methoxybenzyl)-6-methylpyrimidin-4-yl-2,4,6-trimethylbenzenesulfonate To a solution of diethyl (3-(2-(4-((2-amino-4-hydroxy-6-methylpyrimidin-5-yl)methyl)-3-methoxyphenoxy)ethoxy)-1,1-difluoropropyl)phosphonate (1 equiv.) in THF (0.40 M) was added 1,4-diazabicyclo[2.2.2]octane (1.8 equiv.) and 2,4,6-trimethylbenzene-1-sulfonyl chloride (1.3 equiv.). The reaction mixture was allowed to stir at room temperature for 18 h after which it was quenched with aqueous HCl (0.10 N). The resulting mixture was transferred to a separatory funnel and washed with chloroform three times. The combined organic layers were dried over anhydrous $Na_2SO_4$ and the volatiles were removed in vacuo. The resulting residue was purified by a COMBIFLASH™ system using a gradient of 0-5% MeOH/DCM to provide the title compound (41%) as a solid.

Step 5: diethyl (3-(2-(4-((2-amino-4-methyl-6-(pentylamino)pyrimidin-5-yl)methyl)-3-methoxyphenoxy)ethoxy)-1,1-difluoropropyl)phosphonate To a solution of 2-amino-5-(4-(2-(3-(diethoxyphosphoryl)-3,3-difluoropropoxy)ethoxy)-2-methoxybenzyl)-6-methylpyrimidin-4-yl 2,4,6-trimethylbenzenesulfonate (1 equiv.) in EtOAc (0.20 M) was added TFA (1.1 equiv.) and amylamine (3.3 equiv.). The reaction mixture was then heated to 100° C. for 18 h. At this point the reaction mixture was allowed to cool to room temperature and the volatiles were removed in vacuo. The resulting residue was purified by a COMBIFLASH™ system using a gradient of 0-10% MeOH/DCM to provide the title compound (76%) as a solid.

Step 6: (3-(2-(4-((2-amino-4-methyl-6-(pentylamino)pyrimidin-5-yl)methyl)-3-methoxyphenoxy)ethoxy)-1,1-difluoropropyl)phosphonic acid To a solution of diethyl (3-(2-(4-((2-amino-4-methyl-6-(pentylamino)pyrimidin-5-yl)methyl)-3-methoxyphenoxy)ethoxy)-1,1-difluoropropyl)phosphonate (1 equiv.) in $CH_2Cl_2$ (0.10 M) at 0° C. was slowly added trimethylsilyl bromide (10 equiv.). After 1 h the ice-bath was removed and the reaction mixture was allowed to stir at 22° C. for 18 h. At this point the volatiles were removed in vacuo and the resulting residue was purified by Reverse Phase-HPLC using a 20-90% 0.5 mM $NH_4OAc$ (in MeCN) to 10 mM $NH_4OAc$ (in water) gradient to deliver the title compound (70%) as a solid.
$^1$H NMR (Methanol-d4): δ 6.81 (d, 1H, J=8.4 Hz), 6.62 (s, 1H), 6.48 (d, 1H, J=8.4 Hz), 4.09 (t, 2H, J=4.4 Hz), 3.90 (s, 3H), 3.86 (t, 2H, J=7.6 Hz), 3.79 (t, 2H, J=4.4 Hz), 3.67 (s, 2H), 3.43 (t, 2H, J=7.2 Hz), 2.30 (s, 3H), 2.22 (t, 2H, J=7.6 Hz), 2.06-2.01 (m, 2H), 1.33-1.10 (m, 4H), 0.88 (t, 3H, J=7.6 Hz). LRMS [M+H]=533.3.
Formula (III)
The starting compound for preparing compound 19 was (5R,9R)-9-(dodecanoyloxy)-1-(9H-fluoren-9-yl)-3,12-dioxo-2,11-dioxa-7-thia-4-azatricosane-5-carboxylic acid ("TLR2-pre"), prepared as follows:

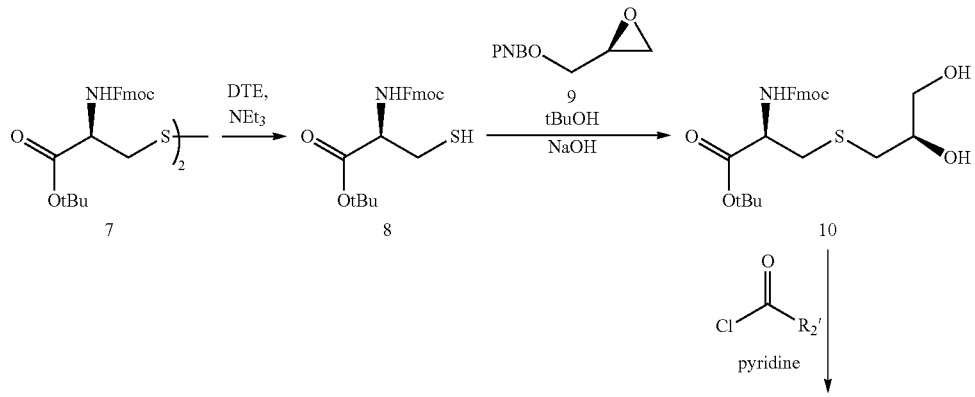

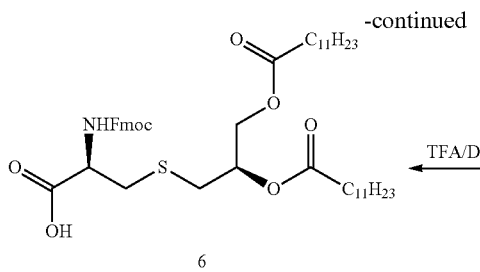

6

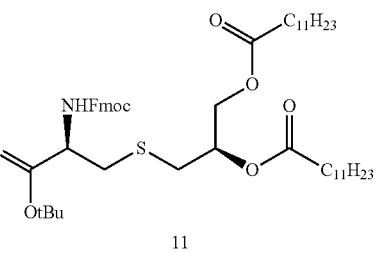

11

Step 1: (R)-tert-butyl 2-(((9H-fluoren-9-yl)methoxy)carbonylamino)-3-mercaptopropanoate (8)

A solution of (N-Fmoc-Cys-OtBu)$_2$ (7, 1 eq), NEt$_3$ (3 eq) and DTE (1,4-Dithioerythritol, 2.5 eq) in DCM (0.1 M) was stirred at room temperature until complete reduction (1.5 hours). The reaction mixture was diluted in DCM, washed three times with 5% citric acid, twice with water, and once with brine. The organic layer was dried over anhydrous Na$_2$SO$_4$ and concentrated en vacuo. The resulting crude was purified by flash chromatography on a COMBIFLASH® system (ISCO) using 0-30% EtOAc/Hex to give the title product as colorless viscous oil.

Step 2: (R)-tert-butyl 2-(((9H-fluoren-9-yl)methoxy)carbonylamino)-3-((R)-2,3-dihydroxypropylthio)propanoate (10)

A solution of (2S)-(+)-glycidyl-4-nitrobenzoate (9, 1.1 eq) and 1M NaOH (1.1 eq) in tBuOH (0.1 M) was stirred at room temperature until complete hydrolysis of the nitrobenzoate (30 minutes). To the resulting mixture, a solution of (R)-tert-butyl 2-(((9H-fluoren-9-yl)methoxy)carbonylamino)-3-mercaptopropanoate (8, 1 eq) in tBuOH (1 M) was introduced. The reaction was stirred at room temperature for 15 hours. The reaction mixture was concentrated en vacuo to remove tBuOH and dissolved in EtOAc. The EtOAc solution was washed three times with water, and once with brine. The resulting crude was purified by flash chromatography on a COMBIFLASH® system (ISCO) using 0-90% EtOAc/Hex to give the title product as colorless viscous oil.

Step 3: (R)-3-((R)-2-(((9H-fluoren-9-yl)methoxy)carbonylamino)-3-tert-butoxy-3-oxopropylthio)propane-1,2-diyl didodecanoate (11)

A solution of (R)-tert-butyl 2-(((9H-fluoren-9-yl)methoxy)carbonylamino)-3-((R)-2,3-dihydroxypropylthio)propanoate (10, 1 eq) in DCM (0.1 M) was cooled in an ice bath. Pyridine (3.7 eq) was added followed by dodecanoyl chloride (3.7 eq). The reaction mixture was stirred for 10 minutes then warmed up to room temperature, and stirred for 2 hours. The reaction mixture was diluted with DCM, washed with saturated aqueous NH$_4$Cl. The aqueous phase was back extracted with DCM. The combined organic phases were washed with H$_2$O, and the aqueous phase was back extracted with DCM. The combined organic phases were washed with brine, dried over anhydrous Na$_2$SO$_4$ and concentrated en vacuo. The resulting crude was purified by flash chromatography on a COMBIFLASH® system (ISCO) using 0-30% EtOAc/Hex to give the title product as a white solid.

Step 4: (5R,9R)-9-(dodecanoyloxy)-1-(9H-fluoren-9-yl)-3,12-dioxo-2,11-dioxa-7-thia-4-azatricosane-5-carboxylic acid ("TLR2-pre")

A solution of (R)-3-((R)-2-(((9H-fluoren-9-yl)methoxy)carbonylamino)-3-tert-butoxy-3-oxopropyl thio)propane-1, 2-diyl didodecanoate (11) in 40% TFA in DCM (0.3 M) was stirred at room temperature until complete deprotection of tert-butyl group (2 hr). The reaction mixture was diluted in MTBE, washed three times with 1M citric acid (adjusted to pH3), and once with 1:2 1N HCl/brine. The organic layer was dried over anhydrous Na$_2$SO$_4$ and concentrated en vacuo. The resulting waxy solid was used without further purification.

This material was used for preparing compounds 17, 19 and 22. For instance, compound 19 was prepared as follows:

Step 1: diethyl 2-(2-(2-iodoethoxy)ethoxy)ethylphosphonate 1,2-bis(2-iodoethoxy)ethane (1.0 eq) was mixed with triethyl phosphate (1 eq) then heated to 160° C. for 20 minutes by microwave. The crude mixture was purified by flash chromatography on a COMBIFLASH™ system using 85-100% EtOAc/Hex to give diethyl 2-(2-(2-iodoethoxy)ethoxy)ethylphosphonate as a colorless oil.

Step 2: diethyl 2-(2-(2-azidoethoxy)ethoxy)ethylphosphonate

To a solution of diethyl 2-(2-(2-iodoethoxy)ethylphosphonate (1 eq) in EtOH (0.2 M) was added sodium azide (5 eq) in water (1.4 M). The reaction mixture was heated at reflux overnight. The mixture was then diluted with water, extracted with EtOAc (3 times). The combined organic layers were washed brine, dried over anhydrous Na$_2$SO$_4$, and concentrated en vacuo. The crude material was purified by flash chromatography on a COMBIFLASH™ system using 0-5% MeOH/DCM to give diethyl 2-(2-(2-azidoethoxy)ethoxy) ethylphosphonate as colorless oil.

Step 3: diethyl 2-(2-(2-aminoethoxy)ethoxy)ethylphosphonate

Diethyl 2-(2-(2-azidoethoxy)ethoxy)ethylphosphonate (1 eq) was dissolved in EtOH (0.1 M). Pd(OH)$_2$ (0.05 eq) was added to the reaction. Hydrogen gas was introduced via a balloon; and the reaction was stirred for 2 hours at room temperature. The mixture was filtered through Celite and washed with MeOH. The solvent was removed en vacuo and the crude material was purified by flash chromatography on a COMBIFLASH™ system using 0-10% MeOH/DCM with 0.5% NH$_3$ to give diethyl 2-(2-(2-aminoethoxy)ethoxy)ethylphosphonate as a colorless oil.

Step 4: (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester To a solution of TLR2-pre (1 eq) in DCM (0.1M) was added diethyl 2-(2-(2-aminoethoxy)ethoxy)ethylphosphonate (1.3 eq), DIEA (2.5 eq) and HBTU (1.2 eq). The reaction was stirred at room temperature for 2 hours. The crude mixture was purified by flash chromatography by flash chromatography on a COMBIFLASH™ system using 70-100% EtOAc/Hex to give (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester.

Step 5: (11R,15R)-11-amino-15-(dodecanoyloxy)-10,18-dioxo-3,6,17-trioxa-13-thia-9-azanonacosyl phosphoryl diethyl ester To a solution of (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester (1 eq) was added 20% piperidine (50 eq) in acetonitrile. The resulting mixture was diluted with DCM and sonicated for 3 minutes. To the mixture was added to toluene and then concentrated en vacuo. The crude mixture was purified by flash chromatography on a COMBIFLASH™ system using 100% EA followed by 0-10% MeOH in DCM to give (11R,15R)-11-amino-15-(dodecanoyloxy)-10,18-dioxo-3,6,17-trioxa-13-thia-9-azanonacosyl phosphoryl diethyl ester.

Step 6: (11R,15R)-11-amino-15-(dodecanoyloxy)-10,18-dioxo-3,6,17-trioxa-13-thia-9-azanonacosyl phosphonic acid To a solution of (11R,15R)-11-amino-15-(dodecanoyloxy)-10,18-dioxo-3,6,17-trioxa-13-thia-9-azanonacosyl phosphoryl diethyl ester (1 eq) in DCM (0.1 M) was added trimethylsilyl bromide (10 eq). The reaction mixture was stirred at room temperature overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give (11R,15R)-11-amino-15-(dodecanoyloxy)-10,18-dioxo-3,6,17-trioxa-13-thia-9-azanonacosyl phosphonic acid as a white solid.

Compounds 17, 19 and 22 were tested for binding to Al—H in 100 mM histidine buffer at pH 6.5. Binding to Al—H was >80% in all three cases. Further compounds which are useful for adsorbing to Al—H are the "TLR2p" compounds mentioned above. The interaction of four of these (compounds 63-66) with Al—H was tested in the same way as for compounds 17, 19 and 22; binding was again >80% in all cases.

Impact of Adsorption on Behaviour of Immunopotentiators

Cellular Uptake

The autofluorescence of compound 1 was exploited to follow its uptake by human PBMCs after adsorption to Al—H. FACS was used to monitor uptake.

Various concentrations of compound 1 were incubated with cells overnight at 37° C. with or without Al—H The presence of Al—H, to which compound 1 is adsorbed, produced a large shift in the FACS pattern, with a dose response, and increased fluorescence was detected specifically in monocytes. Thus the Al—H particles can enhance the cellular uptake of adsorbed compound 1 in comparison to the free compound in solution. Moreover, the results show that the adsorbed compound is retained for longer in the cells after entry.

The same uptake has been seen in other cell types too.

Pre-treatment of cells with cytochalasin D resulted in a lower fluorescence intensity associated with compound 2, compared to untreated cells, indicating that the process of interaction and internalization of the adsorbed compound is actively mediated by monocytes.

Addition of trypan blue is able to "quench" compound 2's fluorescence, but trypan blue is not able to permeate live cells. Cells which were not pre-treated with cytochalasin D remained highly fluorescent after treatment with trypan blue, meaning that compound 2 is located inside the cells. Cellular uptake was time-dependent.

Figure 20:
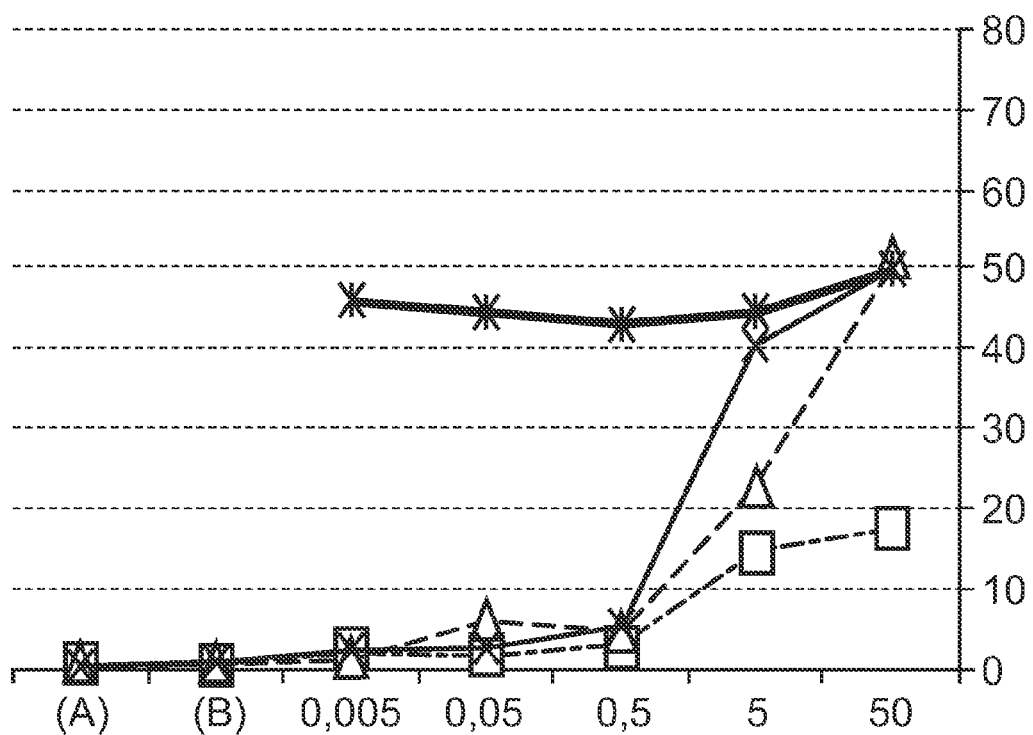
FIG. 20 shows the % of CD40-positive cells. Lines are: *=LPS; X=Al—H and compound 2, serially diluted; triangle=Al—H and compound 2, with fixed Al$^{+++}$ dose; and square=soluble compound 2 without Al—H. (A) is a negative control of medium alone. (B) is a negative control of buffer alone when testing soluble compound 2 or Al—H alone when testing adsorbed compound 2. The other values on the X-axis are the amount of test compound.
Figure 21:
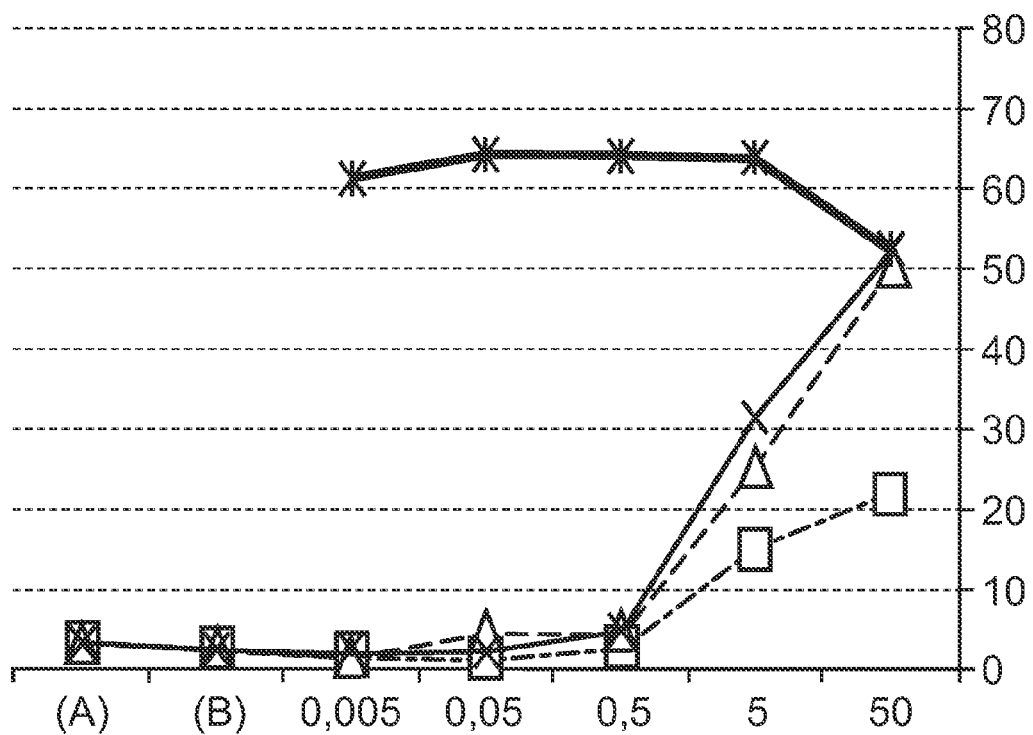
FIG. 21 shows the % of CD80-positive cells. The format is the same as in FIG. 20.

Monocyte activation markers CD40 and CD80 were studied in response to compounds 1, 2 and 5, either alone or adsorbed to Al—H, or to LPS (positive control). The adsorbed compounds were tested at 5 different concentrations, either at a fixed Al$^{+++}$ dose or with simple dilution. FIG. 20 shows CD40 activation and FIG. 21 shows CD80 activation using compound 2; both markers indicate greater activation in the presence of adsorbed SMIP than with soluble SMIP. The same trend was seen with compounds 1 and 5.

The cytokine activation profile of compound 2 was compared in soluble and adsorbed form. There was no significant observable difference in IL-8, IL-6, TNF-α or IL-1β responses.

Thus adsorption of compound 2 to Al—H results in an enhanced uptake of the SMIP into the cell, and in a higher degree of cell activation when compared to incubation with unadsorbed SMIP. Cellular uptake of SMIP is mediated by an active process of internalization that is time- and dose-dependent.

Systemic Exposure after In Vivo Delivery

Compounds 1, 2, 3 and 5 are administered to Balb/C mice by intramuscular injection at 100 μg (4 mg/kg), either with buffer alone or after adsorption to an Al—H adjuvant. Systemic serum exposure of the compounds is followed for 24 hours. As shown in FIGS. 1 to 4, whereas the unadsorbed compounds have a high initial serum concentration which rapidly declines, adsorbed compounds show a much flatter response which is sustained for a longer period. Similar systemic serum exposure profiles were seen in rats.

Despite the longer period of exposure, for these compounds the overall systemic exposure can be reduced by adsorption, as separately measured by AUC for compounds 2 and 5:

|  | 2 | 5 |
|---|---|---|
| Compound | 8846 | 9834 |
| +Al-H | 4553 | 13908 |

Similarly to FIGS. 1-4, FIG. 23 shows serum exposure of compounds (A) 6 (B) 67 (C) 68 and (D) 71 for 24 hours after injection. AUCs were as follows (nM·hr), and for these four compounds were in all cases higher when adsorbed:

|  | 6 | 67 | 68 | 71 |
|---|---|---|---|---|
| Compound | 7176 | 3573 | 1391 | 2093 |
| +Al-H | 13424 | 8110 | 2759 | 4219 |

Figure 16:
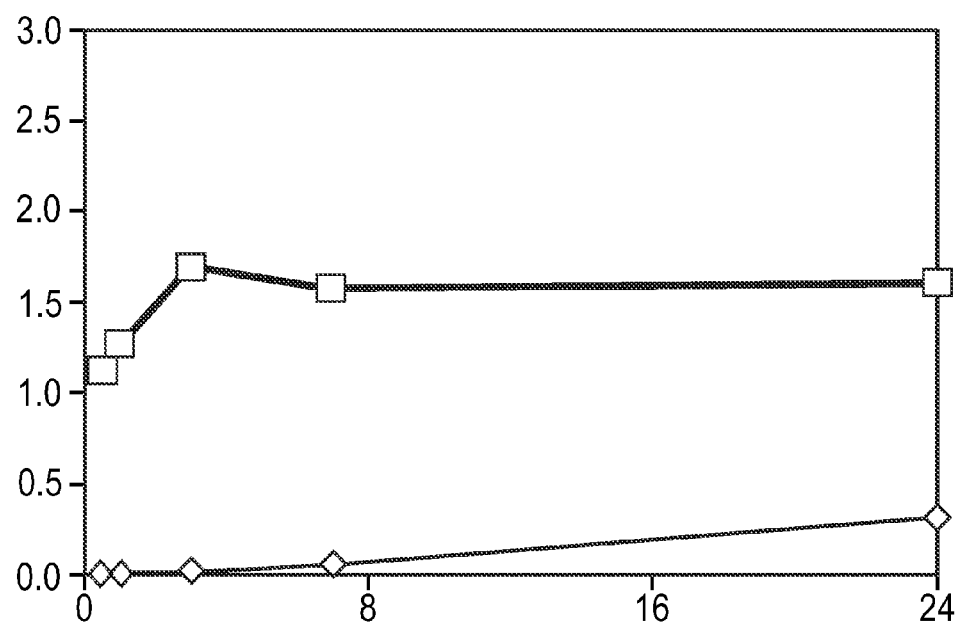
FIG. 16 shows serum levels (µM) over time (hours) of compound 74 after 100 µg i.m. injection.

FIG. 16 shows similar data for a TLR2 agonist (compound 74). AUCs of this compound and compound 80, both TLR2 agonists of interest, were reduced by adsorption to Al—H:

|  | 74 | 80 |
|---|---|---|
| Compound | 37425 | 20749 |
| +Al-H | 3389 | 7264 |

Cmax values (nM) were as follows, in general showing a reduction when adsorbed:

|  | TLR7 | | | | | | TLR2 | |
| --- | --- | --- | --- | --- | --- | --- | --- | --- |
|  | 2 | 5 | 6 | 67 | 68 | 71 | 74 | 80 |
| Compound | 5600 | 9273 | 6124 | 4057 | 2122 | 2603 | 1937 | 2823 |
| +Al—H | 465 | 3319 | 5521 | 4514 | 1721 | 1807 | 317 | 180 |

Figure 10:
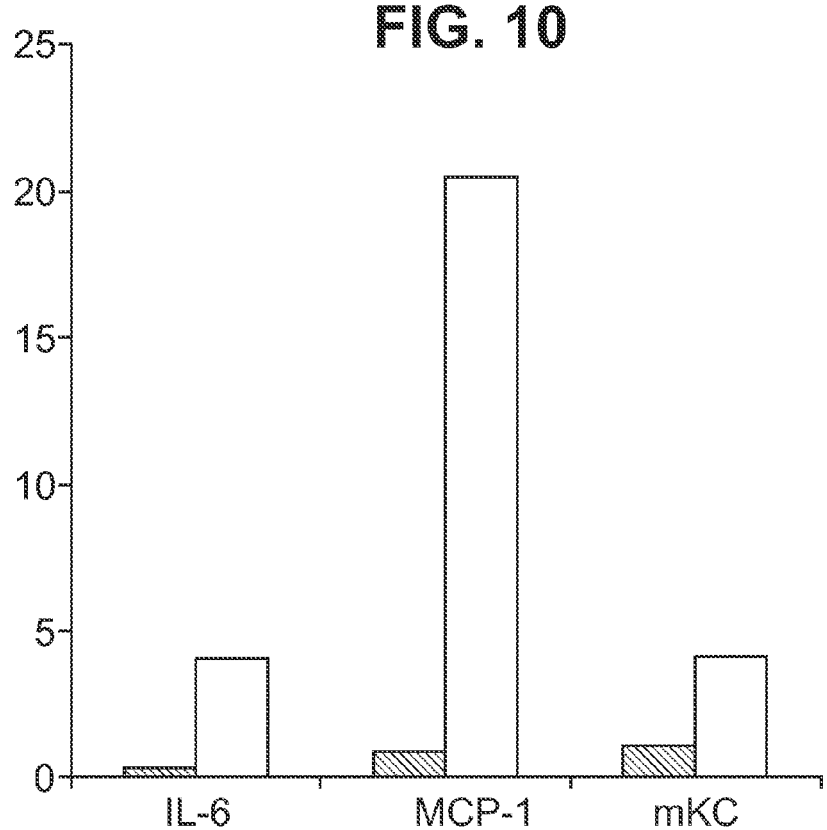
FIGS. 10 and 11 show the fold-increase, compared to vehicle alone, of serum cytokines after administration of compound 1 or compound 2. Each cytokine shows two bars: the left-hand bar shows levels after receiving Al—H-adsorbed compound, whereas the right-hand bar shows levels after receiving the compound alone.
Figure 11:
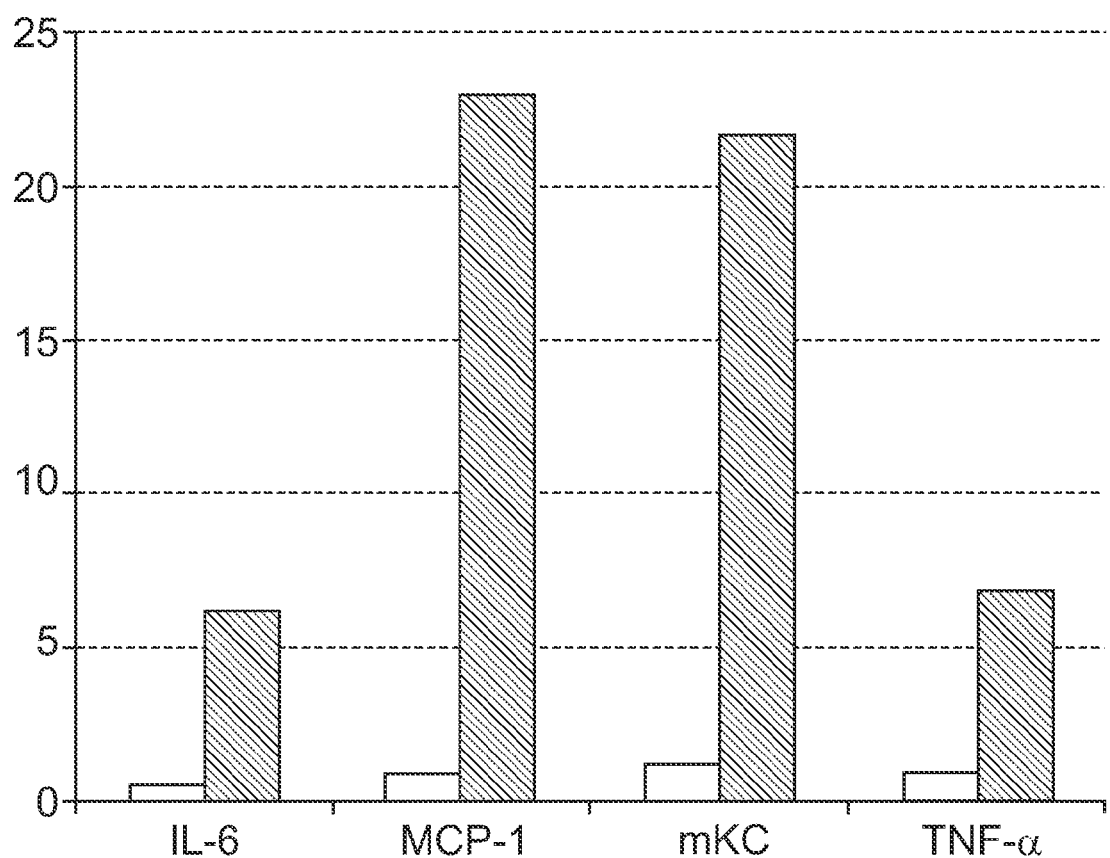

Serum cytokines are measured 24 hours after immunization with compound 1, with or without Al—H, or with buffer alone. Levels of IL-6 and mKC are both about ~4-fold higher after administration of compound 1 without Al—H, and levels of MCP-1 are ~20-fold higher (compared to vehicle alone). In contrast, when administered in combination with Al—H the levels are increased to a lesser degree, being <2-fold higher (see FIG. 10; see also FIG. 11 for results with compound 2). For compounds 67, 68 & 71 systemic cytokines were generally reduced or unaffected by adsorption to Al—H, whereas for compound 6 levels of several cytokines (e.g. IFN-γ, IL1-β, IL12-p40) were enhanced.

Figure 25:
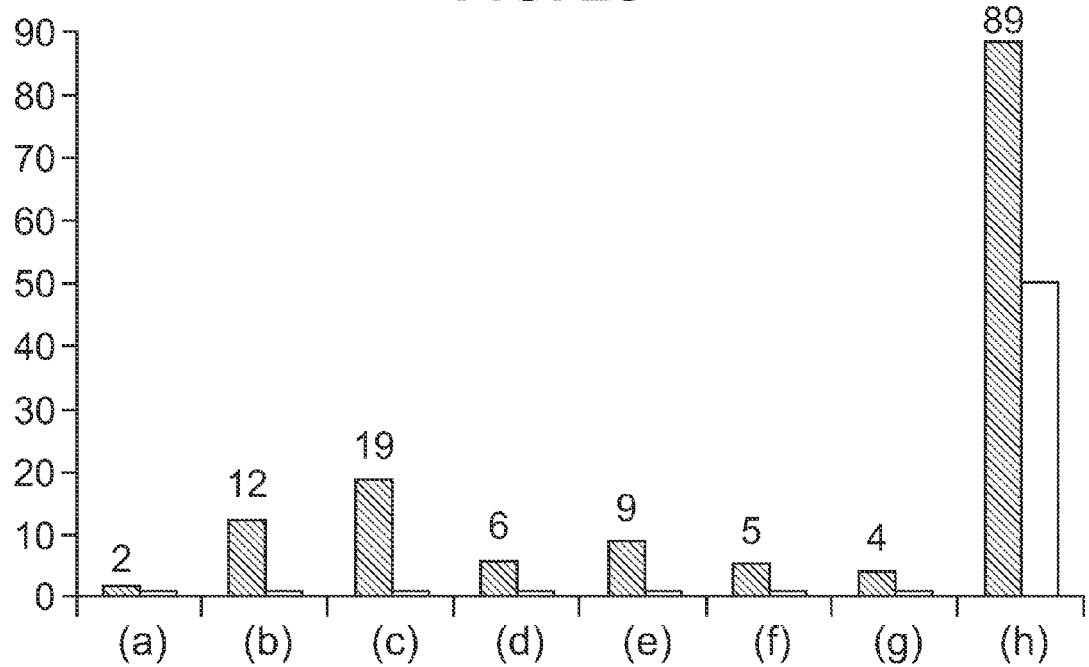
FIG. 25 shows B cell activation (% of CD19$^+$ cells which are CD69$^+$) in response to compounds 67 (b & e), 68 (c & f) & 71 (d & g) when administered with histidine buffer (soluble; b, c & d) or with Al—H (adsorbed; e, f & g). Resiquimod was used as a positive control (h), and buffer alone as a negative control (a). For all of a-h, the left-hand bar shows cells in inguinal lymph nodes and the right-hand bar shows cells in the spleen.

Adsorption of compound 1 to Al—H decreases both the proportion of CD4+ T-cells which are also CD69+ and the proportion of CD19+ B-cells which are also CD86+, and this effect is seen in both the spleen and in draining lymph nodes. For example, adsorption reduces the proportion of CD86+ B-cells from ~0.75% to ~15%. A similar reduction in activation of B cells is seen when compounds 6, 67 & 68 are adsorbed to Al—H (FIG. 25 e.g. compare group f to group c). Thus for all tested TLR7 agonists adsorption to Al—H reduces general activation of B cells.

Figure 1:
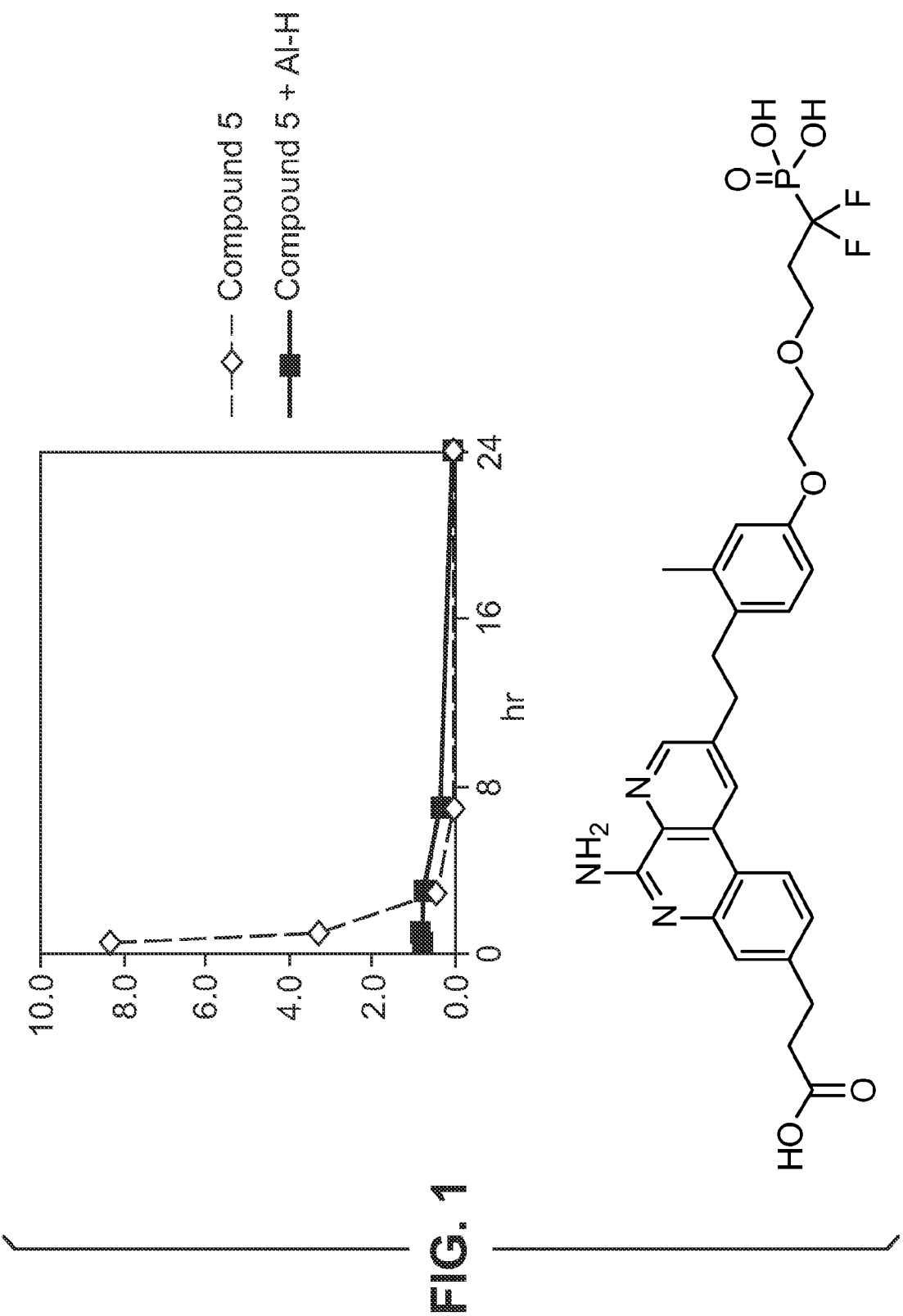
FIGS. 1 to 4 show a the serum concentration (µM) of compounds 2, 5, 1 & 3 either free or adsorbed, over a 24 hour period after intramuscular injection.
Figure 2:
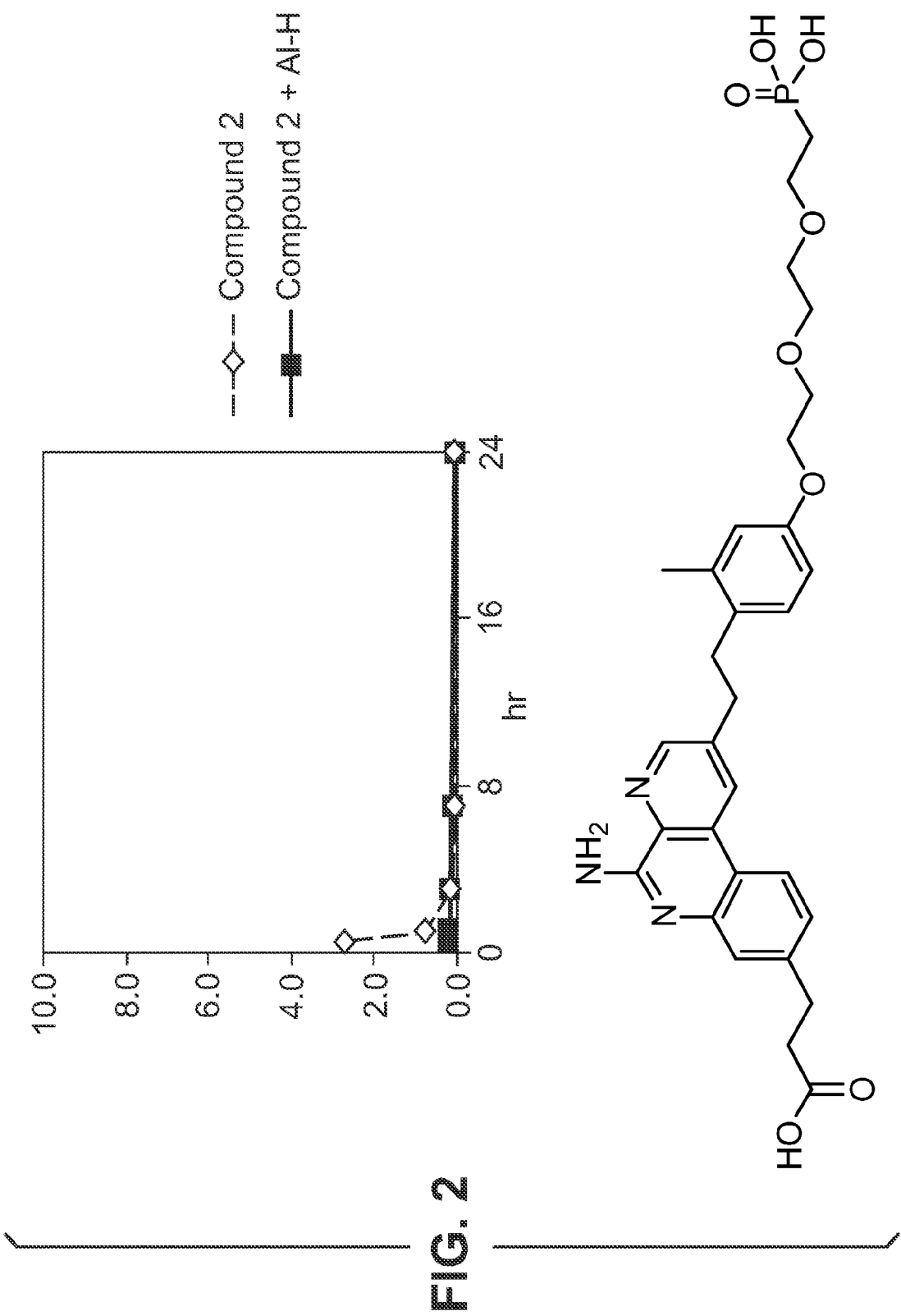
Figure 3:
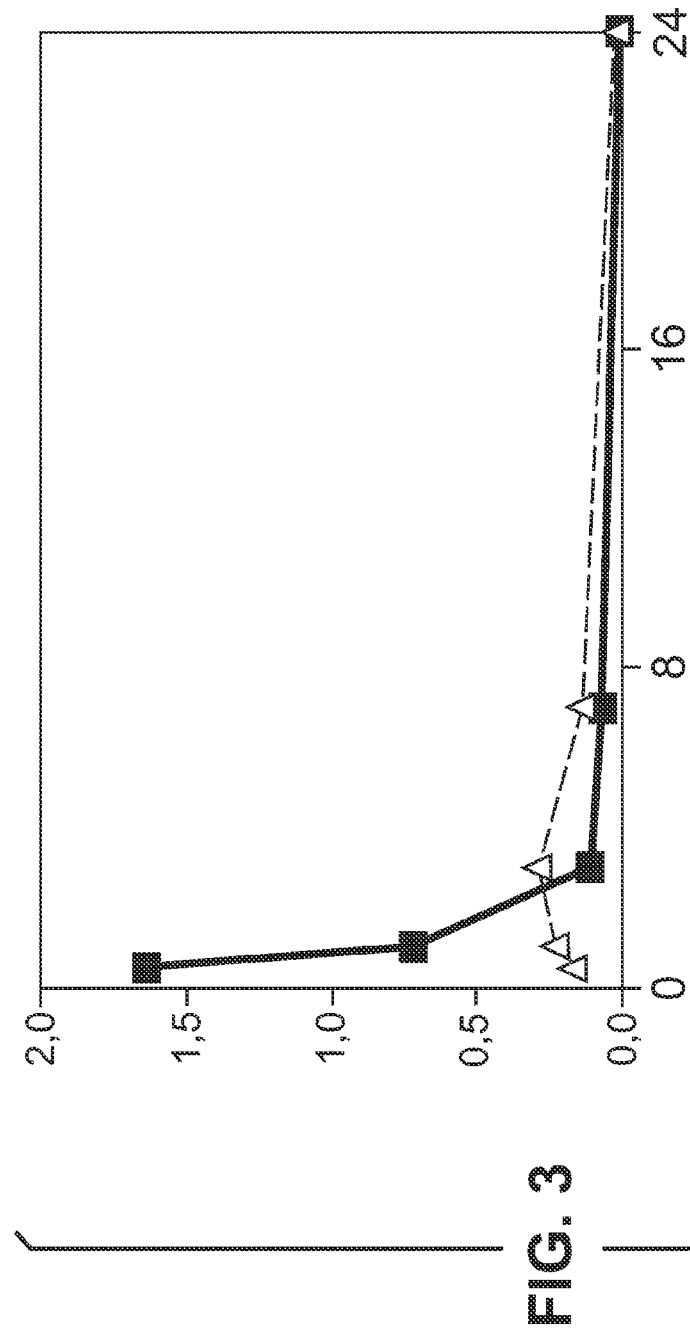
Figure 3:
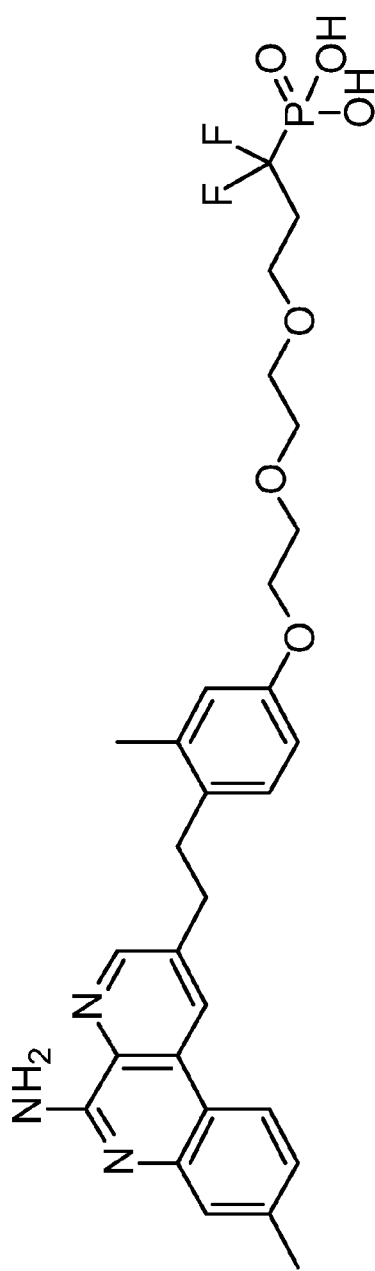
Figure 4:
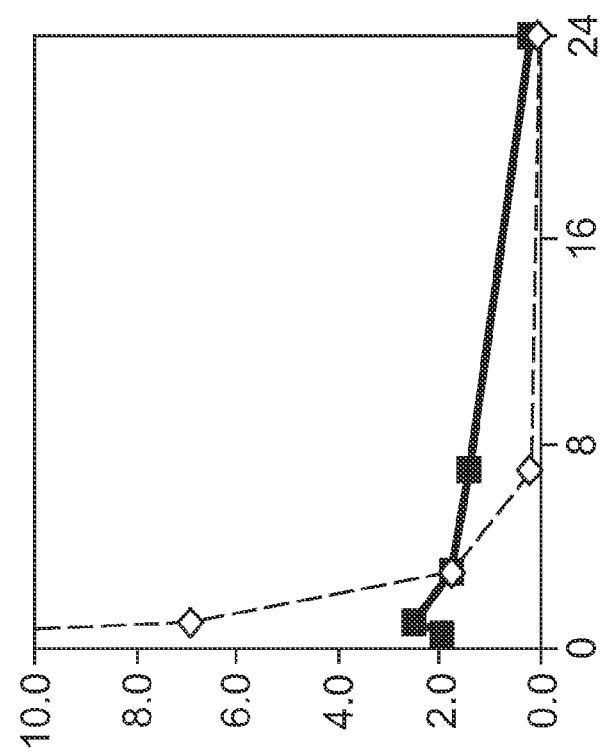
Figure 4:
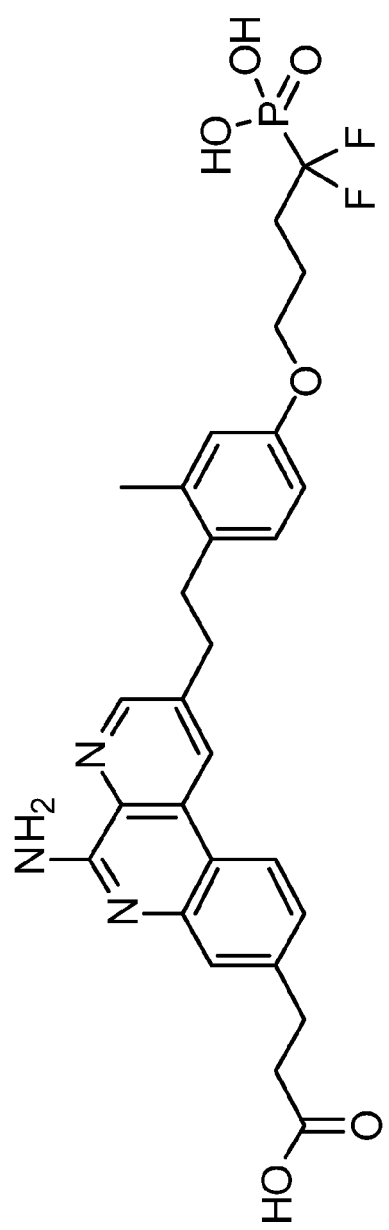
Figure 5:
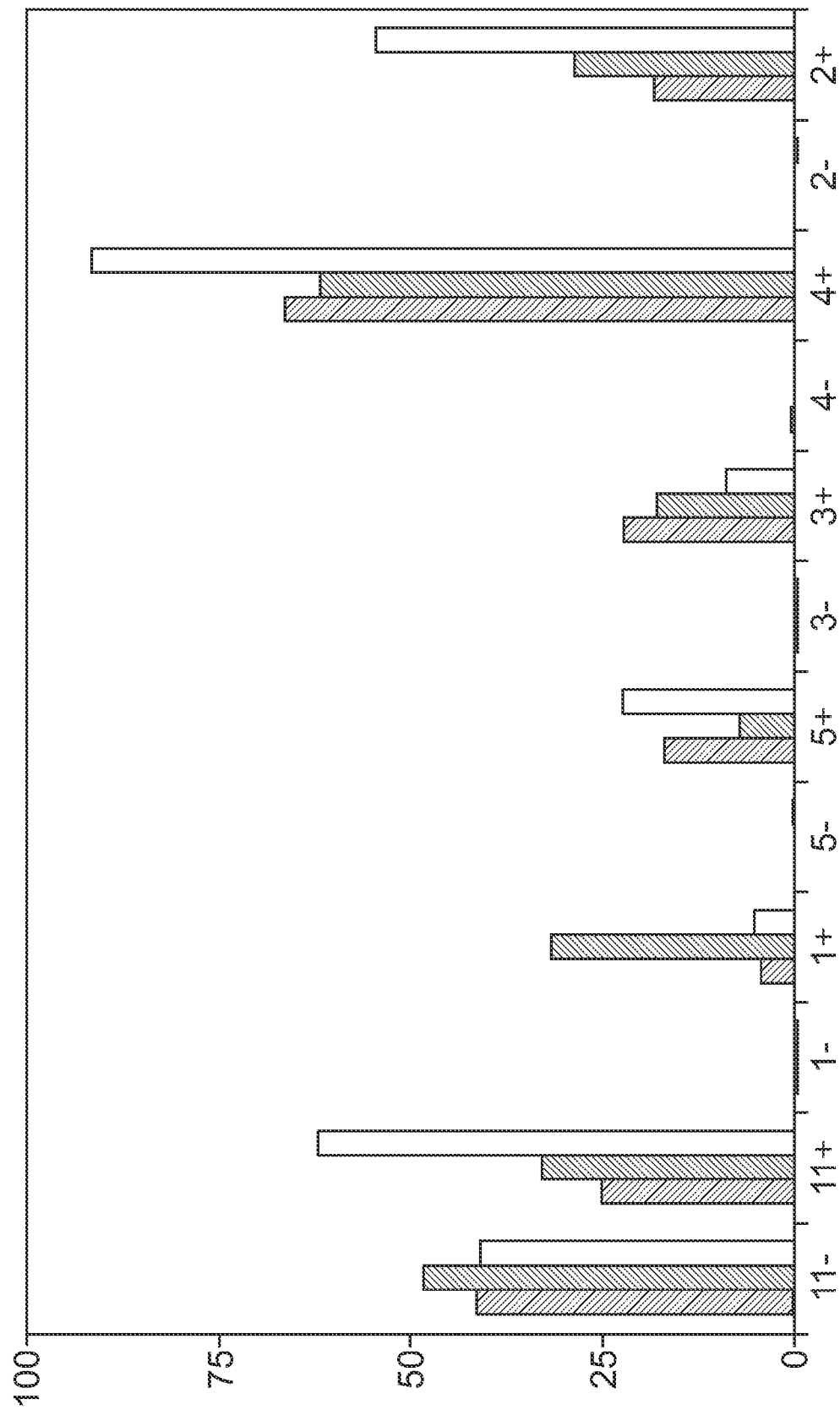
FIG. 5 shows muscle levels (µM) of compounds 24 hours after injection. The x-axis shows the compound number; + indicates adsorption to Al—H, whereas − indicated the absence of Al—H. Each bar represents a single animal, with 3 animals per group.

Muscle levels of compounds 1, 2, 3, 4, 5 & 13 are measured 24 hours after intramuscular injection (100 µg) in Balb/C mice (3 per group) in combination with protein antigens, with or without Al—H. Except for compound 13, the phospho-compounds are undetectable if injected without Al—H, but are readily detected if injected with Al—H (see FIG. 5). Compound 13 is poorly soluble in histidine buffer, pH 6.8, which explains its different behaviour. The soluble 'parent' compounds, without modifications to favour adsorption, are also cleared from muscle very rapidly.

Figure 24:
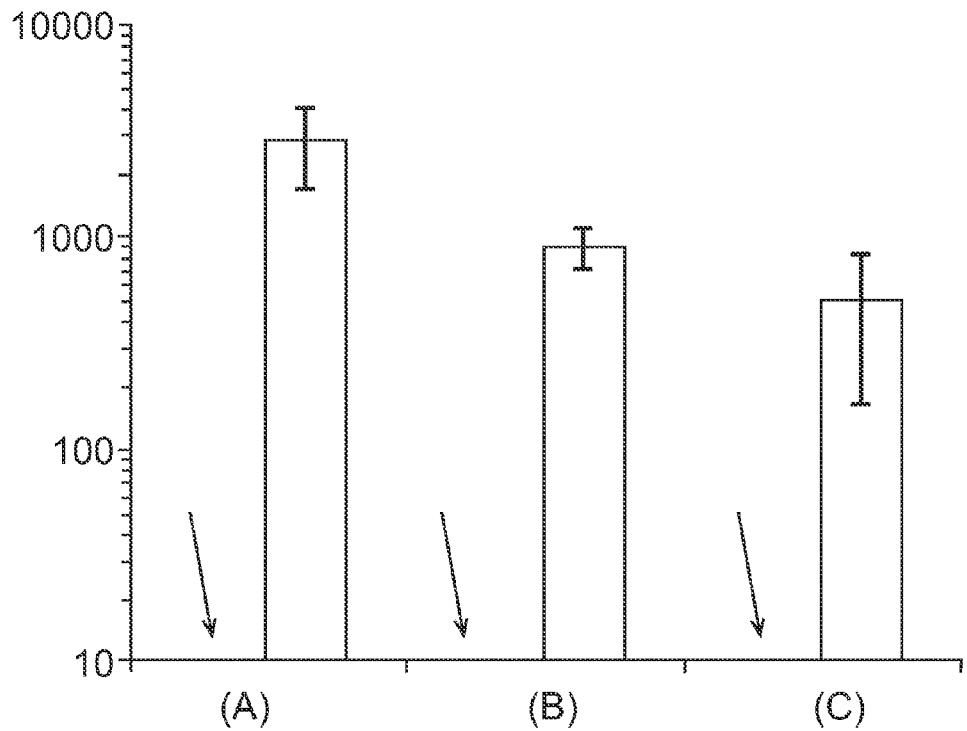
FIG. 24 shows muscle levels (nM in quadriceps) of compounds (A) 67 (B) 71 and (C) 68 after intramuscular injection of 100 µg compound 24 hours earlier when adsorbed to Al—H. Arrows show the absence of detectable levels for unadsorbed compounds.

Results from similar experiments with compounds 67, 68 and 71 are shown in FIG. 24; again, the compounds are undetectable 24 hours after injection in free form (arrows), but are readily detected if injected with Al—H. Similar results were obtained for compound 6, which again was undetectable in muscle after 24 hours, and also could not be detected in inguinal lymph nodes or in liver. Levels of compound in muscle 24 hours after injection for various compounds were as follows (nM):

|  | TLR7 | | | | | | TLR2 | | | |
| --- | --- | --- | --- | --- | --- | --- | --- | --- | --- | --- |
|  | 2 | 5 | 6 | 67 | 68 | 71 | 22 | 72 | 74 | 80 |
| Compound | 0 | 0 | 0 | 0 | 0 | 0 | 0 | 0 | 27843 | 5072 |
| +Al—H | 20393 | 4214 | 2773 | 2876 | 502 | 924 | 25344 | 14484 | 49027 | 47151 |

Thus for all tested compounds adsorption to Al—H retains higher levels of the soluble phosphonates at the local injection sites.

In summary, adsorption of these SMIPs to Al—H modifies their local and systemic post-delivery behaviour in vivo. Adsorption has been shown to: (i) increase cellular uptake of SMIPs; (ii) increase residence time of SMIPs at sites of intramuscular injection, where they can continue to exert an immunostimulatory effect; (iii) reduce levels of general B cell activation, thus advantageously minimising general and non-specific immunostimulation; (iv) decrease Cmax; and (v) modify serum exposure profiles, with the potential either to increase or decrease overall systemic exposure thus achieving useful in vivo properties as desired e.g. for widespread prophylactic immunisations, adsorption can be used to reduce systemic exposure and cytokine stimulation, or for emergency immunotherapeutic situations it can be used to increase systemic exposure. The use of adsorption to modify the in vivo behaviour of SMIPs in this way has not previously been reported.

Model of In Vivo Desorption

Figure 13:
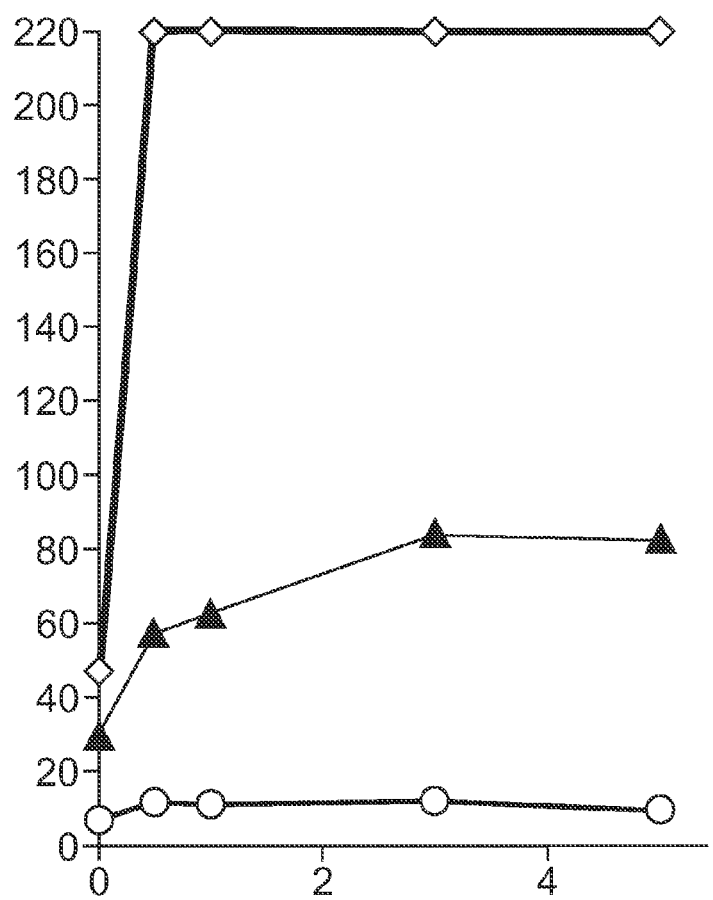
FIG. 13 shows the concentration (µM) of compound 3 over a period of 5 hours after incubation with SIF (♦), buffer (●) or a plasma/buffer mixture (▲).

It is known that antigens can desorb from aluminium salts after being exposed to interstitial or lymph fluids [89, 90]. Al—H-adsorbed phosphonate compounds were incubated at 37° C. with a histidine buffer, a mixture of plasma and a histidine buffer, or with a simulated interstitial fluid (SIF) and adsorption was followed for 5 hours. FIG. 13 shows an example desorption profile (compound 3). For six tested compounds the proportion of desorbed antigen after 5 hours was as follows:

| Compound | SIF | Plasma/His buff | His buff |
| --- | --- | --- | --- |
| 13* | 4% | 9% | 2% |
| 1 | 90% | 43% | 2% |
| 3 | 100% | 49% | 5% |
| 2 | 84% | 59% | 3% |
| 5 | 100% | 73% | 4% |
| 4 | 100% | 81% | 4% |

*Results with compound 13 were unreliable.

In histidine buffer alone, all phosphonates exhibit strong binding to Al—H, with only 2-6% being unbound after 5 hours. In plasma, however, the phosphonates quickly dissociate from Al—H, and dissociation was even more rapid in SIF. Moreover, in SIF the rate of dissociation qualitatively correlates with the systemic exposure of a compound as seen after intramuscular injection. Thus, for example, compounds 3 and 4 had the highest serum exposure and fastest dissociation in SIF.

Toxicology

There were no concerns following repeat-dose local tolerability and toxicity study in male rats for compound 2 adsorbed to Al—H. The formulation was not associated with body weight loss, elevation in body temperature or adverse clinical observations.

Effect of Adsorption on Immunogenicity—Meningococcus B

Reference 40 discloses a vaccine for serogroup B meningococcus ('MenB') made from three separate polypeptides ('5CVMB'). These polypeptides can adsorb to Al—H, and SDS-PAGE is used to check if this adsorption can still occur after adsorption of compound 1 to the Al—H.

Compound 1 is dissolved in 10 mM NaOH at 0.5 mg/ml final concentration, then combined with excess Al—H at a 1:6 weight ratio in the presence of 10 mM histidine (final concentration). The pH is adjusted to 9.2 and the mixture is gently agitated for 3 hours at room temperature, allowing the reaction to occur. The mixture was centrifuged at 5000 g for 10 minutes and the supernatant discarded. The pellet (Al—H with adsorbed compound 1) is resuspended in the initial buffer to obtain the starting concentration of Al—H. The pH was adjusted to 6.5. The modified Al—H is then used for the formulation with the MenB antigens. For comparison, antigens are also formulated in parallel with 'plain' Al—H.

Figure 6:
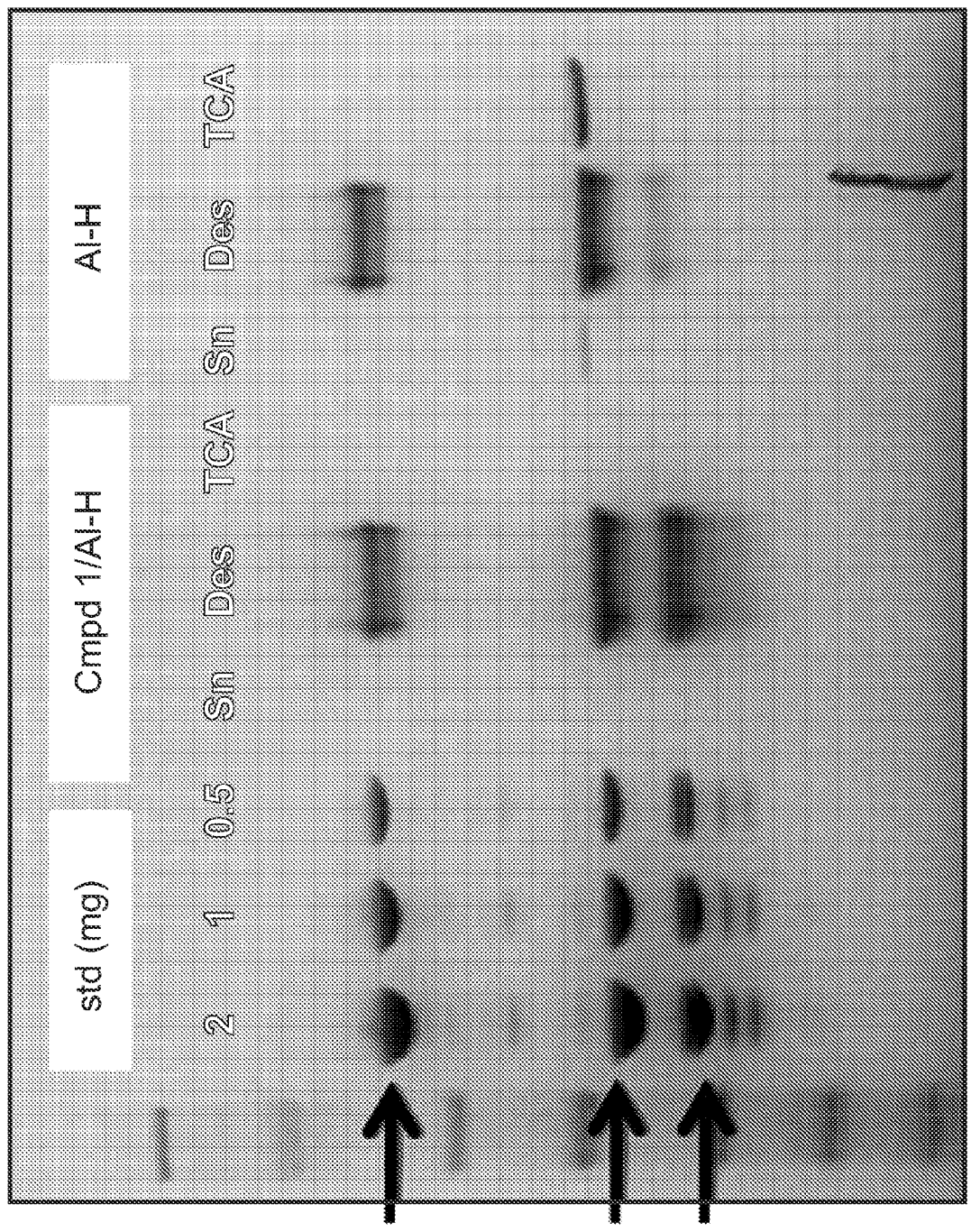
FIG. 6 shows SDS-PAGE of a mixture of MenB antigens. The lanes marked 'std' show purified antigen standards at three concentrations. Antigens were formulated with Al—H alone or Al—H to which compound 1 had been adsorbed. 'Sn' shows supernatant after adsorption; 'Des' shows supernatants after desorption treatment; 'TCA' shows supernatants after precipitation.

The formulated antigens are centrifuged and the supernatant is tested by SDS-PAGE for presence of the three polypeptides. In further tests, supernatants are treated with trichloroacetic acid (TCA) to precipitate proteins. In further tests, formulated antigens are treated with 0.5 M phosphate buffer prior to analysis, to desorb any adsorbed antigens. FIG. 6 shows SDS-PAGE of supernatants. Pre-adsorption of compound to the Al—H does not prevent adsorption of the MenB antigens. Further studies showed that antigen adsorption still occurred even with a 5-fold excess of TLR agonist.

Similar tests are performed with compounds 3 and 4. HPLC analysis shows that neither compound is observed in the supernatant after mixing with aluminium hydroxide, but they are recovered after desorption treatment with 0.5M $KH_2PO_4$. SDS-PAGE analysis of MenB antigen binding to Al—H after pre-adsorption with compound 3 or 4 again shows that the antigens are completely adsorbed.

Figure 7:
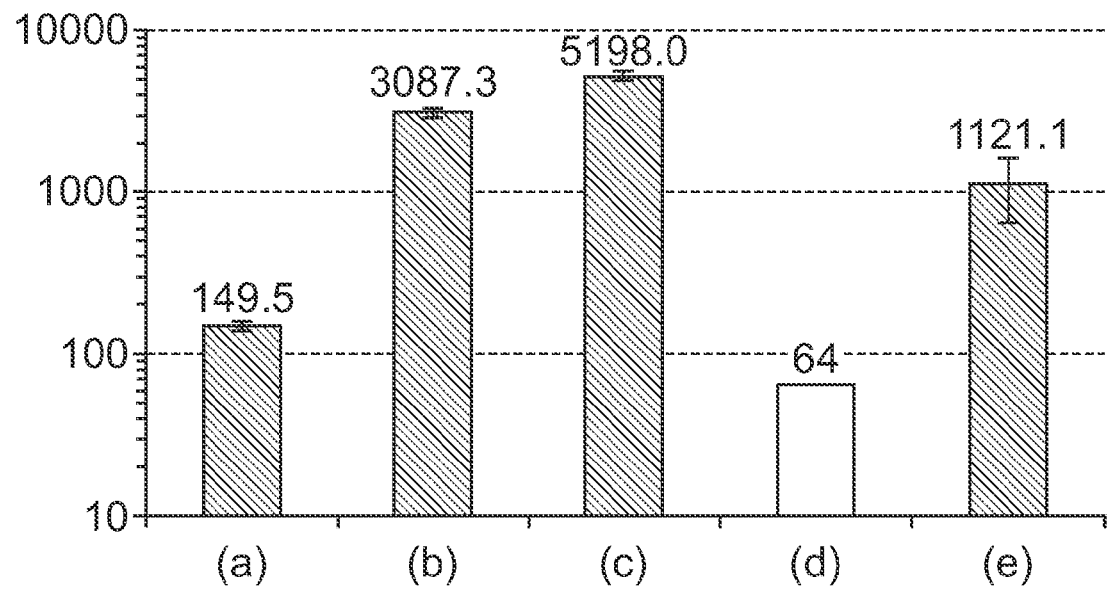
FIG. 7 shows SBA titers against strain NZ98 using 5CVMB formulated with (a) Al—H alone, (b) Al—H+25 µg compound 1, (c) Al—H+100 µg compound 1, (d) compound 1 alone, or (e) Al—H and MenB outer membrane vesicles.

The MenB antigens are tested for in vivo immunogenic potency using a serum bactericidal antibody (SBA) assay. FIG. 7 shows bactericidal titers against strain NZ98 of sera obtained after immunization with 5CVMB combined with (a) Al—H alone, (b) Al—H+25 µg compound 1, (c) Al—H+100 µg compound 1, (d) compound 1 alone, or (e) Al—H and MenB outer membrane vesicles. Pre-adsorption of compound 1 to Al—H gives a large increase in SBA titer, and much greater than would be expected based on results seen with compound 1 alone. Thus, although general stimulation of B cells is reduced by adsorption (see above), MenB-specific antibody responses are enhanced.

Figure 8:
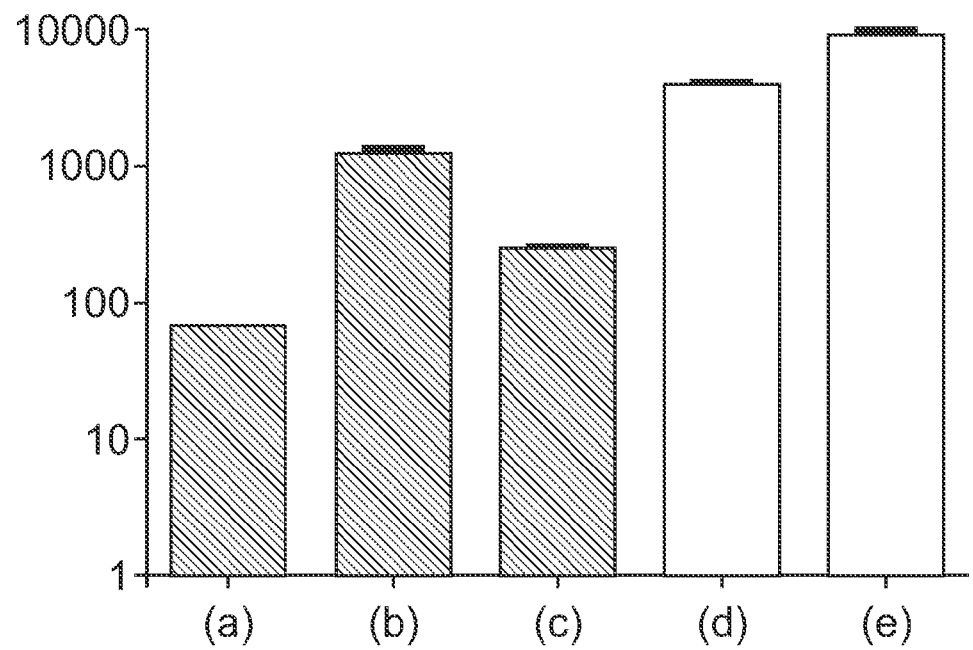
FIG. 8 shows SBA titers against NZ98 using 5CVMB formulated with (a) no adjuvant, (b) Al—H+OMV, (c) 100 µg compound 2, (d) 25 µg compound 2+Al—H, or (e) 100 µg compound 2+Al—H.
Figure 9:
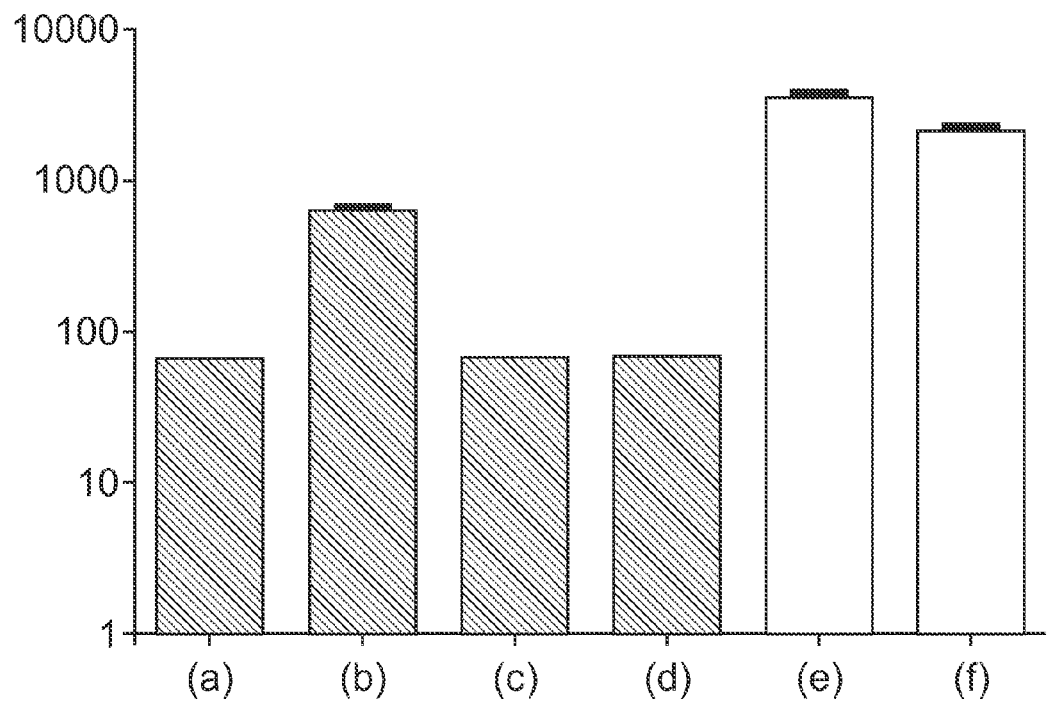
FIG. 9 shows SBA titers against NZ98 using 5CVMB formulated with (a) no adjuvant, (b) Al—H and vesicles, (c) 100 µg compound 5, (d) 25 µg compound 5 (e) 100 µg compound 5+Al—H, or (f) 25 µg compound 5+Al—H.

Similar effects are seen with other phospho-modified compounds of the invention. For instance, FIG. 8 shows results with compound 2, and FIG. 9 shows results with compound 5 (both sera tested against strain NZ98). These two compounds are selected for further evaluation.

Compound 2 is pre-adsorbed to Al—H to investigate strain coverage of sera obtained after immunization with a modified 5CVMB in which the GNA2091/1870 fusion protein is replaced by the '936-10A-10A' protein disclosed in ref. 91 (SEQ ID NO: 126 therein; SEQ ID NO: 4 herein). The following table shows titers against five different strains after formulating the three polypeptides with (a) Al—H alone, (b) Al—H+25 µg outer membrane vesicles, (c) Al—H with 100 µg of compound 2, (d) Al—H with 25 µg of compound 2, (e) Al—H with 5 µg of compound 2, or (f) Al—H+a particulate TLR9 agonist:

|     | MC58   | NZ98  | 961-5945 | UK355 | 599    |
|-----|--------|-------|----------|-------|--------|
| (a) | 16384  | 1024  | 16384    | 256   | 65536  |
| (b) | 32768  | 4096  | 8192     | 2048  | >65536 |
| (c) | >65536 | 16384 | 32768    | 4096  | >65536 |
| (d) | 32768  | 2048  | 16384    | 1024  | >65536 |
| (e) | >65536 | 4096  | 8192     | 2048  | >65536 |
| (f) | >65536 | 8192  | 16384    | 2048  | >65536 |

Thus compound 2 improves the strain coverage compared to Al—H alone.

With a wider panel of 17 strains the percentage coverage with titers >1024 or >4096 was as follows, with the best coverage seen using Al—H+compound 2:

|       | (a)   | (b)   | (c)   | (f)   |
|-------|-------|-------|-------|-------|
| >4096 | ~20%  | ~60%  | ~75%  | ~50%  |
| >1024 | ~45%  | ~80%  | >95%  | ~90%  |

The 5CVMB vaccine was also tested in CD-1 mice with TLR7 agonist compounds 6, 67, 68 & 71. The antigens were administered at days 0 & 14 with (a) buffer (b) the agonist compound (c) Al—H alone (d) the agonist compound+Al—H or (e) as a positive control for compound 6 only, resiquimod+Al—H. SBA titers at day 28 are as follows:

|    | (a) | (b) | (c) | (d)  | (e)  |
|----|-----|-----|-----|------|------|
| 6  | 64  | 282 | 256 | 4016 | 1033 |
| 67 | 64  | 64  | 244 | 949  | —    |
| 68 | 64  | —   | 244 | 404  | —    |
| 71 | 64  | 65  | 244 | 1653 | —    |

Thus the activity of all tested TLR7 agonist compounds is greatly enhanced by adsorption to Al—H (group (d) better than group (b) in all cases), and vice versa (group (d) better than group (c)).

In addition to modifying the in vivo pharmacokinetics and retention of SMIPs, in some cases adsorption to insoluble metal salts can thus improve immunostimulatory activity.

Effect of Adsorption on Immunogenicity—*Staphylococcus aureus*

The "Combo-1" vaccine from reference 39 includes a mixture of four polypeptides (EsxAB, Sta006, Sta011, and Hla-H35L) and this combination is effective for immunising against *S. aureus*. Reference 39 tested Combo-1 with an Al—H adjuvant, and it was decided to test Al—H in combination with adsorbed compound 2. Experiments used Balb/C mice (3 intramuscular injections) and considered IgG titers, T cell responses and protective efficacy.

FIG. 19 shows IgG titers against the individual polypeptides in Combo-1. For all four polypeptides the titer obtained using the Al—H/compound 2 adjuvant combination was higher than the titer obtained using Al—H alone (**, p<0.05). Similar results were seen using Al—H with 1, 5, 25 or 50 µg of compound 2.

To evaluate the quality of recall-specific T cell responses, spleen cells from the mice were stimulated with the Combo-1 polypeptides. Cytokine production in $CD4^+$ T helper cells was assessed by looking at cytokine release. The use of Al—H/compound 2 gave more antigen-specific $CD4^+$ T cells that 1.0 produce TNF-α, IL-2 and IFN-γ compared to immunisation with unadjuvanted antigens or with antigens adjuvanted with Al—H alone. The percentage of antigen-specific $CD4^+$ T cells that produce IL-4 and IL-13 was higher (although not statistically significant) when using Al—H compared to unadjuvanted Combo-1, but immunization using the Al—H/compound 2 combination reduced this effect at all doses except the lowest, indicating that the Th2-polarizing effect of Al—H was counterbalanced by the Th1-polarizing effect of the TLR7 agonist.

Protective efficacy against *S. aureus* was assessed using a sepsis model, monitored for 15 days after challenge with Newman strain. Results from two experiments with 10 µg of each polypeptide were pooled. The proportion of animals surviving after 15 days, and the median survival length, were:

| Antigen | Adjuvant | % survival | Survival days |
|---|---|---|---|
| — | — | 0 | 1 |
| — | Al-H | 4 | 1 |
| — | Al-H + 50 µg cmpd 2 | 12.5 | 1 |
| Combo-1 | — | 33.5 | 7 |
| Combo-1 | Al-H | 21 | 7.5 |
| Combo-1 | Al-H + 50 µg cmpd 2 | 97 | 15 |
| Combo-1 | Al-H + 25 µg cmpd 2 | 75 | 15 |
| Combo-1 | Al-H + 5 µg cmpd 2 | 67 | 15 |
| Combo-1 | Al-H + 1 µg cmpd 2 | 66.5 | 15 |

Survival was better, with statistical significance, when using the Al—H/compound 2 combination.

The positive effects on meningococcus B immunogenicity are therefore also seen with *S. aureus*.

Effect of Adsorption on Immunogenicity—Viral Antigens

Figure 15:
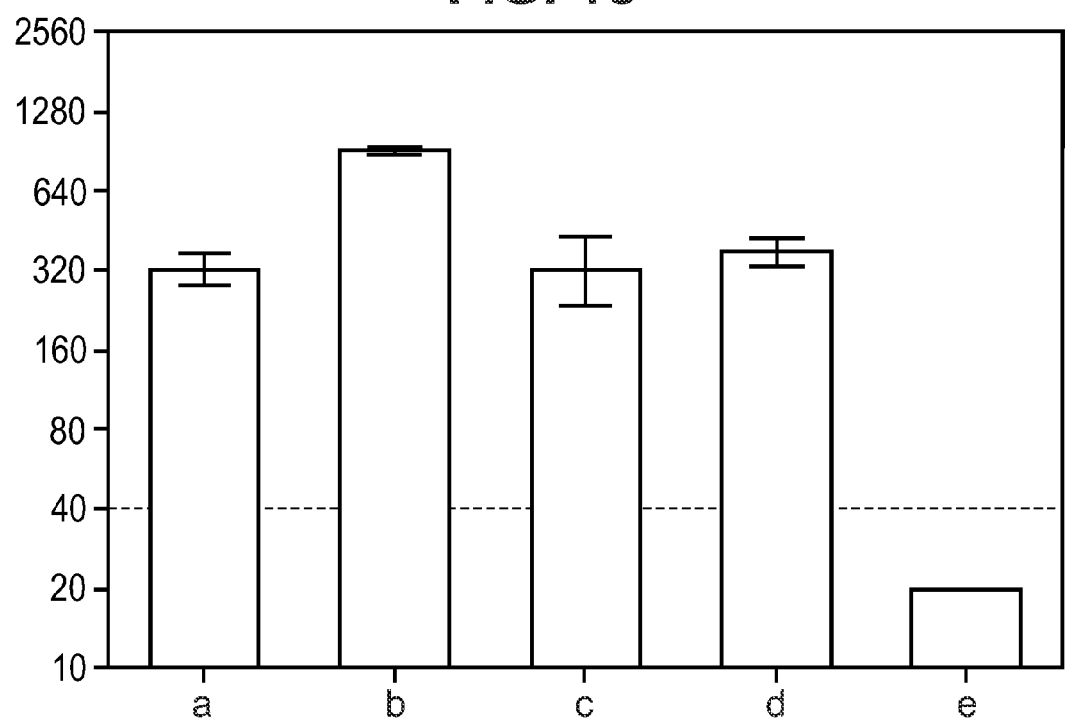
FIG. 15 shows neutralization titers against RSV in mice using RSV F/antigen formulated with (a) Al—H, (b) Al—H and 25 µg of compound 2, (c) Al—H and 25 µg of a different TLR4 agonist, (d) Al—H and a particulate TLR9 agonist consisting of an immunostimulatory oligonucleotide complexed with a polycationic oligopeptide, or (e) no adjuvant.
Figure 18:
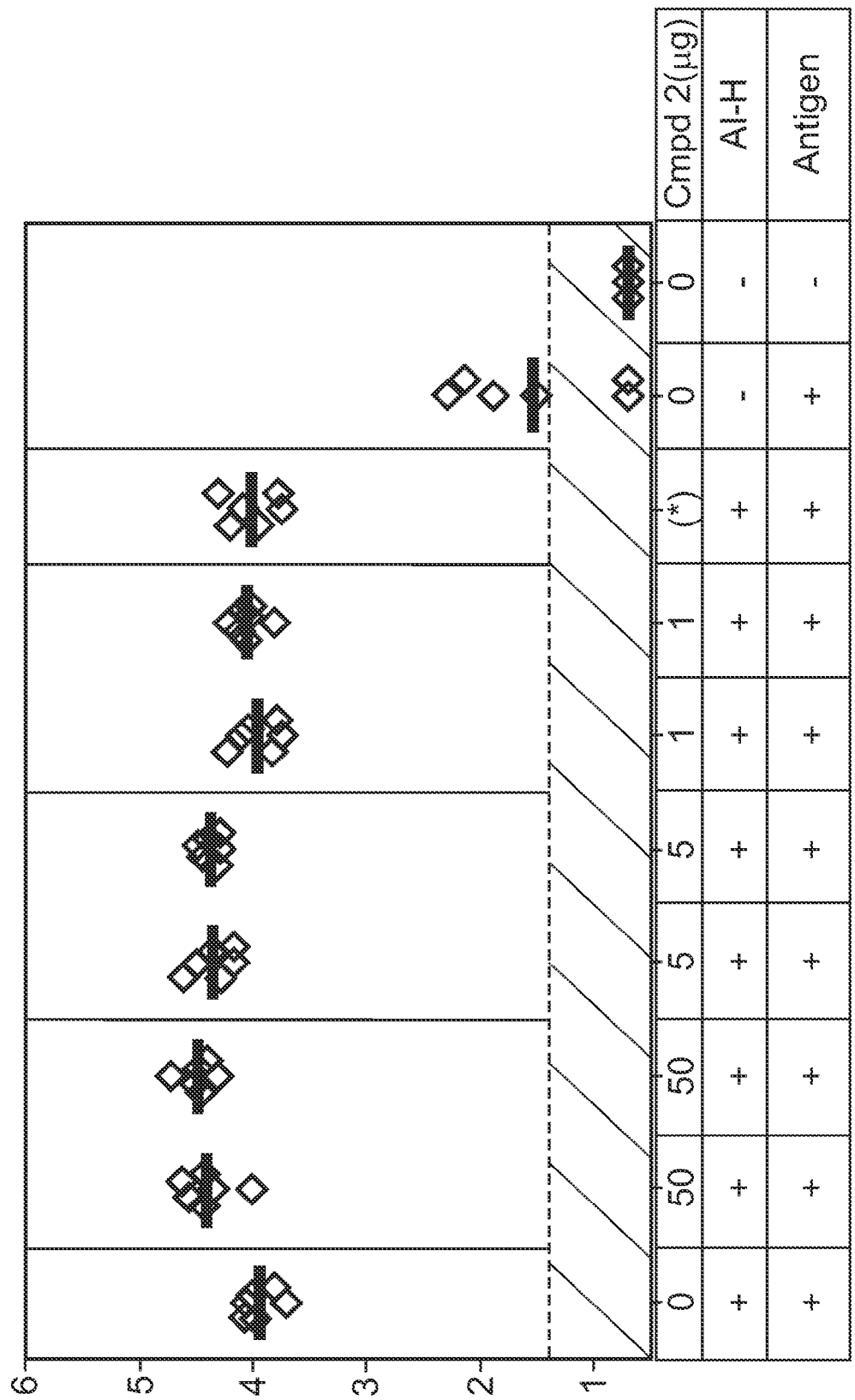
FIG. 18 shows F-specific IgG titers in mice using Al—H with compound 2 at the indicated amounts. The data marked as (*) used a particulate TLR9 agonist for comparison.
Figure 19A:
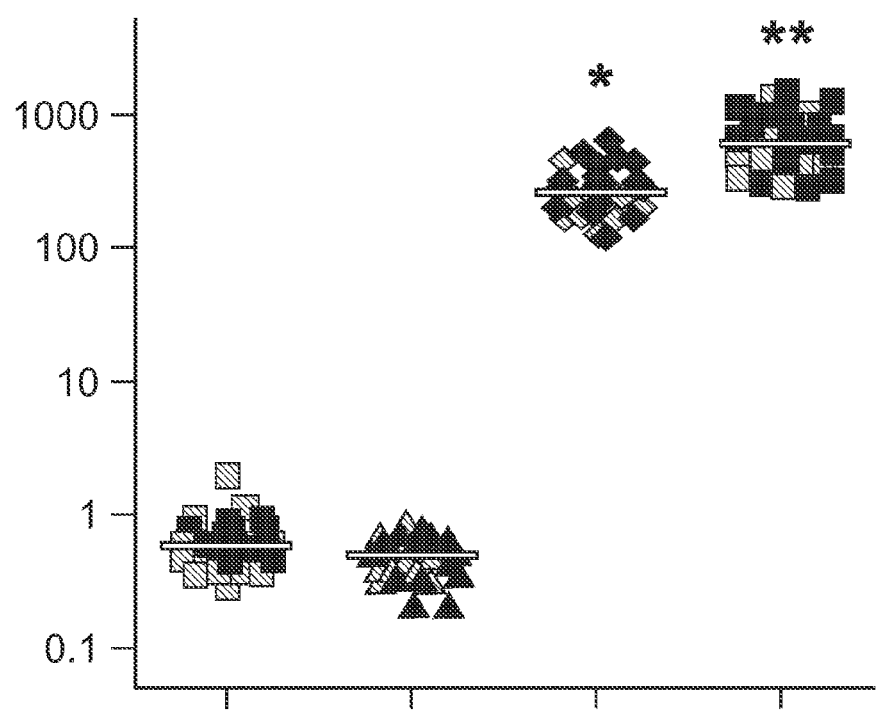
FIG. 19 shows IgG titers, after 3 intramuscular injections, against (A) Hla-H35L (B) EsxAB (C) Sta006 (D) Sta011. In each panel the four groups are, from left to right: Al—H adjuvant alone; Al—H+compound 2; Combo-1+Al—H; Combo-1+Al—H+compound 2. A * indicates a statistically significant difference (p<0.05) against adjuvant alone. A ** indicates a statistically significant difference (p<0.05) against Combo-1+Al—H.
Figure 19B:
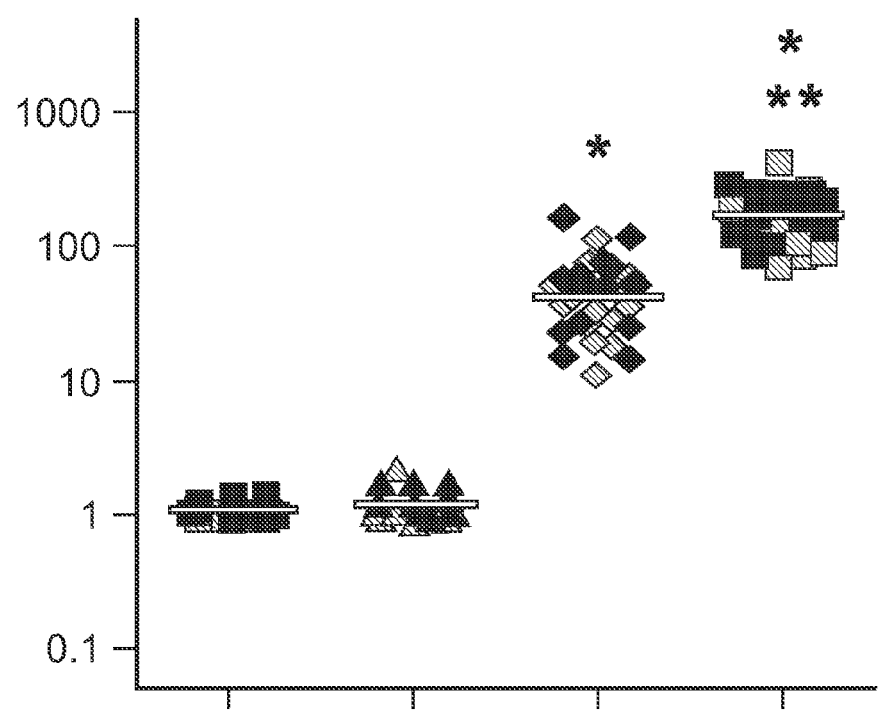
Figure 19C:
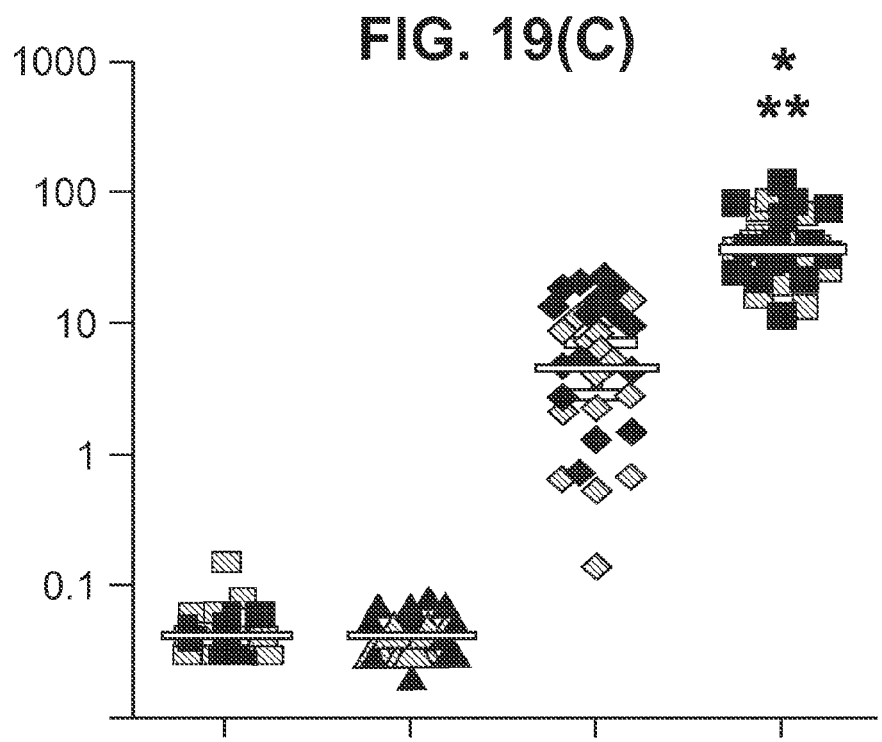
Figure 19D:
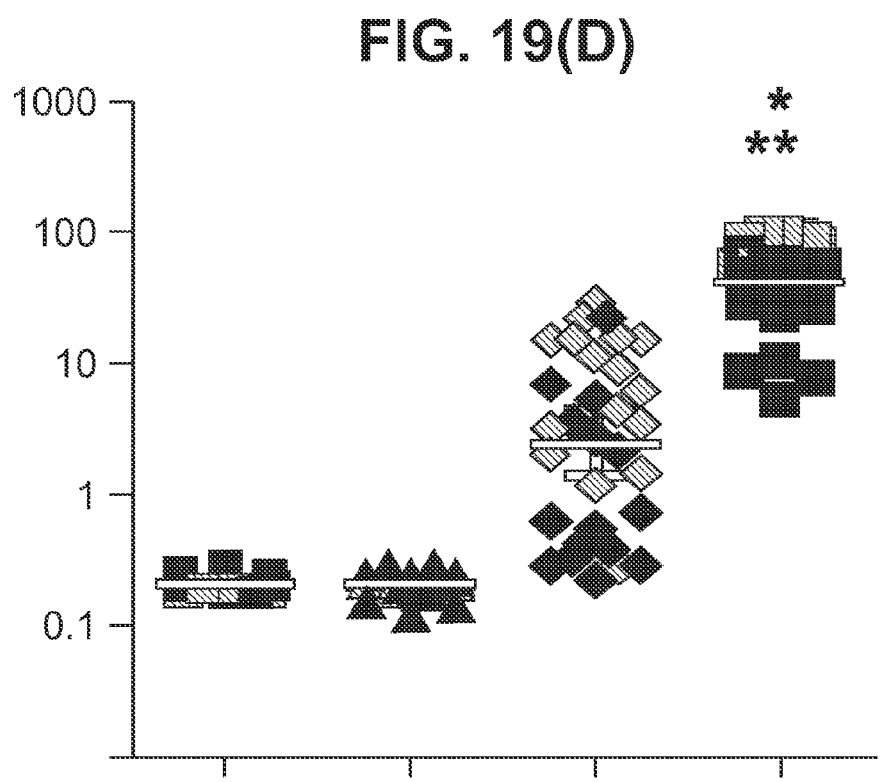

Trimeric F glycoprotein of respiratory syncytial virus (RSV) is formulated with various adjuvants, including compounds 2, 5 and example 161 from reference 4 (25 µg or 100 µg per dose), with or without Al—H. Balb/C mice (6 per group) are immunized at days 0 and 21 and immune responses are assessed at days 35 and 42. The formulation was well tolerated in various test animals. FIG. 18 shows F-specific IgG titers (GMT, 6 mice per group) 3 weeks after a single dose of 2 µg trimeric F protein. Neutralization titers at day 35 are shown in FIG. 15, including comparisons to other adjuvants. Compound 2 plus Al—H increased both total IgG titers and neutralization titers compared to Al—H alone, and the enhancement was higher than that observed for other TLR agonists.

TLR7 agonists disclosed above were also useful for enhancing the immunogenicity of HIV gp120 when adsorbed to Al—H and then administered to monkeys. Results were better than with Al—H alone.

Figure 26:
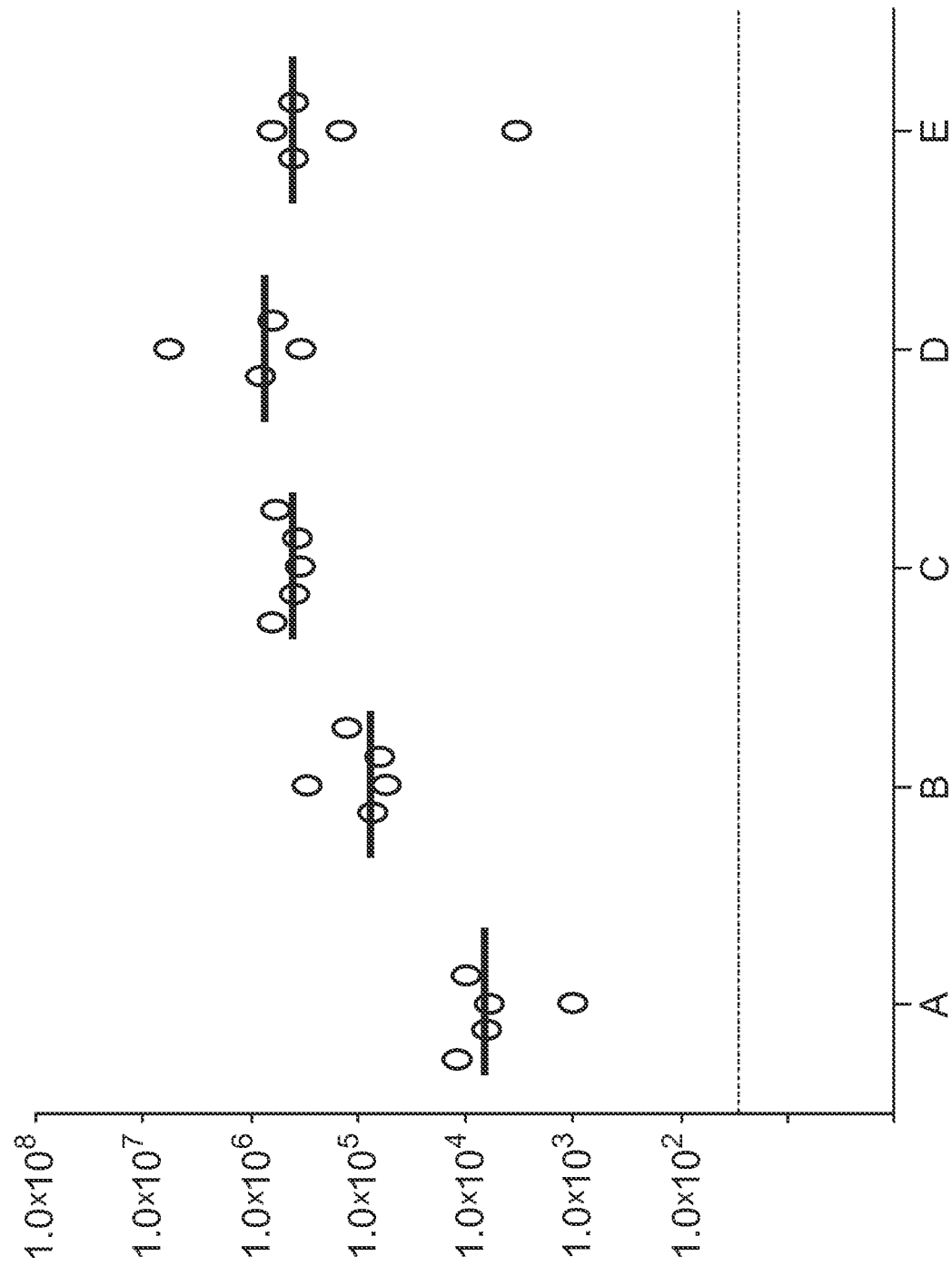
FIG. 26 shows gp140-specific IgG titers at day 35 after immunisations on days 0 & 21. Adjuvants were: (A) unadjuvanted; (B) Al—H; (C) Al—H+a TLR4 agonist; (D) compound 2 adsorbed to Al—H; (E) MF59 emulsion.

Compound 2 (10 µg/dose) was adsorbed to Al—H (100 µg Al$^{+++}$/dose) and tested as an adjuvant with o-gp140ΔV2 from South African HIV subtype C strain TV1. Immunisations used 101.1 g protein in BALB/c mice (5 per group) on days 0 & 21 (50 µl in a single quad muscle). Other adjuvants were also tested. FIG. 26 shows that the best results were obtained using compound 2 adsorbed to Al—H.

Figure 17A:
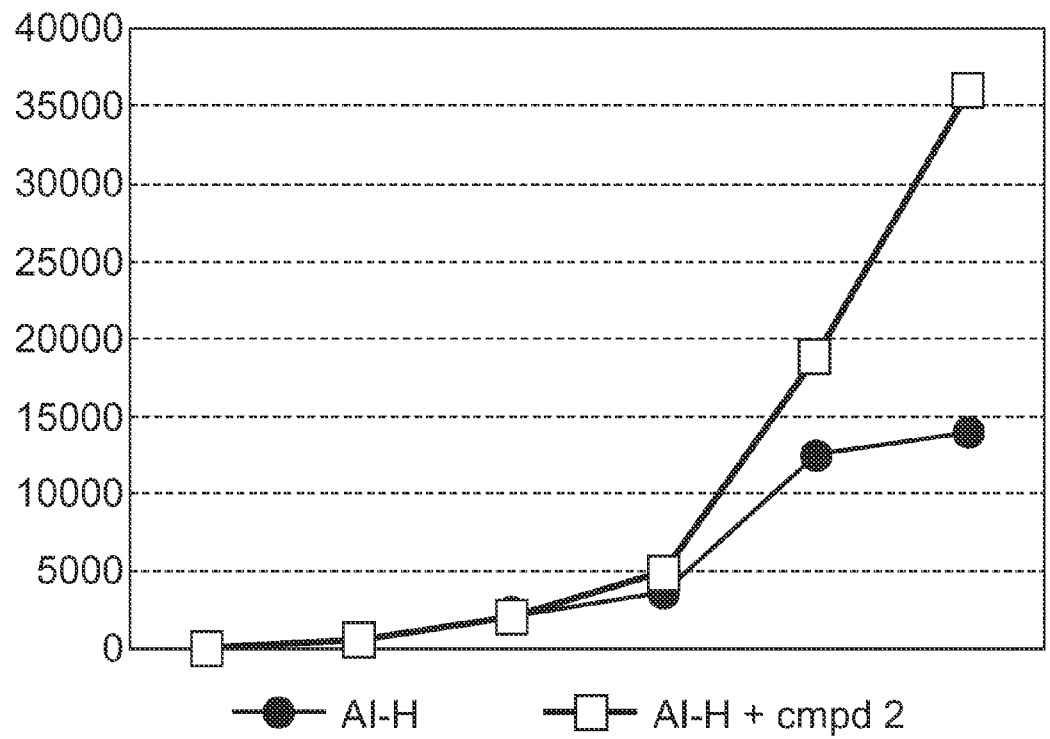
FIG. 17A shows total IgG titers at 6 time points after immunisation with influenza virus hemagglutinin adjuvanted with Al—H alone (circles) or Al—H+compound 2 (squares). The time points at 7, 11, 16 and 21 days after the first dose, then 7 & 14 days after the second dose.
Figure 17B:
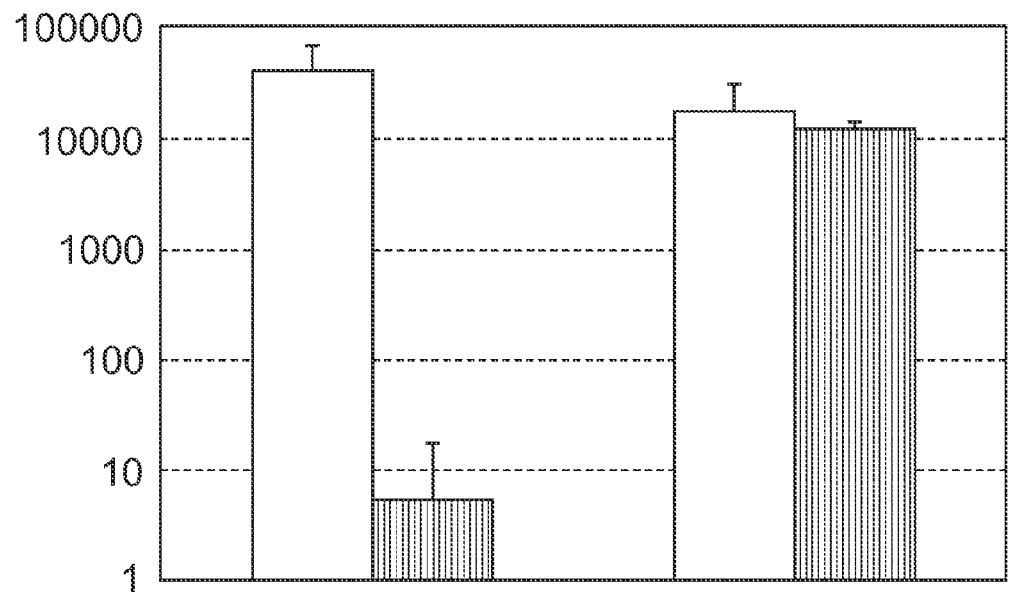
FIG. 17B shows IgG titers 14 days after the second dose. The left-hand pair of bars shows titers where the adjuvant was Al—H alone, whereas the right-hand pair of bars is in the Al—H/cmpd 2 group. In each pair the left-hand bar shows IgG1 titers and the right-hand bar shows IgG2a titers.

Al—H was used to adjuvant influenza virus hemagglutinin, with or without adsorbed compound 2. Animals received 2 doses of adjuvanted antigen. As shown in FIG. 17A, total IgG titers were similar in the two groups after the first dose, but after the second dose the presence of compound 2 led to higher titers. In addition, FIG. 17B shows that Al—H alone favoured an IgG1 isotype response (Th2-type) whereas the addition of compound 2 led to a balanced IgG1/IgG2a response (Th1/Th2).

The positive effects on immunogenicity with bacterial antigens are therefore also seen with viruses.

Comparison with Other Adjuvants

The INFANRIX HEXA™ product from GlaxoSmithKline contains ≥30 IU diphtheria toxoid, ≥40 IU tetanus toxoid, an acellular pertussis component (25/25/8 µg of PT/FHA/pertactin), 10 µg HBsAg, a trivalent IPV component (40/8/32 DU of types 1/2/3), and 10 µg Hib conjugate. The vaccine is presented as a 5-valent aqueous vaccine which is used to reconstitute the Hib conjugate from its lyophilised form, to give a 0.5 ml aqueous unit dose for human infants which contains 0.95 mg aluminium hydroxide and 1.45 mg aluminium phosphate.

To investigate alternative adjuvants a 6-valent mixture was adjuvanted with Al—H alone (2 mg/ml, in histidine buffer), with Al—H adsorbed to compound 1 (1 mg/ml), or with the MF59 oil-in-water emulsion (mixed at equal volume with antigens). An adjuvant-free control was also prepared. Antigen concentrations were as follows (per ml):

| DT | TT | PT | FHA | Pertactin |
|---|---|---|---|---|
| 36.9 Lf | 14.8 Lf | 36.9 µg | 36.9 µg | 11.8 µg |
| IPV Type 1 | IPV Type 2 | IPV Type 3 | HBsAg | Hib |
| 59.1 DU | 11.8 DU | 47.3 DU | 14.8 µg | 14.8 µg |

The same adjuvants were also used with a 3-valent D-T-Pa mixture (same concentrations).

Osmolarity and pH were measured after combining the components in order to ensure physiological acceptability. For all 3-valent compositions the pH was between 6.2 and 7.1 and osmolarity was between 290-320 mOsm/kg. For all 6-valent compositions the pH was between 5.5 and 6.8 and osmolarity was between 260-320 mOsm/kg. A buffer control had pH 7.3 and 276 mOsm/kg.

The integrity and immunogenicity of the combined antigens were also tested. None of antigens showed an altered analytical profile after being formulated as combinations i.e. the antigens and adjuvants are physically compatible together.

With Al—H alone all antigens adsorbed well to the adjuvant. With the complex of Al—H+compound 1 all antigens adsorbed well, except that pertactin was partially desorbed.

Mice (female Balb/c, 4 weeks old) were immunised intramuscularly with 100 µl of each composition (i.e. ⅕ human dose) at days 0 and 28. Sera were collected 14 days after each injection. After the second immunisation IgG antibody titers were as follows:

|  | No adjuvant | Al-H | MF59 | Al-H/cmpd1 | Infanrix-6 |
|---|---|---|---|---|---|
| 3-valent vaccines | | | | | |
| DT | 750 | 21626 | 15693 | 23395 | — |
| TT | 13120 | 17868 | 22458 | 23131 | — |
| Pertactin | 639 | 7209 | 10258 | 12857 | — |
| PT | 2501 | 8270 | 7212 | 9938 | — |
| FHA | 3982 | 12057 | 14098 | 23008 | — |
| 6-valent vaccine | | | | | |
| DT | 1751 | 18914 | 13982 | 23102 | 21581 |
| TT | 12729 | 16756 | 22229 | 23267 | 15998 |
| Pertactin | 333 | 6299 | 9363 | 5153 | 10809 |
| PT | 3069 | 3384 | 4823 | 6484 | 6052 |
| FHA | 4558 | 7206 | 16201 | 19383 | 11051 |
| Hib | 177 | 813 | 1266 | 2153 | 1269 |
| HBsAg | 1058 | 1598 | 2288 | 4501 | 1113 |

Thus for all of these antigens the inclusion of an adjuvant increased IgG antibody titers. The best titers were seen when using the complex of Al-h and compound 1. The next best were with MF59, which gave better results than aluminium hydroxide alone. The titers obtained using the adsorbed complex were better for all antigens than those seen with Infanrix Hexa, except for pertactin.

Furthermore, the data show that the good results achieved with the 3-valent vaccine are maintained even after IPV, Hib and HBsAg are added.

IgG responses were also investigated by subclass. For most of the antigens in the 6-valent vaccines the adjuvants had little effect on IgG1 titers, but they did increase IgG2a and IgG2b titers. The best IgG2a and IgG2b titers were obtained with the adsorbed complex, and then with MF59.

The increased titers seen with the complex compared with Al—H alone, or with the mixture of aluminium salts seen in Infanrix Hexa™, mean that the total amount of aluminium per dose can be reduced while maintaining enhancement of immune responses.

Reduction of Antigen Doses

Experiments were designed to investigate whether the adjuvant complex could be used to reduce the amount of antigen per dose. 10-fold, 50-fold and 100-fold dilutions (relative to human dosing i.e. to deliver 1 µg, 0.2 µg or 0.1 µg HBsAg to each mouse per 100 µl dose) of the 6-valent antigen combinations were made while adjuvant concentration was maintained.

For all 6-valent compositions the pH was between 6.1 and 7.0 and osmolarity was between 275-320 mOsm/kg. A buffer control had pH 7.3 and 285 mOsm/kg.

Mice were immunised in the same way as discussed above. Total serum IgG titers after 2 immunisations were as follows:

|  | No adjuvant | | | Al—H | | | MF59 | | | Al—H + cmpnd 1 | | |
| --- | --- | --- | --- | --- | --- | --- | --- | --- | --- | --- | --- | --- |
|  | 1/10 | 1/50 | 1/100 | 1/10 | 1/50 | 1/100 | 1/10 | 1/50 | 1/100 | 1/10 | 1/50 | 1/100 |
| DT | 459 | 2043 | 137 | 18357 | 13106 | 7541 | 17431 | 6003 | 8736 | 21913 | 16807 | 13724 |
| TT | 7602 | 7929 | 1700 | 17595 | 9664 | 5531 | 22791 | 12062 | 13015 | 23570 | 12237 | 13183 |
| Pertactin | 827 | 2154 | 341 | 10880 | 8135 | 4181 | 17159 | 7288 | 10591 | 17098 | 10748 | 8952 |
| PT | 3612 | 5645 | 2129 | 5287 | 3266 | 1068 | 7200 | 3659 | 5493 | 9051 | 4203 | 2717 |
| FHA | 2305 | 4161 | 101 | 8997 | 4471 | 1442 | 19197 | 5179 | 4492 | 22151 | 8293 | 3252 |
| Hib | 171 | 352 | 109 | 1380 | 796 | 251 | 3147 | 573 | 2415 | 3056 | 1440 | 1815 |
| HBsAg | 525 | 412 | 129 | 1034 | 685 | 226 | 4885 | 1103 | 1983 | 5270 | 1526 | 950 |

Thus the presence of adjuvants allowed a dose reduction of 5-fold or 10-fold while maintaining IgG titers which are comparable or higher to unadjuvanted antigens. MF59 and the adsorbed complex in particular are useful for dose sparing of antigens in this manner.

Adjuvant Dosing

With the 100-fold antigen dilution the amount of adjuvant was also reduced. The complex of Al—H and compound 1 was prepared at 3 strengths having 2 mg/ml Al—H with either 5 µg, 25 µg or 100 µg of compound 1 per dose. For comparison a 1:100 antigen dose was tested in unadjuvanted form or with Al—H alone. A 1:100 dilution of INFANRIX HEXA was also used for comparison.

For all 6-valent compositions the pH was between 6.2 and 7.3 and osmolarity was between 270-320 mOsm/kg. A buffer control had pH 7.3 and 280 mOsm/kg.

Mice were immunised as before. Total serum IgG titers after 2 immunisations were as follows:

|  | No adjuvant | Infanrix Hexa | Al—H | Al—H + compound 1 | | |
| --- | --- | --- | --- | --- | --- | --- |
|  |  |  |  | 100 | 25 | 5 |
| DT | 584 | 6282 | 10849 | 21571 | 20865 | 11788 |
| TT | 3426 | 5415 | 6857 | 16041 | 15124 | 6236 |
| Pertactin | 48 | 3017 | 6053 | 6158 | 6697 | 3815 |

|  | No adjuvant | Infanrix Hexa | Al—H | Al—H + compound 1 | | |
| --- | --- | --- | --- | --- | --- | --- |
|  |  |  |  | 100 | 25 | 5 |
| PT | 3351 | 1751 | 2699 | 2476 | 2696 | 3079 |
| FHA | 262 | 7886 | 5626 | 7369 | 8634 | 6120 |
| Hib | 126 | 109 | 310 | 936 | 792 | 390 |
| HBsAg | 88 | 240 | 369 | 4062 | 2308 | 1154 |

Thus lower amounts of the complex still retain good adjuvanticity and can induce higher IgG antibody titers than those induced by unadjuvanted 6-valent antigen formulations. By reducing the amount of adjuvant, while maintaining immunological efficacy, the safety profile of a vaccine can be improved which is particularly important in pediatric settings.

Adjuvant Dilution

Compound 2 was adsorbed to Al—H as disclosed above. This adsorbed material was then mixed with plain Al—H. Flow cytometry showed a shift of fluorescence for the entire Al—H population, indicating redistribution of the adsorbed compound onto the new Al—H.

To study the potential for redistribution a two-chamber experiment was prepared. The two chambers were separated by a membrane with a 8-10 kDa cutoff. In a control experiment Al—H was placed in chamber 1 and the same volume of PBS was placed in chamber 2. No leakage of Al—H from chamber 1 into chamber 2 was observed. In the test experiment compound 2+Al—H was placed in chamber 1 and the same volume of Al—H was placed in chamber 2. Flow cytometry, based on the intrinsic fluorescence of compound 2, showed that the compound had crossed from chamber 1 to chamber 2.

Similar experiments were performed with phosphorylated hexaacyl disaccharide, a synthetic analog of monophosphoryl lipid A (MPL), using NMR. The experiments showed that MPL can pass through the membrane from chamber 1, and adsorb to Al—H in chamber 2.

Thus a bulk mixture of Al—H and an adsorbed SMIP can be prepared at a high SMIP concentration, and this bulk can be diluted with plain Al—H to give a desired SMIP strength. This arrangement can simplify manufacture of several different strengths of day-to-day adjuvant from a single bulk.

Extemporaneous Mixing of Antigen and Adjuvant

The modified 5CVMB combination was prepared in lyophilised form [92] with 10% sucrose, 3.84 mg/ml NaCl and 10 mM phosphate buffer (pH 7.0). This material was reconstituted with an aqueous adjuvant component with 500 µg/ml of compound 2, 3 mg/ml Al—H, 2% sucrose, 6.25 mg/ml NaCl and 10 mM histidine buffer (pH 6.3).

This material was compared to an aqueous formulation of the same materials (500 µg/ml compound 2, 10 mM histidine buffer pH 6.3, 6.25 mg/ml NaCl, 2% sucrose, 3 mg/ml Al—H).

The TLR7 agonist remained adsorbed to Al—H after mixing with the lyophilised antigens.

Antigen adsorption was checked after mixing (time 0) and after 24 hours of storage at 2-8° C. or at room temperature. Antigen adsorption was comparable in the lyophilised/reconstituted formulation and in the fully-aqueous formulation. Both formulations were stable for 24 hours.

Thus antigens and adjuvant can be stored separately for extemporaneous mixing at the point of use.

It will be understood that the invention has been described by way of example only and modifications may be made whilst remaining within the scope and spirit of the invention.

REFERENCES

[1] U.S. Pat. No. 4,666,886.
[2] WO2009/118296.
[3] WO2008/005555.
[4] WO2009/111337.
[5] WO2009/067081.
[6] WO2007/040840.
[7] WO2010/014913.
[8] Burrell et al. (1999) *Vaccine* 17:2599-603.
[9] PCT/US2011/029661.
[10] WO2011/027222.
[11] WO2007/034917.
[12] WO2007/034173.
[13] WO2008/114817.
[14] US2009/0105212.
[15] US2009/0118263.
[16] US2009/0143400.
[17] US2009/0192153.
[18] WO2007/093901.
[19] WO2009/019553.
[20] US2009/0221631.
[21] WO2008/004948.
[22] WO2008/135791.
[23] US2009/0099216.
[24] US2009/0202484.
[25] WO2008/101867.
[26] WO2010/077613.
[27] US2010/0143301.
[28] Iyer et al. (2004) *Vaccine* 22:1475-9.
[29] Morefield et al. (2005) *Vaccine* 23:1502-6.
[30] Levesque & de Alwis (2005) *Human Vaccines* 1:70-3.
[31] Romero Méndez et al. (2007) *Vaccine* 25:825-33.
[32] *Vaccine Design* . . . (1995) eds. Powell & Newman. ISBN: 030644867X. Plenum.
[33] Clausi et al. (2008) *J Pharm Sci* DOI 10.1002/jps.21390.
[34] Treanor et al. (1996) *J Infect Dis* 173:1467-70.
[35] Keitel et al. (1996) *Clin Diagn Lab Immunol* 3:507-10.
[36] WO03/097091.
[37] Cassone & Torosantucci (2006) *Expert Rev Vaccines* 5:859-67.
[38] WO2010/140119.
[39] WO2010/119343.
[40] Giuliani et al. (2006) *Proc Natl Acad Sci USA*. 103: 10834-9.
[41] WO95/27787.
[42] WO03/010317.
[43] WO2007/110700.
[44] WO2006/138004.
[45] WO2005/084306.
[46] WO2005/002619.
[47] WO03/049762.
[48] WO02/02606.
[49] WO00/37494.
[50] WO2008/020330.
[51] WO2006/091517.
[52] WO2006/089264.
[53] Covacci & Rappuoli (2000) *J. Exp. Med.* 19:587-592.
[54] WO93/18150.
[55] Covacci et al. (1993) *Proc. Natl. Acad. Sci. USA* 90:5791-5795.
[56] Tummuru et al. (1994) *Infect. Immun.* 61:1799-1809.
[57] Marchetti et al. (1998) *Vaccine* 16:33-37.
[58] Telford et al. (1994) *J. Exp. Med.* 179:1653-1658.
[59] Evans et al. (1995) *Gene* 153:123-127.
[60] WO96/01272 & WO96/01273, especially SEQ ID NO:6.
[61] WO97/25429.
[62] Rappuoli et al. (1991) *TIBTECH* 9:232-238.
[63] Nencioni et al. (1991) *Infect Immun.* 59(2): 625-30.
[64] Dasarai et al. (2011) *J Gen Virol* PMID: 21307228.
[65] Zhang et al. (2001) *J. Biol. Chem.* 276:39577-85.
[66] Earl et al. (2001) *J Virol* 75:645-53.
[67] Barnett et al. (2001) *J Virol* 75:5526-40.
[68] *MMWR Morb Mortal Wkly Rep* 1998 Jan. 16; 47(1):12, 19.
[69] Harper et al. (2004) *Lancet* 364(9447):1757-65.
[70] U.S. Pat. No. 6,699,474.
[71] WO2007/060548.
[72] WO2010/144734.
[73] WO2004/032958.
[74] Rosenberg et al. (2010) *J Immunol* 184:136.20.
[75] WO2010/003009.
[76] WO2009/081172.
[77] *Remington: The Science and Practice of Pharmacy* (Gennaro, 2000; 20th edition, ISBN: 0683306472)
[78] De Libero et al, *Nature Reviews Immunology*, 2005, 5: 485-496.
[79] U.S. Pat. No. 5,936,076.
[80] Oki et al, *J. Clin. Investig.*, 113: 1631-1640.
[81] US2005/0192248.
[82] Yang et al, *Angew. Chem. Int. Ed.*, 2004, 43: 3818-3822.
[83] WO2008/047174.
[84] WO2008/047249.
[85] WO2005/102049.
[86] Goff et al, *J. Am. Chem., Soc.*, 2004, 126: 13602-13603.
[87] WO03/105769.
[88] US2011/0053893.
[89] Chang et al. (2001) *Vaccine* 19:2884-9.
[90] Shi et al. (2002) *Vaccine* 20:80-5.
[91] WO2011/024072.
[92] WO2009/050586.

The invention claimed is:

1. A composition, comprising a TLR7 agonist of formula (C) and an insoluble metal salt, wherein at least 50% by mass of the TLR7 agonist of formula (C) is adsorbed to the metal salt, and wherein formula (C) is:

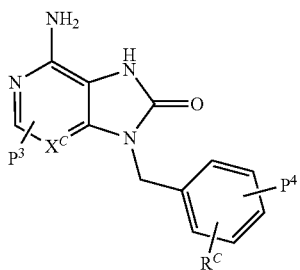

(C)

wherein:
$P^3$ is selected from H, $C_1$-$C_6$alkyl, $CF_3$, $-((CH_2)_pO)_q(CH_2)_pO_s-$ and $-Y$-$L$-$X$-$P(O)(OR^X)(OR^Y)$; and $P^4$ is selected from H, $C_1$-$C_6$alkyl, $-C_1$-$C_6$alkylaryl and $-Y$-$L$-$X$-$P(O)(OR^X)(OR^Y)$; with the proviso that at least one of $P^3$ and $P^4$ is $-Y$-$L$-$X$-$P(O)(OR^X)(OR^Y)$;
$R^X$ and $R^Y$ are independently selected from H and $C_1$-$C_6$alkyl;
$R^C$ is selected from H and $C_1$-$C_6$alkyl;
$X^C$ is selected from CH and N;

X is selected from a covalent bond, O and NH;
Y is selected from a covalent bond, O, C(O), S and NH;
L is selected from, a covalent bond, $C_1$-$C_6$alkylene, $C_1$-$C_6$alkenylene, arylene, heteroarylene, $C_1$-$C_6$alkyleneoxy and $-((CH_2)_pO)_q(CH_2)_p-$ each optionally substituted with 1 to 4 substituents independently selected from halo, OH, $C_1$-$C_4$alkyl, $-OP(O)(OH)_2$ and $-P(O)(OH)_2$;
each p is independently selected from 1, 2, 3, 4, 5 and 6;
q is selected from 1, 2, 3 and 4; and
s is selected from 0 and 1.

2. The composition of claim 1, wherein the compound of formula (C) is one of the following compounds:

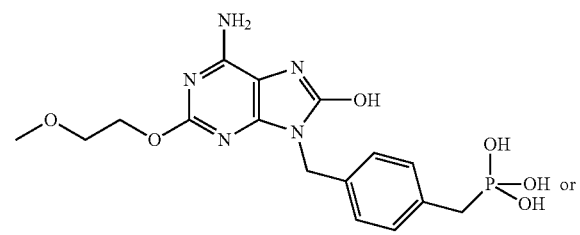

-continued

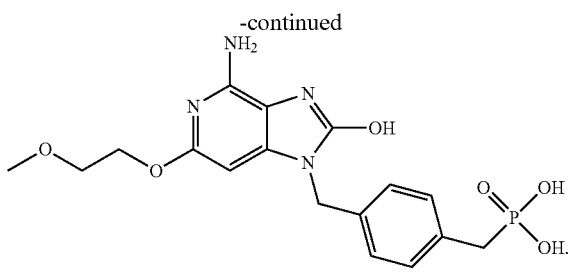

3. The composition of claim 1, wherein $P^3$ is selected from $C_1$-$C_6$alkyl, $CF_3$, —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is CH; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is 1 or 2.

4. The composition of claim 1, wherein $P^3$ is selected from $C_1$-$C_6$alkyl, $CF_3$, —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is N; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

5. The composition of claim 1, wherein the compound of formula (C) is not a compound in which $P^4$ is —Y-L-X—P(O)(OR$^X$)(OR$^Y$).

6. The composition of claim 1, wherein $P^4$ is selected from H, $C_1$-$C_6$alkyl, —$C_1$-$C_6$alkylaryl.

7. The composition of claim 1, wherein X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

8. The composition of claim 1, wherein X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

9. The composition of claim 1, wherein the compound of formula (C) has a structure according to formula (C'), shown below:

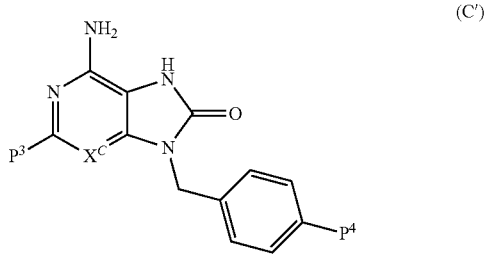

(C')

wherein:
$P^3$ is selected from H, $C_1$-$C_6$alkyl, $CF_3$, —$((CH_2)_pO)_q(CH_2)_pO_s$— and —Y-L-X—P(O)(OR$^X$)(OR$^Y$); and $P^4$ is selected from H, $C_1$-$C_6$alkyl, —$C_1$-$C_6$alkylaryl and —Y-L-X—P(O)(OR$^X$)(OR$^Y$); with the proviso that at least one of $P^3$ and $P^4$ is —Y-L-X—P(O)(OR$^X$)(OR$^Y$);
$R^X$ and $R^Y$ are independently selected from H and $C_1$-$C_6$alkyl;
$X^C$ is selected from CH and N;
X is selected from a covalent bond, O and NH;
Y is selected from a covalent bond, O, C(O), S and NH;
L is selected from a covalent bond, $C_1$-$C_6$alkylene, $C_1$-$C_6$alkenylene, arylene, heteroarylene, $C_1$-$C_6$alkyleneoxy and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$;
each p is independently selected from 1, 2, 3, 4, 5 and 6;
q is selected from 1, 2, 3 and 4; and
s is selected from 0 and 1.

10. The composition of claim 9, wherein $P^3$ is selected from $C_1$-$C_6$alkyl, $CF_3$, —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is CH; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is 1 or 2.

11. The composition of claim 9, wherein $P^3$ is selected from $C_1$-$C_6$alkyl, $CF_3$, —$((CH_2)_pO)_q(CH_2)_pO_s$— and —Y-L-X—P(O)(OR$^X$)(OR$^Y$); $P^4$ is selected from —$C_1$-$C_6$alkylaryl and —Y-L-X—P(O)(OR$^X$)(OR$^Y$); $X^C$ is N; X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; q is selected from 1 and 2.

12. The TLR7 agonist as claimed in claim 9, selected from formulae (D) or (D'), wherein $P^5$ is selected from $C_1$-$C_6$alkyl, and —Y-L-X—P(O)(OR$^X$)(OR$^Y$).

13. The TLR7 agonist as claimed in claim 9, selected from formulae (E) or (E'), wherein $X^E$ is $CH_2$, $P^8$ is $C_1$-$C_6$alkoxy optionally substituted with —Y-L-X—P(O)(OR$^X$)(OR$^Y$).

14. The TLR7 agonist as claimed in claim 9, selected from formula (E) or (E'), wherein $P^9$ is —NH$C_1$-$C_6$alkyl optionally substituted with OH and $C_1$-$C_6$alkyl, and —Y-L-X—P(O)(OR$^X$)(OR$^Y$).

15. The composition of claim 9, selected from formulae (C) or (C'), which is not a compound in which $P^4$ is —Y-L-X—P(O)(OR$^X$)(OR$^Y$).

16. The composition of claim 9, wherein $P^4$ is selected from H, $C_1$-$C_6$alkyl, —$C_1$-$C_6$alkylaryl.

17. The composition of claim 9, wherein X is O; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

18. The composition of claim 9, wherein X is a covalent bond; L is selected from $C_1$-$C_6$alkylene and —$((CH_2)_pO)_q(CH_2)_p$— each optionally substituted with 1 to 4 substituents independently selected from halo, OH, $C_1$-$C_4$alkyl, —OP(O)(OH)$_2$ and —P(O)(OH)$_2$; each p is independently selected from 1, 2 and 3; and q is selected from 1 and 2.

* * * * *

SEQUENCE LISTING

<160> NUMBER OF SEQ ID NOS: 5

<210> SEQ ID NO 1
<211> LENGTH: 327
<212> TYPE: PRT

<213> ORGANISM: Artificial Sequence
<220> FEATURE:
<223> OTHER INFORMATION: Immunogen for Neisseria meningitidis

<400> SEQUENCE: 1

```
Ala Thr Asn Asp Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
        35                  40                  45

Thr Ala Ala Asp Val Glu Ala Asp Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325
```

<210> SEQ ID NO 2
<211> LENGTH: 644
<212> TYPE: PRT
<213> ORGANISM: Artificial Sequence
<220> FEATURE:
<223> OTHER INFORMATION: Immunogen for Neisseria meningitidis -
      fusion protein

<400> SEQUENCE: 2

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
                100                 105                 110

Gly Glu Ser Glu Gln Pro Ala Asn Gln Pro Asp Met Ala Asn Thr Ala
            115                 120                 125

Asp Gly Met Gln Gly Asp Pro Ser Ala Gly Gly Glu Asn Ala Gly
        130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Ser Ala Arg Ser Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
```

```
                405                 410                 415
Gly Asn Gly Phe Lys Gly Thr Trp Thr Glu Asn Gly Gly Asp Val
            420                 425                 430

Ser Gly Lys Phe Tyr Gly Pro Ala Gly Glu Val Ala Gly Lys Tyr
            435                 440                 445

Ser Tyr Arg Pro Thr Asp Ala Glu Lys Gly Gly Phe Gly Val Phe Ala
450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
610                 615                 620

Val Asn Val Gly Met Thr Lys Ser Val Arg Ile Asp Ile Gln Ile Glu
625                 630                 635                 640

Ala Ala Lys Gln

<210> SEQ ID NO 3
<211> LENGTH: 434
<212> TYPE: PRT
<213> ORGANISM: Artificial Sequence
<220> FEATURE:
<223> OTHER INFORMATION: Immunogen for Neisseria meningitidis -

```
        115                 120                 125

Ala Thr Arg Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205

Gly Leu Gln Ser Leu Thr Leu Asp Gln Ser Val Arg Lys Asn Glu Lys
    210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
        275                 280                 285

Gln Thr Glu Gln Ile Gln Asp Ser Glu His Ser Gly Lys Met Val Ala
    290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 4
<211> LENGTH: 686
<212> TYPE: PRT
<213> ORGANISM: Artificial Sequence
<220> FEATURE:
<223> OTHER INFORMATION: Immunogen for Neisseria meningitidis -
      fusion protein

<400> SEQUENCE: 4

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
```

-continued

```
            35                  40                  45
Thr Lys Gly Tyr Thr Pro Gln Ile Ser Val Val Gly Tyr Asp Arg His
 50                  55                  60
Leu Leu Leu Leu Gly Gln Val Ala Thr Glu Gly Lys Gln Phe Val
 65                  70                  75                  80
Gly Gln Ile Ala Arg Ser Glu Gln Ala Ala Gly Val Tyr Asn Tyr
                     85                  90                  95
Ile Thr Val Ala Ser Leu Pro Arg Thr Ala Gly Asp Ile Ala Gly Asp
                100                 105                 110
Thr Trp Asn Thr Ser Lys Val Arg Ala Thr Leu Leu Gly Ile Ser Pro
                115                 120                 125
Ala Thr Arg Ala Arg Val Lys Ile Val Thr Tyr Gly Asn Val Thr Tyr
                130                 135                 140
Val Met Gly Ile Leu Thr Pro Glu Glu Gln Ala Gln Ile Thr Gln Lys
145                 150                 155                 160
Val Ser Thr Thr Val Gly Val Gln Lys Val Ile Thr Leu Tyr Gln Asn
                165                 170                 175
Tyr Val Gln Arg Gly Ser Gly Gly Gly Val Ala Ala Asp Ile Gly
                180                 185                 190
Ala Gly Leu Ala Asp Ala Leu Thr Ala Pro Leu Asp His Lys Asp Lys
                195                 200                 205
Gly Leu Gln Ser Leu Thr Leu Asp Gln Ser Val Arg Lys Asn Glu Lys
                210                 215                 220
Leu Lys Leu Ala Ala Gln Gly Ala Glu Lys Thr Tyr Gly Asn Gly Asp
225                 230                 235                 240
Ser Leu Asn Thr Gly Lys Leu Lys Asn Asp Lys Val Ser Arg Phe Asp
                245                 250                 255
Phe Ile Arg Gln Ile Glu Val Asp Gly Gln Leu Ile Thr Leu Glu Ser
                260                 265                 270
Gly Glu Phe Gln Val Tyr Lys Gln Ser His Ser Ala Leu Thr Ala Phe
                275                 280                 285
Gln Thr Glu Gln Ile Gln Asp Ser Glu His Ser Gly Lys Met Val Ala
                290                 295                 300
Lys Arg Gln Phe Arg Ile Gly Asp Leu Gly Gly Glu His Thr Ala Phe
305                 310                 315                 320
Asn Gln Leu Pro Asp Gly Lys Ala Glu Tyr Arg Gly Thr Ala Phe Gly
                325                 330                 335
Ser Asp Asp Ala Gly Gly Lys Leu Thr Tyr Thr Ile Asp Phe Thr Lys
                340                 345                 350
Lys Gln Gly Asn Gly Lys Ile Glu His Leu Lys Ser Pro Glu Leu Asn
                355                 360                 365
Val Glu Leu Ala Ser Ala Glu Ile Lys Ala Asp Gly Lys Ser His Ala
                370                 375                 380
Val Ile Leu Gly Asp Val Arg Tyr Gly Ser Glu Glu Lys Gly Ser Tyr
385                 390                 395                 400
Ser Leu Gly Ile Phe Gly Gly Arg Ala Gln Glu Val Ala Gly Ser Ala
                405                 410                 415
Glu Val Lys Thr Val Asn Gly Ile Arg His Ile Gly Leu Ala Ala Lys
                420                 425                 430
Gln Gly Ser Gly Gly Gly Val Ala Ala Asp Ile Gly Ala Gly Leu
                435                 440                 445
Ala Asp Ala Leu Thr Ala Pro Leu Asp His Lys Asp Lys Gly Leu Gln
450                 455                 460
```

```
Ser Leu Thr Leu Asp Gln Ser Val Arg Lys Asn Glu Lys Leu Lys Leu
465                 470                 475                 480

Ala Ala Gln Gly Ala Glu Lys Thr Tyr Gly Asn Gly Asp Ser Leu Asn
                485                 490                 495

Thr Gly Lys Leu Lys Asn Asp Lys Val Ser Arg Phe Asp Phe Ile Arg
            500                 505                 510

Gln Ile Glu Val Asp Gly Gln Leu Ile Thr Leu Glu Ser Gly Glu Phe
        515                 520                 525

Gln Val Tyr Lys Gln Ser His Ser Ala Leu Thr Ala Phe Gln Thr Glu
    530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
                565                 570                 575

Pro Asp Gly Lys Ala Glu Tyr Arg Gly Thr Ala Phe Gly Ser Asp Asp
            580                 585                 590

Ala Gly Gly Lys Leu Thr Tyr Thr Ile Asp Phe Thr Lys Lys Gln Gly
        595                 600                 605

Asn Gly Lys Ile Glu His Leu Lys Ser Pro Glu Leu Asn Val Glu Leu
    610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Glu Lys Gly Ser Tyr Ser Leu Gly
                645                 650                 655

Ile Phe Gly Gly Arg Ala Gln Glu Val Ala Gly Ser Ala Glu Val Lys
            660                 665                 670

Thr Val Asn Gly Ile Arg His Ile Gly Leu Ala Ala Lys Gln
        675                 680                 685

<210> SEQ ID NO 5
<211> LENGTH: 776
<212> TYPE: PRT
<213> ORGANISM: Artificial Sequence
<220> FEATURE:
<223> OTHER INFORMATION: Immunogen for Neisseria meningitidis -
      fusion protein

<400> SEQUENCE: 5

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr

```
            130              135                 140
Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Gly Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Val Ala Ala Asp Ile Gly Ala
            260                 265                 270

Gly Leu Ala Asp Ala Leu Thr Ala Pro Leu Asp His Lys Asp Lys Gly
        275                 280                 285

Leu Gln Ser Leu Thr Leu Asp Gln Ser Val Arg Lys Asn Glu Lys Leu
    290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
            340                 345                 350

Glu Phe Gln Val Tyr Lys Gln Ser His Ser Ala Leu Thr Ala Phe Gln
        355                 360                 365

Thr Glu Gln Ile Gln Asp Ser Glu His Ser Gly Lys Met Val Ala Lys
    370                 375                 380

Arg Gln Phe Arg Ile Gly Asp Ile Ala Gly Glu His Thr Ser Phe Asp
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
            420                 425                 430

Lys Gln Gly Asn Gly Lys Ile Glu His Leu Lys Ser Pro Glu Leu Asn
        435                 440                 445

Val Asp Leu Ala Ala Ala Asp Ile Lys Pro Asp Gly Lys Arg His Ala
    450                 455                 460

Val Ile Ser Gly Ser Val Leu Tyr Asn Gln Ala Glu Lys Gly Ser Tyr
465                 470                 475                 480

Ser Leu Gly Ile Phe Gly Gly Lys Ala Gln Glu Val Ala Gly Ser Ala
                485                 490                 495

Glu Val Lys Thr Val Asn Gly Ile Arg His Ile Gly Leu Ala Ala Lys
            500                 505                 510

Gln Gly Ser Gly Pro Asp Ser Asp Arg Leu Gln Arg Arg Val Ala
        515                 520                 525

Ala Asp Ile Gly Thr Gly Leu Ala Asp Ala Leu Thr Ala Pro Leu Asp
    530                 535                 540

His Lys Asp Lys Gly Leu Lys Ser Leu Thr Leu Glu Asp Ser Ile Pro
545                 550                 555                 560
```

```
Gln Asn Gly Thr Leu Thr Leu Ser Ala Gln Gly Ala Glu Lys Thr Phe
                565             570                 575
Lys Ala Gly Asp Lys Asp Asn Ser Leu Asn Thr Gly Lys Leu Lys Asn
            580             585                 590
Asp Lys Ile Ser Arg Phe Asp Phe Val Gln Lys Ile Glu Val Asp Gly
            595             600             605
Gln Thr Ile Thr Leu Ala Ser Gly Glu Phe Gln Ile Tyr Lys Gln Asn
            610             615             620
His Ser Ala Val Val Ala Leu Gln Ile Glu Lys Ile Asn Asn Pro Asp
625                 630                 635                 640
Lys Thr Asp Ser Leu Ile Asn Gln Arg Ser Phe Leu Val Ser Gly Leu
                645             650                 655
Gly Gly Glu His Thr Ala Phe Asn Gln Leu Pro Gly Gly Lys Ala Glu
            660             665             670
Tyr His Gly Lys Ala Phe Ser Ser Asp Asp Pro Asn Gly Arg Leu His
            675             680             685
Tyr Ser Ile Asp Phe Thr Lys Lys Gln Gly Tyr Gly Arg Ile Glu His
            690             695             700
Leu Lys Thr Leu Glu Gln Asn Val Glu Leu Ala Ala Ala Glu Leu Lys
705             710             715                 720
Ala Asp Glu Lys Ser His Ala Val Ile Leu Gly Asp Thr Arg Tyr Gly
            725             730             735
Ser Glu Glu Lys Gly Thr Tyr His Leu Ala Leu Phe Gly Asp Arg Ala
            740             745             750
Gln Glu Ile Ala Gly Ser Ala Thr Val Lys Ile Gly Glu Lys Val His
            755             760             765
Glu Ile Gly Ile Ala Gly Lys Gln
770             775
```